United States Patent
Charrier et al.

(10) Patent No.: US 10,822,331 B2
(45) Date of Patent: *Nov. 3, 2020

(54) PROCESSES FOR PREPARING ATR INHIBITORS

(71) Applicant: Vertex Pharmaceuticals Incorporated, Boston, MA (US)

(72) Inventors: Jean-Damien Charrier, Abingdon (GB); John Studley, Abingdon (GB); Francoise Yvonne Theodora Marie Pierard, Abingdon (GB); Steven John Durrant, Abingdon (GB); Benjamin Joseph Littler, Carlsbad, CA (US); Robert Michael Hughes, San Diego, CA (US); David Andrew Siesel, San Diego, CA (US); Paul Angell, Carlsbad, CA (US); Armando Urbina, San Diego, CA (US); Yi Shi, Natick, MA (US)

(73) Assignee: VERTEX PHARMACEUTICALS INCORPORATED, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/233,641

(22) Filed: Dec. 27, 2018

(65) Prior Publication Data

US 2019/0202818 A1    Jul. 4, 2019

Related U.S. Application Data

(62) Division of application No. 15/849,241, filed on Dec. 20, 2017, now Pat. No. 10,208,027, which is a
(Continued)

(51) Int. Cl.
*C07D 413/04* (2006.01)
*C07D 413/14* (2006.01)
(Continued)

(52) U.S. Cl.
CPC .......... *C07D 413/04* (2013.01); *C07C 251/48* (2013.01); *C07D 241/20* (2013.01); *C07D 413/14* (2013.01)

(58) Field of Classification Search
CPC .. C07D 413/04; C07D 413/14; C07D 241/20; C07D 309/14; C07C 251/48;
(Continued)

(56) References Cited

U.S. PATENT DOCUMENTS 4,309,430 A   1/1982  Bock et al.
5,143,824 A   9/1992  Yamakawa et al.
(Continued)

FOREIGN PATENT DOCUMENTS

CN    1551869 A    12/2004
CN    101001606 A    7/2007
(Continued)

OTHER PUBLICATIONS

Abdel-Magid, "Inhibitors of ATR Kinase for Treatment of Cancer," ACS Medicinal Chemistry Letters, vol. 4, No. 8, Jun. 2013 (pp. 688-689).
(Continued)

*Primary Examiner* — John M Mauro
(74) *Attorney, Agent, or Firm* — Dechert LLP; Andrea L. C. Reid

(57) ABSTRACT

The present invention relates to processes and intermediates for preparing compounds useful as inhibitors of ATR kinase, such as aminopyrazine-isoxazole derivatives and related molecules. The present invention also relates to compounds useful as inhibitors of ATR protein kinase. The invention relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and solid forms of the compounds of this invention.

The compounds of this invention have formula I or II:

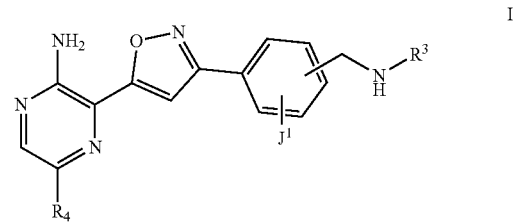

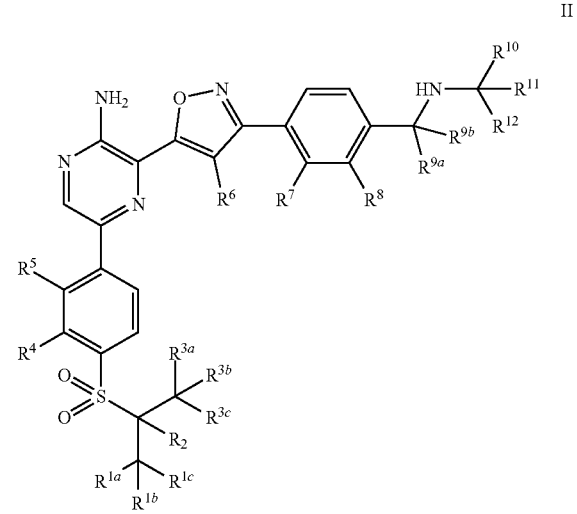

35 Claims, 20 Drawing Sheets

Related U.S. Application Data division of application No. 14/678,489, filed on Apr. 3, 2015, now Pat. No. 9,862,709, which is a division of application No. 13/631,759, filed on Sep. 28, 2012, now Pat. No. 9,035,053.

(60) Provisional application No. 61/541,865, filed on Sep. 30, 2011.

(51) Int. Cl.

| | | |
|---|---|---|
| C07D 241/20 | (2006.01) | |
| C07C 251/48 | (2006.01) | |
| C07D 241/14 | (2006.01) | |
| C07D 309/14 | (2006.01) | |
| C07B 59/00 | (2006.01) | |
| A61K 31/497 | (2006.01) | |
| A61P 35/00 | (2006.01) | |

(58) Field of Classification Search
CPC ... C07C 269/06; C07B 2200/05; C07B 59/00; A61K 31/497; A61P 35/00
See application file for complete search history.

(56) References Cited

U.S. PATENT DOCUMENTS

| | | | |
|---|---|---|---|
| 6,420,367 | B1 | 7/2002 | Ueda et al. |
| 6,469,002 | B1 | 10/2002 | Ohshima et al. |
| 6,660,753 | B2 | 12/2003 | Van Wagenen et al. |
| 6,790,935 | B1 | 9/2004 | Mutter et al. |
| 6,858,600 | B2 | 2/2005 | Hamilton et al. |
| 6,992,087 | B2 | 1/2006 | Verhoest et al. |
| 7,041,672 | B2 | 5/2006 | Verhoest et al. |
| 7,043,079 | B2 | 5/2006 | Malvar et al. |
| 7,145,002 | B2 | 12/2006 | Brands et al. |
| 7,199,123 | B2 | 4/2007 | Munchhof |
| 7,277,118 | B2 | 10/2007 | Foote |
| 7,385,626 | B2 | 6/2008 | Aggarwal et al. |
| 7,394,926 | B2 | 7/2008 | Bryll et al. |
| 7,452,993 | B2 | 11/2008 | Arnold et al. |
| 7,574,131 | B2 | 8/2009 | Chang et al. |
| 7,622,583 | B2 | 11/2009 | Ungashe et al. |
| 7,626,021 | B2 | 12/2009 | Arnold et al. |
| 7,700,601 | B2 | 4/2010 | Chan et al. |
| 7,704,995 | B2 | 4/2010 | Buhr et al. |
| 7,829,558 | B2 | 11/2010 | Arnold et al. |
| 7,872,031 | B2 | 1/2011 | Lauffer et al. |
| 7,902,197 | B2 | 3/2011 | Elworthy et al. |
| 7,932,254 | B2 | 4/2011 | DuBois et al. |
| 7,939,531 | B2 | 5/2011 | Bamberg et al. |
| 7,981,893 | B2 | 7/2011 | Mortensen et al. |
| 8,063,032 | B2 | 11/2011 | Chytil et al. |
| 8,106,197 | B2 | 1/2012 | Cui et al. |
| 8,410,112 | B2 | 4/2013 | Charrier et al. |
| 8,492,582 | B2 | 7/2013 | Yokotani et al. |
| 8,765,751 | B2 | 7/2014 | Charrier et al. |
| 8,841,308 | B2 | 9/2014 | Charrier et al. |
| 8,841,337 | B2 | 9/2014 | Charrier et al. |
| 8,841,449 | B2 | 9/2014 | Charrier et al. |
| 8,841,450 | B2 | 9/2014 | Charrier et al. |
| 8,846,686 | B2 | 9/2014 | Charrier et al. |
| 8,846,917 | B2 | 9/2014 | Charrier et al. |
| 8,846,918 | B2 | 9/2014 | Charrier et al. |
| 8,853,217 | B2 | 10/2014 | Charrier et al. |
| 8,877,759 | B2 | 11/2014 | Charrier et al. |
| 8,912,198 | B2 | 12/2014 | Charrier et al. |
| 8,962,631 | B2 | 2/2015 | Charrier et al. |
| 8,969,356 | B2 | 3/2015 | Charrier et al. |
| 8,999,632 | B2 | 4/2015 | Falcon et al. |
| 9,035,053 | B2 * | 5/2015 | Charrier ............ C07D 413/04 544/405 |
| 9,062,008 | B2 | 6/2015 | Charrier et al. |
| 9,096,584 | B2 | 8/2015 | Charrier et al. |
| 9,334,244 | B2 | 5/2016 | Charrier et al. |
| 9,340,546 | B2 | 5/2016 | Ahmad et al. |
| 9,365,557 | B2 | 6/2016 | Charrier et al. |
| 9,650,381 | B2 | 5/2017 | Ahmad et al. |
| 9,670,215 | B2 | 6/2017 | Ahmad et al. |
| 10,208,027 | B2 | 2/2019 | Charrier et al. |
| 2002/0064314 | A1 | 5/2002 | Comaniciu et al. |
| 2002/0068828 | A1 | 6/2002 | Schnatterer et al. |
| 2002/0158984 | A1 | 10/2002 | Brodsky et al. |
| 2002/0180759 | A1 | 12/2002 | Park et al. |
| 2002/0195563 | A1 | 12/2002 | Lida et al. |
| 2003/0008882 | A1 | 1/2003 | Hamilton et al. |
| 2003/0055085 | A1 | 3/2003 | Wagenen et al. |
| 2003/0199511 | A1 | 10/2003 | Li et al. |
| 2004/0034037 | A1 | 2/2004 | Harbeson et al. |
| 2004/0075741 | A1 | 4/2004 | Berkey et al. |
| 2004/0100560 | A1 | 5/2004 | Stavely et al. |
| 2004/0175042 | A1 | 9/2004 | Kroeker et al. |
| 2004/0180905 | A1 | 9/2004 | Munchhof |
| 2004/0202382 | A1 | 10/2004 | Pilu |
| 2004/0252193 | A1 | 12/2004 | Higgins |
| 2004/0264793 | A1 | 12/2004 | Okubo |
| 2005/0116968 | A1 | 6/2005 | Barrus et al. |
| 2005/0123902 | A1 | 6/2005 | Meneses et al. |
| 2005/0207487 | A1 | 9/2005 | Monroe |
| 2005/0261339 | A1 | 11/2005 | Ohi et al. |
| 2005/0276765 | A1 | 12/2005 | Nghiem et al. |
| 2006/0046991 | A1 | 3/2006 | Cui et al. |
| 2006/0083440 | A1 | 4/2006 | Chen |
| 2006/0142307 | A1 | 6/2006 | Hellberg et al. |
| 2006/0211709 | A1 | 9/2006 | Buhr et al. |
| 2007/0032501 | A1 | 2/2007 | Augeri et al. |
| 2007/0037794 | A1 | 2/2007 | Ungashe et al. |
| 2007/0092245 | A1 | 4/2007 | Bazakos et al. |
| 2007/0120954 | A1 | 5/2007 | Allen et al. |
| 2007/0149547 | A1 | 6/2007 | Bonnefous et al. |
| 2007/0254868 | A1 | 11/2007 | Lauffer et al. |
| 2007/0270420 | A1 | 11/2007 | Harbeson et al. |
| 2007/0287711 | A1 | 12/2007 | Arnold et al. |
| 2008/0132698 | A1 | 6/2008 | Fagnou et al. |
| 2008/0176892 | A1 | 7/2008 | Heinrich et al. |
| 2009/0001843 | A1 | 1/2009 | Enomoto et al. |
| 2009/0005381 | A1 | 1/2009 | Brown et al. |
| 2009/0143410 | A1 | 6/2009 | Patel |
| 2009/0156512 | A1 | 6/2009 | Umemura et al. |
| 2009/0215724 | A1 | 8/2009 | DuBois et al. |
| 2009/0215750 | A1 | 8/2009 | Bamberg et al. |
| 2009/0215785 | A1 | 8/2009 | DuBois et al. |
| 2009/0215788 | A1 | 8/2009 | Elworthy et al. |
| 2009/0306087 | A1 | 12/2009 | Ibrahim et al. |
| 2010/0036118 | A1 | 2/2010 | Arnold et al. |
| 2010/0168138 | A1 | 7/2010 | DeGoey et al. |
| 2010/0179194 | A1 | 7/2010 | Mihara et al. |
| 2010/0190980 | A1 | 7/2010 | Umemiya et al. |
| 2010/0204214 | A1 | 8/2010 | Chytil et al. |
| 2010/0222318 | A1 | 9/2010 | Charrier et al. |
| 2010/0233091 | A1 | 9/2010 | Neumann et al. |
| 2010/0249387 | A1 | 9/2010 | Inouye |
| 2011/0015231 | A1 | 1/2011 | Al-Abed et al. |
| 2011/0059936 | A1 | 3/2011 | Lauffer et al. |
| 2011/0098325 | A1 | 4/2011 | Raynham et al. |
| 2011/0275797 | A1 | 11/2011 | Yokotani et al. |
| 2011/0288067 | A1 | 11/2011 | Hendricks et al. |
| 2011/0288097 | A1 | 11/2011 | Hendricks et al. |
| 2012/0025805 | A1 | 2/2012 | Matsushita et al. |
| 2012/0027874 | A1 | 2/2012 | Charrier et al. |
| 2012/0035407 | A1 | 2/2012 | Charrier et al. |
| 2012/0035408 | A1 | 2/2012 | Charrier et al. |
| 2012/0040020 | A1 | 2/2012 | Charrier et al. |
| 2012/0046295 | A1 | 2/2012 | Charrier et al. |
| 2012/0065247 | A1 | 3/2012 | Thompson et al. |
| 2012/0115874 | A1 | 5/2012 | Wang et al. |
| 2012/0122884 | A1 | 5/2012 | Charrier et al. |
| 2012/0177748 | A1 | 7/2012 | Charrier et al. |
| 2012/0178756 | A1 | 7/2012 | Charrier et al. |
| 2012/0178915 | A1 | 7/2012 | Xu |
| 2012/0220587 | A1 | 8/2012 | Emde et al. |
| 2012/0225857 | A1 | 9/2012 | Augeri et al. |
| 2013/0017273 | A1 | 1/2013 | Everitt et al. |
| 2013/0018035 | A1 | 1/2013 | MacCormick et al. |

(56) References Cited

U.S. PATENT DOCUMENTS

| | | |
|---|---|---|
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0107093 A1 | 4/2014 | Charrier et al. |
| 2014/0113005 A1 | 4/2014 | Charrier et al. |
| 2014/0134596 A1 | 5/2014 | Falcon et al. |
| 2014/0163000 A1 | 6/2014 | Ahmad et al. |
| 2014/0187529 A1 | 7/2014 | Shetty et al. |
| 2014/0249157 A1 | 9/2014 | Ahmad et al. |
| 2014/0356456 A1 | 12/2014 | Pollard et al. |
| 2015/0031661 A1 | 1/2015 | Charrier et al. |
| 2015/0051187 A1 | 2/2015 | Charrier et al. |
| 2015/0158872 A1 | 6/2015 | Charrier et al. |
| 2015/0239874 A1 | 8/2015 | Charrier et al. |
| 2015/0247866 A1 | 9/2015 | Falcon et al. |
| 2015/0274710 A1 | 10/2015 | Charrier et al. |
| 2015/0353560 A1 | 12/2015 | Ahmad et al. |
| 2015/0359797 A1 | 12/2015 | Helleday et al. |
| 2016/0030424 A1 | 2/2016 | Pollard et al. |
| 2016/0271129 A1 | 9/2016 | Charrier et al. |
| 2016/0311809 A1 | 10/2016 | Charrier et al. |
| 2016/0347754 A1 | 12/2016 | Ahmad et al. |
| 2017/0349596 A1 | 5/2017 | Ahmad et al. |
| 2018/0072735 A1 | 3/2018 | Ahmad et al. |
| 2018/0155346 A1 | 6/2018 | Ahmad et al. |
| 2018/0170922 A1 | 6/2018 | Charrier et al. |

FOREIGN PATENT DOCUMENTS

| | | |
|---|---|---|
| CN | 101479255 A | 7/2009 |
| CN | 101537007 A | 9/2009 |
| CN | 101652354 A | 2/2010 |
| CN | 101671336 A | 3/2010 |
| CN | 103373996 A | 10/2013 |
| EP | 313724 A2 | 5/1989 |
| EP | 1217000 A1 | 6/2002 |
| EP | 2157090 A1 | 2/2010 |
| JP | 62270623 A2 | 11/1987 |
| JP | 63208520 A2 | 8/1988 |
| JP | H02-72370 A | 3/1990 |
| JP | H02-72372 A | 3/1990 |
| JP | H03-74370 A | 3/1991 |
| JP | H10-77286 A | 3/1998 |
| JP | 2002072370 A | 3/2002 |
| JP | 2002072372 A | 3/2002 |
| JP | 2002518389 A | 6/2002 |
| JP | 2003074370 A | 3/2003 |
| JP | 2003516974 A | 5/2003 |
| JP | 2005511531 A | 4/2005 |
| JP | 2005530760 A | 10/2005 |
| JP | 2006156445 A | 6/2006 |
| JP | 2006516124 A | 6/2006 |
| JP | 2006519232 A | 8/2006 |
| JP | 2006519833 A | 8/2006 |
| JP | 2006520794 A | 9/2006 |
| JP | 2006521357 A | 9/2006 |
| JP | 2007524682 A | 8/2007 |
| JP | 2008510790 A | 4/2008 |
| JP | 2008510792 A | 4/2008 |
| JP | 2008517945 A | 5/2008 |
| JP | 2008525453 A | 7/2008 |
| JP | 2008543754 A | 12/2008 |
| JP | 2009503103 A | 1/2009 |
| JP | 2009027904 A | 2/2009 |
| JP | 2009530233 A | 8/2009 |
| JP | 2009532356 A | 9/2009 |
| JP | 2009533327 A | 9/2009 |
| JP | 2009541247 A | 11/2009 |
| JP | 2009541268 A | 11/2009 |
| JP | 2010506934 A | 3/2010 |
| JP | 2010509356 A | 3/2010 |
| JP | 2010077286 A | 4/2010 |
| JP | 2010513433 A | 4/2010 |
| JP | 2010180180 A | 8/2010 |
| JP | 2011500778 A | 1/2011 |
| JP | 2011042639 A | 3/2011 |
| JP | 2012508260 A | 4/2012 |
| JP | 2012513398 A | 6/2012 |
| JP | 2012533248 A | 12/2012 |
| JP | 2013501720 A | 1/2013 |
| JP | 2013505900 A | 2/2013 |
| JP | 2013517264 A | 5/2013 |
| JP | 2013525476 A | 6/2013 |
| JP | 2014510072 A | 4/2014 |
| JP | 2014518545 A | 7/2014 |
| JP | 2014165380 A | 9/2014 |
| NZ | 593316 A | 6/2013 |
| NZ | 593969 A | 11/2013 |
| WO | WO-1997043267 A1 | 11/1997 |
| WO | WO-1998042701 A1 | 10/1998 |
| WO | WO-1999044609 A1 | 9/1999 |
| WO | WO-2000004014 A1 | 1/2000 |
| WO | WO-2000076982 A1 | 12/2000 |
| WO | WO-2001044206 A1 | 6/2001 |
| WO | WO-2002009648 A2 | 2/2002 |
| WO | WO-2002080899 A1 | 10/2002 |
| WO | WO-2003004472 A1 | 1/2003 |
| WO | WO-2003004475 A1 | 1/2003 |
| WO | WO-2003032971 A1 | 4/2003 |
| WO | WO-2003045924 A1 | 6/2003 |
| WO | WO-2003076422 A1 | 9/2003 |
| WO | WO-2003080610 A1 | 10/2003 |
| WO | WO-2003087057 A1 | 10/2003 |
| WO | WO-2003092686 A1 | 11/2003 |
| WO | WO-2003093297 A2 | 11/2003 |
| WO | WO-2003101968 A1 | 12/2003 |
| WO | WO-2004000318 A2 | 12/2003 |
| WO | WO-2004000820 A2 | 12/2003 |
| WO | WO-2004033431 A2 | 4/2004 |
| WO | WO-2004055005 A1 | 7/2004 |
| WO | WO-2004055006 A1 | 7/2004 |
| WO | WO-2004076412 A2 | 9/2004 |
| WO | WO-2004080982 A1 | 9/2004 |
| WO | WO-2004084813 A2 | 10/2004 |
| WO | WO-2004084824 A2 | 10/2004 |
| WO | WO-2004085409 A2 | 10/2004 |
| WO | WO-2004103279 A2 | 12/2004 |
| WO | WO-2004103369 A1 | 12/2004 |
| WO | WO-2004103991 A1 | 12/2004 |
| WO | WO-2005028475 A2 | 3/2005 |
| WO | WO-2005058876 A1 | 6/2005 |
| WO | WO-2005079802 A1 | 9/2005 |
| WO | WO-2005123672 A2 | 12/2005 |
| WO | WO-2006015124 A2 | 2/2006 |
| WO | WO-2006021886 A1 | 3/2006 |
| WO | WO-2006047504 A1 | 5/2006 |
| WO | WO-2006053342 A2 | 5/2006 |
| WO | WO-2006058074 A1 | 6/2006 |
| WO | WO-2006067462 A1 | 6/2006 |
| WO | WO-2006071548 A2 | 7/2006 |
| WO | WO-2006075152 A1 | 7/2006 |
| WO | WO-2006088837 A2 | 8/2006 |
| WO | WO-2006114180 A1 | 11/2006 |
| WO | WO-2006120573 A2 | 11/2006 |
| WO | WO-2006124874 A2 | 11/2006 |
| WO | WO-2006135604 A2 | 12/2006 |
| WO | WO-2007015632 A1 | 2/2007 |
| WO | WO-2007016674 A2 | 2/2007 |
| WO | WO-2007058850 A2 | 5/2007 |
| WO | WO-2007063012 A1 | 6/2007 |
| WO | WO-2007066805 A1 | 6/2007 |
| WO | WO-2007076360 A1 | 7/2007 |
| WO | WO-2007095588 A1 | 8/2007 |

(56) References Cited

FOREIGN PATENT DOCUMENTS

| | | |
|---|---|---|
| WO | WO-2007096151 A2 | 8/2007 |
| WO | WO-2007096764 A2 | 8/2007 |
| WO | WO-2007096765 A1 | 8/2007 |
| WO | WO-2007102770 A1 | 9/2007 |
| WO | WO-2007111904 A2 | 10/2007 |
| WO | WO-2007126964 A2 | 11/2007 |
| WO | WO-2007147746 A1 | 12/2007 |
| WO | WO-2007147874 A1 | 12/2007 |
| WO | WO-2008025820 A1 | 3/2008 |
| WO | WO-2008037477 A1 | 4/2008 |
| WO | WO-2008038010 A1 | 4/2008 |
| WO | WO-2008040651 A1 | 4/2008 |
| WO | WO-2008051493 A2 | 5/2008 |
| WO | WO-2008060907 A2 | 5/2008 |
| WO | WO-2008071456 A2 | 6/2008 |
| WO | WO-2008074997 A1 | 6/2008 |
| WO | WO-2008079291 A2 | 7/2008 |
| WO | WO-2008079903 A1 | 7/2008 |
| WO | WO-2008079906 A1 | 7/2008 |
| WO | WO-2008103277 A2 | 8/2008 |
| WO | WO-2008106692 A1 | 9/2008 |
| WO | WO-2008122375 A2 | 10/2008 |
| WO | WO-2008124850 A1 | 10/2008 |
| WO | WO-2008141065 A1 | 11/2008 |
| WO | WO-2008144463 A1 | 11/2008 |
| WO | WO-2008144464 A1 | 11/2008 |
| WO | WO-2008156174 A1 | 12/2008 |
| WO | WO-2008157191 A2 | 12/2008 |
| WO | WO-2009005638 A2 | 1/2009 |
| WO | WO-2009007390 A2 | 1/2009 |
| WO | WO-2009012482 A2 | 1/2009 |
| WO | WO-2009014637 A2 | 1/2009 |
| WO | WO-2009016460 A2 | 2/2009 |
| WO | WO-2009024825 A1 | 2/2009 |
| WO | WO-2009037247 A1 | 3/2009 |
| WO | WO-2009053737 A2 | 4/2009 |
| WO | WO-2009099982 A1 | 8/2009 |
| WO | WO-2009106885 A1 | 9/2009 |
| WO | WO-2009111280 A1 | 9/2009 |
| WO | WO-2009115517 A2 | 9/2009 |
| WO | WO-2010015803 A1 | 2/2010 |
| WO | WO-2010016005 A1 | 2/2010 |
| WO | WO-2010017055 A2 | 2/2010 |
| WO | WO-2010048131 A1 | 4/2010 |
| WO | WO-2010054398 A1 | 5/2010 |
| WO | WO-2010063634 A1 | 6/2010 |
| WO | WO-2010068483 A2 | 6/2010 |
| WO | WO-2010071837 A1 | 6/2010 |
| WO | WO-2010073034 A1 | 7/2010 |
| WO | WO-2010075200 A1 | 7/2010 |
| WO | WO-2011006074 | 7/2010 |
| WO | WO-2011008830 A1 | 1/2011 |
| WO | WO-2011017513 A1 | 2/2011 |
| WO | WO-2011035855 A1 | 3/2011 |
| WO | WO-2011044157 A1 | 4/2011 |
| WO | WO-2011086531 A2 | 7/2011 |
| WO | WO-2011117145 A2 | 9/2011 |
| WO | WO-2011124998 A1 | 10/2011 |
| WO | WO-2011130689 A1 | 10/2011 |
| WO | WO-2011138751 A2 | 11/2011 |
| WO | WO-2011143399 A1 | 11/2011 |
| WO | WO-2011143419 A1 | 11/2011 |
| WO | WO-2011143422 A1 | 11/2011 |
| WO | WO-2011143423 A2 | 11/2011 |
| WO | WO-2011143425 A2 | 11/2011 |
| WO | WO-2011143426 A1 | 11/2011 |
| WO | WO-2011144584 A1 | 11/2011 |
| WO | WO-2011144585 A1 | 11/2011 |
| WO | WO-2012127347 A1 * | 9/2012 ........... C07D 261/04 |
| WO | WO-2012158785 A1 | 11/2012 |
| WO | WO-2013049722 A1 | 4/2013 |
| WO | WO-2013049726 A2 | 4/2013 |
| WO | WO-2013049859 A1 | 4/2013 |

OTHER PUBLICATIONS

Adamczyk et al., "Synthesis of 3,7-dihydroimidazo[1,2a]pyrazine-3-ones and their chemiluminescent properties," Tetrahedron, vol. 59, No. 41, 2003 (pp. 8129-8142).

Ammar et al., "3-Ethoxycarbonylmethylenequinoxalin-2-one in heterocyclic synthesis. Part 1: Synthesis of new substituted and condensed quinoxalines," Afinidad, vol. 62, No. 516, 2005 (pp. 151-160).

Bastin et al., "Salt Selection and Optimisation Procedures for Pharmaceutical New Chemical Entities," Organic Process Research and Development, American Chemical Society, vol. 4, No. 5, 2000 (pp. 42735).

Biss et al., "Selective tumor killing based on specific DNA-damage response deficiencies," Cancer Biology & Therapy, Mar. 2012, (pp. 239-246).

Bracher et al., "Total Synthesis of the Indolizidinium Alkaloid Ficuseptine," European Journal of Organic Chemistry, 2002 (pp. 2288-2291).

Buscemi et al., "DNA damage-induced cell cycle regulation and function of novel Chk2 phosphoresidues," Molecular and Cellular Biology, vol. 26, No. 21, Nov. 2006 Nov, (pp. 7832-7845) Epub Aug. 28, 2006.

Britain, H. G., ed. "Polymorphism in pharmaceutical solids," CRC Press, 2009, Chapters 7 (p. 233-281) and 12 (p. 436-480).

Bryn, S. et al. "Pharmaceuticals Solids: A Strategic Approach to Regulatory Considerations," Pharmaceutical Research, vol. 12, No. 7, Jul. 1, 1995 (pp. 945-954).

Caira, "Crystalline Polymorphism of Organic Compounds" Topics in Current Chemistry, Design of Organic Solids, vol. 198, 1998 (pp. 163-208).

Campone et al., "Phase I and pharmacokinetic trial of AP5346, a DACH-platinum-polymer conjugate, administered weekly for three out of every 4 weeks to advanced solid tumor patients," Cancer Chemother Pharmacol, vol. 60, No. 4, Sep. 2007 (pp. 523-533) Epub Feb. 17, 2007.

Charrier et al, "Discovery of potent and selective inhibitors of ataxia telangiectasia mutated and Rad3 related (ATR) protein kinase as potential anticancer agents," Journal Medicinal Chemistry, vol. 54, No. 7, Apr. 14, 2011 (pp. 2320-2330) doi: 10.1021/jm101488z. Epub Mar. 17, 2011.

Charrier et al., "Discovery of Potent and Selective Inhibitors of ATR (Ataxia Telangiectasia Mutated and Rad3 Related) as Potential AntiCancer Agents," Supplementary Information, Apr. 14, 2011 (pp. 47).

Charrier, "Discovery of potent and selective inhibitors of Ataxia Telangiectasia mutated and Rad3 related (ATR) protein kinase as potential anticancer agents," Presentation, ACS Denver 2011. Aug. 28, 2011. 21 pages.

Chen et al., "Development of biomarker of ATR activity in surrogate human tissues," Newcastle University, Poster. Nov. 2012. 1 page.

Chen et al., "Targeting the S and G2 checkpoint to treat cancer," Drug Discovery Today, vol. 17, No. 5-6, Mar. 2012, (pp. 194-202) doi: 10.1016/j.drudis.2011.12.009. Epub Dec. 15, 2011.

Clark et al., "Mass spectrometry of pyrrolo [2, 3-b] pyrazines and pyrazino [2, 3-b]indole," Organic Mass Spectrometry, vol. 12, No. 7, 1977 (pp. 421-423).

Curtin, "Inhibiting the DNA damage response as a therapeutic manoeuvre in cancer," British Jouranl of Pharmacology, vol. 169, No. 8, Aug. 2013 (pp. 1745-1765).

Curtin, "Inhibiting the DNA damage response as a therapeutic manoeuvre in cancer," British Journal Pharmacology, 2013 (pp. 1-52).

Darabantu et al., "Synthesis of new polyaza heterocycles," Part 42, Diazines, Tetrahedron, vol. 61, No. 11, 2005 (pp. 2897-2905).

De Wergifosse et al., "Coelenterazine: a two-stage antioxidant in lipid micelles" Free Radical Biology and Medicine, vol. 36, No. 3, 2004 (pp. 278-287).

Dias et al., "Synthesis of 2,6-diphenylpyrazine derivatives and their DNA binding and cytotoxic properties," European Journal of Medicinal Chemistry, vol. 40, 2005 (pp. 1206-1213).

(56) References Cited

OTHER PUBLICATIONS

El-Emary, "Synthesis and Biological Activity of Some New Pyrazolo[3,4-b]pyrazines," Journal Chinese Chemical Society (Taipei, Taiwan), vol. 53, No. 2, 2006 (pp. 391-401).
Erickson et al., "Structure-guided expansion of kinase fragment libraries driven by support vector machine models," Biochim Biophys Acta., vol. 1804, No. 3, Mar. 2010 (pp. 642-652).
Fernandes et al., "Synthesis and Biological Activity of Heterocyclic Derivatives derived from Ethyl-2-hydroxy-quinoxaline-3-carboxylate," Journal of Indian Chemistry Society, vol. 63, No. 4, 1986 (pp. 427-429).
Finlay et al., "Modulation of DNA repair by pharmacological inhibitors of the PIKK protein kinase family," Bioorganic Medicinal Chemistry Letters, vol. 22, No. 17, Sep. 1, 2012 (pp. 5352-5359).
Fokas et al., "Targeting ATR in DNA damage response and cancer therapeutics," Cancer Treat Review, vol. 40, No. 1, Feb. 2014 (pp. 109-117).
Fokas et al., "Targeting ATR in vivo using the novel inhibitor VE-822 results in selective sensitization of pancreatic tumors to radiation," Cell Death Disease, vol. 3, edition 441, Dec. 6, 2012.
Foote, K.M., "Drugging ATR: progress in the development of specific inhibitors for the treatment of cancer," Future medicinal chemistry 7.7, 2015 (pp. 873-891).
Gentili et al., "Alpha2-adrenoreceptors profile modulation. 4. From antagonist to agonist behavior," Journal of Medincinal Chemistry, vol. 51, No. 14, Jul. 24, 2008 ( pp. 4289-4299).
Golub T.R., "Molecular classification of cancer: class discovery and class prediction by gene expression monitoring," Science vol. 286, No. 5439, 1999 ( pp. 531-537).
Goto et al., "Squid bioluminescence I. Structure of watasenia oxyluciferin, a possible light-emitter in the bioluminescence of watasenia scintillans," Tetrahedron Letters, vol. 15, No. 26, 1974 (pp. 2321-2324).
Hall-Jackson et al., "ATR is a caffeine-sensitive, DNA-activated protein kinase with a substrate specificity distinct from DNA-PK," Oncogene, vol. 18, No. 48, Nov. 18, 1999 (pp. 6707-6713).
Hancock et al., "Characteristics and significance of the amorphous state in pharmaceutical systems," Journal Pharmaceutical Sciences, vol. 86, No. 1, Jan. 1997 (pp. 1-12).
Hart et al., "Renilla Reinformis Bioluminescence: Luciferase-Catalyzed Production of Nonradiating Excited States from Luciferin Analogues and Elucidation of the Excited State Species Involved in Energy Transfer to Renilla Green Fluorescent Protein," Biochemistry, vol. 18, 1979 (pp. 2204-2210).
Hickson et al., "Identification and characterization of a novel and specific inhibitor of the ataxia-telangiectasia mutated kinase ATM," Cancer Research, vol. 64, No. 24, Dec. 15, 2004 (pp. 9152-9159).
Hilfiker et al., "Relevance of Solid-state Properties for Pharmaceutical Products," Polymorphism in the Pharmaceutical Industry, 2006 (pp. 1-19).
Hilton et al., "Identification and characterisation of 2-aminopyridine inhibitors of checkpoint kinase 2," Bioorganic & Medicinal Chemistry, vol. 18, No. 2, Jan. 5, 2010 (pp. 707-718).
Hirano et al., "Bioluminescent properties of fluorinated semisynthetic aequorins," Tetrahedron Letters, vol. 39, No. 31, 1998 (pp. 5541-5544).
International Search Report and Written Opinion dated Apr. 23, 2013 for Application No. PCT/US2012/058127.
International Search Report and Written Opinion dated Aug. 10, 2012 for Application No. PCT/US2012/032438.
International Search Report and Written Opinion dated Aug. 23, 2013 for Application No. PCT/US2013/035466.
International Search Report and Written Opinion dated Dec. 20, 2013 for Application No. PCT/US2013/063254.
International Search Report and Written Opinion dated Dec. 28, 2011 for Application No. PCT/US2011/036245.
International Search Report and Written Opinion dated Feb. 1, 2013 for Application No. PCT/US2012/064426.
International Search Report and Written Opinion dated Feb. 1, 2013 for Application No. PCT/US2012/064430.
International Search Report and Written Opinion dated Feb. 15, 2013 for Application No. PCT/US2012/064421.
International Search Report and Written Opinion dated Feb. 26, 2013 for Application No. PCT/US2012/064433.
International Search Report and Written Opinion dated Feb. 27, 2014 for Application No. PCT/US2013/064920.
International Search Report and Written Opinion dated Jan. 11, 2012 for Application No. PCT/US2011/036243.
International Search Report and Written Opinion dated Jan. 30, 2013 for Application No. PCT/US2012/058117.
International Search Report and Written Opinion dated Jan. 30, 2013 for Application No. PCT/US2012/064435.
International Search Report and Written Opinion dated Jan. 8, 2013 for Application No. PCT/US2012/058374.
International Search Report and Written Opinion dated Jul. 19, 2011 for Application No. PCT/US2011/036246.
International Search Report and Written Opinion dated Jun. 17, 2011 for Application No. PCT/US2011/036214.
International Search Report and Written Opinion dated Jun. 28, 2011 for Application No. PCT/US2011/036242.
International Search Report and Written Opinion dated Nov. 12, 2012 for Application No. PCT/US2012/058119.
International Search Report and Written Opinion dated Nov. 12, 2012 for Application No. PCT/US2012/058121.
International Search Report and Written Opinion dated Oct. 12, 2011 for Application No. PCT/US2011/036239.
International Search Report and Written Opinion dated Mar. 4, 2010 for Application No. PCT/US2009/068827.
International Search Report and Written Opinion dated Mar. 15, 2010 for Application No. PCT/US2009/063922.
Jia et al., "A Facile Preparation of 2,6-Diarylpyrazines," Heteroatom Chemistry, vol. 9, No. 3, 1998 (pp. 341-345).
Jiang et al., "Synthesis and cytotoxicity evaluation of novel indolylpyrimidines and indolylpyrazines as potential antitumor agents," Bioorganic & Medicinal Chemistry, vol. 9, No. 5, May 2001 (pp. 1149-1154).
Jones et al., "A Suzuki Coupling Approach to Pyrazines Related to Coelenterazin," Synlett, vol. 6, 1996 (pp. 509-510).
Kao et al., "Inhibition of y-H2AX after ionizing radiation as a biological surrogate of impaired upstream DNA damage signaling and radiosensitivity," Journal Cancer Molecular, vol. 5, No. 2, 2010 (pp. 49-54).
Katritzky et al., "Efficient synthesis of 3,5-functionalized isoxazoles and isoxazolines via 1,3-dipolar cycloaddition reactions of 1-propargyl- and 1-allylbenzotriazoles," Journal of Heterocyclic Chemistry, vol. 37, No. 6, 2000 (pp. 1505-1510).
Kim et al., "Substrate specificities and identification of putative substrates of ATM kinase family members," Journal Biology Chemistry, vol. 274, No. 53, Dec. 31, 1999 (pp. 37538-37543).
Klicnar et al., "Studien in der chinoxalinreihe III. Synthese, reaktionen and ir-spektren einiger 3-hydroxy-2-carboxymethylchinoxalin-derivate", Collection Czechoslovak Chemical Communications, vol. 30, No. 9, 1965 (pp. 3092-3101).
Kumar et al., "Salt selection in drug development," Pharmaceutical Technology, vol. 32, No. 3, 2008 (pp. 12846).
Kumpaty et al., "Synthesis of N-methyl secondary amines," Synthetic Communications, vol. 33, No. 8, 2003 (pp. 1411-1416).
Kurasawa et al., "Revised Structure for the Product from the Reaction of 3-Hydrazinocarbonylmethylene-2-oxo-1,2,3,4-tetrahydroquinoxaline with Nitrous Acid," Chemical Pharmaceutical Bulletin, vol. 32, No. 10, 1984 (pp. 4140-4143).
Lala, "Role of nitric oxide in tumor progression: lessons from experimental tumors." Cancer and Metastasis Reviews 17.1, 1998 (pp. 91-106).
Lima et al., "Bioisosterism: a useful strategy for molecular modification and drug design," Current Medicinal Chemistry, vol. 12, No. 1, 2005 (pp. 23-49).
Ling et al., "Mechanism of Cell Cycle G2/M Arrest in Human Gastric Cancer BGC823 Cells Induced by Diallyl Disulfide," Chinese Journal of Clinical Oncology, vol. 3, Feb. 28, 2010 (pp. 121-125).
Liu et al., "Chemical Biology Foundation," Science Press, Sep. 30, 2010 (pp. 213-218).

(56) References Cited

OTHER PUBLICATIONS

Luo et al., "Molecular dynamics-based self-organizing molecular field analysis on 3-amino-6-arylpyrazines as the ataxia telangiectasia mutated and Rad3 related (ATR) protein kinase inhibitors," Medicinal Chemistry Research, 2013 (pp. 1-12).
March, March's Advanced Organic Chemistry, 2007, John Wiley and Sons, Chapter 16.
McKenna, G., et al., "Evaluation of the first potent and highly selective inhibitor of ATR inhibitor, VE-821: an approach to selectively sensitize cancer cells to ionizing and hypoxia", Poster, Mar. 31, 2012.
McKenna, G., et al., "Evaluation of the first potent and highly selective inhibitor of ATR kinase. an approach to selectively sensitize cancer cells to ionizing radiation and hypoxia", Abstract, Mar. 31, 2012.
Middleton et al., "ATR as a Therapeutic Target," Cancer Drug Discovery and Development. 2013. Author's Proof 20 pages.
Middleton et al., "ATR as a Therapeutic Target. In: Advances in DNA Repair in Cancer Therapy," Cancer Drug Discovery and Development, vol. 72, 2013 (pp. 211-228).
Middleton et al., "Chemosensitisation By, and Single Agent Activity of, ATR Inhibitor VE-821 in Human Breast Cancer Cells," European Journal of Cancer, vol. 1, Nov. 1, 2012, (pp. 85-86).
Morgan et al., "Mechanism of radiosensitization by the Chk1/2 inhibitor AZD7762 involves abrogation of the G2 checkpoint and inhibition of homologous recombinational DNA repair," Cancer Research, vol. 70, No. 12, Jun. 15, 2010 (pp. 4972-4981).
Muslimovic et al., "An optimized method for measurement of gamma-H2AX in blood mononuclear and cultured cells," Nature Protocols, vol. 3, No. 7, 2008 (pp. 1187-1193).
Nakamura et al., "Bimodal Chemiluminescence of 8-Chlorostyryl-6-phenylethynylimidazopyrazinone: Large Bathochromic Shift Caused by a Styryl Group at 8-Position," Tetrahedron Letters, vol. 39, 1998 (pp. 301-304).
Non-Final Office Action dated Aug. 8, 2013 in U.S. Appl. No. 13/631,727.
Non-Final Office Action dated Aug. 8, 2013 in U.S. Appl. No. 13/631,732.
Nowotnik, et al., "ProLindac (AP5346): a review of the development of an HPMA DACH platinum PolyA82:A102mer Therapeutic," Advanced Drug Delivery Reviews, vol. 61, No. 13, Nov. 12, 2009 (pp. 1214-1219).
Patani et al., "Bioisosterism: A Rational Approach in Drug Design," Chemical Reviews, vol. 96, No. 8, Dec. 19, 1996 (pp. 3147-3176).
Peasland et al., "Identification and evaluation of a potent novel ATR inhibitor, NU6027, in breast and ovarian cancer cell lines," British Journal of Cancer, vol. 105, No. 3, Jul. 2011 (pp. 372-381).
Pires et al., "Targeting radiation-resistant hypoxic tumour cells through ATR inhibition," British Journal of Cancer, vol. 107, No. 2, Jul. 10, 2012 (pp. 291-299).
Pollard et al., "Defining optimal dose schedules for ATR inhibitors in combination with DNA damaging drugs: Informing clinical studies of VX-970, the first-in-class ATR inhibitor," Proceedings, AACR Annual Meeting. Apr. 16-20, 2016.
Pollard, Inhibition of the DNA Damage Response Kinase, ATR, as a Promising Anti-Cancer Approach. Presentation, Mar. 8, 2012. 28 pages.
Prevo et al., "The novel ATR inhibitor VE-821 increases sensitivity of pancreatic cancer cells to radiation and chemotherapy," Cancer Biology & Therapy, vol. 11, Sep. 13, 2012 (pp. 1072-1081).
Qi et al., "Chemi- and Bio-luminescence of Coelenterazine Analogues with Phenyl Homologues at the C-2 Position," Journal Chemistry Society, Perkin Trans 1. 1992 (pp. 1607-1611).
Reaper et al., "Selective killing of ATM- or p53-deficient cancer cells through inhibition of ATR," Nature Chemical Biology, vol. 7, No. 7, Apr. 13, 2011 (pp. 428-430).
Reaper, et al., "Selective killing of ATM- or p53-deficient cancer cells through inhibition of ATR" Nature Chemical Biology, Supplementary Information, vol. 7, No. 7, Apr. 13, 2011 (pp. 428-430).
Reaper, et al., "Evaluation of a potent and highly selective inhibitor of ATR kinase: an approach to selectively sensitize cancer cells to genotoxic drugs", Abstract, Mar. 31, 2012.
Reaper, et al., "Evaluation of a Potent and Highly Selective Inhibitor of ATR Kinase: An Approach to Selectively Sensitize Cancer Cells to Genotoxic Drugs", Poster, Mar. 31, 2012.
Reaper, et al., "Selective Killing of ATM- or p53-deficient cancer cells through inhibition of ATR", Presentation, Nov. 21, 2011.
Reaper, et al., "Selective Killing of ATM- or p53-deficient cancer cells through inhibition of ATR", Presentation, Nov. 29, 2011.
Reaper, et al., "Selective Killing of ATM- or p53-deficient cancer cells through inhibition of ATR", Supplementary Information, Nature Chemical Biology, Apr. 13, 2011 (DOI: 10.1038/NCHEMBI0.573).
Redon et al., "γ-H2AX as a biomarker of DNA damage induced ionizing radiation in human peripheral blood lymphocytes and artificial skin," Advances in Space Research, vol. 43, No. 8, 2009 (pp. 1171-1178).
Registry (STN), 2004, RN 726138-31-4.
Richards et al., "An Autoinhibitory Tyrosine Motif in the Cell-Cycle-Regulated Nek7 Kinase Is Released through Binding of Nek9," Molec Cell., vol. 36, 2009 (pp. 560-570).
Saito et al., "Synthesis and in vitro evaluation of botryllazine B analogues as a new class of inhibitor against human aldose reductase," Tetrahedron, vol. 65, No. 15 2009 (pp. 3019-3026).
Sarkaria et al., "Inhibition of ATM and ATR kinase activities by the radio sensitizing agent, caffeine," Cancer Research, vol. 59, No. 17, Sep. 1, 1999 (pp. 4375-4382).
Schultheiss et al., "Facile Synthesis of Diarylpyrazines Using Suzuki Coupling of Dichloropyrazines with Aryl Boronic Acids," Heterocycles, vol. 60, No. 8, 2003 (pp. 1891-1897).
Serajuddin, "Salt formation to improve drug solubility," Advanced Drug Delivery Reviews, vol. 59, No. 7, 2007 (pp. 603-616).
Sevilla et al., "Microwave-assisted synthesis of 1,3-dihydro41,2,5]thiadiazolo [3,4-b]pyrazine-2,2-dioxides,". Tetrahedron Letters, vol. 47, No. 48, 2006 (pp. 8603-8606).
Shimomura et al., "Semi-synthetic aequorins with improved sensitivity to Ca2+ ions," Biochemistry Journal, vol. 261, No. 3, Aug. 1, 1989 (pp. 913-920).
Sugimoto et al., "Imidazopteridines. I. Synthesis of Imidazo[1,2-c]pteridine and Its Alkyl Derivatives," Bulletin Chemistry Society Japan, vol. 50, No. 10, 1977 (pp. 2744-2747).
Teranishi et al., "Synthesis and Chemiluminescence of Coelenterazine (Oplophorus Luciferin) Analogues," Bulletin Chem Society Japan, vol. 63, No. 11, 1990 (pp. 3132-3140).
Tutin, "Syntheses in the epinephrine series. Part II. The formation and properties of some 2 : 5- and 2 : 6-substituted pyrazines and their conversion into amino-ketones and imino-diketones," Journal Chemistry Society Transaction, vol. 97, 1910 (pp. 2495-2524).
Vicent, "Polymer Anticancer Drug Conjugates: Use as Single Agents and as Combination Therapy," 2007 AACR Annual Meeting. Apr. 14-18, 2007 (pp. 56-62).
Ward et al., "Histone H2AX is phosphorylated in an ATR-dependent manner in response to replicational stress," Journal of Biological Chemistry, vol. 6, No. 51, Dec. 21, 2001, (pp. 47759-47762).
Wu et al., "Chemi- and bioluminescence of coelenterazine analogues with a conjugated group at the C-8 position," Tetrahedron Letters, vol. 42, No. 16, 2001 (pp. 2997-3000).
Wuts et al., "Protection for the Amino Group. Chapter 7. In: Greene's Protective Groups in Organic Synthesis," 4th Edition. John Wiley & Sons, Inc. 2007. 235 pages.
Wuts et al., "Protection for the Carbonyl Group. Chapter 4. In: Greene's Protective Groups in Organic Synthesis," 4th Edition. John Wiley & Sons, Inc. 2007. 106 pages.
U.S. Appl. No. 15/967,110 of Charrier et al., filed Apr. 30, 2018.
U.S. Appl. No. 15/693,521 of Falcon et al., filed Sep. 1, 2017.
U.S. Appl. No. 15/763,366 of Pollard et al., filed Mar. 26, 2018.
Bavin et al., "Pharmaceutical Solids: A Strategic Approach to Regulatory Considerations", Pharma Res.; 1996; vol. 12. No. 7, pp. 945-954.
Berge et al., January "Pharmaceutical Salts", Drug Development, 1977; vol. 66, No. 1, pp. 1-19.
Buteau, K.C., "Deuterated Drugs: Unexpected Nonobvious?", Journal of High Technology Law, 2009; pp. 22-74.

(56) References Cited

OTHER PUBLICATIONS

Carlson et al., "An integrated high throughput workflow for pre-formulations: Polymorph and salt selection studies", Pharm. Chem, Drug Development, 1994; pp. 524-527.
Foster A.B., "Deuterium isotope effects in studies of drug metabolism", Trends in Pharmacological Sciences, 1984; vol. 5, pp. 524-527.
Foster A.B., "Deuterium Isotope Effects in the Metabolism of Drugs and Xenobiotics: Implications for Drug Design", Advances in Drug Research, 1985; vol. 14, pp. 1-40.
Sato, Kentaro, "Expanded Use of Deuterium", Wako Organic Square, 2010; vol. 33, pp. 1-3.

* cited by examiner

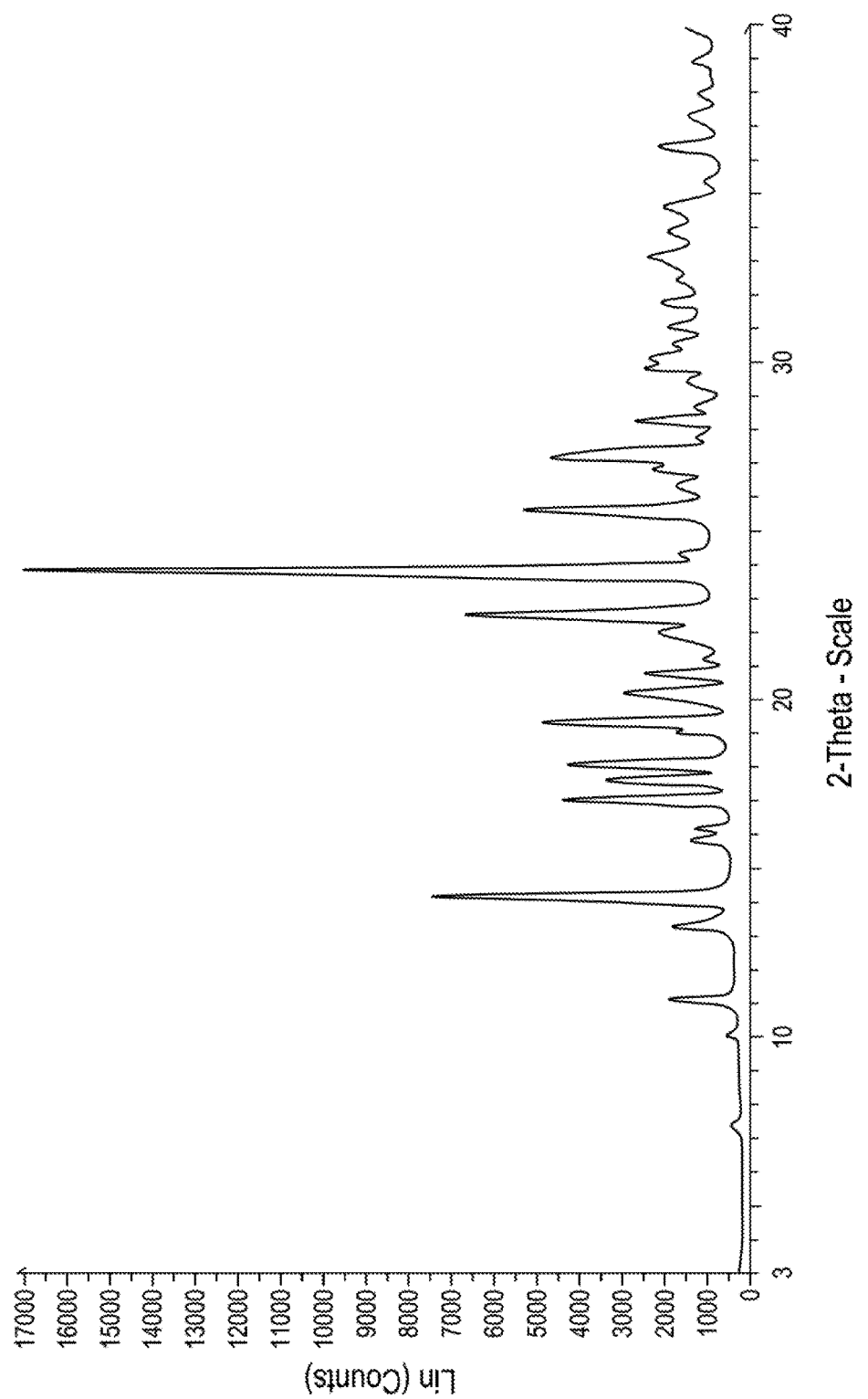

ORTEP plot of the asymmetric unit of the Compound I-2 free form single crystal structure ORTEP plot of the asymmetric unit of the Compound I-2 • HCl anhydrous structure

PROCESSES FOR PREPARING ATR INHIBITORS

CROSS REFERENCE TO RELATED APPLICATIONS

This application is a divisional of U.S. application Ser. No. 15/849,241, filed Dec. 20, 2017, which is a divisional of U.S. application Ser. No. 14/678,489, filed Apr. 3, 2015, which is a divisional of U.S. application Ser. No. 13/631,759, filed Sep. 28, 2012, which application claims the benefit under 35 U.S.C. § 119(e) of U.S. Provisional Application No. 61/541,865, filed on Sep. 30, 2011, the contents of all of which are incorporated herein in their entireties by reference thereto.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

For all of these reasons, there is a need for the development of potent and selective ATR inhibitors for the treatment of cancer, either as single agents or as combination therapies with radiotherapy or genotoxic chemotherapy. Furthermore, it would be desirable to have a synthetic route to ATR inhibitors that is amenable to large-scale synthesis and improves upon currently known methods.

ATR peptide can be expressed and isolated using a variety of methods known in the literature (see e.g., Ünsal-Kaçmaz et al, *PNAS* 99: 10, pp6673-6678, May 14, 2002; see also Kumagai et al. *Cell* 124, pp943-955, Mar. 10, 2006; Unsal-Kacmaz et al. *Molecular and Cellular Biology*, February 2004, p1292-1300; and Hall-Jackson et al. *Oncogene* 1999, 18, 6707-6713).

DESCRIPTION OF THE FIGURES

FIG. 1a: XRPD Compound I-2 free base

SUMMARY OF THE INVENTION

Figure 1B:
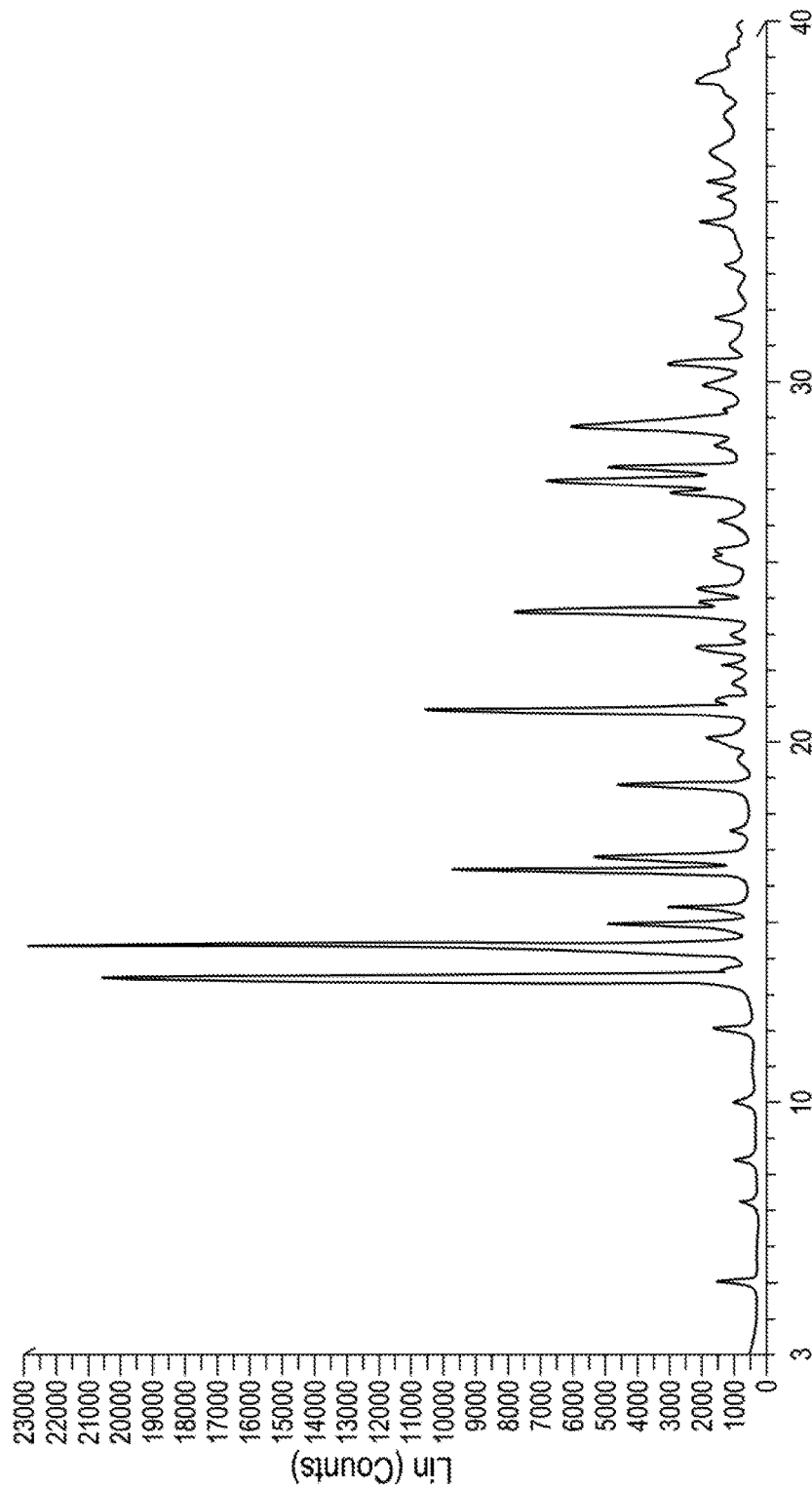
FIG. 1b: XRPD Compound I-2.HCl

The present invention relates to processes and intermediates for preparing compounds useful as inhibitors of ATR kinase, such as aminopyrazine-isoxazole derivatives and related molecules. Aminopyrazine-isoxazole derivatives are useful as ATR inhibitors and are also useful for preparing ATR inhibitors. The present invention also relates to solid forms of ATR inhibitors as well as deuterated ATR inhibitors.

One aspect of the invention provides a process for preparing a compound of formula I:

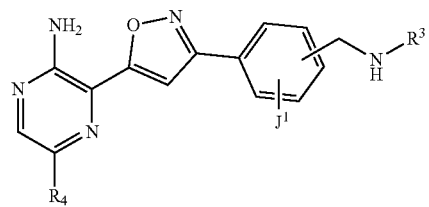

comprising preparing a compound of formula 4:

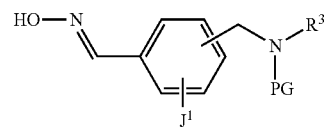

from a compound of formula 3:

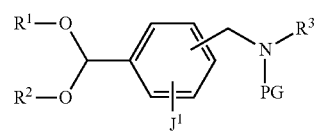

under suitable oxime formation conditions.

Another aspect comprises preparing a compound of formula 4:

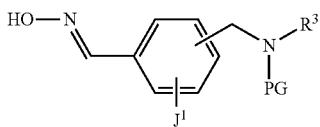
4 from a compound of formula 3:

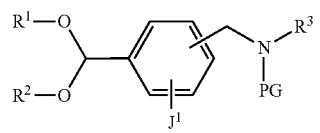
3 under suitable oxime formation conditions.

Another aspect of the present invention comprises a compound of formula II:

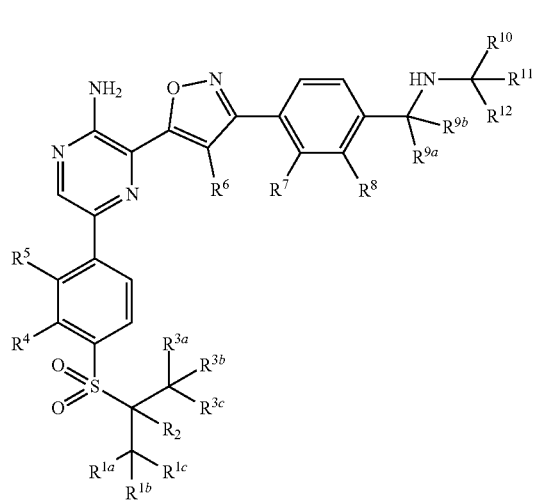
II or a pharmaceutically acceptable salt thereof, wherein each $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11}$, $R^{12}$, and $R^{13}$ is independently hydrogen or deuterium, and at least one of $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10}$, $R^{11}$, $R^{12}$, and $R^{13}$ is deuterium.

Yet another aspect of the invention provides solid forms of a compound of formula I-2:

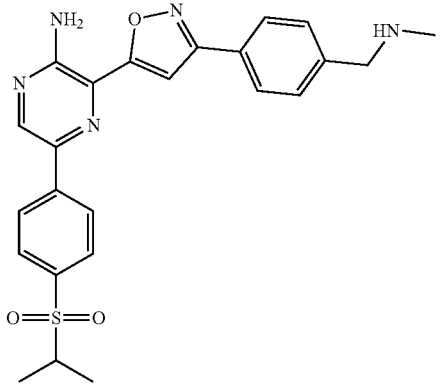
I-2

Other aspects of the invention are set forth herein.

The present invention has several advantages over previously known methods. First, the present process has fewer number of total synthetic steps compared with previously disclosed processes. Second, the present process has improved yields over previously disclosed processes. Third, the present process is effective for compounds wherein $R^3$ is a wide range of groups, such as alkyl groups or a large, hindered moiety, such as a ring. Fourth, the present process comprises intermediates which are more stable and have a longer shelf life. In certain embodiments, the non-acidic formation of the oxime group in the present process allows the preservation of acid-sensitive protecting groups such as Boc or CBz during the course of the synthesis. In other embodiments, the process is more easily scaled up to larger quantities due to the elimination of chromatography as a purification step.

DETAILED DESCRIPTION OF THE INVENTION

One aspect of the invention provides a process for making a compound of preparing a compound of formula 4:

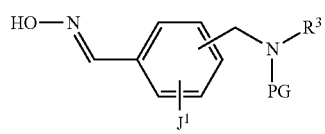
4 from a compound of formula 3:

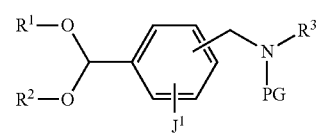
3 under suitable oxime formation conditions;
wherein
  $R^1$ is $C_{1-6}$alkyl;
  $R^2$ is $C_{1-6}$alkyl;
  or $R^1$ and $R^2$, together with the oxygen atoms to which they are attached, form an optionally substituted 5 or 6 membered saturated heterocyclic ring having two oxygen atoms;
  $R^3$ is hydrogen, $C_{1-6}$alkyl, or a 3-6 membered saturated or partially unsaturated heterocyclyl having 1-2 heteroatoms selected from the group consisting of oxygen, nitrogen, and sulfur; wherein the heterocyclyl is optionally substituted with 1 occurrence of halo or $C_{1-3}$alkyl;
  $J^1$ is halo, $C_{1-4}$alkyl, or $C_{1-4}$alkoxy;
  PG is a carbamate protecting group.

Another aspect provides a process for preparing a compound of formula I:

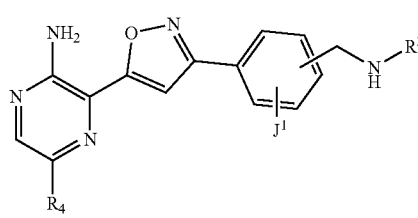
I comprising the steps of:
preparing a compound of formula 4:

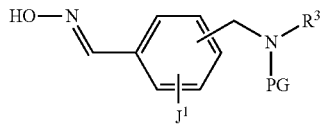   4 from a compound of formula 3:

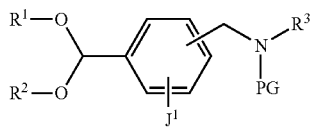   3 under suitable oxime formation conditions;
wherein
$R^1$ is $C_{1-6}$alkyl;
$R^2$ is $C_{1-6}$alkyl;
or $R^1$ and $R^2$, together with the oxygen atoms to which they are attached, form an optionally substituted 5 or 6 membered saturated heterocyclic ring having two oxygen atoms;
$R^3$ is hydrogen, $C_{1-6}$alkyl, or a 3-6 membered saturated or partially unsaturated heterocyclyl having 1-2 heteroatoms selected from the group consisting of oxygen, nitrogen, and sulfur; wherein the heterocyclyl is optionally substituted with 1 occurrence of halo or $C_{1-3}$alkyl;
$R^4$ is

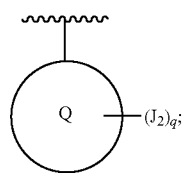

Q is phenyl, pyridyl, or an N-alkylated pyridine;
$J^1$ is H, halo, $C_{1-4}$alkyl, or $C_{1-4}$alkoxy;
$J^2$ is halo; CN; phenyl; oxazolyl; or a $C_{1-6}$aliphatic group wherein up to 2 methylene units are optionally replaced with O, NR", C(O), S, S(O), or S(O)$_2$; said $C_{1-6}$aliphatic group is optionally substituted with 1-3 fluoro or CN;
q is 0, 1, or 2;
PG is a carbamate protecting group.
Another embodiment further comprises the step of protecting a compound of formula 2:

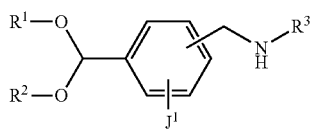   2 under suitable protection conditions to form the compound of formula 3.

Another embodiment further comprises the step of reacting a compound of formula 1:

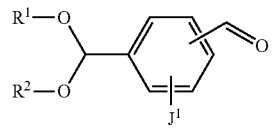   1 with a suitable amine under suitable reductive amination conditions to form a compound of formula 2.
In some embodiments, the suitableamine is NHCH$_3$. In other embodiments, the suitable amine is

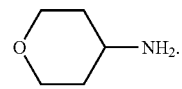

Another embodiment further comprises the step of reacting a compound of formula 4:

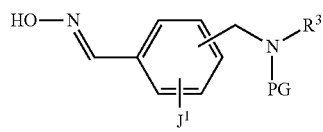   4 under suitable isoxazole formation conditions to form a compound of formula 5:

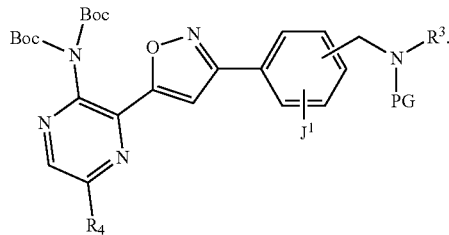   5

Another embodiment further comprises the step of reacting a compound of formula 5 under suitable coupling conditions followed by suitable deprotection conditions to form a compound of formula I.
In some embodiments, PG is Boc or Cbz. In some embodiments, PG is Boc.
In other embodiments, $R^1$ is ethyl and $R^2$ ethyl.
In yet other embodiments, $R^3$ is CH$_3$ or

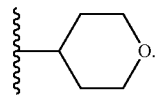

In some embodiments, $R^4$ is

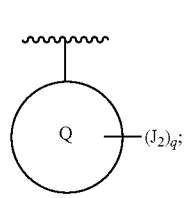

wherein Q is phenyl. In some embodiments, Q is substituted in the para position with $J_2$, wherein q is 1.

In some embodiments, $J^1$ is H or halo. In some embodiments, $J^1$ is H. In other embodiments, $J^1$ is halo.

In other embodiments, $J^2$ is a $C_{1-6}$aliphatic group wherein up to 1 methylene unit is optionally replaced with $S(O)_2$. In some embodiments, $J^2$ is —$S(O)_2$—($C_{1-5}$alkyl). In some embodiments, q is 1.

According to another embodiment,
$R^1$ is ethyl;
$R^2$ is ethyl;
$R^3$ is $CH_3$ or

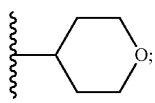

PG is Boc or Cbz;
$J^1$ is H;
$R^4$ is

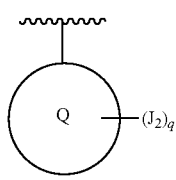

wherein Q is phenyl; $J^2$ is —$S(O)_2$—$CH(CH_3)_2$;
q is 1;
In some embodiments, $R^3$ is $CH_3$. In some embodiments, $R^3$ is $CH_3$. In yet another embodiments, $R^3$ is $CH_3$ or

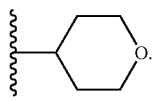 [SMILES: *C1CCOCC1]

According to another embodiment,
$R^1$ is ethyl;
$R^2$ is ethyl;
$R^3$ is

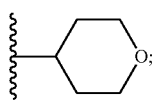

PG is Boc;
$J^1$ is H;
$R^4$ is

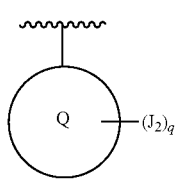

wherein Q is pyridyl; $J^2$ is

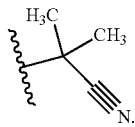

q is 1;
In some embodiments, $R^4$ is

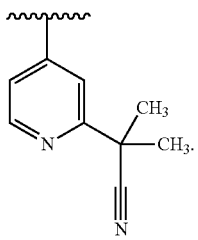 [SMILES: *c1ccnc(C(C)(C)C#N)c1]

Reactions Conditions

In some embodiments, the suitable oxime formation conditions consist of either a single step sequence or a two step sequence.

In some embodiments, the two step sequence consists of first deprotecting the ketal group in the compound of formula 3 into an aldehyde under suitable deprotection conditions, and then forming the oxime of formula 4 under suitable oxime formation conditions. In some embodiments, suitable deprotection conditions comprise adding catalytic amounts of para-toluenesulfonic acid (pTSA), acetone, and water; and suitable oxime formation conditions comprise mixing together hydroxylamine, a catalytic amount of acid, a dehydrating agent, and an alcoholic solvent. In other embodiments, the acid is pTSA or HCl, the dehydrating agent is molecular sieves or dimethoxyacetone, and the alcoholic solvent is methanol or ethanol.

In other embodiments, the single step sequence comprises adding $NH_2OH\cdot HCl$ and a mixture of THF and water. In other embodiments, the sequence comprises adding $NH_2OH\cdot HCl$ with a mixture of 2-methyl tetrahydrofuran and water optionally buffered with $Na_2SO_4$. In some embodiments, 1 equivalent of the compound of formula 3 is combined with a 1.1 equivalents of $NH_2OH\cdot HCl$ in a 10:1 v/v mixture of THF and water. In some embodiments, 1 equivalent of the compound of formula 3 is combined with a 1.1 equivalents of $NH_2OH\cdot HCl$ in a 10:1 v/v mixture of 2-methyl tetrahydrofuran and water optionally buffered with $Na_2SO_4$.

In other embodiments, the protection conditions are selected from the group consisting of
R—OCOCl, a suitable tertiary amine base, and a suitable solvent; wherein R is $C_{1-6}$alkyl optionally substituted with phenyl;
$R(CO_2)OR'$, a suitable solvent, and optionally a catalytic amount of base, wherein R is and R' are each independently $C_{1-6}$alkyl optionally substituted with phenyl;
$[RO(C=O)]_2O$, a suitable base, and a suitable solvent.

In some embodiments, the suitable base is $Et_3N$, diisopropylamine, and pyridine; and the suitable solvent is selected from a chlorinated solvent, an ether, or an aromatic hydrocarbon. In other embodiments, the suitable base is $Et_3N$, the suitable solvent is a chlorinated solvent selected from DCM. In yet other embodiments, the protection conditions comprise adding 1.20 equivalents of (Boc)$_2$O and 1.02 equivalents of Et$_3$N in DCM.

According to another embodiment suitable coupling conditions comprise adding a suitable metal and a suitable base in a suitable solvent. In other embodiments, the suitable metal is Pd[P(tBu)$_3$]$_2$; the suitable solvent is a mixture of acetonitrile and water; and the suitable base is sodium carbonate. In yet other embodiments, the suitable coupling conditions comprise adding 0.1 equivalents of Pd[P(tBu)$_3$]2; 1 equivalent of boronic acid or ester; and 2 equivalents of sodium carbonate in a 2:1 ratio v/v of acetonitrile/water at 60-70° C.

According to another embodiment, suitable deprotection conditions comprise combining the compound of formula 5 with a suitable acid in a suitable solvent. In some embodiments, the suitable acid is selected from para-toluenesulfonic acid (pTSA), HCl, TBAF, H$_3$PO$_4$, or TFA and the suitable solvent is selected from acetone, methanol, ethanol, CH$_2$Cl$_2$, EtOAc, THF, 2-MeTHF, dioxane, toluene, or diethylether.

According to another embodiment, suitable isoxazole-formation conditions consists of two steps, the first step comprising reacting the compound of formula 4 under suitable chlorooxime formation conditions to form a chlorooxime intermediate; the second step comprising reacting the chlorooxime intermediate with acetylene under suitable cycloaddition conditions to form a compound of formula 5.

According to another embodiment, suitable chlorooxime formation conditions are selected from N-chlorosuccinimide and suitable solvent or potassium peroxymonosulfate, HCl, and dioxane.

In some embodiments, the suitable solvent is selected from a nonprotic solvent, an aromatic hydrocarbon, or an alkyl acetate. According to another embodiment, the suitable chlorooxime formation conditions are 1.05 equivalents of N-chlorosuccinimide in isopropylacetate at 40-50° C.

According to another embodiment, suitable cycloaddition conditions consist of a suitable base and a suitable solvent. In some embodiments, the suitable base is selected from pyridine, DIEA, TEA, t-BuONa, and K$_2$CO$_3$ and the suitable solvent is selected from acetonitrile, tetrahydrofuran, 2-methyltetrahydrofuran, MTBE, EtOAc, i-PrOAc, DCM, toluene, DMF, and methanol. In other embodiments, the suitable base is selected from Et$_3$N and the suitable solvent is selected from DCM.

According to another embodiment, the second step comprises reacting 1 equivalent of acetylene with 1.2 equivalents of the chlorooxime intermediate and 1.3 equivalents of Et$_3$N in DCM at room temperature.

According to another embodiment, suitable isoxazole-formation conditions comprise combining the compound of formula 4 with an oxidant in a suitable solvent. In some embodiments, said oxidant is [bis(trifluoroacetoxy)iodo]benzene and said solvent is a 1:1:1 mixture of methanol, water, and dioxane.

Synthesis of Compounds I-2 and I-3

One embodiment provides a process for preparing a compound of formula I-2:

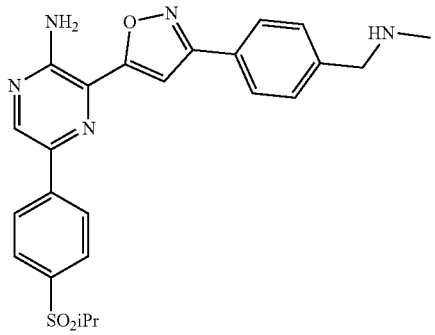

comprising one or more of the following steps:
a) Reacting a compound of formula 1b:

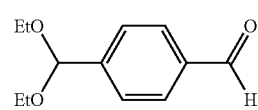

with methylamine under suitable reductive amination conditions to form a compound of formula 2b:

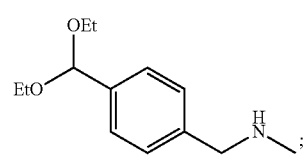

b) reacting a compound of formula 2b under suitable Boc protection conditions to form the compound of formula 3b:

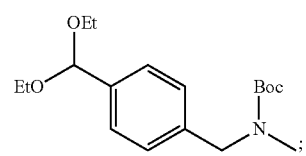

c) reacting a compound of formula 3b under suitable oxime formation conditions to form the compound of formula 4-i:

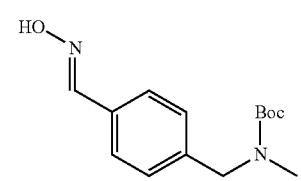

d) reacting a compound of formula 4-i under suitable chlorooxime formation conditions to form the compound of formula 4-ii:

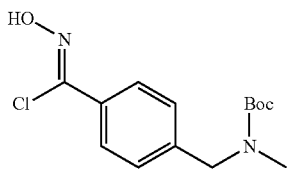

4-ii e) reacting the compound of formula 4-ii with a compound of formula 4-iii

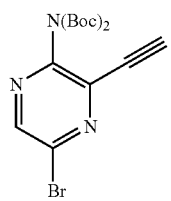

4-iii under suitable cycloaddition conditions to form a compound of formula 4-iv:

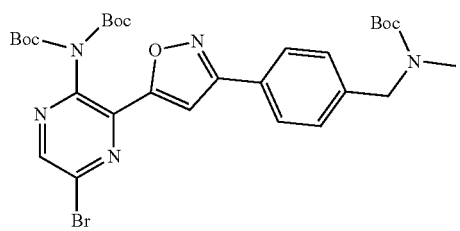

4-iv f) reacting a compound of formula 4-iv with a compound of formula A-5-i:

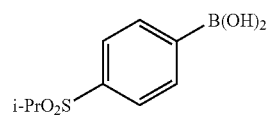

A-5-i under suitable coupling conditions to form the compound of formula 5-i:

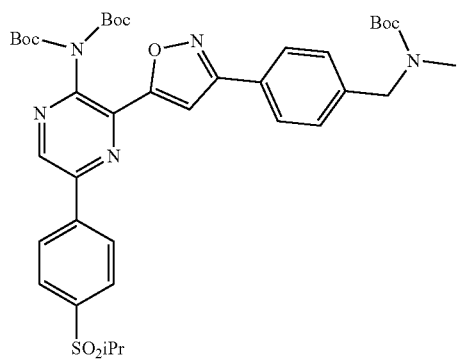

5-i g) deprotecting a compound of formula 5-i under suitable Boc deprotection conditions optionally followed by treatment under basic aqueous conditions to form a compound of formula I-2.

Another embodiment provides a process for preparing a compound of formula I-3:

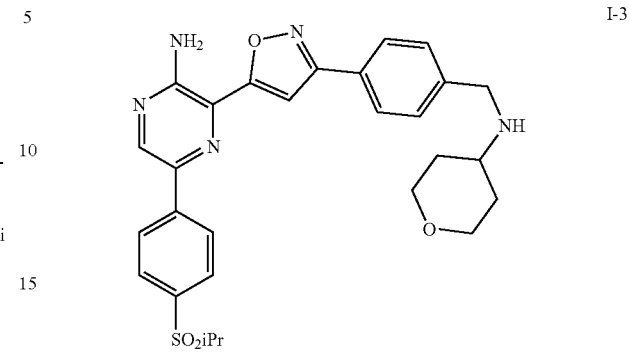

I-3 comprising one or more of the following steps:

a) Reacting a compound of formula A-1:

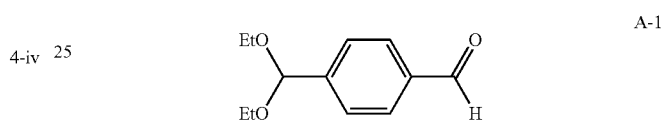

A-1 with tetrahydro-2H-pyran-4-amine under suitable reductive amination conditions to form a compound of formula A-2:

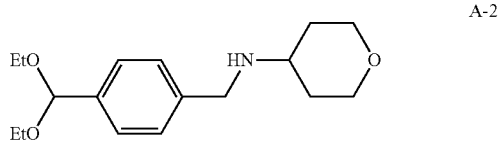 [SMILES: CCOC(OCC)c1ccc(CNC2CCOCC2)cc1]

A-2 b) reacting a compound of formula A-2 under suitable Boc protection conditions to form the compound of formula A-3:

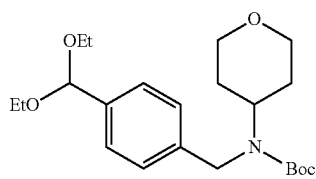

A-3 c) reacting a compound of formula A-3 under suitable oxime formation conditions to form the compound of formula A-4:

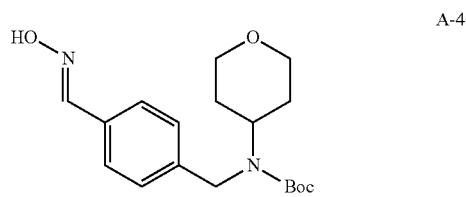 [SMILES: CC(C)(C)OC(=O)N(Cc1ccc(/C=N/O)cc1)C1CCOCC1]

A-4 d) reacting a compound of formula A-4:

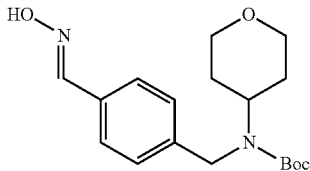

under suitable chlorooxime formation conditions to form the compound of formula A-4-i:

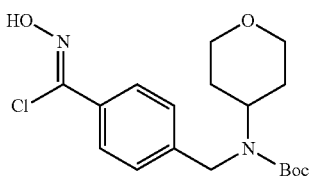

e) reacting the compound of formula A-4-i with a compound of formula A-4-ii:

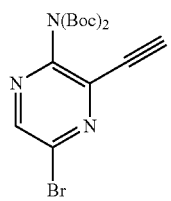

under suitable cycloaddition conditions to form the compound of formula A-5:

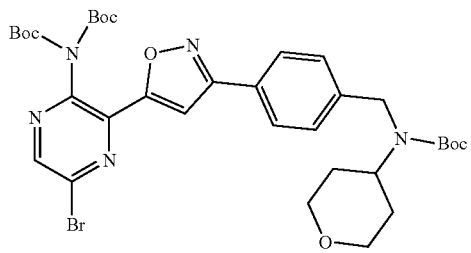

f) reacting a compound of formula A-5 with a compound of formula A-5-i:

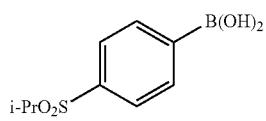

under suitable coupling conditions to form the compound of formula A-6:

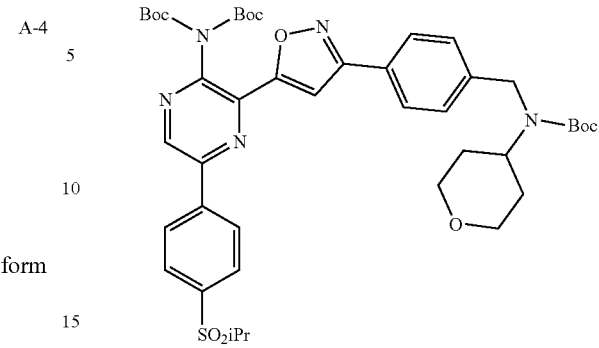

g) deprotecting a compound of formula A-6 under suitable Boc deprotection conditions optionally followed by treatment under basic aqueous conditions to form a compound of formula I-3.

Suitable coupling conditions comprise combining a suitable palladium catalyst with a suitable base in a suitable solvent. Suitable palladium catalyst include, but are not limited to, $Pd[P(tBu)_3]_2$, $Pd(dtbpf)Cl_2$, $Pd(PPh_3)_2Cl_2$, $Pd(PCy_3)_2Cl_2$, $Pd(dppf)Cl_2$, and $Pd(dppe)Cl_2$. Suitable solvents include, but are not limited to. toluene, MeCN, water, EtOH, IPA, 2-Me-THF, or IPAc. Suitable bases include, but are not limited to, $K_2CO_3$, $Na_2CO_3$, or $K_3PO_4$.

Suitable oxime formation conditions consist of either a single step sequence or a two step sequence. The two step sequence consists of first deprotecting the ketal group in the compound of formula A-3 into an aldehyde under suitable deprotection conditions, and then forming the oxime of formula A-4 under suitable oxime formation conditions.

The single step sequence comprises, for example, comprise mixing together hydroxylamine, an acid, an organic solvent, and water. In some embodiments, $NH_2OH.HCl$ is added to a mixture of THF and water. In some embodiments, 1 equivalent of the compound of formula 3-A is combined with a 1.1 equivalents of $NH_2OH.HCl$ in a 10:1 v/v mixture of THF/water.

Suitable deprotection conditions comprise adding an acid, acetone, and water. Suitable acids include pTSA or HCl, tsuitable organic solvents include chlorinated solvents (e.g., dichloromethane (DCM), dichloroethane (DCE), $CH_2Cl_2$, and chloroform); an ether (e.g., THF, 2-MeTHF and dioxane); an aromatic hydrocarbons (e.g., toluene and xylenes, or other aprotic solvents.

Suitable cycloaddition conditions comprise a suitable base (e.g., pyridine, DIEA, TEA, t-BuONa, or $K_2CO_3$) and a suitable solvent (e.g., acetonitrile, tetrahydrofuran, 2-methyltetrahydrofuran, MTBE, EtOAc, i-PrOAc, DCM, toluene, DMF, and methanol.

Suitable chlorooxime formation conditions comprise adding HCl in dioxame to a solution of the oxime in the presence of NCS in a suitable solvent selected from a nonprotic solvents (DCM, DCE, THF, and dioxane), aromatic hydrocarbons (e.g. toluene, xylenes), and alkyl acetates (e.g., isopropyl acetate, ethyl acetate).

Suitable Boc deprotection conditions comprises adding a suitable Boc deprotecting agent (e.g, TMS-Cl, HCl, TBAF, $H_3PO_4$, or TFA) and a suitable solvent (e.g., acetone, toluene, methanol, ethanol, 1-propanol, isopropanol, $CH_2Cl_2$, EtOAc, isopropyl acetate, tetrahydrofuran, 2-methyltetraydrofuran, dioxane, and diethylether). In some embodiments, the suitable Boc deprotection conditions comprises adding a suitable Boc deprotecting agent selected from HCl, TFA and a suitable solvent selected from acetone, toluene, isopropyl acetate, tetrahydrofuran, or 2-methyltetraydrofuran.

Suitable Boc protection conditions include (Boc)$_2$O, a suitable base, and a suitable solvent. Suitable bases include, but are not limited to, Et$_3$N, diisopropylamine, and pyridine. Suitable solvents include, but are not limited to, chlorinated solvents (e.g., dichloromethane (DCM), dichloroethane (DCE), CH$_2$Cl$_2$, and chloroform); an ether (e.g., THF, 2-MeTHF and dioxane); an aromatic hydrocarbons (e.g., toluene and xylenes, or other aprotic solvents. In some embodiments, the suitable base is Et$_3$N, the suitable solvent is DCM, tetrahydrofuran or 2-methyltetrahydrofuran. In certain embodiments, the protection conditions comprise adding 1.05 equivalents of (Boc)$_2$O in 2-methyltetrahydrofuran or DCM.

Suitable reductive amination conditions comprise adding a reducing agent selected from NaBH$_4$ NaBH$_4$, NaBH$_3$CN, or NaBH(OAc)$_3$ in the presence of a solvent selected from dichloromethane (DCM), dichloroethane (DCE), an alcoholic solvent selected from methanol, ethanol, 1-propanol, isopropanol, or a nonprotic solvent selected from dioxane, tetrahydrofuran, or 2-methyltetrahydrofuran and optionally a base selected from Et$_3$N or diisopropylethylamine. In some embodiments, the suitable reductive amination conditions comprise adding 1.2 equivalents of NaBH$_4$ caplets in the presence Et$_3$N in MeOH.

Another aspect of the present invention provides a compound of Formula II:

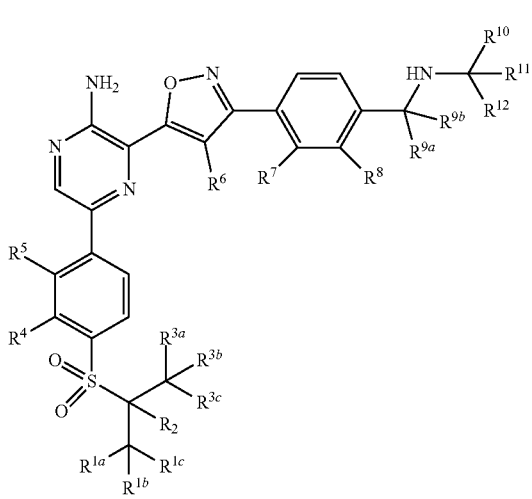

II or a pharmaceutically acceptable salt thereof, wherein each $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10a}$, $R^{10b}$, and $R^{10c}$ is independently hydrogen or deuterium, and at least one of $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, $R^{9b}$, $R^{10a}$, $R^{10b}$, and $R^{10c}$ is deuterium.

In some embodiments, $R^{9a}$ and $R^{9b}$ are the same. In other embodiments, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are deuterium or hydrogen. In yet another embodiment, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10}$, $R^{11a}$, $R^{11b}$, $R^{12a}$, $R^{12b}$, $R^{13a}$, $R^{13b}$, $R^{14a}$, and $R^{14b}$ are hydrogen.

In one embodiment, $R^{9a}$, $R^{9b}$, $R^{10a}$, $R^{10b}$, and $R^{10c}$ are the same. In another embodiment, $R^{9a}$, $R^{9b}$, $R^{10a}$, $R^{10b}$, and $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, and $R^8$ are deuterium or hydrogen. In some embodiments, $R^{9a}$, $R^{9b}$, $R^{10a}$, $R^{10b}$, and $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, and $R^8$ are hydrogen.

In other embodiments, $R^{10a}$, $R^{10b}$, and $R^{10c}$ are the same. In one embodiment, $R^{11a}$, $R^{10b}$, and $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, R, $R^{9a}$, and $R^{9b}$ are deuterium or hydrogen. In yet another embodiment, $R^{10a}$, $R^{10b}$, and $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, R, $R^{9a}$, and $R^{9b}$ are hydrogen.

In some embodiments, $R^{1a}$, $R^{1b}$, $R^{1c}$, $R^2$, $R^{3a}$, $R^{3b}$, and $R^{3c}$ are the same. In another embodiment $R^{1a}$, $R^{1b}$, $R^{1c}$, $R^2$, $R^{3a}$, $R^{3b}$, and $R^{3c}$ are deuterium, and $R^4$, $R^5$, $R^6$, $R^7$, $R^8$, $R^{9a}$, $R^{9b}$, $R^{10a}$, $R^{10b}$, and $R^{10c}$ are deuterium or hydrogen. In yet another embodiment, $R^{1a}$, $R^{1b}$, $R^{1c}$, $R^2$, $R^{3a}$, $R^{3b}$, and $R^{3c}$ are deuterium, and $R^4$, $R^5$, $R^6$, $R^7$, $R^8$, $R^{9a}$, $R^{9b}$, $R^{10a}$, $R^{10b}$, and $R^{10c}$ are deuterium.

In another embodiment, $R^6$ is deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{9a}$, $R^{9b}$, $R^{10a}$, $R^{10b}$, and $R^{10c}$ are deuterium or hydrogen. In yet another embodiment, $R^6$ is deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{9a}$, $R^{9b}$, $R^{10a}$, $R^{10b}$, and $R^{10c}$ are hydrogen.

In other embodiments, $R^2$ is deuterium, and $R^{1a}$, $R^{1b}$, $R^{1c}$, $R^{3a}$, $R^{3b}$, and $R^{3c}$, $R^4$, $R^5$, $R^6$, $R^7$, $R^8$, $R^{9a}$, $R^{9b}$, $R^{10a}$, $R^{10b}$, and $R^{10c}$ are deuterium or hydrogen. In another embodiment, $R^2$ is deuterium, and $R^{1a}$, $R^{1b}$, $R^{1c}$, $R^{3a}$, $R^{3b}$, and $R^{3c}$, $R^4$, $R^5$, $R^6$, $R^7$, $R^8$, $R^{9a}$, $R^{9b}$, $R^{10a}$, and $R^{10c}$ are hydrogen.

In another embodiment, $R^7$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{9a}$, $R^{9b}$, $R^{10a}$, $R^{10b}$, and $R^{10c}$ are deuterium or hydrogen. In other embodiments, $R^7$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{9a}$, $R^{9b}$, $R^{10a}$, $R^{10b}$, $R^{10c}$ are hydrogen.

In yet another embodiment, $R^8$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^{9a}$, $R^{9b}$, $R^{10a}$, $R^{10b}$, and $R^{10c}$ are deuterium or hydrogen. In another embodiment, $R^8$ is deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^{9a}$, $R^{9b}$, $R^{10a}$, $R^{10b}$, $R^{10c}$ are hydrogen.

In some embodiments, at least one of $R^{10a}$, $R^{10b}$, or $R^{10c}$ are the same. In another embodiment, at least one of $R^{10a}$, $R^{10b}$, or $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, and $R^{9b}$ are deuterium or hydrogen. In yet another embodiment, at least one of $R^{10a}$, $R^{10b}$, or $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, and $R^{9b}$ are hydrogen.

In some embodiments, at least two of $R^{10a}$, $R^{10b}$, or $R^{10c}$ are the same. In another embodiment, at least two of $R^{10a}$, $R^{10b}$, or $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, and $R^{9b}$ are deuterium or hydrogen. In yet another embodiment, at least two of $R^{10a}$, $R^{10b}$, or $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{9a}$, and $R^{9b}$ are hydrogen.

In another embodiment, $R^{1a}$, $R^{1b}$, $R^{1c}$, $R^{3a}$, $R^{3b}$, and $R^{3c}$ are the same. In some embodiments, $R^{1a}$, $R^{1b}$, $R^{1c}$, $R^{3a}$, $R^{3b}$, and $R^{3c}$ are deuterium, and $R^2$, $R^4$, $R^5$, $R^6$, $R^7$, R, $R^{9a}$, $R^{9b}$, $R^{10a}$, $R^{10b}$, and $R^{10c}$ are deuterium or hydrogen. In yet another embodiment, $R^{1a}$, $R^{1b}$, $R^{1c}$, $R^{3a}$, $R^{3b}$, and $R^{3c}$ is deuterium, and $R^2$, $R^4$, $R^5$, $R^6$, $R^7$, $R^8$, $R^{9a}$, $R^{9b}$, $R^{10a}$, $R^{10b}$, and $R^{10c}$ are hydrogen.

In yet another embodiment, $R^4$ is deuterium, and $R^{1a}$, $R^{1b}$, $R^{1c}$, $R^2$, $R^{3a}$, $R^{3b}$, $R^{3c}R^5$, $R^6$, $R^7$, $R^8$, $R^{9a}$, $R^{9b}$, $R^{10a}$, $R^{10b}$, and $R^{10c}$ are deuterium or hydrogen. In other embodiments, $R^4$ is deuterium, and $R^{1a}$, $R^{1b}$, $R^{1c}$, $R^2$, $R^{3a}$, $R^{3b}$, $R^{3c}$, $R^5$, $R^6$, $R^7$, $R^8$, $R^{9a}$, $R^{9b}$, $R^{1a}$, $R^{10b}$, and $R^{10c}$ are hydrogen.

In another embodiment, $R^5$ is deuterium, and $R^{1a}$, $R^{1b}$, $R^{1c}$, $R^2$, $R^{3a}$, $R^{3b}$, $R^{3c}$, $R^4$, $R^6$, $R^7$, $R^8$, $R^{9a}$, $R^{9b}$, $R^{10a}$, $R^{10b}$, and $R^{10c}$ are deuterium or hydrogen. In yet another embodiment, $R^5$ is deuterium, and $R^{1a}$, $R^{1b}$, $R^{1c}$, $R^2$, $R^{3a}$, $R^{3b}$, $R^{3c}$, $R^4$, $R^6$, $R^7$, $R^8$, $R^{9a}$, $R^{9b}$, $R^{10a}$, $R^{10b}$, and $R^{10c}$ are hydrogen.

In another embodiment, at least one of $R^{9a}$ or $R^{9b}$ are the same. In other embodiments, at least one of $R^{9a}$ or $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10a}$, $R^{10b}$, and $R^{10c}$ are deuterium or hydrogen. In some embodiments, at least one of $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^7$, $R^8$, $R^{10a}$, $R^{10b}$, $R^{10c}$ are hydrogen.

In one embodiment, $R^6$, $R^{9a}$ and $R^{9b}$ are the same. In some embodiments, $R^6$, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{10a}$, $R^{10b}$, $R^{10c}$ are deuterium or hydrogen. In other embodiments, $R^6$, $R^{9a}$ and $R^{9b}$ are deuterium, and $R^{1a}$, $R^{1b}$, $R^{1c}$, $R^2$, $R^{3a}$, $R^{3b}$, $R^{3c}$, $R^4$, $R^5$, $R^7$, $R^8$, $R^{10a}$, $R^{10b}$, and $R^{10c}$ are hydrogen.

In some embodiments, $R^2$, $R^{10a}$, $R^{10b}$, and $R^{10c}$ are the same. In another embodiment, $R^2$, $R^{10a}$, $R^{10b}$, and $R^{10c}$ are deuterium, and $R^{1a}$, $R^{1b}$, $R^{1c}$, $R^{3a}$, $R^{3b}$, $R^{3c}$, $R^4$, $R^5$, $R^6$, $R^7$, $R^8$, $R^{9a}$, and $R^{9b}$ are deuterium or hydrogen. In yet another embodiment, $R^2$, $R^{10a}$, $R^{10b}$, and $R^{10c}$ are deuterium, and $R^{1a}$, $R^{1b}$, $R^{1c}$, $R^{3a}$, $R^{3b}$, $R^{3c}$, $R^4$, $R^5$, $R^6$, $R^7$, $R^8$, $R^{9a}$, and $R^{9b}$ are hydrogen.

In some embodiments, $R^7$ and at least two of $R^{10a}$, $R^{10b}$, or $R^{10c}$ are the same. In another embodiment, $R^7$ and at least two of $R^{10a}$, $R^{10b}$, or $R^{10c}$ are deuterium, and $R^{1a}$, $R^{1b}R^{1c}$, $R^2$, $R^{3a}$, $R^{3b}$, $R^{3c}$, $R^4$, $R^5$, $R^6$, $R^8$, $R^{9a}$, and $R^{9b}$ are deuterium or hydrogen. In yet another embodiment, $R^7$ and at least two of $R^{10a}$, $R^{10b}$, or $R^{10c}$ are deuterium, and $R^{1a}$, $R^{1b}$, $R^{1c}$, $R^2$, $R^{3a}$, $R^{3b}$, $R^{3c}$, $R^4$, $R^5$, $R^6$, $R^8$, $R^{9a}$, and $R^{9b}$ are hydrogen.

In some embodiments, $R^{1a}$, $R^{1b}$, $R^{1c}$, $R^2$, $R^{3a}$, $R^{3b}$, $R^{3c}$, and at least one of $R^{10a}$, $R^{10b}$, or $R^{10c}$ are the same. In another embodiment, $R^{1a}$, $R^{1b}$, $R^{1c}$, $R^2$, $R^{3a}$, $R^{3b}$, $R^{3c}$, and at least one of $R^{10a}$, $R^{10b}$, or $R^{10c}$ are deuterium, and $R^4$, $R^5$, $R^6$, $R^7$, $R^8$, $R^{9a}$, and $R^{9b}$ are deuterium or hydrogen. In yet another embodiment, $R^{1a}$, $R^{1b}$, $R^{1c}$, $R^2$, $R^{3a}$, $R^{3b}$, $R^{3c}$, and at least one of $R^{10a}$, $R^{10b}$, or $R^{10c}$ are deuterium, and $R^4$, $R^5$, $R^6$, $R^7$, $R^8$, $R^{9a}$, and $R^{9b}$ are hydrogen.

In some embodiments, $R^{1a}$, $R^{1b}$, $R^{1c}$, $R^{3a}$, $R^{3b}$, $R^{3c}$, and $R^5$ are the same. In another embodiment, $R^{1a}$, $R^{1b}$, $R^{1c}$, $R^{3a}$, $R^{3b}$, $R^{3c}$, and $R^5$ are deuterium, and $R^2$, $R^4$, $R^6$, $R^7$, $R^8$, $R^{9a}$, $R^{9b}$, $R^{10a}$, $R^{10b}$, and $R^{10c}$ are deuterium or hydrogen. In yet another embodiment, $R^{1a}$, Rib $R^{1c}$, $R^{3a}$, $R^{3b}$, $R^{3c}$, and $R^5$ are deuterium, and $R^2$, $R^4$, $R^6$, $R^7$, $R^8$, $R^{9a}$, $R^{9b}$, $R^{10a}$, $R^{10b}$, and $R^{10c}$ are hydrogen.

In other embodiments, $R^4$ and $R^6$ are the same. In another embodiment, $R^4$ and $R^6$ are deuterium, and $R^{1a}$, $R^{1b}$, $R^{1c}$, $R^2$, $R^{3a}$, $R^{3b}$, $R^{3c}$, $R^5$, $R^7$, $R^8$, $R^{9a}$, $R^{9b}$, $R^{10a}$, $R^{10b}$, and $R^{10c}$ are deuterium or hydrogen. In yet another embodiment, $R^4$ and $R^6$ are deuterium, and $R^{1a}$, $R^{1b}$, $R^{1c}$, $R^2$, $R^{3a}$, $R^{3b}$, $R^{3c}$, $R^5$, $R^7$, $R^8$, $R^{9a}$, $R^{9b}$, $R^{10a}$, $R^{10b}$, and $R^{10c}$ are hydrogen.

In one embodiment, $R^2$, $R^5$, $R^{9a}$, and $R^{9b}$ are the same. In some embodiments, $R^2$, $R^5$, $R^{9a}$, and $R^{9b}$ are deuterium, and $R^{1a}$, $R^{1b}$, $R^{1c}$, $R^{3a}$, $R^{3b}$, $R^{3c}$, $R^4$, $R^6$, $R^7$, $R^8$, $R^{10a}$, $R^{1b}$, and $R^{10c}$ are deuterium or hydrogen. In another embodiment, $R^2$, $R^5$, $R^{9a}$, and $R^{9b}$ are deuterium, and $R^{1a}$, $R^{1b}$, $R^{1c}$, $R^{3a}$, $R^{3b}$, $R^{3c}$, $R^4$, $R^6$, $R^7$, R, $R^{10a}$, $R^{10b}$, and $R^{10c}$ are hydrogen.

In yet another embodiment, $R^{1a}$, $R^{1b}$, $R^{1c}$, $R^2$, $R^{3a}$, $R^{3b}$, $R^{3c}$, $R^5$, $R^6$, $R^{9a}$, $R^{9b}$, $R^{10a}$, $R^{10b}$, and $R^{10c}$ are the same. In some embodiments, $R^{1a}$, $R^{1b}$, $R^{1c}$, $R^2$, $R^{3a}$, $R^{3b}$, $R^{3c}$, $R^5$, $R^6$, $R^{9a}$, $R^{9b}$, $R^{10a}$, $R^{10b}$, and $R^{10c}$ are deuterium, and $R^4$, $R^7$, and $R^8$ are deuterium or hydrogen. In other embodiments, $R^{1a}$, $R^{1b}$, $R^{1c}$, $R^2$, $R^{3a}$, $R^{3b}$, $R^{3c}$, $R^5$, $R^6$, $R^{9a}$, $R^{9b}$, $R^{10a}$, $R^{10b}$, and $R^{10c}$ is deuterium, and $R^4$, $R^7$, and $R^8$ are hydrogen.

In some embodiments, the variables are as depicted in the compounds of the disclosure including compounds in the tables below.

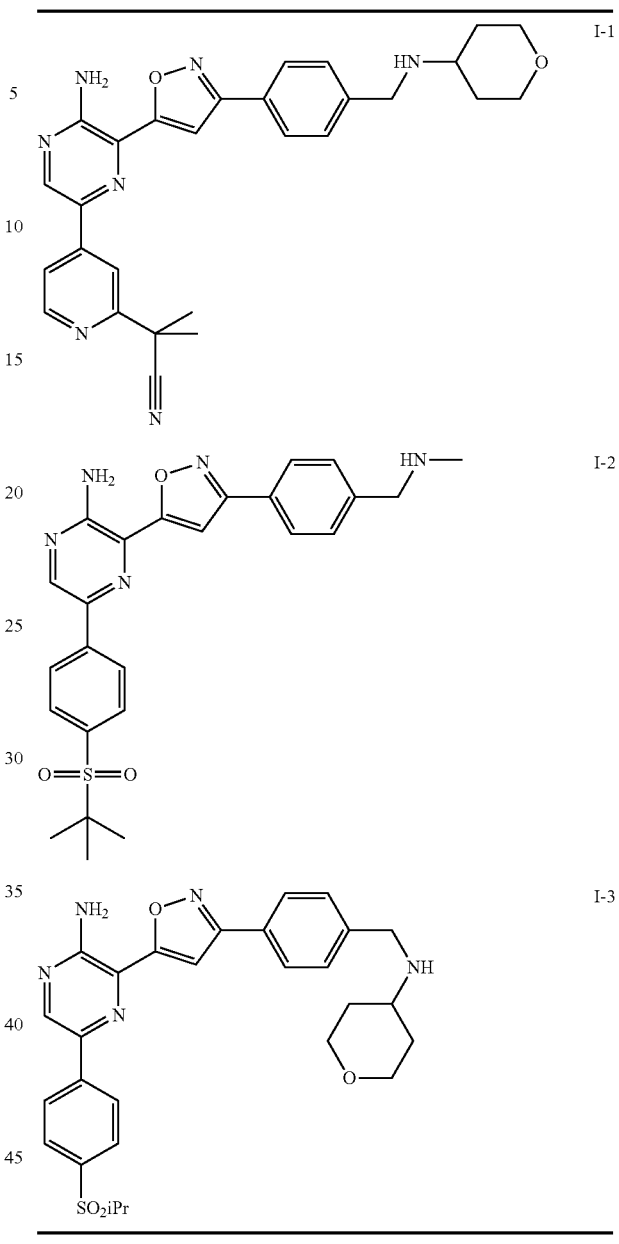

TABLE I

I-1

I-2

I-3

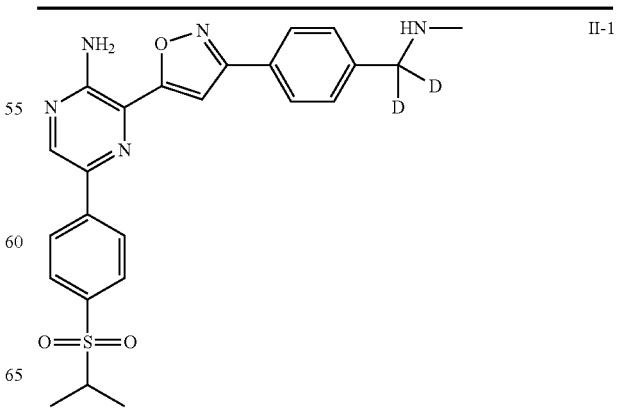

TABLE II

II-1

TABLE II-continued
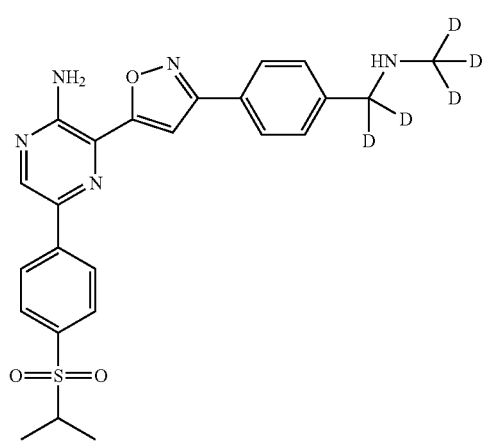 [SMILES: [2H]C([2H])([2H])NC([2H])([2H])c1ccc(-c2cc(-c3nc(-c4ccc(S(=O)(=O)C(C)C)cc4)cnc3N)on2)cc1]
II-2
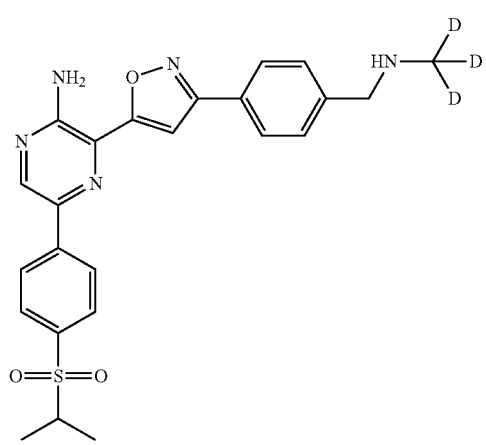 [SMILES: [2H]C([2H])([2H])NCc1ccc(-c2cc(-c3nc(-c4ccc(S(=O)(=O)C(C)C)cc4)cnc3N)on2)cc1]
II-3
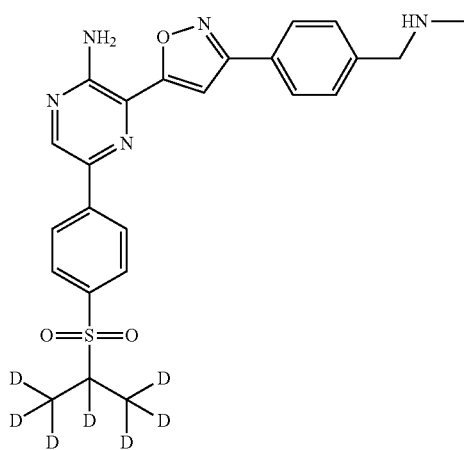 [SMILES: [2H]C([2H])([2H])C([2H])(C([2H])([2H])[2H])S(=O)(=O)c1ccc(-c2cnc(N)c(-c3cc(-c4ccc(CNC)cc4)no3)n2)cc1]
II-4
TABLE II-continued
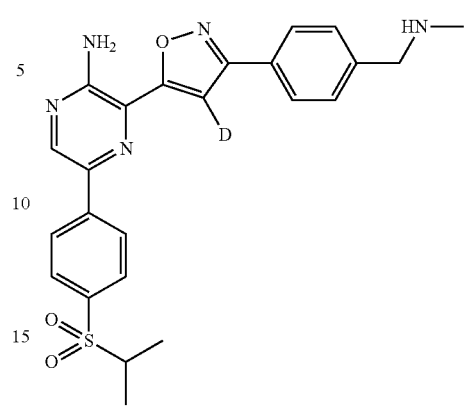
II-5
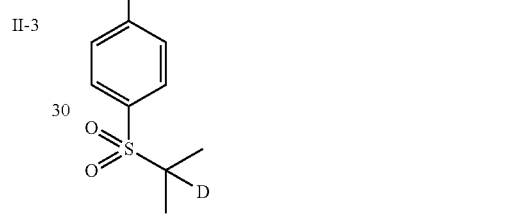
II-6
II-7
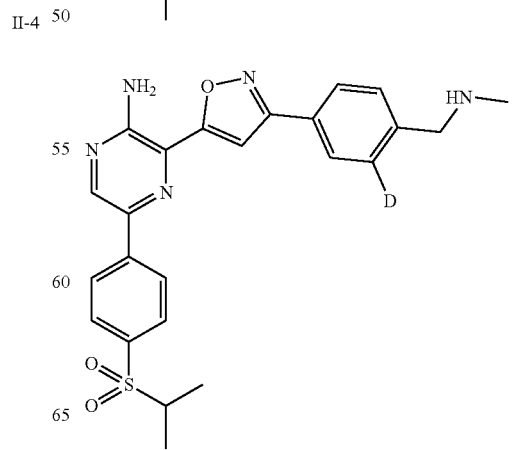
II-8

TABLE II-continued
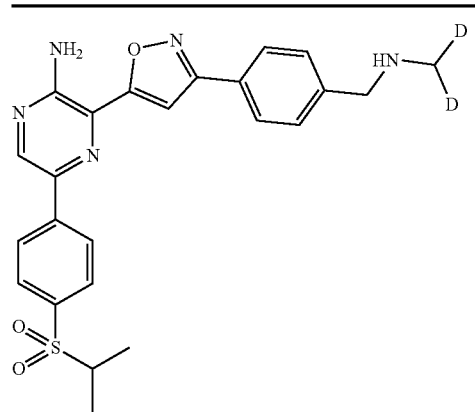
II-9
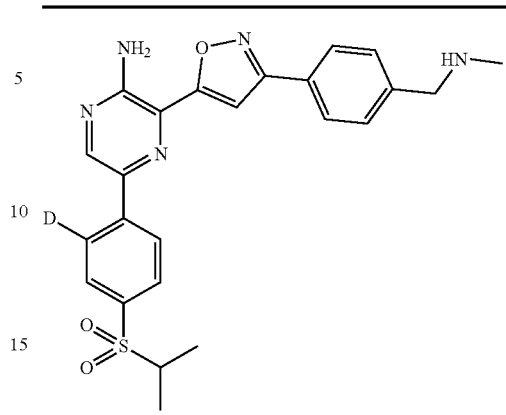
II-13
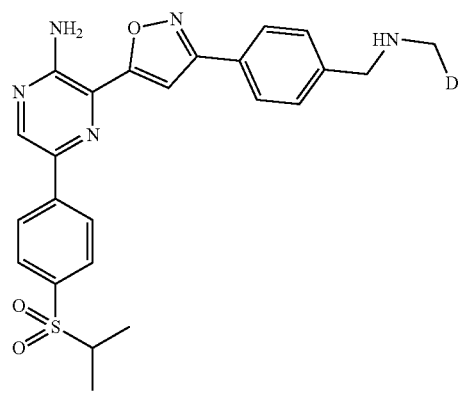 [SMILES: [2H]CNCc1ccc(-c2cc(-c3nc(-c4ccc(S(=O)(=O)C(C)C)cc4)cnc3N)on2)cc1]
II-10
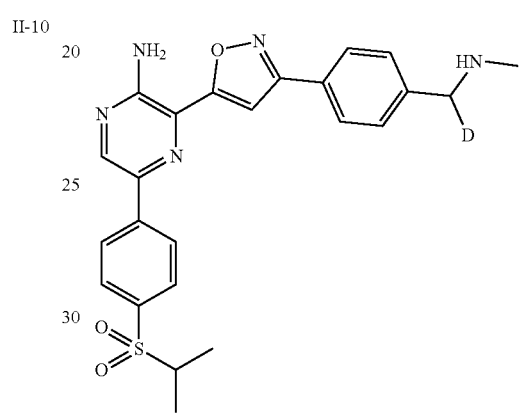
II-14
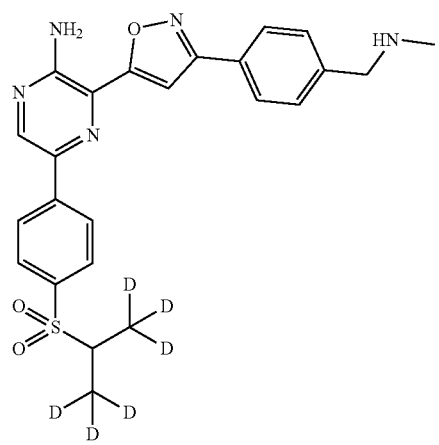 [SMILES: [2H]C([2H])([2H])C(C([2H])([2H])[2H])S(=O)(=O)c1ccc(-c2cnc(N)c(-c3cc(-c4ccc(CNC)cc4)no3)n2)cc1]
II-11
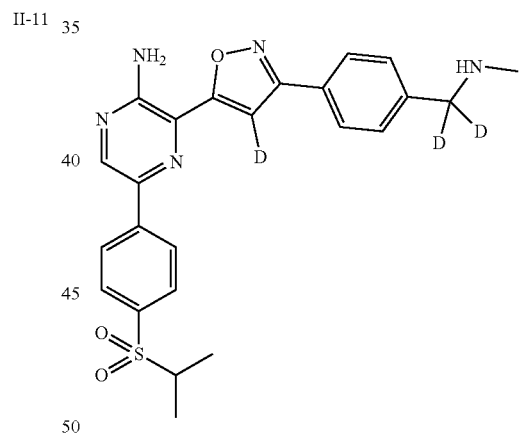
II-15
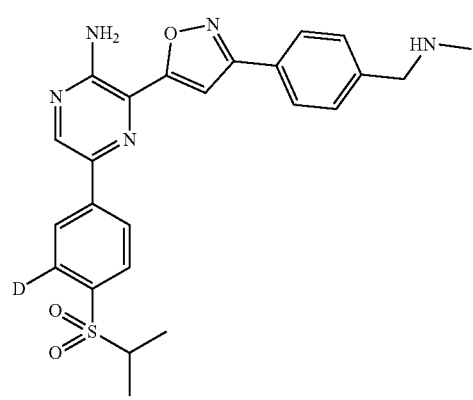 [SMILES: [2H]c1cc(-c2cnc(N)c(-c3cc(-c4ccc(CNC)cc4)no3)n2)ccc1S(=O)(=O)C(C)C]
II-12
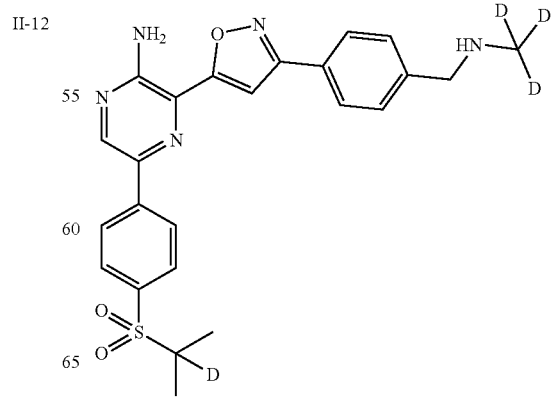
II-16

TABLE II-continued

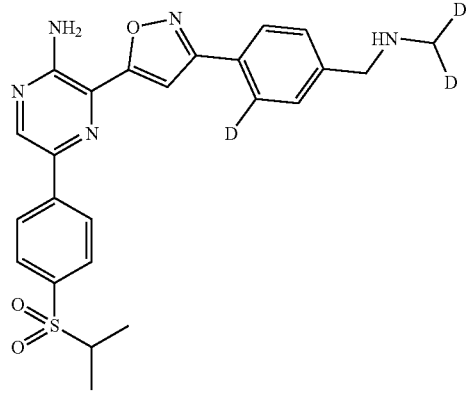 [SMILES: [2H]c1cc(CNC([2H])[2H])ccc1-c1cc(-c2nc(-c3ccc(S(=O)(=O)C(C)C)cc3)cnc2N)on1]

II-17

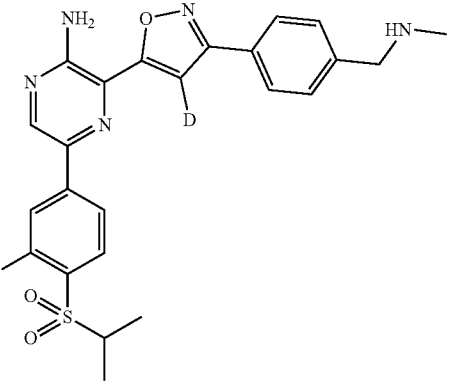

II-20

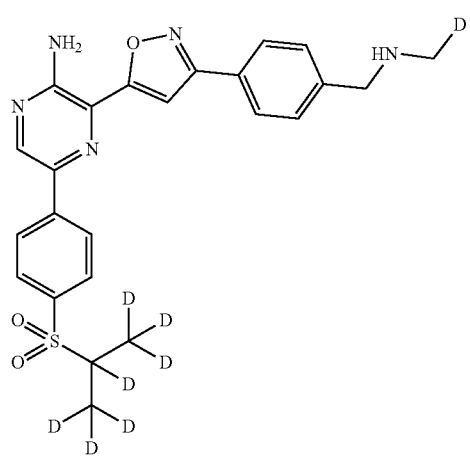 [SMILES: [2H]CNCc1ccc(-c2cc(-c3nc(-c4ccc(S(=O)(=O)C([2H])(C([2H])([2H])[2H])C([2H])([2H])[2H])cc4)cnc3N)on2)cc1]

II-18

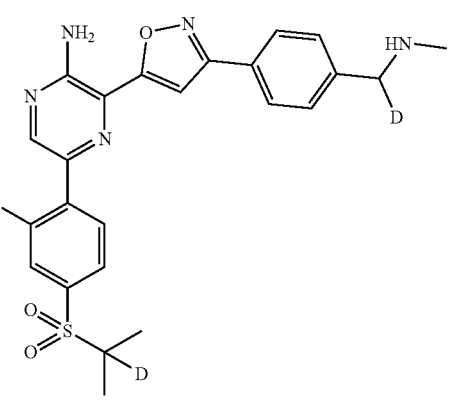

II-21

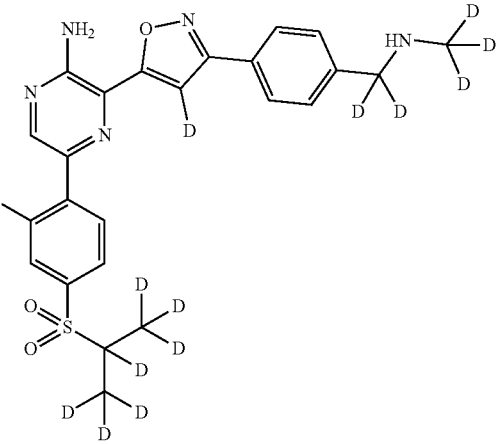

II-22

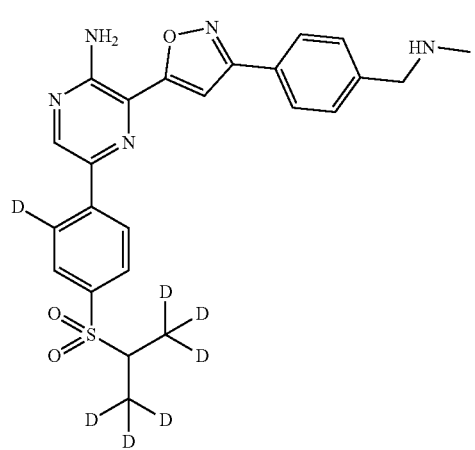 [SMILES: [2H]c1cc(S(=O)(=O)C(C([2H])([2H])[2H])C([2H])([2H])[2H])ccc1-c1cnc(N)c(-c2cc(-c3ccc(CNC)cc3)no2)n1]

II-19

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example ii below, for instance, $J^1$ can be bonded to the 5-membered ring (on the nitrogen atom, for instance), and to the 6-membered ring.

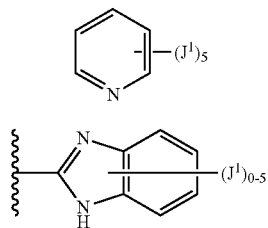

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$— cyclopropyl, CH$_2$CH$_2$CH(CH$_3$)-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

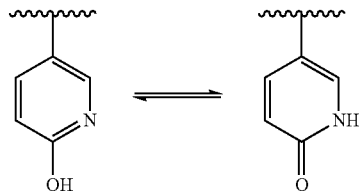 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N≡N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

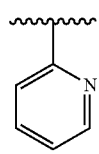

also represents

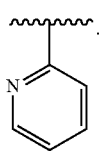

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

"D" and "d" both refer to deuterium.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Processes

Processes and compounds described herein are useful for producing ATR inhibitors that contain an aminopyrazine-isoxazole core. The general synthetic procedures shown in schemes herein are useful for generating a wide array of chemical species which can be used in the manufacture of pharmaceutical compounds.

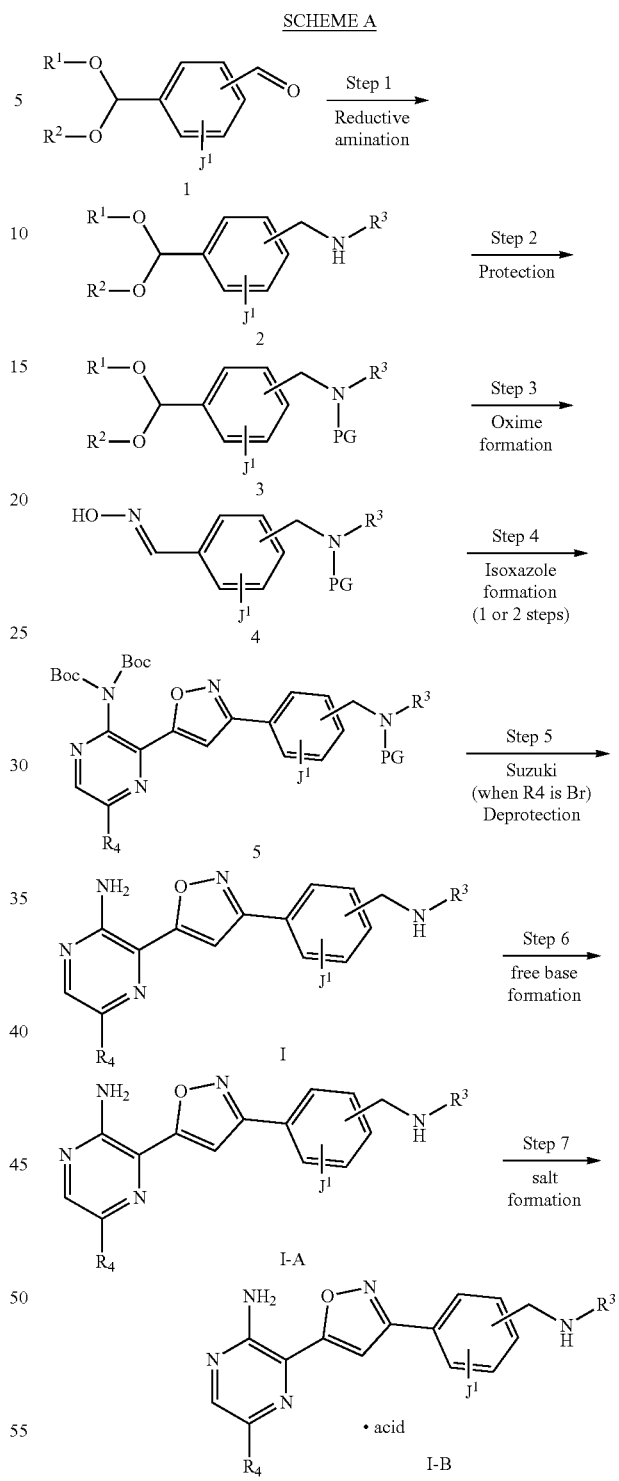

SCHEME A

Step 1

The compound of formula I can be made according to the steps outlined in Scheme A. Step 1 depicts the use of a readily available aldehyde/ketal as a starting point for the preparation of compounds of formula I, I-A, and I-B. Reductive amination between compound 1 and a suitable primary amine, under conditions known to those skilled in the art leads to compound 2 where a benzylamine motif has been installed. For example, imines can be formed by combining an amine and an aldehyde in a suitable solvent, such as dichloromethane (DCM), dichloroethane (DCE), an alcoholic solvent (e.g., methanol, ethanol), or a nonprotic solvent (e.g., dioxane or tetrahydrofuran (THF)). These imines can then be reduced by known reducing agents including, but not limited to, $NaBH_4$, $NaBH_3CN$, and $NaBH(OAc)_3$ (see JOC 1996, 3849). In some embodiments, 1.05 equivalents of amine is combined with 1 equivalent of aldehyde in methanol. In other embodiments, 1.2 equivalents of amine is combined with 1 equivalent of aldehyde in methanol. This step is then followed by reduction with 0.6 to 1.4 (such as 1.2) equivalents of $NaBH_4$. In some cases, if an amine salt is used, base (e.g., $Et_3N$ or diisopropylethylamine) can also be added.

Step 2

Step 2 depicts the protection of the benzylamine 1 prepared above, using a carbamate-based protecting group, under suitable protection conditions known to those skilled in the art. Various protecting groups, such as Cbz and Boc, can be used. Protection conditions include, but are not limited to the following:
 a) R—OCOCl, a suitable tertiary amine base, and a suitable solvent; wherein R is $C_{1-6}$alkyl optionally substituted with phenyl;
 b) R(CO_2)OR', a suitable solvent, and optionally a catalytic amount of base, wherein R is and R' are each independently $C_{1-6}$alkyl optionally substituted with phenyl;
 c) [RO(C=O)]_2O, a suitable base, and a suitable solvent.

Examples of suitable bases include, but are not limited to, $Et_3N$, diisopropylamine, and pyridine. Examples of suitable solvents include chlorinated solvents (e.g., dichloromethane (DCM), dichloroethane (DCE), $CH_2Cl_2$, and chloroform), ethers (e.g., THF, 2-MeTHF, and dioxane), aromatic hydrocarbons (e.g., toluene, xylenes) and other aprotic solvents.

In some embodiments, protection can be done by reacting the benzylamine with $(Boc)_2O$ and $Et_3N$ in DCM. In some embodiments, 1.02 equivalents of $(Boc)_2O$ and 1.02 equivalents of $Et_3N$ 1.02 are used. In another embodiment, protection can be done by reacting the benzylamine with $(Boc)_2O$ in 2-MeTHF. In some embodiments, 1.05 equivalents of $(Boc)_2O$ are used.

Step 3

Step 3 shows how the ketal functional group in 3 is then converted into the oxime 4 in a single step. This direct conversion from ketal to oxime is not extensively described in the literature and it will be appreciated that this step could also be conducted in a two-step sequence, transiting through the aldehyde after deprotection of the ketal using methodologies known to those skilled in the art.

Oxime formation conditions comprise mixing together hydroxylamine, acid, optionally a dehydrating agent, and an alcoholic solvent. In some embodiments, the acid is a catalytic amount. In some embodiments, the acid is pTSA or HCl, the dehydrating agent is molecular sieves or dimethoxyacetone, and the alcoholic solvent is methanol or ethanol. In some embodiments, the hydroxylamine hydrochloride is used in which case no additional acid is required. In other embodiments, the desired product is isolated via a biphasic work up and optionally precipitation or crystallization. If a biphasic work up is used, a dehydrating agent is not needed.

In another embodiment, the oxime formation conditions comprise of mixing together hydroxylamine, an acid, an organic solvent and water. Examples of suitable organic solvents include chlorinated solvents (e.g., dichloromethane (DCM), dichloroethane (DCE), $CH_2Cl_2$, and chloroform), ethers (e.g., THF, 2-MeTHF and dioxane), aromatic hydrocarbons (e.g., toluene, xylenes) and other aprotic solvents. In some embodiments, 1.5 equivalents of hydroxylamine hydrochloride are used, the organic solvent is 2-MeTHF and the water is buffered with $Na_2SO_4$. In another embodiment, 1.2 equivalents of hydroxylamine hydrochloride are used, the organic solvent is THF.

In some embodiments, suitable deprotection conditions comprise adding catalytic amounts of para-toluenesulfonic acid (pTSA), acetone, and water; and then forming the oxime using conditions known to one skilled in the art. In other embodiments, a single step sequence is used. In some embodiments, the single step sequence comprises adding $NH_2OH.HCl$ and a mixture of THF and water. In some embodiments, 1 equivalent of the compound of formula 3 is combined with a 1.1 equivalents of $NH_2OH.HCl$ in a 10:1 v/v mixture of THF/water.

Step 4

Step 4 illustrates how the oxime 4 is then transformed and engaged in a [3+2] cycloaddition to for the isoxazole 5. This transformation can be conducted in one pot but requires two distinct steps. The first step is an oxidation of the oxime functional group into a nitrone, or a similar intermediate with the same degree of oxidation, for example a chlorooxime. This reactive species then reacts with an alkyne in a [3+2] cycloaddition to form the isoxazole adduct.

In some embodiments, the suitable isoxazole-formation conditions consists of two steps, the first step comprising reacting the compound of formula 4 under suitable chlorooxime formation conditions to form a chlorooxime intermediate; the second step comprising reacting the chlorooxime intermediate with acetylene under suitable cycloaddition conditions to form a compound of formula 5.

In some embodiments, the chlorooxime formation conditions are selected from
 a) N-chlorosuccinimide and suitable solvent;
 b) potassium peroxymonosulfate, HCl, and dioxane; and
 c) Sodium hypochlorite and a suitable solvent Examples of suitable solvents include, but are not limited to, nonprotic solvents (e.g., DCM, DCE, THF, 2-MeTHF, MTBE and dioxane), aromatic hydrocarbons (e.g. toluene, xylenes), and alkyl acetates (e.g., isopropyl acetate, ethyl acetate).

Isolation of the product can be achieved by adding an antisolvent to a solution of a compound of formula 5. Examples of suitable solvents for isolating the chlorooxime intermediate include mixtures of suitable solvents (EtOAc, IPAC) with hydrocarbons (e.g., hexanes, heptane, cyclohexane), or aromatic hydrocarbons (e.g., toluene, xylenes). In some embodiments, heptane is added to a solution of chlorooxime in IPAC.

Suitable cycloaddition conditions consist of combining the chlorooxime with acetylene with a suitable base and a suitable solvent. Suitable solvents include protic solvents, aprotic solvents, polar solvents, and nonpolar solvents. Examples of suitable solvent include, but are not limited to, acetonitrile, tetrahydrofuran, 2-methyltetrahydrofuran, MTBE, EtOAc, i-PrOAc, DCM, toluene, DMF, and methanol. Suitable bases include, but are not limited to, pyridine, DIEA, TEA, t-BuONa, and $K_2CO_3$. In some embodiments, suitable cycloaddition conditions comprise adding 1.0 equivalents of chlorooxime, 1.0 equivalents of acetylene, 1.1 equivalents of Et3N in DCM.

Isolation of the product can be achieved by adding an antisolvent to a solution of a compound of formula 5. Examples of suitable solvents for isolating the chlorooxime include mixtures of suitable solvents (EtOAc, IPAC) with hydrocarbons (e.g., hexanes, heptane, cyclohexane), or aromatic hydrocarbons (e.g., toluene, xylenes). In some embodiments, heptane is added to a solution of chlorooxime in IPAC.

Step 5

Step 5 depicts the final step(s) of the preparation of compounds of formula I. When the R4 group is bromo, intermediate 5 can be subjected to a Suzuki cross-coupling with boronic acid or esters, under conditions known to those skilled in the art, to form compounds where R4 an aryl, heteroaryl or alternative moieties resulting from the metal-assisted coupling reaction. When intermediate 5 is suitably functionalised, a deprotection step can be carried out to remove the protecting groups and generate the compounds of formula I.

Metal assisted coupling reactions are known in the art (see e.g., Org. Proc. Res. Dev. 2010, 30-47). In some embodiments, suitable coupling conditions comprise adding 0.1 equivalents of Pd[P(tBu)$_3$]2; 1 equivalent of boronic acid or ester; and 2 equivalents of sodium carbonate in a 2:1 ratio v/v of acetonitrile/water at 60-70° C. In other embodiments, suitable coupling conditions comprise adding 0.010-0.005 equivalents Pd(dtbpf)Cl$_2$, 1 equivalent of boronic acid or ester, and 2 equivalents of potassium carbonate in a 7:2 v/v of toluene and water at 70° C.

The final product can treated with a metal scavenger (silica gel, functionalized resins, charcoal) (see e.g., Org. Proc. Res. Dev. 2005, 198-205). In some embodiments, the solution of the product is treated with Biotage MP-TMT resin.

The product can also be isolated by crystallization from an alcoholic solvent (e.g. methanol, ethanol, isopropanol). In some embodiments the solvent is ethanol. In other embodiments the solvent is isopropanol.

Deprotection of Boc groups is known in the art (see e.g. *Protecting Groups in Organic Synthesis*, Greene and Wuts). In some embodiments, suitable deprotection conditions are hydrochloric acid in acetone at 35-45° C. In other embodiments, suitable deprotection conditions are TFA in DCM.

Step 6

Step 6 illustrates how compounds of formula I are converted to compounds of formula I-A using a base under suitable conditions known to those skilled in the art. In some embodiments, isolation of the free-base form of compounds of formula I may be achieved by adding suitable base, such as NaOH to an alcoholic acidic solution of compounds of formula I to precipitate the product.

Step 7

Step 7 illustrates how compounds of formula I-A are converted to compounds of formula I-B using an acid under suitable conditions known to those skilled in the art.

In some embodiments suitable conditions involve adding aqueous HCl, to a suspension of compounds of formula I-A in acetone at 35° C. then heating at 50° C.

SCHEME B: Formation of d1-boronate

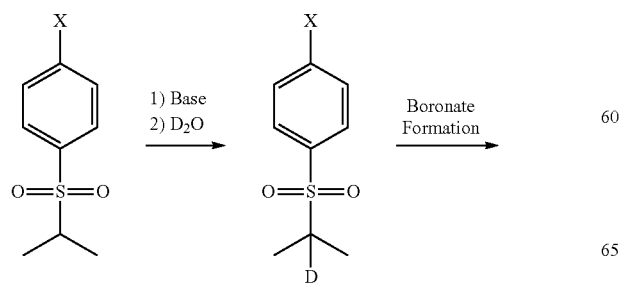

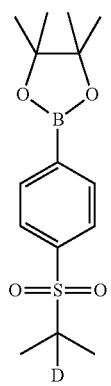

Scheme B shows a general synthetic method for the preparation of d1-boronate intermediates. A suitable 1-halo-(isopropylsulfonyl)benzene is treated with a base such as, but not limited to NaH, LiHMDS or KHMDS followed by quenching of the anion with deuterium source such as D$_2$O. The halogen is then transformed into a suitable boronate derivative via, for example, metal mediated cross-coupling catalyzed by, for instance, Pd($^t$Bu$_3$)$_2$ or Pd(dppf)Cl$_2$.DCM.

SCHEME C: Formation of d6-boronate

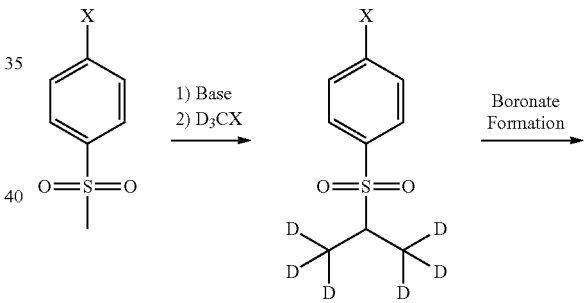

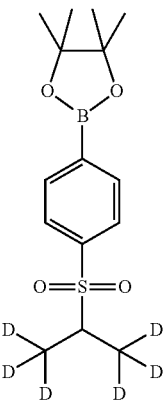

Scheme C shows a general synthetic method for the preparation of d6-boronate intermediates. A suitable 1-halo- (methylsulfonyl)benzene is treated with a base such as, but not limited to NaH, LiHMDS or KHMDS followed by quenching of the anion with deuterium source such as D₃Cl. This reaction is repeated until the desired amount of deuterium has been incorporated into the molecule. The halogen is then transformed into a suitable boronate derivative via, for example, metal mediated cross-coupling catalyzed by, for instance, Pd(ᵗBu₃)₂ or Pd(dppf)Cl₂.DCM.

SCHEME D: Formation of d7-boronate

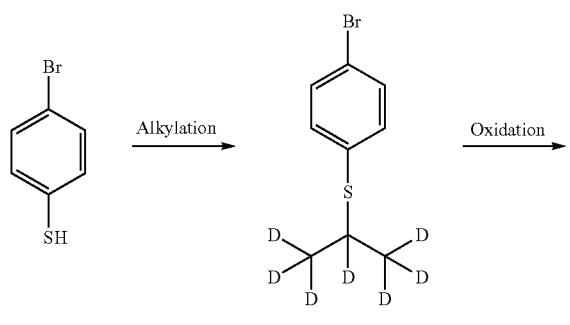

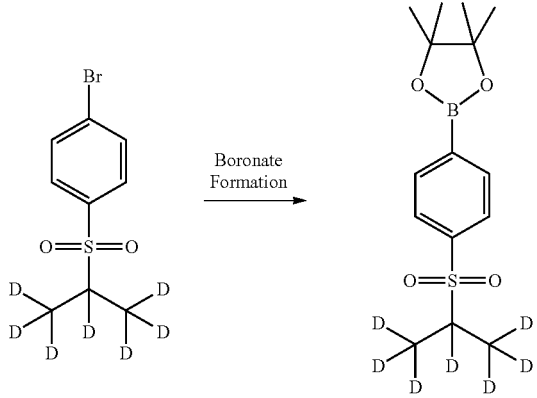

Scheme D shows a general synthetic method for the preparation of d7-boronate intermediates. 4-Bromobenzenethiol is treated with a base such as, but not limited to NaH, LiHMDS or KHMDS followed by quenching of the anion with deuterium source such as 1,1,1,2,3,3,3-heptadeuterio-2-iodo-propane. The sulfide is then oxidized to the corresponding sulfone using, for example, mCPBA or Oxone. The halogen is then transformed into a suitable boronate derivative via, for example, metal mediated cross-coupling catalyzed by, for instance, Pd(ᵗBu₃)₂ or Pd(dppf)Cl₂.DCM.

SCHEME E: Formation of aryl ring deuterated boronate

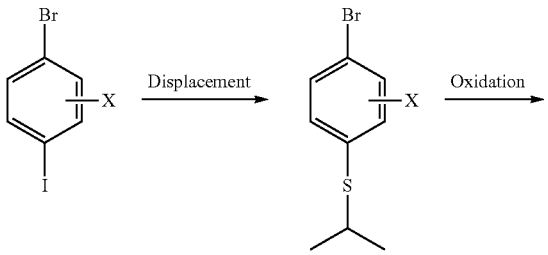

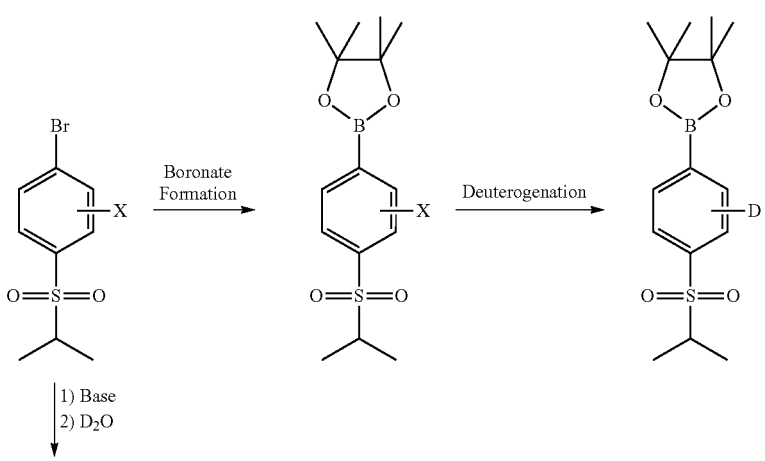

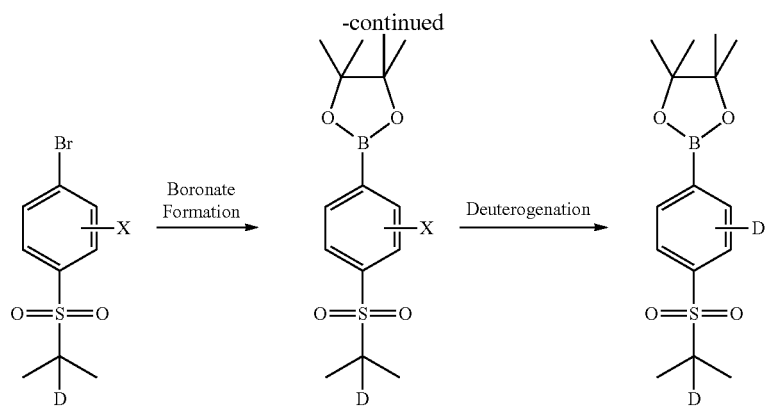

Scheme E shows a general synthetic method for the preparation of boronate intermediates where the aryl ring is substituted with a deuterium. A suitable 1-iodo-4-bromo-aryl derivative is treated with a substituted thiol such as propane-2-thiol under metal catalyzed coupling conditions using a catalyst such as CuI. The sulfide is then oxidized to the corresponding sulfone using, for example, mCPBA or Oxone. The bromide is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas. In addition, the 1-bromo-(isopropylsulfonyl)benzene can be treated with a base such as, but not limited to NaH, LiHMDS or KHMDS followed by quenching of the anion with deuterium source such as D$_2$O. The bromide is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas.

SCHEME F: Formation of aryl ring deuterated boronate

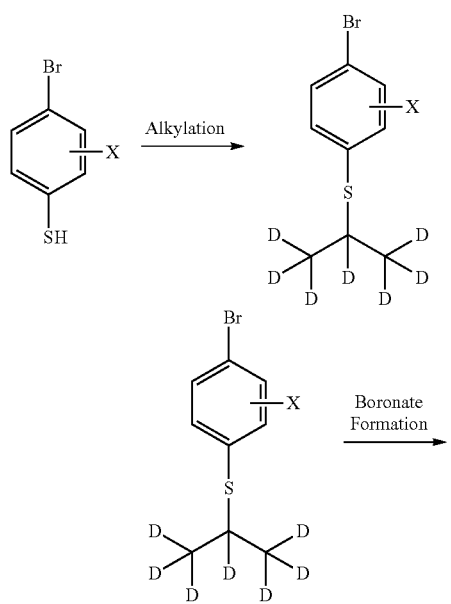

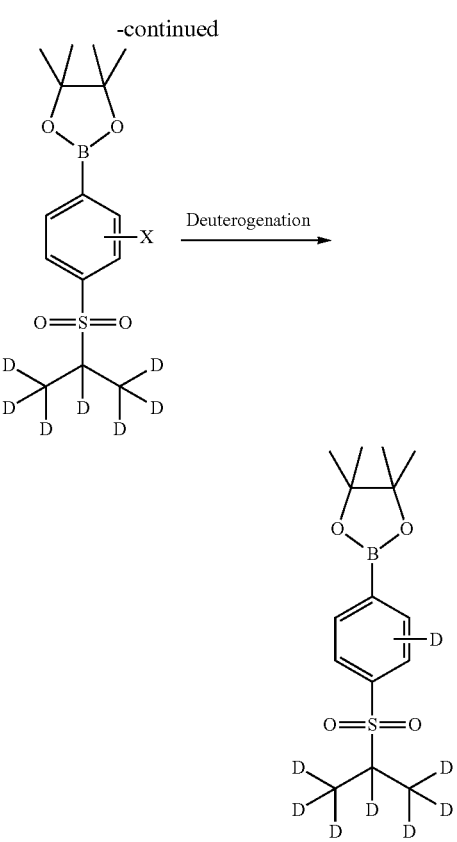

Scheme F shows another general synthetic method for the preparation of boronate intermediates where the aryl ring is substituted with a deuterium. A substituted 4-bromobenzenethiol is treated with a base such as, but not limited to NaH, LiHMDS or KHMDS followed by quenching of the anion with deuterium source such as 1,1,1,2,3,3,3-heptadeuterio-2-iodo-propane. The sulfide is then oxidized to the corresponding sulfone using, for example, mCPBA or Oxone. The halogen is then transformed into a suitable boronate derivative via, for example, metal mediated cross-coupling catalyzed by, for instance, Pd($^t$Bu$_3$)$_2$ or Pd(dppf)Cl$_2$.DCM. The remaining substituent is then converted into deuterium by, for instance, metal catalyzed halogen-deuterium exchange using a suitable metal catalyst, such as Pd on C under an atmosphere of deuterium gas.

SCHEME G: Formation of aryl ring deuterated boronate

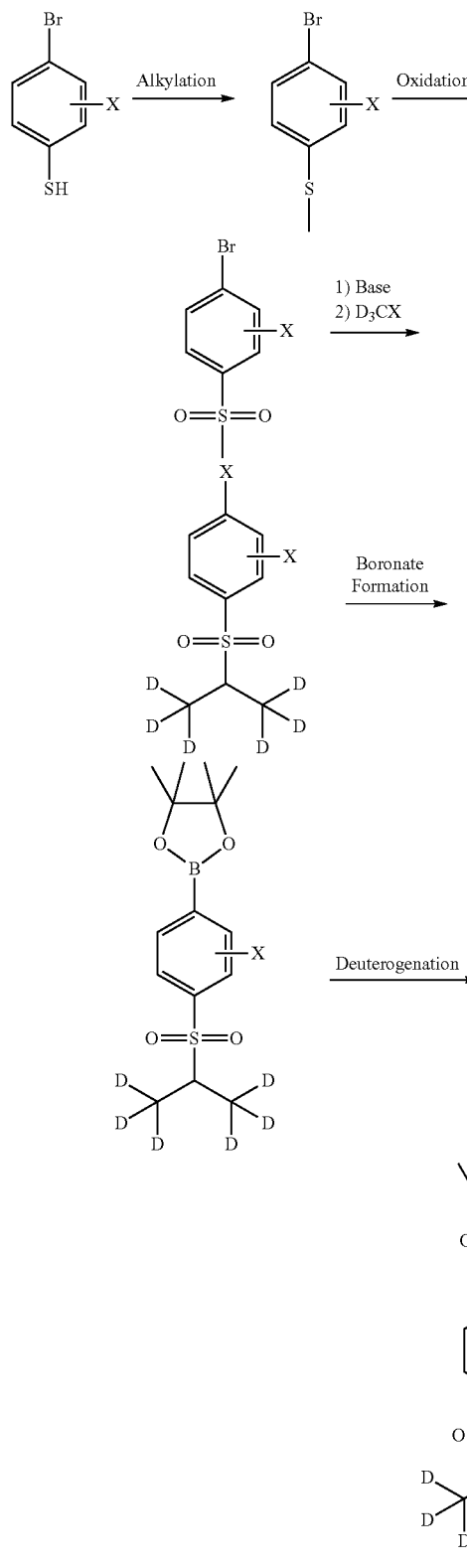

NaH, LiHMDS or KHMDS followed by quenching of the anion with for instance MeI. The sulfide is then oxidized to the corresponding sulfone using, for example, mCPBA or Oxone. The sulfone is treated with a base such as, but not limited to NaH, LiHMDS or KHMDS followed by quenching of the anion with deuterium source such as $D_3Cl$. This reaction is repeated until the desired amount of deuterium has been incorporated into the molecule. The halogen is then transformed into a suitable boronate derivative via, for example, metal mediated cross-coupling catalyzed by, for instance, $Pd(^tBu_3)_2$ or $Pd(dppf)Cl_2.DCM$. The remaining substituent is then converted into deuterium by, for instance, metal catalyzed halogen-deuterium exchange using a suitable metal catalyst, such as Pd on C under an atmosphere of deuterium gas.

SCHEME H: Formation of aryl ring deuterated oxime intermediates

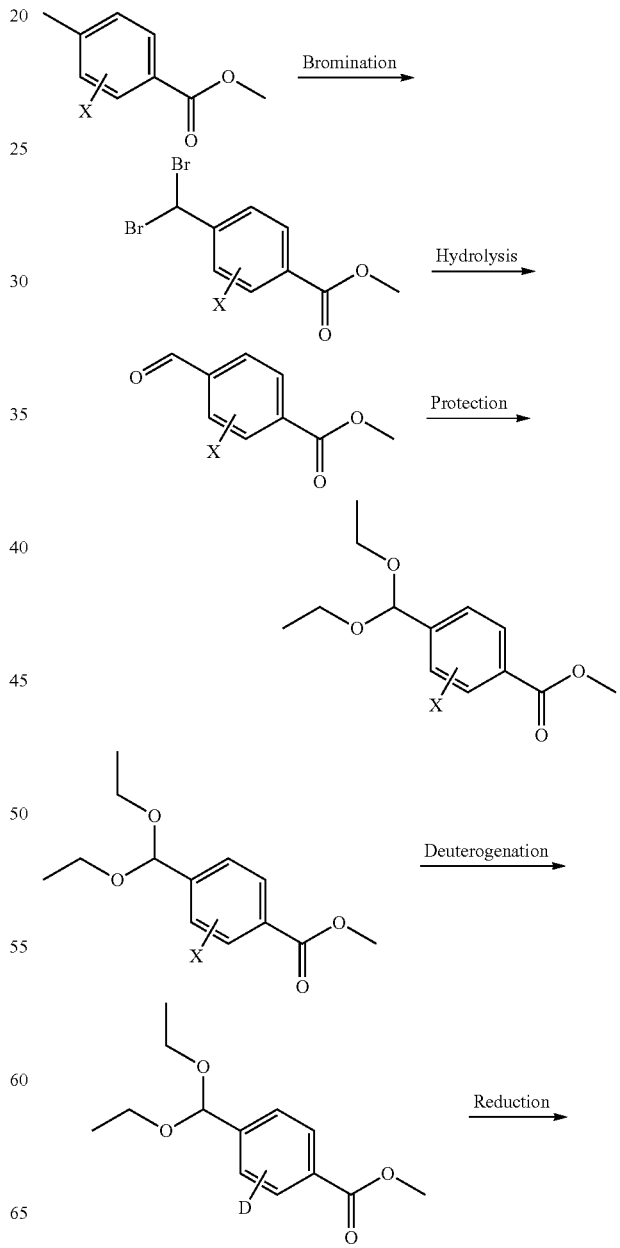

Scheme G shows another general synthetic method for the preparation of boronate intermediates where the aryl ring is substituted with a deuterium. A substituted 4-bromobenzenethiol is treated with a base such as, but not limited to -continued

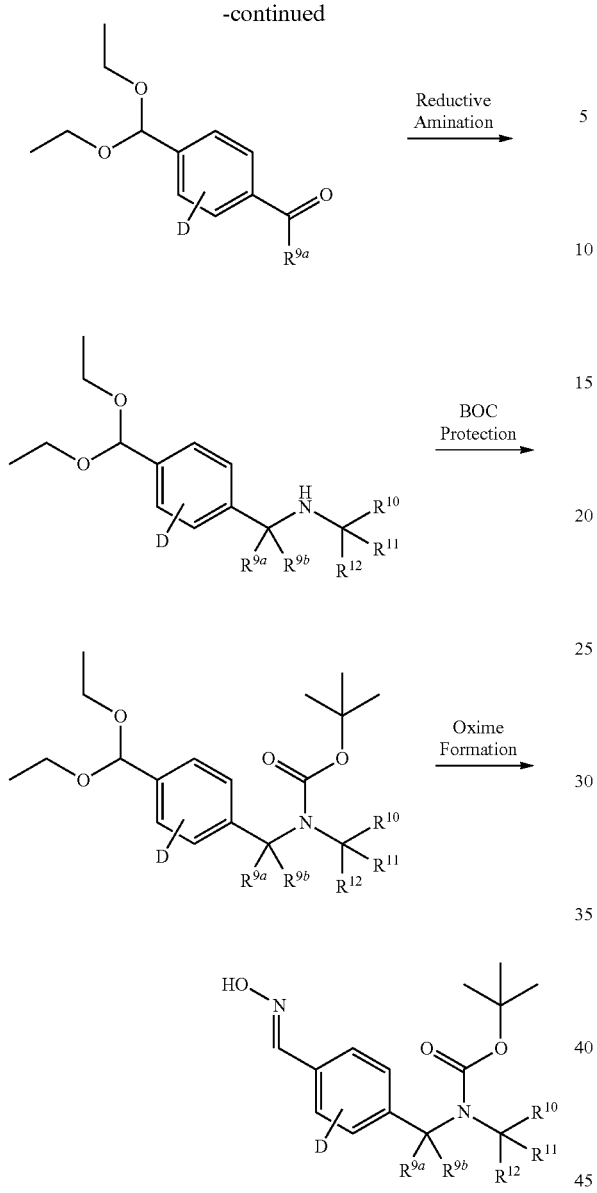

Scheme H shows a general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using AgNO₃ in acetone/water. Protection of the aldehyde as a suitable acetal, for instance the diethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. The ester functionality can be reduced using reagents such as LiAlH₄, NaBH₄, NaBD₄ or LiAlD₄ to give corresponding aldehyde. This can be reacted under reductive amination conditions using a suitable amine, such as methylamine or d3-methylamine using a reducing agent such as NaBH₄ or NaBD₄ to give the corresponding amine derivative. This can be protected with, for instance a Boc group and the acetal converted into the oxime using, for instance, hydroxylamine hydrochloride in THF/water.

SCHEME I: Formation of aryl ring deuterated oxime intermediates

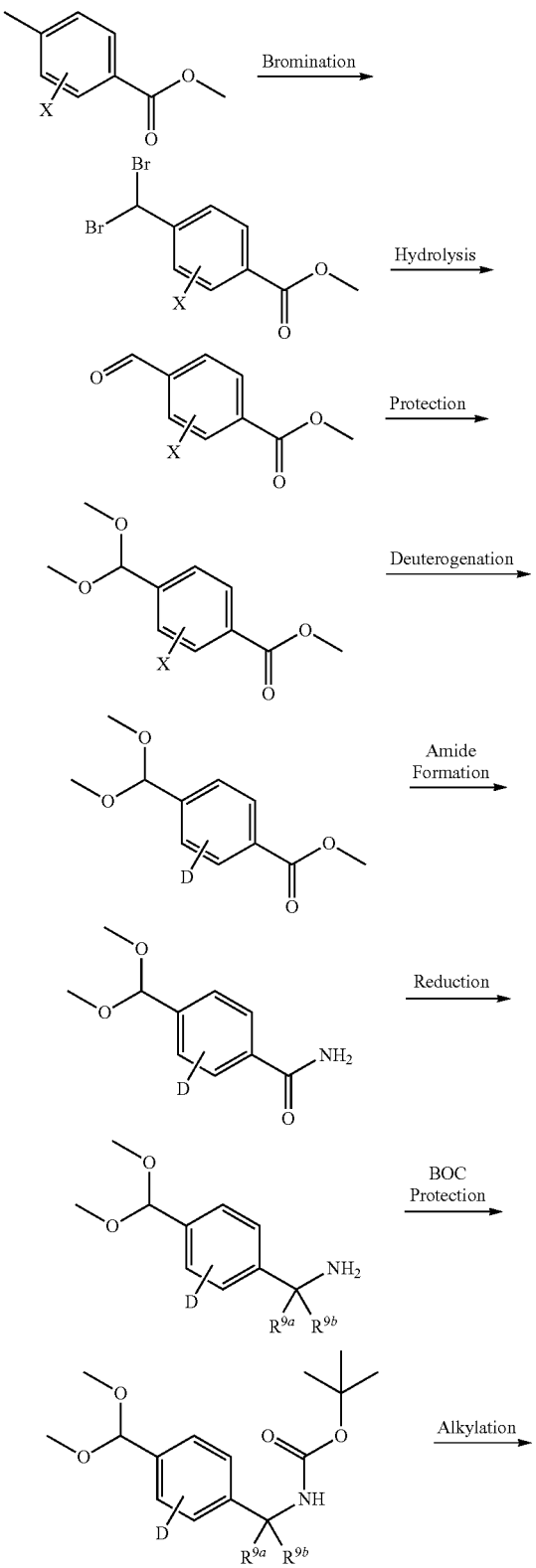

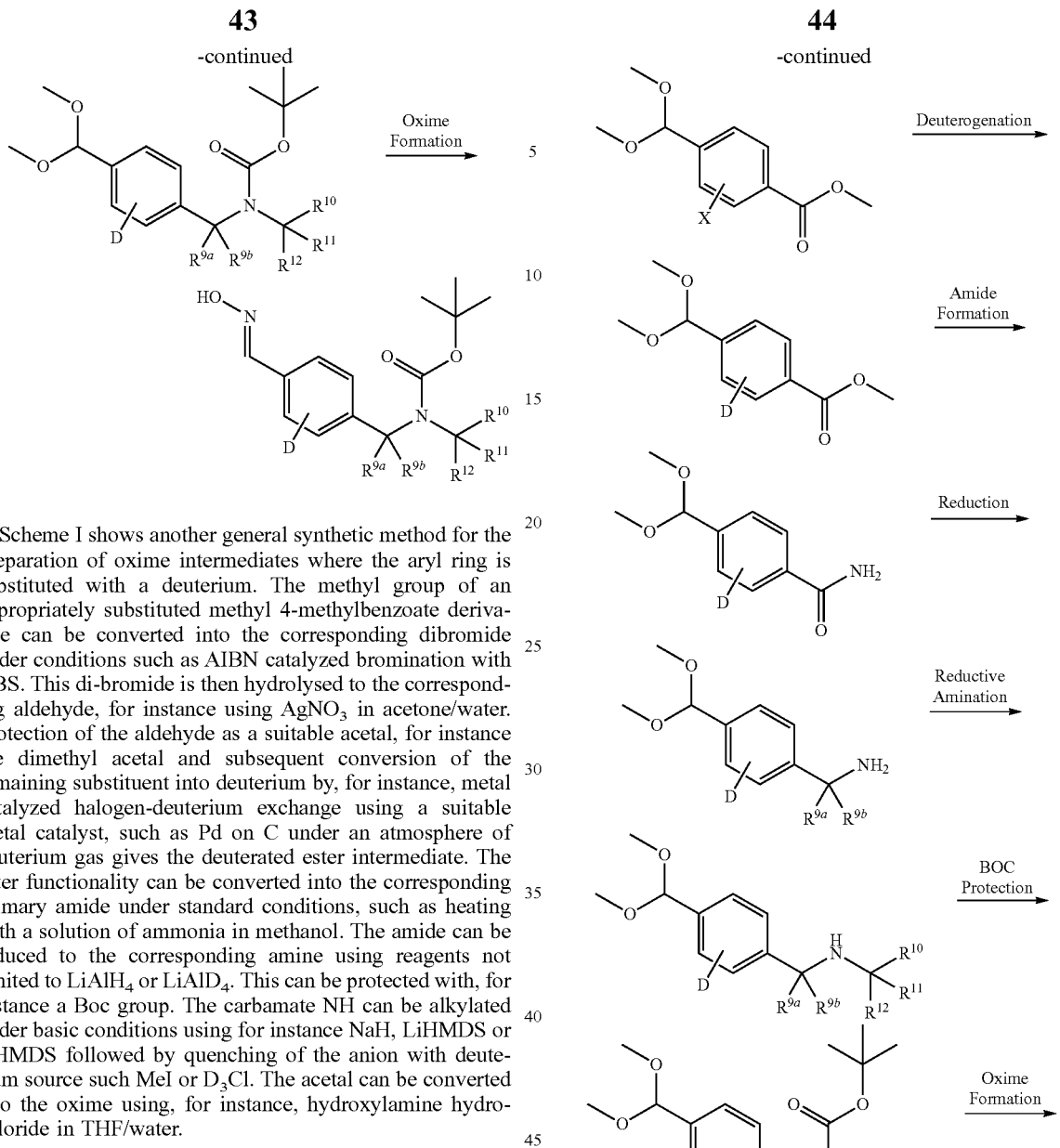

Scheme I shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. The ester functionality can be converted into the corresponding primary amide under standard conditions, such as heating with a solution of ammonia in methanol. The amide can be reduced to the corresponding amine using reagents not limited to $LiAlH_4$ or $LiAlD_4$. This can be protected with, for instance a Boc group. The carbamate NH can be alkylated under basic conditions using for instance NaH, LiHMDS or KHMDS followed by quenching of the anion with deuterium source such MeI or $D_3Cl$. The acetal can be converted into the oxime using, for instance, hydroxylamine hydrochloride in THF/water.

SCHEME J: Formation of aryl ring deuterated oxime intermediates

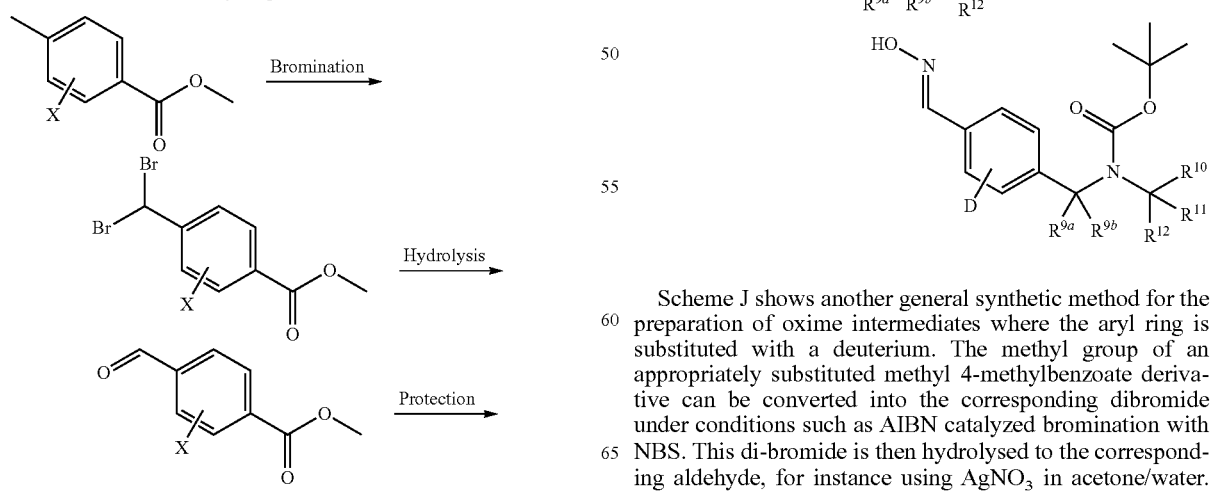

Scheme J shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. The ester functionality can be converted into the corresponding primary amide under standard conditions, such as heating with a solution of ammonia in methanol. The amide can be reduced to the corresponding amine using reagents not limited to $LiAlH_4$ or $LiAlD_4$. This can be reacted under reductive amination conditions using a suitable amine, such as methylamine, d3-methylamine, formaldehyde or d2-formaldehyde using a reducing agent such as $NaBH_4$ or $NaBD_4$ to give the corresponding amine derivative. This can be protected with, for instance a Boc group. The acetal can be converted into the oxime using, for instance, hydroxylamine hydrochloride in THF/water.

SCHEME K: Formation of aryl ring deuterated oxime intermediates

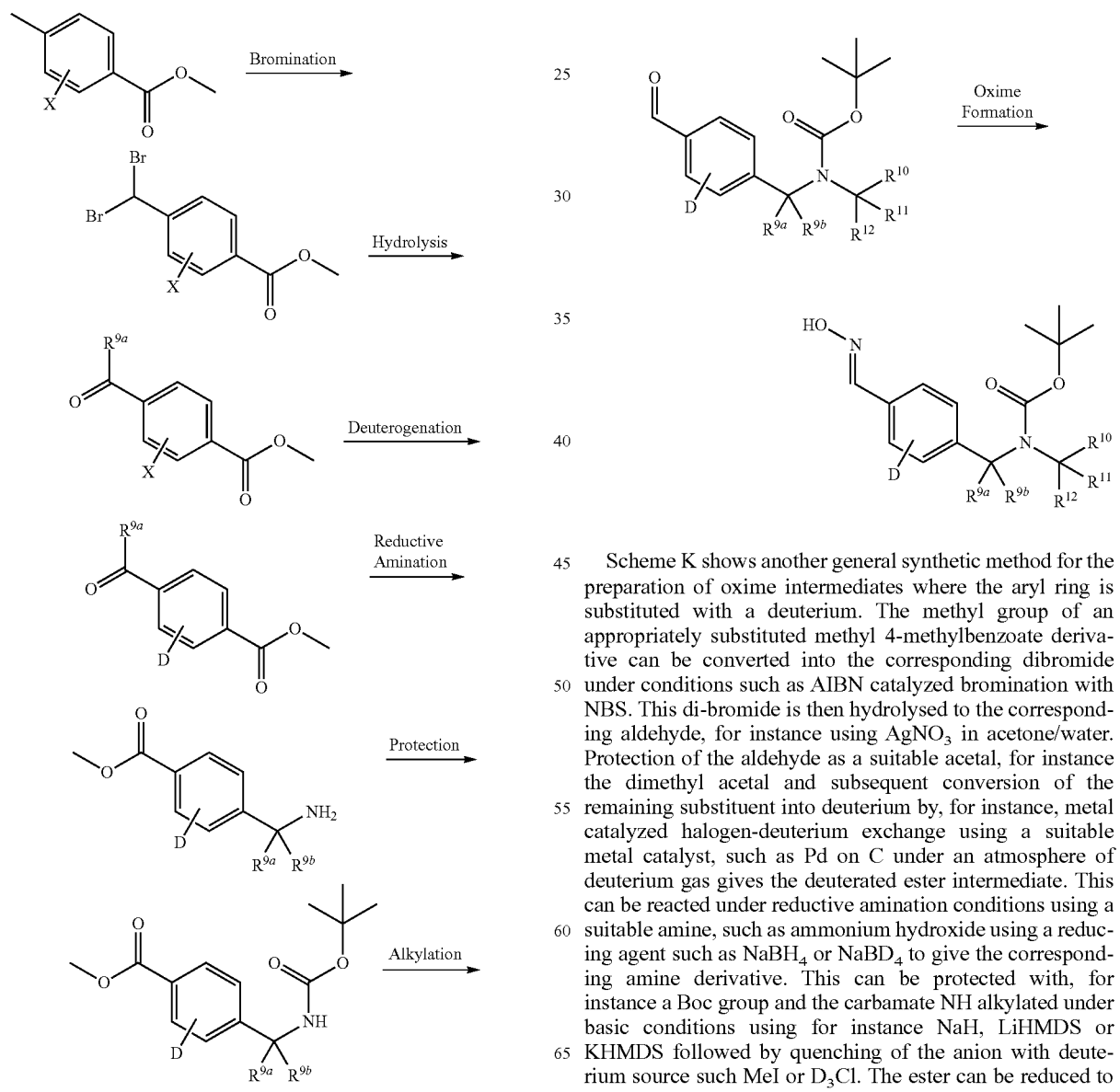

Scheme K shows another general synthetic method for the preparation of oxime intermediates where the aryl ring is substituted with a deuterium. The methyl group of an appropriately substituted methyl 4-methylbenzoate derivative can be converted into the corresponding dibromide under conditions such as AIBN catalyzed bromination with NBS. This di-bromide is then hydrolysed to the corresponding aldehyde, for instance using $AgNO_3$ in acetone/water. Protection of the aldehyde as a suitable acetal, for instance the dimethyl acetal and subsequent conversion of the remaining substituent into deuterium by, for instance, metal catalyzed halogen-deuterium exchange using a suitable metal catalyst, such as Pd on C under an atmosphere of deuterium gas gives the deuterated ester intermediate. This can be reacted under reductive amination conditions using a suitable amine, such as ammonium hydroxide using a reducing agent such as $NaBH_4$ or $NaBD_4$ to give the corresponding amine derivative. This can be protected with, for instance a Boc group and the carbamate NH alkylated under basic conditions using for instance NaH, LiHMDS or KHMDS followed by quenching of the anion with deuterium source such MeI or $D_3Cl$. The ester can be reduced to the corresponding alcohol using a suitable reducing agent such as LiBH$_4$ or NaBH$_4$. The alcohol can be oxidized to the aldehyde using reagents such as MnO$_2$ or Dess-Martin periodane. The acetal can be converted into the oxime using, for instance, aqueous hydroxylamine.

SCHEME L: Formation of deuterated oxime intermediates

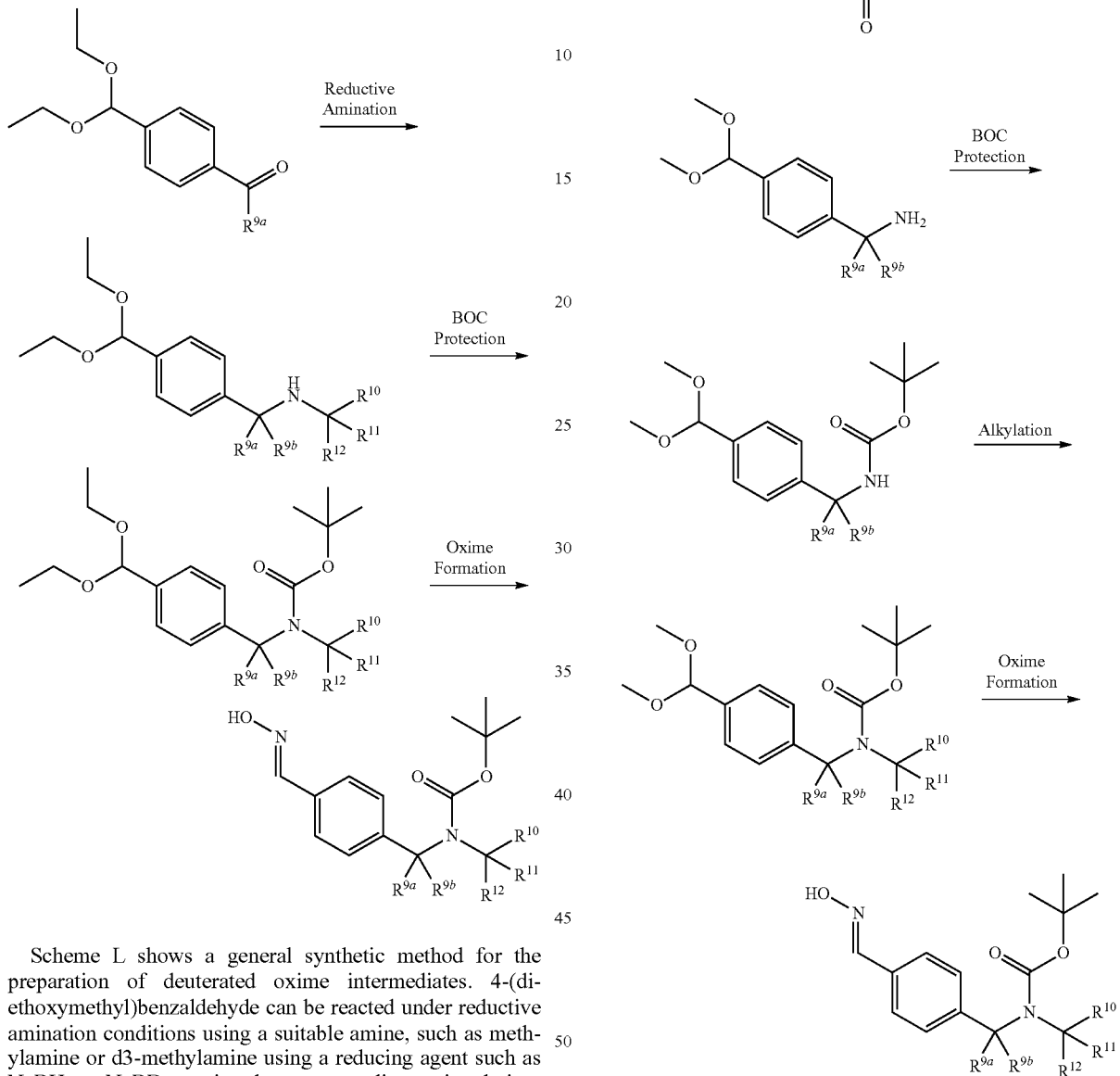

Scheme L shows a general synthetic method for the preparation of deuterated oxime intermediates. 4-(diethoxymethyl)benzaldehyde can be reacted under reductive amination conditions using a suitable amine, such as methylamine or d3-methylamine using a reducing agent such as NaBH$_4$ or NaBD$_4$ to give the corresponding amine derivative. This can be protected with, for instance a Boc group and the acetal converted into the oxime using, for instance, hydroxylamine hydrochloride in THF/water.

SCHEME M: Formation of deuterated oxime intermediates

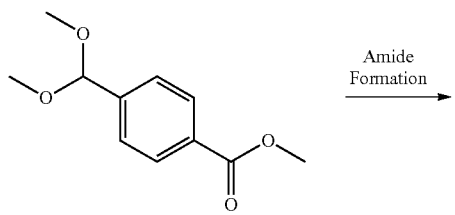

Scheme M shows another general synthetic method for the preparation of deuterated oxime intermediates. The ester functionality of methyl 4-(dimethoxymethyl)benzoate can be converted into the corresponding primary amide under standard conditions, such as heating with a solution of ammonia in methanol. The amide can be reduced to the corresponding amine using reagents not limited to LiAlH$_4$ or LiAlD$_4$. This can be protected with, for instance a Boc group. The carbamate NH can be alkylated under basic conditions using for instance NaH, LiHMDS or KHMDS followed by quenching of the anion with deuterium source such MeI or D$_3$Cl. The acetal can be converted into the oxime using, for instance, hydroxylamine hydrochloride in THF/water.

SCHEME N: Formation of deuterated oxime intermediates

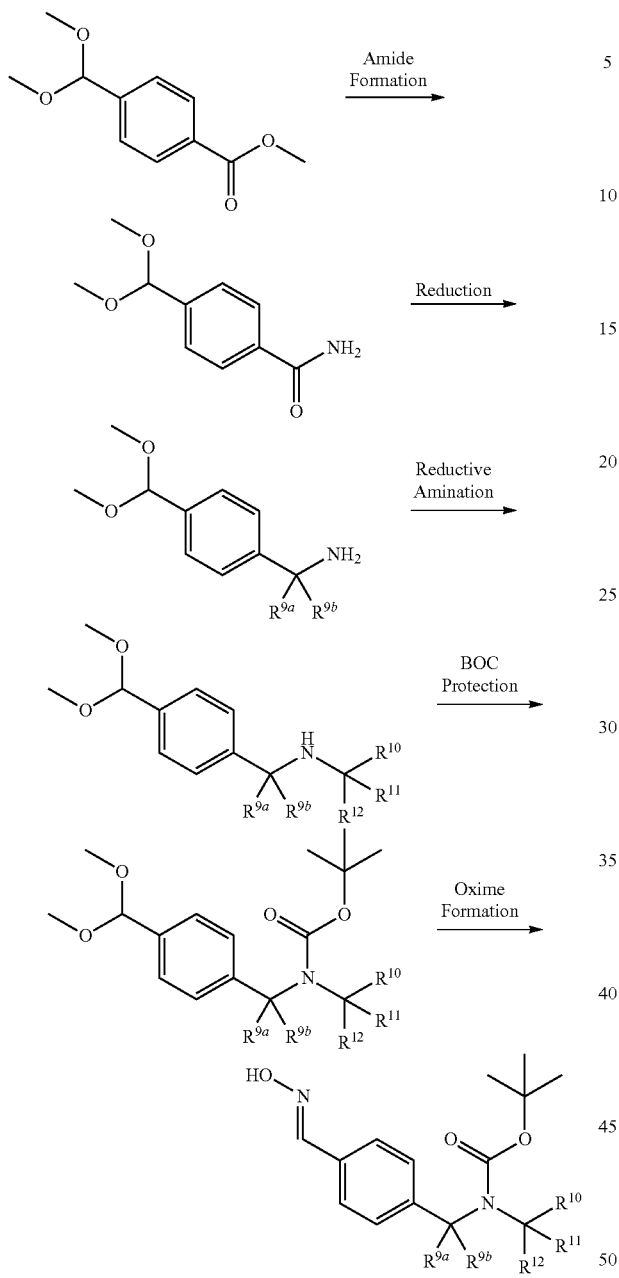

SCHEME O: Formation of deuterated oxime intermediates

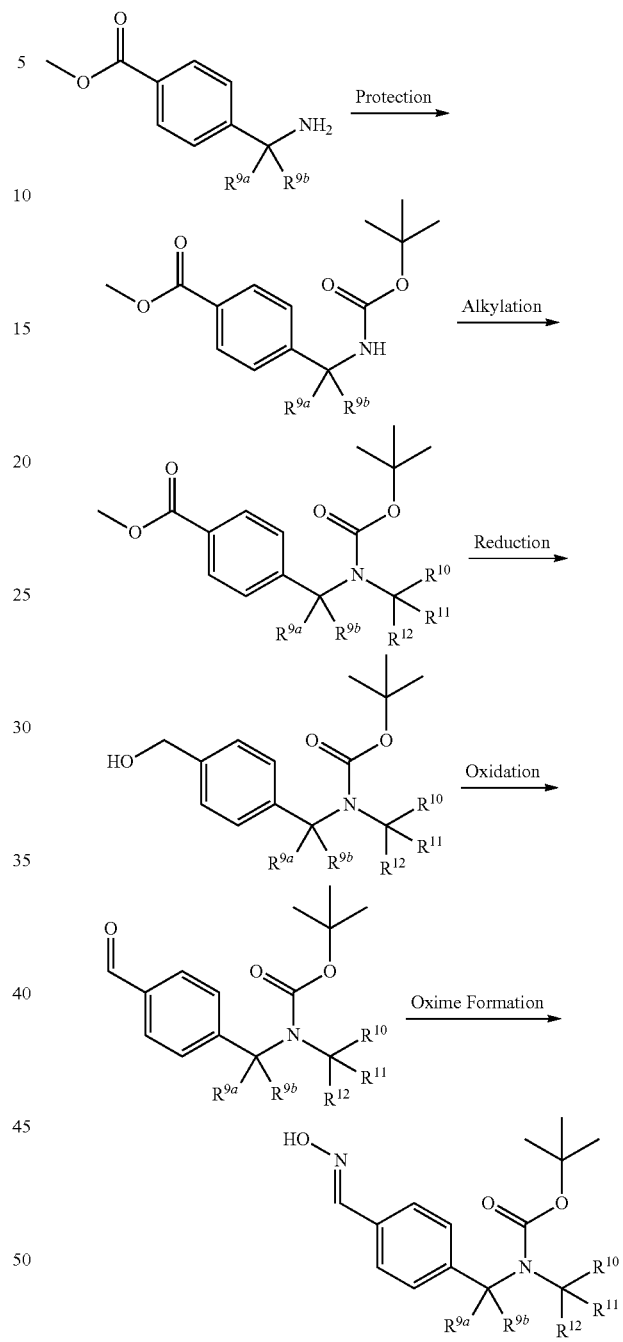

Scheme N shows another general synthetic method for the preparation of deuterated oxime intermediates. The ester functionality of methyl 4-(dimethoxymethyl)benzoate can be converted into the corresponding primary amide under standard conditions, such as heating with a solution of ammonia in methanol. The amide can be reduced to the corresponding amine using reagents not limited to $LiAlH_4$ or $LiAlD_4$. This can be reacted under reductive amination conditions using a suitable amine, such as methylamine, d3-methylamine, formaldehyde or d2-formaldehyde using a reducing agent such as $NaBH_4$ or $NaBD_4$ to give the corresponding amine derivative. This can be protected with, for instance a Boc group. The acetal can be converted into the oxime using, for instance, hydroxylamine hydrochloride in THF/water.

Scheme O shows another general synthetic method for the preparation of deuterated oxime intermediates. A 4-substituted benzylamine can be protected with, for instance a Boc group. The carbamate NH can be alkylated under basic conditions using for instance NaH, LiHMDS or KHMDS followed by quenching of the anion with deuterium source such MeI or $D_3Cl$. The ester can be reduced to the corresponding alcohol using a suitable reducing agent such as $LiBH_4$ or $NaBH_4$. The alcohol can be oxidized to the aldehyde using reagents such as $MnO_2$ or Dess-Martin periodane. The acetal can be converted into the oxime using, for instance, aqueous hydroxylamine.

SCHEME P: Formation of isoxazole derrivatives

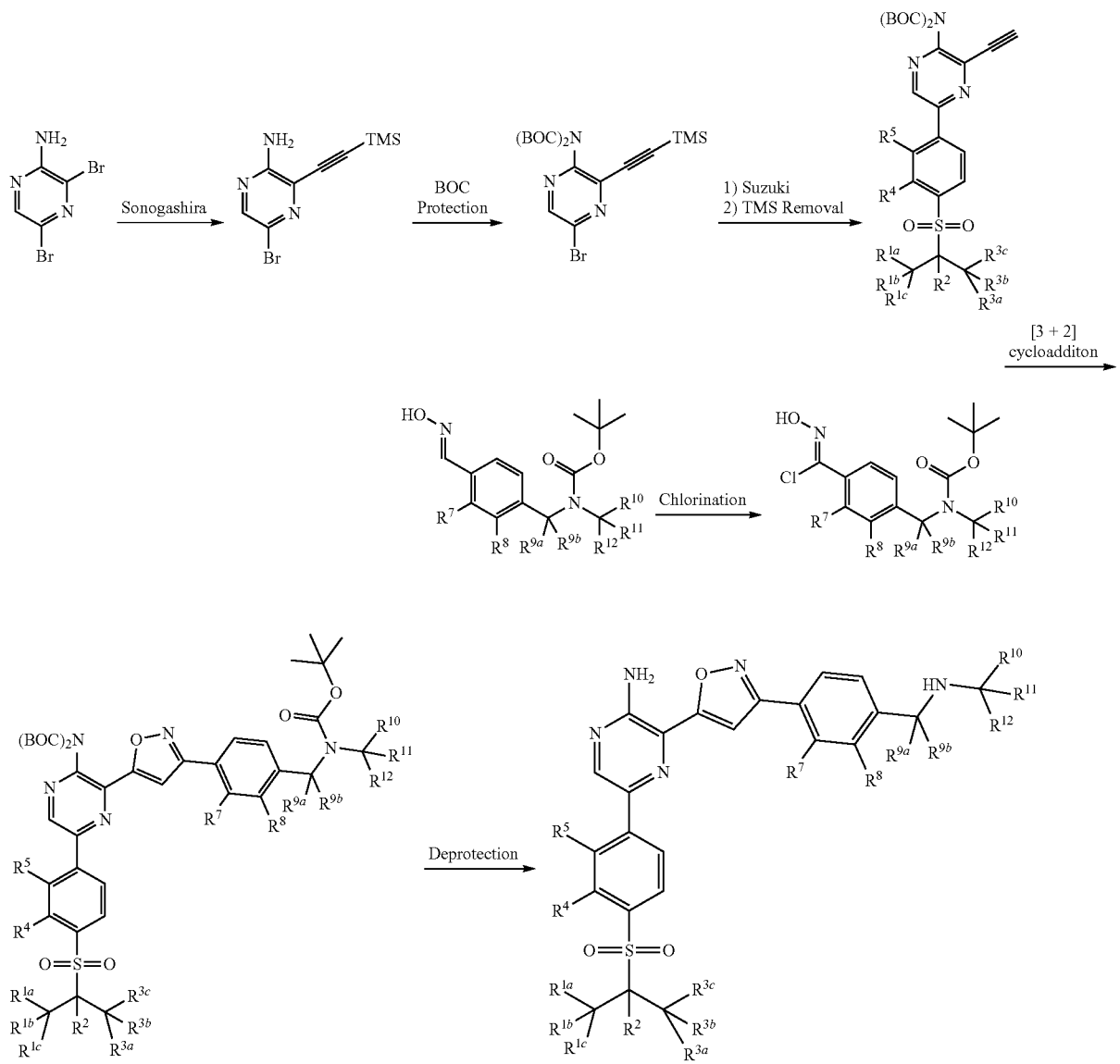

Scheme P shows a general synthetic method for the preparation of deuterated pyrazine-isoxazole derivatives. 3,5-Dibromopyrazin-2-amine is converted into the corresponding silyl-protected alkyne under standard Sonagashira conditions utilizing, for example, Pd(PPh$_3$)$_4$ and CuI as catalysts. The pyrazine NH$_2$ can then be protected as, for example the di-Boc derivative. Coupling of the pyrazine bromide with a boronate, for instance those outlined in Schemes 1 to 6 above, under standard Suzuki cross-coupling conditions followed by removal of the silyl protecting group give the desired alkyne intermediate. Oximes, such as those outline in Schemes 7 to 14 above, can be converted into the corresponding chlorooximes using, for instance, NCS. The alkyne and chlorooxime intermediates can undergo a [3+2] cycloaaditon to give corresponding isoxazole under standard conditions, for instance by the addition of Et$_3$N. The Boc protecting groups can be removed under acidic conditions such as TFA in DCM or HCl in MeOH/DCM to give the deuterated pyrazine isoxale derivatives.

SCHEME Q: Formation of deuterated isoxazole derrivatives

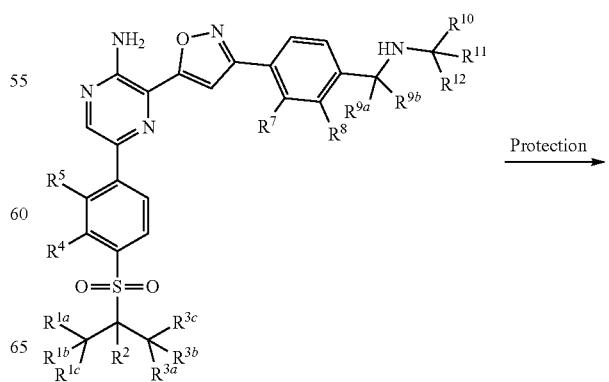

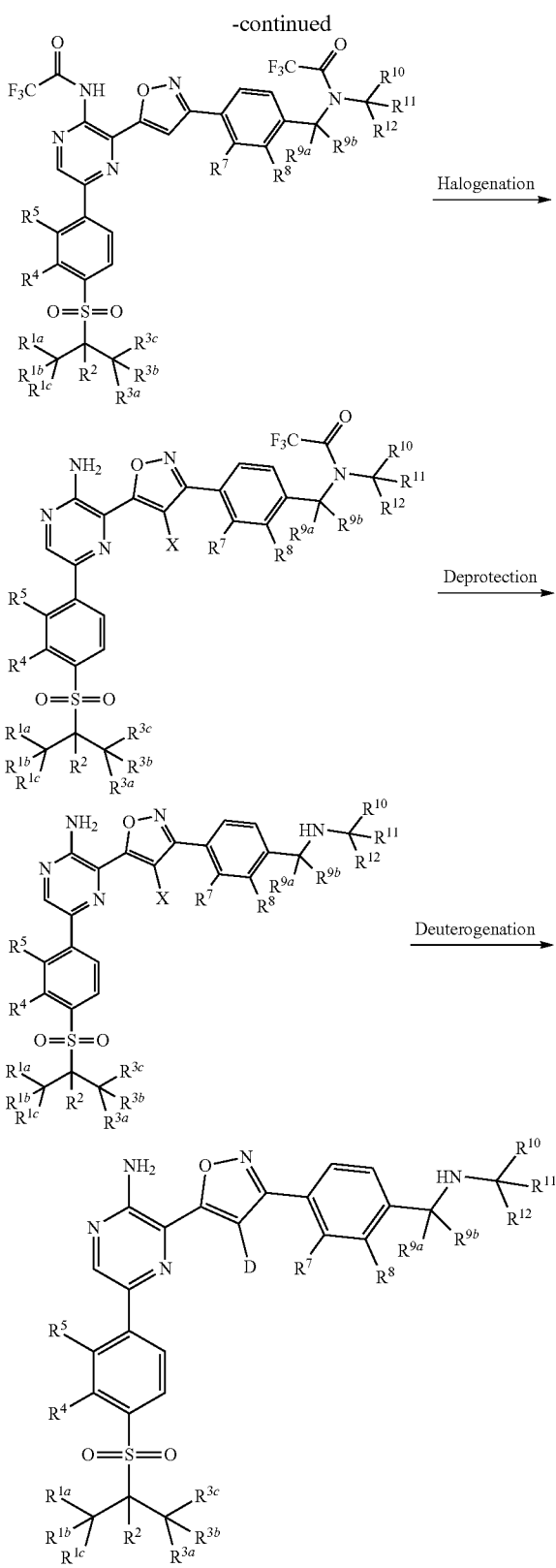

Scheme Q shows a general synthetic method for the preparation of deuterated isoxazole derivatives. The pyrazine $NH_2$ and benzylamineamine NH can be protected under standard conditions using trifluoroacetic anhydride. Halogenation of the isoxazole ring with, for example NIS followed by removal of the trifluoroacetate protecting group under basic conditions provides the desired halogenated intermediates. The halogen can then be converted into deuterium by, for instance, metal catalyzed halogen-deuterium exchange using a suitable metal catalyst, such as Pd on C under an atmosphere of deuterium gas.

Abbreviations

The following abbreviations are used:

| | |
|---|---|
| ATP | adenosine triphosphate |
| Boc | tert-butyl carbamate |
| Cbz | Carboxybenzyl |
| DCM | dichloromethane |
| DMSO | dimethyl sulfoxide |
| $Et_3N$ | triethylamine |
| 2-MeTHF | 2-methyltetrahydrofuran |
| NMM | N-Methyl morpholine |
| DMAP | 4-Dimethylaminopyridine |
| TMS | Trimethylsilyl |
| MTBE | methyl tertbutyl ether |
| EtOAc | ethyl acetate |
| i-PrOAc | isopropyl acetate |
| IPAC | isopropyl acetate |
| DMF | dimethylformamide |
| DIEA | diisopropylethylamine |
| TEA | triethylamine |
| t-BuONa | sodium tertbutoxide |
| $K_2CO_3$ | potassium carbonate |
| PG | Protecting group |
| pTSA | para-toluenesulfonic acid |
| TBAF | Tetra-n-butylammonium fluoride |
| $^1$HNMR | proton nuclear magnetic resonance |
| HPLC | high performance liquid chromatography |
| LCMS | liquid chromatography-mass spectrometry |
| TLC | thin layer chromatography |
| $R_t$ | retention time |

SCHEMES AND EXAMPLES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). The following generic schemes and examples illustrate how to prepare the compounds of the present disclosure. The examples are for the purpose of illustration only and are not to be construed as limiting the scope of the invention in any way. $^1$H-NMR spectra were recorded at 400 MHz using a Bruker DPX 400 instrument. Mass spec. samples were analyzed on a Micro-Mass Quattro Micro mass spectrometer operated in single MS mode with electrospray ionization.

Example 1: Synthesis of 2-(4-(5-amino-6-(3-(4-((tetrahydro-2H-pyran-4-ylamino)methyl)phenyl) isoxazol-5-yl)pyrazin-2-yl)pyridin-2-yl)-2-methyl-propanenitrile (Compound I-1)

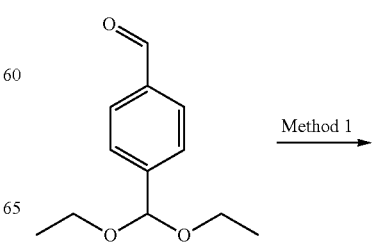

Method 1

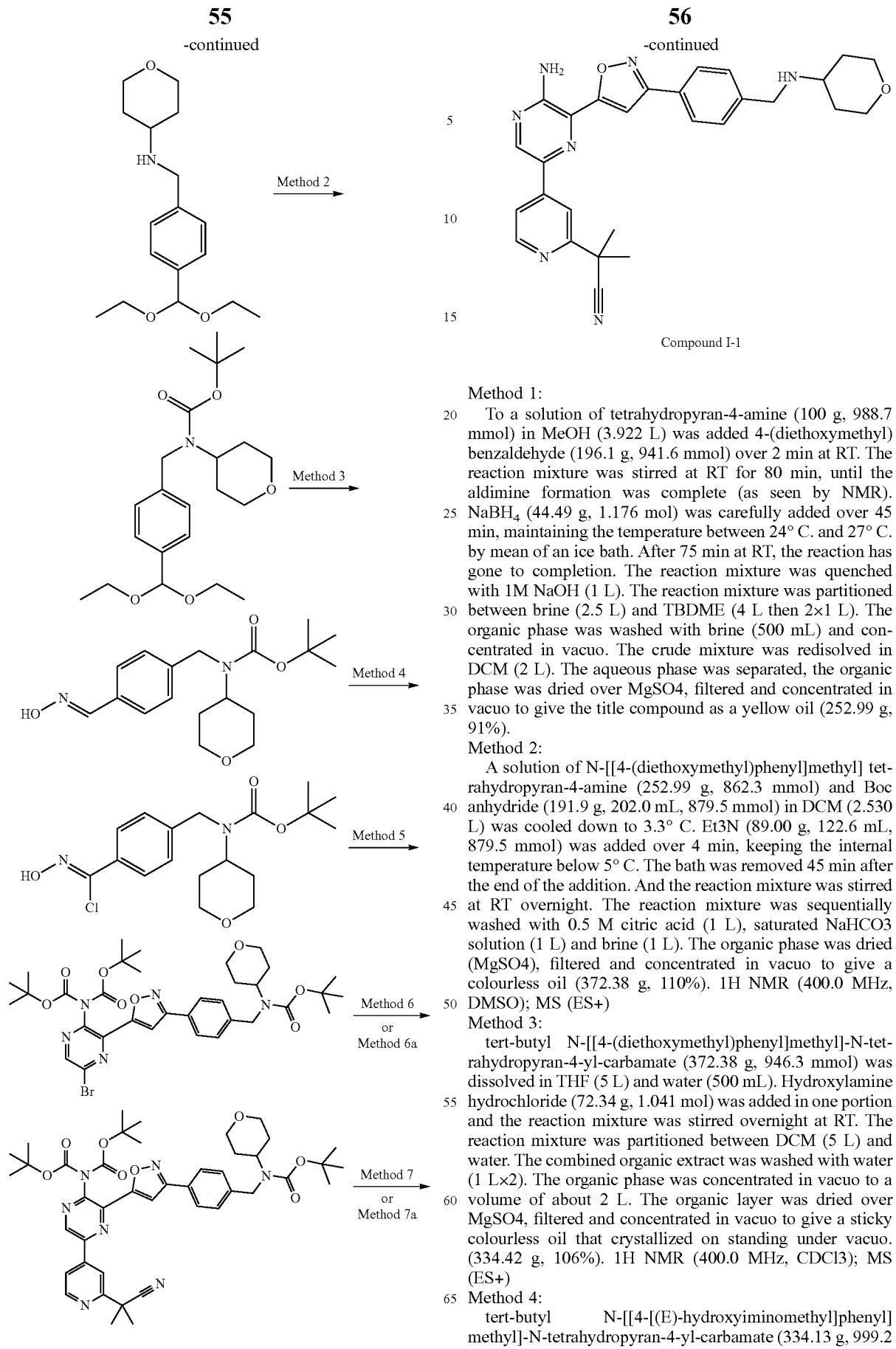

Compound I-1

Method 1:
To a solution of tetrahydropyran-4-amine (100 g, 988.7 mmol) in MeOH (3.922 L) was added 4-(diethoxymethyl)benzaldehyde (196.1 g, 941.6 mmol) over 2 min at RT. The reaction mixture was stirred at RT for 80 min, until the aldimine formation was complete (as seen by NMR). NaBH$_4$ (44.49 g, 1.176 mol) was carefully added over 45 min, maintaining the temperature between 24° C. and 27° C. by mean of an ice bath. After 75 min at RT, the reaction has gone to completion. The reaction mixture was quenched with 1M NaOH (1 L). The reaction mixture was partitioned between brine (2.5 L) and TBDME (4 L then 2×1 L). The organic phase was washed with brine (500 mL) and concentrated in vacuo. The crude mixture was redissolved in DCM (2 L). The aqueous phase was separated, the organic phase was dried over MgSO4, filtered and concentrated in vacuo to give the title compound as a yellow oil (252.99 g, 91%).

Method 2:
A solution of N-[[4-(diethoxymethyl)phenyl]methyl] tetrahydropyran-4-amine (252.99 g, 862.3 mmol) and Boc anhydride (191.9 g, 202.0 mL, 879.5 mmol) in DCM (2.530 L) was cooled down to 3.3° C. Et3N (89.00 g, 122.6 mL, 879.5 mmol) was added over 4 min, keeping the internal temperature below 5° C. The bath was removed 45 min after the end of the addition. And the reaction mixture was stirred at RT overnight. The reaction mixture was sequentially washed with 0.5 M citric acid (1 L), saturated NaHCO3 solution (1 L) and brine (1 L). The organic phase was dried (MgSO4), filtered and concentrated in vacuo to give a colourless oil (372.38 g, 110%). 1H NMR (400.0 MHz, DMSO); MS (ES+)

Method 3:
tert-butyl N-[[4-(diethoxymethyl)phenyl]methyl]-N-tetrahydropyran-4-yl-carbamate (372.38 g, 946.3 mmol) was dissolved in THF (5 L) and water (500 mL). Hydroxylamine hydrochloride (72.34 g, 1.041 mol) was added in one portion and the reaction mixture was stirred overnight at RT. The reaction mixture was partitioned between DCM (5 L) and water. The combined organic extract was washed with water (1 L×2). The organic phase was concentrated in vacuo to a volume of about 2 L. The organic layer was dried over MgSO4, filtered and concentrated in vacuo to give a sticky colourless oil that crystallized on standing under vacuo. (334.42 g, 106%). 1H NMR (400.0 MHz, CDCl3); MS (ES+)

Method 4:
tert-butyl N-[[4-[(E)-hydroxyiminomethyl]phenyl]methyl]-N-tetrahydropyran-4-yl-carbamate (334.13 g, 999.2 mmol) was dissolved in isopropyl acetate (3.0 L) (the mixture was warmed to 40° C. to allow all the solids to go into solution). N-chlorosuccinimide (140.1 g, 1.049 mol) was added portionwise over 5 min and the reaction mixture was heated to 55° C. (external block temperature). After 45 min at 55° C. The reaction had gone to completion. The reaction mixture was cooled down to RT. The solids were filtered off and rinsed with Isopropyl acetate (1 L). Combined organic extract was sequentially washed with water (1.5 L, 5 times) and brine, dried over MgSO4, filtered and concentrated in vacuo to give a viscous yellow oil (355.9 g; 96%). 1H NMR (400.0 MHz, CDCl3); MS (ES+)

Method 5:

Et₃N (76.97 g, 106.0 mL, 760.6 mmol) was added over 20 minutes to a solution of tert-butyl N-(5-bromo-3-ethynyl-pyrazin-2-yl)-N-tert-butoxycarbonyl-carbamate (233.0 g, 585.1 mmol) and tert-butyl N-[[4-[(Z)—C-chloro-N-hydroxy-carbonimidoyl]phenyl]methyl]-N-tetrahydropyran-4-yl-carbamate (269.8 g, 731.4 mmol) in DCM (2.330 L) at RT. During addition of triethylamine, the exotherm was stabilised by cooling the mixture in an ice bath, then the reaction mixture was gradually warmed up to RT and the mixture was stirred at RT overnight. The reaction mixture was sequentially washed with water (1.5 L, 3 times) and brine. The organic extract was dried over MgSO4, filtered and partially concentrated in vacuo. Heptane (1.5 L) was added and the concentration was continued yielding 547.63 g of a yellow-orange solid.

542.12 g was taken up into ~2 vol (1 L) of ethyl acetate. The mixture was heated to 74-75° C. internally and stirred until all the solid went into solution. Heptane (3.2 L) was added slowly via addition funnel to the hot solution keeping the internal temperature between 71° C. and 72° C. At the end of the addition, the dark brown solution was seeded with some recrystallised product, and the reaction mixture was allowed to cool down to RT without any stirring to crystallise O/N. The solid was filtered off and rinsed with heptane (2×250 mL), then dried in vacuo to yield 307.38 g of the title product (72%). %). 1H NMR (400.0 MHz, CDCl3); MS (ES+)

Method 6:

tert-butyl N-[[4-[5-[3-[bis(tert-butoxycarbonyl)amino]-6-bromo-pyrazin-2-yl]isoxazol-3-yl]phenyl]methyl]-N-tetrahydropyran-4-yl-carbamate (303 g, 414.7 mmol) and 2-methyl-2-[4-(4,4,5,5-tetramethyl-1,3,2-dioxaborolan-2-yl)-2-pyridyl] propanenitrile (112.9 g, 414.7 mmol) were suspended in MeCN (2 L) and H₂O (1 L). Na₂CO₃ (414.7 mL of 2 M, 829.4 mmol) followed by Pd[P(tBu)3]2 (21.19 g, 41.47 mmol) were added and the reaction mixture was degassed with N2 for 1 h. The reaction mixture was placed under a nitrogen atmosphere and heated at 70° C. (block temperature) for 4 h (internal temperature fluctuated between 60° C. and 61° C.). The reaction was cooled down to room temperature and stirred at RT overnight. The reaction mixture was partitioned between EtOAc (2 L) and water (500 mL). The combined organic extract was washed with brine (500 mL), filtered through a short pad of celite and concentrated under reduced pressure to a volume of about 3 L. The solution was dried over MgSO4, filtered and partially concentrated in vacuo. iPrOH (1.5 L) was added and the solvent was removed in vacuo to yield the desired product as a light brown foam (405 g).

400 g was taken up into ~5 vol (2 L) of iPrOH and the mixture was heated to 80° C. until all the solid went into solution. The dark brown solution was seeded, and the reaction mixture was allowed to slowly cool down to RT overnight. The solid was filtered off and rinsed with iPrOH (2×250 mL) and Petroleum ether (2×200 mL). The resulting solid was slurried in petroleum ether (2.5 L), filtered off and dried in vacuo. The resulting solid was dissolved in DCM (2.5 L) and stirred slowly for 1 h with 30 g of SPM32 (3-mercaptopropyl ethyl sulfide silica). The silica was filtered through a pad of florisil and rinsed with DCM. The procedure was repeated twice, then the DCM solution was concentrated in vacuo to give 238.02 g of a light yellow solid.

Method 7:

tert-butyl N-[[4-[5-[3-[bis(tert-butoxycarbonyl)amino]-6-[2-(1-cyano-1-methyl-ethyl)-4-pyridyl]pyrazin-2-yl] isoxazol-3-yl]phenyl]methyl]-N-tetrahydropyran-4-yl-carbamate (238 g, 299.0 mmol) was dissolved in DCM (2.380 L). TFA (500 mL, 6.490 mol) was added at RT over 3 min. The reaction mixture was stirred at RT for 3.5 h. The reaction mixture was concentrated under reduced pressure then azeotroped with heptane (2×300 ml). The oil was then slurried in abs. EtOH (2.5 L) and filtered. The solid was dissolved in a mixture of ethanol (1.190 L) and water (1.190 L). potassium carbonate (124.0 g, 897.0 mmol) in water (357.0 mL) was added to the solution and the mixture was stirred at RT overnight.

The solid was filtered off, was washed with water (2.5 L), and dried at 50° C. in vacuo to give 108.82 g of the title compound (Compound I-1) as a yellow powder. (73%)

Methods 6a and 7a

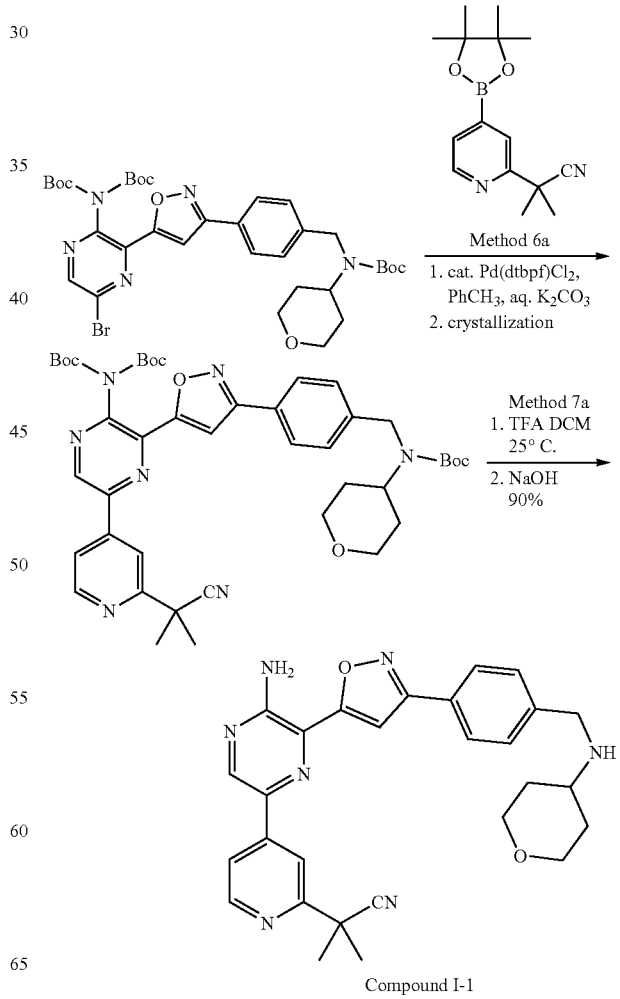

Compound I-1

A mixture of tert-butyl N-[[4-[5-[3-[bis(tert-butoxycarbonyl)amino]-6-bromo-pyrazin-2-yl] isoxazol-3-yl]phenyl]methyl]-N-tetrahydropyran-4-yl-carbamate (110.0 g, 151 mmol), K$_2$CO$_3$ (41.6 g, 301 mmol), and 2-methyl-2-[4-(4,4,5,5-tetramethyl-1,3,2-dioxaborolan-2-yl)-2-pyridyl] propanenitrile (41.0 g, 151 mmol) in toluene (770 mL) and water (220 mL) is stirred and degassed with N$_2$ for 30 min. at 20° C. The catalyst Pd(dtbpf)Cl$_2$ (1.96 g, 3.01 mmol) is added and the mixture is degassed for an additional 10 min. The mixture is heated at 70° C. until the reaction is complete. The mixture is cooled to ambient temperature, diluted with water (220 mL), and filtered through a bed of Celite. The organic phase is concentrated to remove most of the solvent. The concentrate is diluted with i-PrOH (550 mL). The resultant suspension is stirred for at least 1 h and then the solid is collected by filtration to afford a tan powder. The solid is dissolved in toluene (990 mL) and stirred with Biotage MP-TMT resin (18.6 g) for 2 h at ambient temperature. The resin is removed by filtration. The filtrate is concentrated then diluted with i-PrOH (550 mL) and then re-concentrated. Add i-PrOH (550 mL) and stir for 1 h at ambient temperature. Cool the suspension to 5° C. and collect the solid by filtration then dry to afford tert-butyl N-[[4-[5-[3-[bis(tert-butoxycarbonyl)amino]-6-[2-(1-cyano-1-methyl-ethyl)-4-pyridyl]pyrazin-2-yl]isoxazol-3-yl]phenyl]methyl]-N-tetrahydropyran-4-yl-carbamate (Compound I-1) (81.9 g; 68%, yield, 98.7 area % purity by HPLC) as a cream-colored powder.

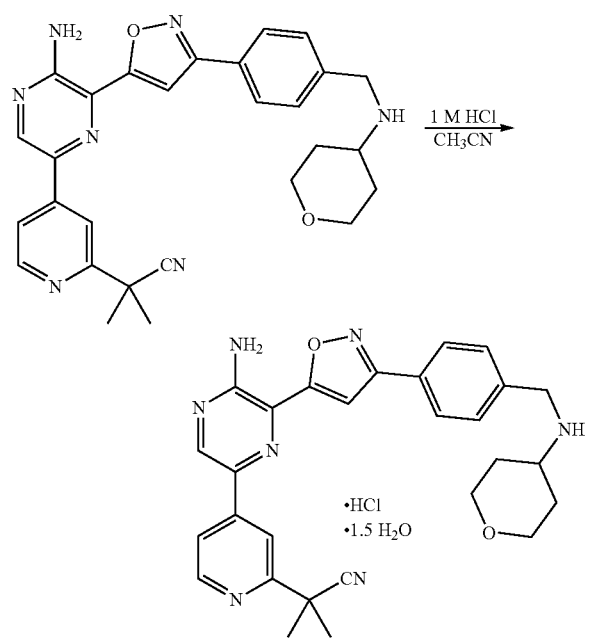

A suspension of tert-butyl N-[[4-[5-[3-[bis(tert-butoxycarbonyl)amino]-6-[2-(1-cyano-1-methyl-ethyl)-4-pyridyl]pyrazin-2-yl]isoxazol-3-yl]phenyl]methyl]-N-tetrahydropyran-4-yl-carbamate (Compound I-1) (36.0 g, 72.6 mmol) in CH$_3$CN (720 mL) is stirred at ambient temperature (20° C.) in a flask equipped with mechanical stirring. A 1 M aqueous solution of HCl (72.6 mL; 72.6 mmol) is added. The suspension is stirred at ambient temperature for 20 h. The solid is collected by filtration. The filter-cake is washed with CH$_3$CN (3×50 mL) then dried under vacuum with high humidity for 2 h to afford Compound I-1.HCl.1.5 H$_2$O (30.6 g; 74%) yield, 98.8 area % purity by HPLC) as a yellow powder. $^1$H NMR (400 MHz, DMSO) δ 9.63 (d, J=4.7 Hz, 2H), 9.05 (s, 1H), 8.69 (d, J=5.2 Hz, 1H), 8.21 (s, 1H), 8.16-8.03 (m, 3H), 7.84 (t, J=4.1 Hz, 3H), 7.34 (br s, 2H), 4.40-4.18 (m, 2H), 3.94 (dd, J=11.2, 3.9 Hz, 2H), 3.32 (t, J=11.2 Hz, 3H), 2.17-2.00 (m, 2H), 1.81 (s, 6H), 1.75 (dd, J=12.1, 4.3 Hz, 2H).

Example 2: Synthesis of 3-[3-[4-[dideuterio(methylamino)methyl]phenyl]isoxazol-5-yl]-5-(4-isopropylsulfonylphenyl)pyrazin-2-amine (Compound II-1)

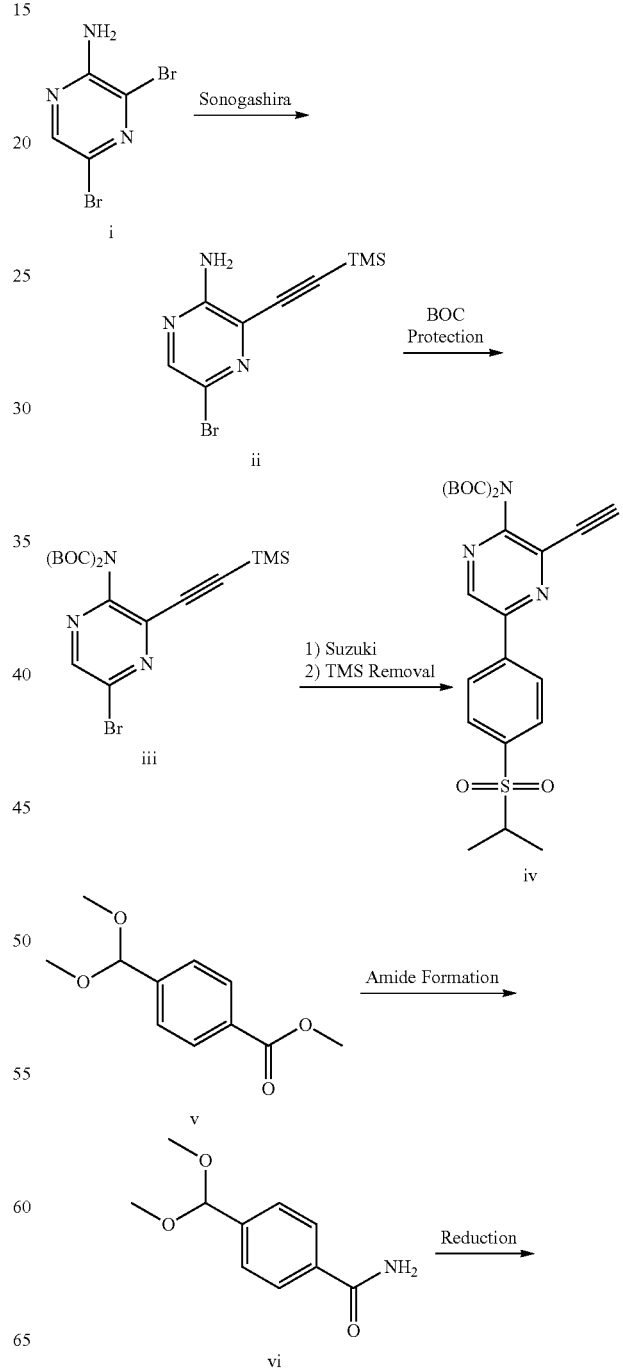

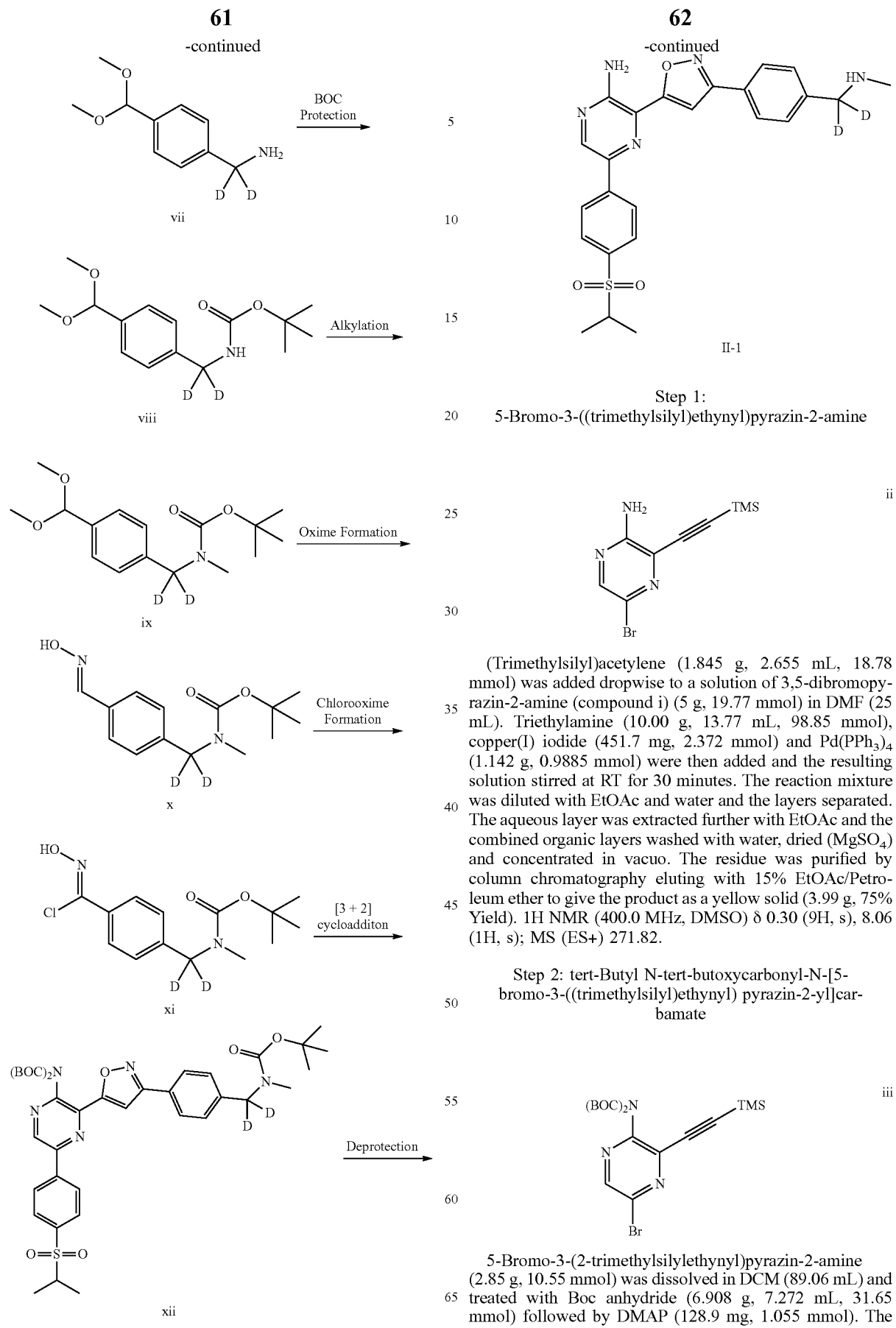

Step 1: 5-Bromo-3-((trimethylsilyl)ethynyl)pyrazin-2-amine (Trimethylsilyl)acetylene (1.845 g, 2.655 mL, 18.78 mmol) was added dropwise to a solution of 3,5-dibromopyrazin-2-amine (compound i) (5 g, 19.77 mmol) in DMF (25 mL). Triethylamine (10.00 g, 13.77 mL, 98.85 mmol), copper(I) iodide (451.7 mg, 2.372 mmol) and Pd(PPh$_3$)$_4$ (1.142 g, 0.9885 mmol) were then added and the resulting solution stirred at RT for 30 minutes. The reaction mixture was diluted with EtOAc and water and the layers separated. The aqueous layer was extracted further with EtOAc and the combined organic layers washed with water, dried (MgSO$_4$) and concentrated in vacuo. The residue was purified by column chromatography eluting with 15% EtOAc/Petroleum ether to give the product as a yellow solid (3.99 g, 75% Yield). 1H NMR (400.0 MHz, DMSO) δ 0.30 (9H, s), 8.06 (1H, s); MS (ES+) 271.82.

Step 2: tert-Butyl N-tert-butoxycarbonyl-N-[5-bromo-3-((trimethylsilyl)ethynyl) pyrazin-2-yl]carbamate 5-Bromo-3-(2-trimethylsilylethynyl)pyrazin-2-amine (2.85 g, 10.55 mmol) was dissolved in DCM (89.06 mL) and treated with Boc anhydride (6.908 g, 7.272 mL, 31.65 mmol) followed by DMAP (128.9 mg, 1.055 mmol). The reaction was allowed to stir at ambient temperature for 2 hours. The mixture was then diluted with DCM and NaHCO₃ and the layers separated. The aqueous layer was extracted further with DCM, dried (MgSO₄), filtered and concentrated in vacuo. The resultant residue was purified by column chromatography eluting with dichloromethane to give the desired product as a colourless oil (4.95 g, 99% Yield). 1H NMR (400.0 MHz, DMSO) δ 0.27 (9H, s), 1.42 (18H, s), 8.50 (1H, s); MS (ES+) 472.09.

Step 3: tert-Butyl N-(3-ethynyl-5-(4-(isopropylsul-fonyl)phenyl)pyrazin-2-yl)N-tertbutoxycarbonyl-carbamate tert-butyl

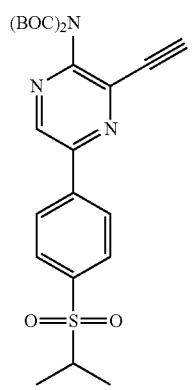

N-[5-Bromo-3-(2-trimethylsilylethynyl)pyrazin-2-yl]-N-tertbutoxycarbonylcarbamate (3 g, 6.377 mmol) and (4-isopropylsulfonylphenyl)boronic acid (1.491 g, 6.536 mmol) were dissolved in MeCN/water (60/12 mL). K₃PO₄ (2.706 g, 12.75 mmol) was added and the reaction mixture was degassed with a flow of nitrogen (5 cycles). Pd[P(tBu)₃]₂ (162.9 mg, 0.3188 mmol) was added and the resulting mixture was stirred at room temperature for 1 h. The reaction mixture was poured quickly into a mixture of ethyl acetate (500 mL), water (90 mL) and 1% aqueous sodium metabisulphite at 4° C., shaken well and the layer separated. The organic fraction was dried over MgSO4, filtered and the filtrate was treated with 3-mercaptopropyl ethyl sulphide on silica (0.8 mmol/g, 1 g), pre-absorbed onto silica gel then purified by column chromatography on silica gel eluting with 30-40% EtOAc/petroleum ether. The solvents were concentrated in vacuo to leave the product as a yellow viscous oil that was triturated with petroleum ether to yield the product as beige crystals (1.95 g, 61% Yield); 1H NMR (400 MHz, DMSO) δ 1.20 (m, 6H), 1.39 (s, 18H), 3.50 (m, 1H), 5.01 (s, 1H), 8.03 (m, 2H), 8.46 (m, 2H) and 9.37 (s, 1H).

Step 4: 4-(Dimethoxymethyl)benzamide

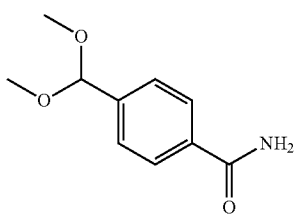

A mixture of methyl 4-(dimethoxymethyl)benzoate (3.8 g, 18.08 mmol) and 7M NH₃ in MeOH (30 mL of 7 M, 210.0 mmol) in a sealed tube was heated at 110° C. for 22 hours. A further portion of 7M NH₃ in MeOH (20 mL of 7 M, 140.0 mmol) was added and the reaction heated at 135° C. for 23 hours. The reaction was cooled to ambient temperature and the solvent removed in vacuo. The residue was re-submitted to the reaction conditions (7M NH₃ in MeOH (30 mL of 7 M, 210.0 mmol) at 115° C.) for a further 16 hours. The solvent was removed in vacuo and the residue trituated from Et₂O. The resultant precipitate was isolated by filtration to give the sub-title compound as a white solid (590 mg, 17% yield). The filtrate was purified by column chromatography (ISCO Companion, 40 g column, eluting with 0 to 100% EtOAc/Petroleum Ether to 10% MeOH/EtOAc, loaded in EtOAc/MeOH) to give a further portion of the sub-title product as a white solid (225 mg, 6% Yield). Total isolated (815 mg, 23% Yield); 1H NMR (400 MHz, DMSO) δ 3.26 (s, 6H), 5.44 (s, 1H), 7.37 (s, 1H), 7.46 (d, J=8.0 Hz, 2H), 7.84-7.91 (m, 2H) and 7.98 (s, 1H) ppm; MS (ES+) 196.0.

Step 5: Dideuterio-[4-(dimethoxymethyl)phenyl] methanamine

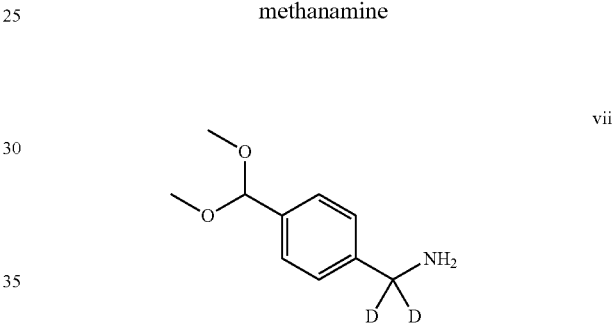

LiDH₄ (12.52 mL of 1 M, 12.52 mmol) was added dropwise to a stirred solution of 4-(dimethoxymethyl)benzamide (815 mg, 4.175 mmol) in THF (20 mL) at 0° C. under an atmosphere of nitrogen. The reaction was heated at reflux for 16 hours then cooled to ambient temperature. The reaction was quenched by the sequential addition of D₂O (1 mL), 15% NaOH in D₂O (1 mL) and D₂O (4 mL). The resultant solid was removed by filtration and washed with EtOAc. The filtrate was concentrated in vacuo and the residue dried by azeotropic distillation with toluene (×3) to give the sub-title compound as a yellow oil (819 mg) that was used without further purification; 1H NMR (400 MHz, DMSO) δ 3.23 (s, 6H), 5.36 (s, 1H) and 7.30-7.35 (m, 4H) ppm; MS (ES+) 167.0.

Step 6: tert-Butyl N-[dideuterio-[4-(dimethoxymethyl)phenyl]methyl]carbamate

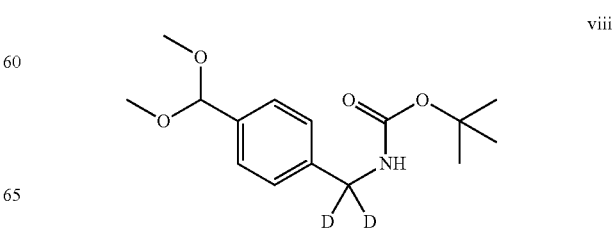

Et₃N (633.7 mg, 872.9 µL, 6.262 mmol) was added to a stirred suspension of dideuterio-[4-(dimethoxymethyl)phenyl]methanamine (765 mg, 4.175 mmol) in THF (15 mL) at 0° C. The reaction was allowed to stir at this temperature for 30 minutes then Boc₂O (956.8 mg, 1.007 mL, 4.384 mmol) was added in portions. The reaction was allowed to warm to ambient temperature and stirred for 18 hours. The solvent was removed in vacuo and the residue was purified by column chromatography (ISCO Companion, 120 g column, eluting with 0 to 50% EtOAc/Petroleum Ether, loaded in DCM) to give the sub-title product as a colourless oil (1.04 g, 88% Yield); 1H NMR (400 MHz, DMSO) δ 1.40 (s, 9H), 3.23 (s, 6H), 5.36 (s, 1H), 7.24 (d, J=8.2 Hz, 2H), 7.33 (d, J=8.0 Hz, 2H) and 7.38 (s, 1H) ppm.

Step 7: tert-Butyl N-[dideuterio-[4-(dimethoxymethyl)phenyl]methyl]-N-methyl-carbamate

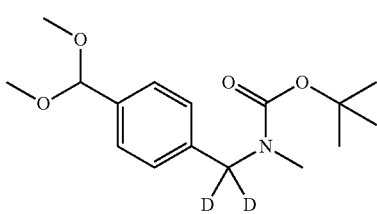

ix

LiHMDS (1M in THF) (1.377 mL of 1 M, 1.377 mmol) was added dropwise to a stirred solution of tert-butyl N-[dideuterio-[4-(dimethoxymethyl)phenyl]methyl]carbamate (300 mg, 1.059 mmol) in THF (5 mL) at −78° C. The solution was stirred at this temperature for 10 minutes then iodomethane (225.4 mg, 98.86 µL, 1.588 mmol) was added dropwise and the mixture allowed to warm to ambient temperature over 1 hour. The reaction was again cooled to −78° C. and LiHMDS (1M in THF) (635.4 µL of 1 M, 0.6354 mmol) was added. After 10 minutes iodomethane (105.2 mg, 46.14 µL, 0.7413 mmol) was added and the reaction allowed to warm to ambient temperature over 6 hours. The mixture was diluted with EtOAc and the organic layer washed with saturated aqueous NaHCO₃ (×2), brine (×1), dried (MgSO4) filtered and concentrated in vacuo. The residue was purified by column chromatography (ISCO Companion, 24 g column, eluting with 0 to 30% EtOAc/Petroleum Ether, loaded in DCM) to give the sub-title product as a colourless oil (200 mg, 63% Yield); 1H NMR (400 MHz, DMSO) δ 1.41 (d, J=27.7 Hz, 9H), 2.76 (s, 3H), 3.24 (s, 6H), 5.37 (s, 1H), 7.23 (d, J=7.9 Hz, 2H) and 7.37 (d, J=8.0 Hz, 2H) ppm.

Step 8: tert-Butyl N-[dideuterio-[4-[hydroxyiminomethyl]phenyl]methyl]-N-(methyl)carbamate

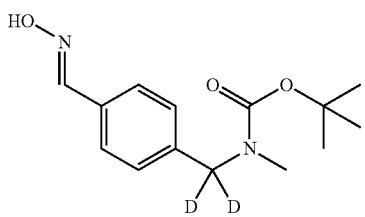

x

Hydroxylamine hydrochloride (51.15 mg, 0.7361 mmol) was added to a stirred solution of tert-butyl N-[dideuterio-[4-(dimethoxymethyl)phenyl]methyl]-N-methyl-carbamate (199 mg, 0.6692 mmol) in THF (10 mL)/water (1.000 mL) and the reaction allowed to stir at ambient temperature for 4 hours. The reaction was partitioned between DCM and brine and the layers separated. The aqueous layer was extracted with DCM (×2) and the combined organic extracts washed with brine (×1), dried (MgSO4), filtered and concentrated in vacuo to give the sub-title compound as a white solid (180 mg, 100% Yield); 1H NMR (400 MHz, DMSO) δ 1.41 (d, J=24.6 Hz, 9H) 2.76 (s, 3H), 7.25 (d, J=8.1 Hz, 2H), 7.58 (d, J=8.0 Hz, 2H), 8.13 (s, 1H) and 11.20 (s, 1H) ppm; MS (ES+) 211.0 (M-Boc).

Step 9: tert-Butyl N-[[4-[chloro-N-hydroxy-carbonimidoyl]phenyl]-dideuterio-methyl]-N-methyl-carbamate

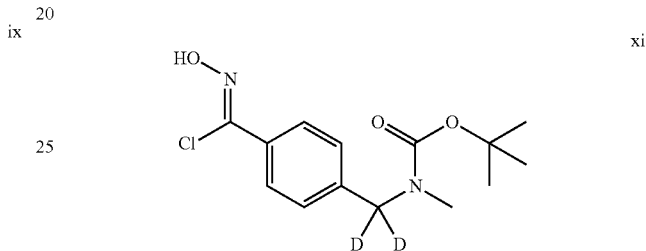

xi tert-Butyl N-[dideuterio-[4-[hydroxyiminomethyl]phenyl]methyl]-N-(methyl)carbamate (178 mg, 0.6683 mmol) in DMF (2 mL) was treated with NCS (89.24 mg, 0.6683 mmol) and the reaction warmed to 65° C. for 1 hour. The reaction was cooled to ambient temperature and diluted with water. The mixture was extracted with EtOAc (×2) and the combined organic extracts washed with brine (×4), dried (MgSO₄), filtered and concentrated in vacuo to give the sub-title compound as a white solid (188 mg, 94% Yield); 1H NMR (400 MHz, DMSO) δ 1.42 (d, J=24.7 Hz, 9H), 2.78 (s, 3H), 7.32 (d, J=8.4 Hz, 2H), 7.78 (d, J=8.2 Hz, 2H) and 12.36 (s, 1H) ppm.

Step 10: tert-Butyl N-[[4-[5-[3-[bis(tert-butoxycarbonyl)amino]-6-(4-isopropylsulfonylphenyl)pyrazin-2-yl]isoxazol-3-yl]phenyl]-dideuterio-methyl]-N-methyl-carbamate

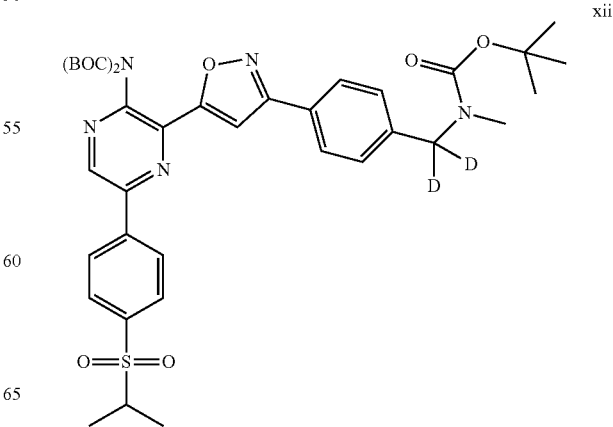

xii

Et₃N (36.31 mg, 50.01 μL, 0.3588 mmol) was added dropwise to a stirred solution of tert-butyl N-tert-butoxycarbonyl-N-[3-ethynyl-5-(4-isopropylsulfonylphenyl)pyrazin-2-yl]carbamate (150 mg, 0.2990 mmol) and tert-Butyl N-[[4-[chloro-N-hydroxy-carbonimidoyl]phenyl]-dideuterio-methyl]-N-methyl-carbamate (89.93 mg, 0.2990 mmol) in anhydrous THF (3 mL) and the reaction mixture heated at 65° C. for 3 hours. The reaction mixture was cooled to ambient temperature and diluted with EtOAc/brine. Water was added until the aqueous layer became clear and the layers were separated. The aqueous layer was extracted with EtOAc (×1) and the combined organic extracts were washed with brine (×1), dried (MgSO₄), filtered and concentrated in vacuo. The residue was purified by column chromatography (ISCO Companion, 40 g column, eluting with 0 to 30% EtOAc/Petroleum Ether, loaded in DCM) to give the subtitle product as a white solid (134 mg, 59% Yield); 1H NMR (400 MHz, DMSO) δ 1.22 (d, J=6.8 Hz, 6H) 1.32 (s, 18H), 1.43 (d, J=23.1 Hz, 9H), 2.82 (s, 3H), 3.56 (pent, 1H), 7.43 (d, J=8.3 Hz, 3H), 8.02-8.03 (m 3H), 8.06-8.11 (m, 2H), 8.62-8.67 (m, 2H) and 9.51 (s, 1H) ppm; MS (ES+) 666.2 (M-Boc).

Step 11: 3-[3-[4-[Dideuterio(methylamino)methyl]phenyl]isoxazol-5-yl]-5-(4-isopropylsulfonylphenyl)pyrazin-2-amine (compound II-1)

3M HCl in MeOH (1.167 mL of 3 M, 3.500 mmol) was added to a stirred solution of tert-butyl N-[[4-[5-[3-[bis(tert-butoxycarbonyl)amino]-6-(4-isopropylsulfonylphenyl)pyrazin-2-yl]isoxazol-3-yl]phenyl]-dideuterio-methyl]-N-methyl-carbamate (134 mg, 0.1750 mmol) in DCM (5 mL) and the reaction heated at reflux for 16 hours. The reaction was cooled to ambient temperature and the resultant precipitate was isolated by filtration and dried under vacuum at 40° C. to give the di-HCl salt of the title compound as a yellow solid (58.8 mg, 62% Yield); 1H NMR (400 MHz, DMSO) δ 1.20 (d, J=6.8 Hz, 6H), 2.60 (t, J=5.4 Hz, 3H), 3.48 (hept, J=6.8 Hz, 1H), 7.22 (br s, 2H), 7.69-7.75 (m, 2H), 7.85 (s, 1H), 7.92-7.99 (m, 2H), 8.08-8.15 (m, 2H), 8.37-8.42 (m, 2H), 8.97 (s, 1H) and 9.10 (d, J=5.8 Hz, 2H) ppm; MS (ES+) 466.2.

Example 3: Synthesis of 3-[3-[4-[dideuterio-(trideuteriomethylamino)methyl]phenyl]isoxazol-5-yl]-5-(4-isopropylsulfonylphenyl)pyrazin-2-amine (Compound II-2)

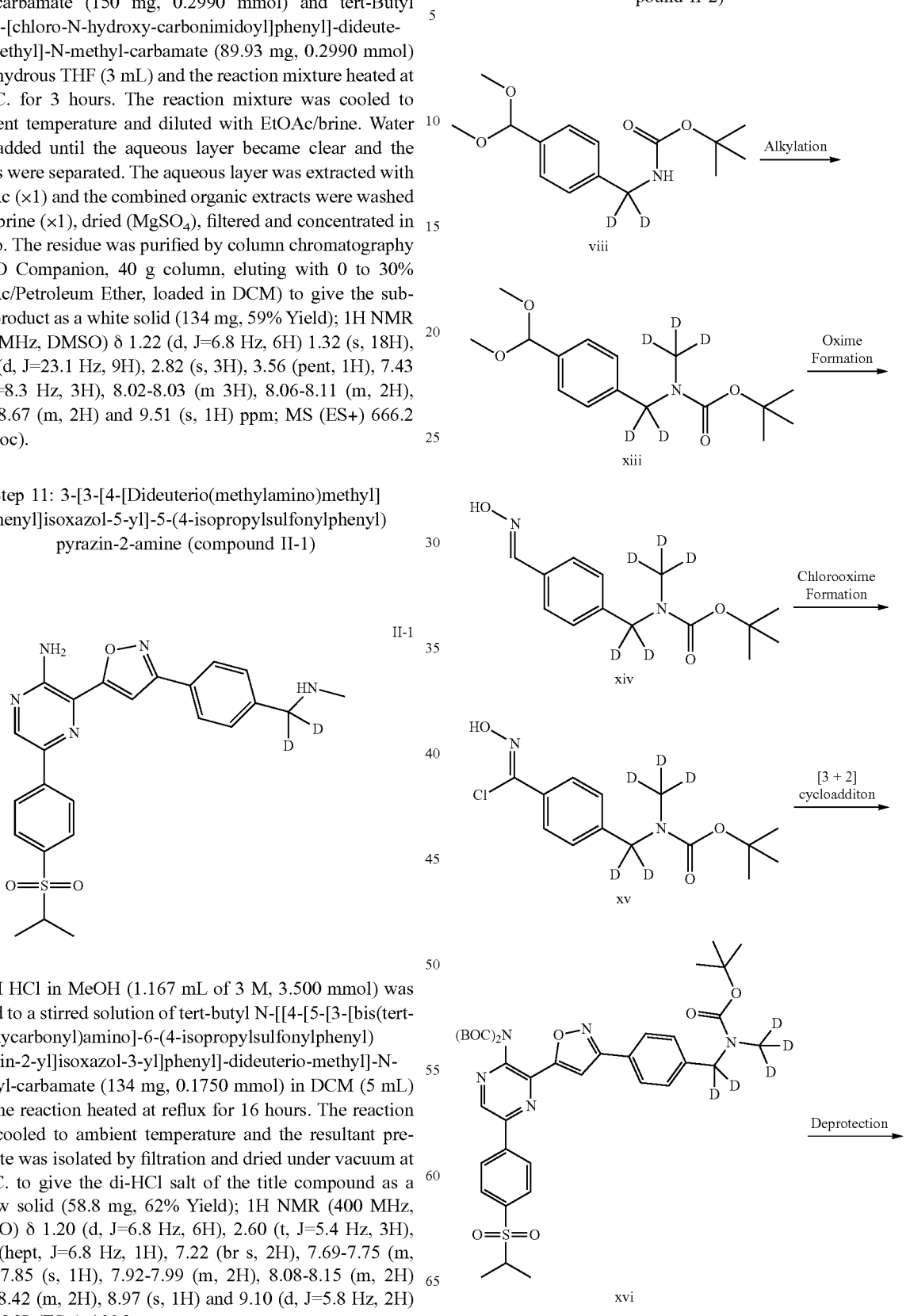

-continued

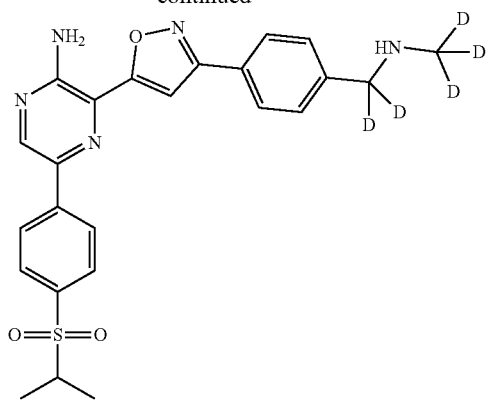

II-2

Step 1: tert-Butyl N-[dideuterio-[4-(dimethoxymethyl)phenyl]methyl]-1-(trideuteriomethyl)carbamate

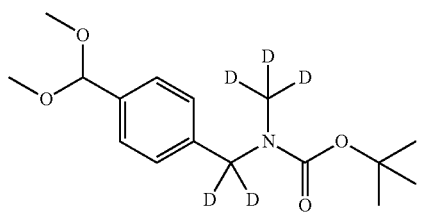

xiii

LiHMDS (1M in THF) (1.181 mL of 1 M, 1.181 mmol) was added dropwise to a sittred solution of tert-butyl N-[dideuterio-[4-(dimethoxymethyl)phenyl]methyl]carbamate (300 mg, 1.059 mmol) in THF (5 mL) at −78° C. The solution was stirred at this temperature for 30 minutes then trideuterio(iodo)methane (198.0 mg, 84.98 µL, 1.366 mmol) was added dropwise and the mixture allowed to warm to ambient temperature over 21 hours. The reaction was again cooled to −78° C. and a further portion of LiHMDS (1M in THF) (635.4 L of 1 M, 0.6354 mmol) was added. After 15 minutes more trideuterio(iodo)methane (76.75 mg, 32.94 µL, 0.5295 mmol) was added and the reaction allowed to warm to ambient temperature over 5 hours. The mixture was diluted with EtOAc and the organic layer washed with saturated aqueous NaHCO₃ (×2), brine (×1), dried (MgSO₄) filtered and concentrated in vacuo. The residue was purified by column chromatography (ISCO Companion, 24 g column, eluting with 0 to 30% EtOAc/Petroleum Ether, loaded in DCM) to give the sub-title product as a colourless oil (213 mg, 67% Yield); 1H NMR (400 MHz, DMSO) δ 1.36-1.42 (m, 9H) 3.22 (s, 6H), 5.35 (s, 1H), 7.21 (d, J=7.8 Hz, 2H) and 7.35 (d, J=7.7 Hz, 2H) ppm.

Step 2: tert-Butyl N-[dideuterio-[4-[hydroxyiminomethyl]phenyl]methyl]-N-(trideuteriomethyl)carbamate

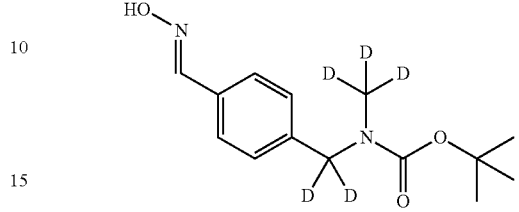

xiv

Hydroxylamine hydrochloride (53.95 mg, 0.7763 mmol) was added to a stirred solution of tert-butyl N-[dideuterio-[4-(dimethoxymethyl)phenyl]methyl]-N-(trideuteriomethyl)carbamate (212 mg, 0.7057 mmol) in THF (10 mL)/water (1.000 mL) and the reaction allowed to stir at ambient temperature for 22 hours. The reaction was partitioned between DCM and brine and the layers separated. The aqueous layer was extracted with DCM (×2) and the combined organic extracts washed with brine (×1), dried (MgSO₄), filtered and concentrated in vacuo to give the sub-title compound as a white solid (190 mg, 100% Yield).); 1H NMR (400 MHz, DMSO) δ 1.41 (d, J=24.2 Hz, 9H)), 7.25 (d, J=8.1 Hz, 2H), 7.58 (d, J=8.0 Hz, 2H), 8.13 (s, 1H) and 11.20 (s, 1H) ppm.

Step 3: tert-Butyl N-[[4-[chloro-N-hydroxy-carbonimidoyl]phenyl]-dideuterio-methyl]-N-(trideuteriomethyl)carbamate

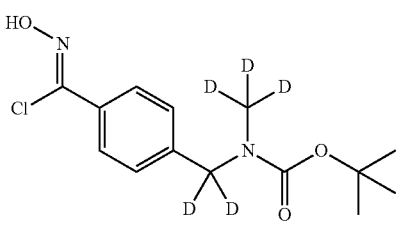

xv tert-Butyl N-[dideuterio-[4-[hydroxyiminomethyl]phenyl]methyl]-N-(trideuteriomethyl)carbamate (190.0 mg, 0.7054 mmol) in DMF (2 mL) was treated with NCS (94.19 mg, 0.7054 mmol) and the reaction warmed to 65° C. for 1 hour. The reaction was cooled to ambient temperature and diluted with water. The mixture was extracted with EtOAc (×2) and the combined organic extracts washed with brine (×4), dried (MgSO4), filtered and concentrated in vacuo to give the sub-title compound as a white solid (198 mg, 93% Yield); 1H NMR (400 MHz, DMSO) δ 1.41 (d, J=26.0 Hz, 9H), 7.32 (d, J=8.3 Hz, 2H), 7.78 (d, J=8.2 Hz, 2H) and 12.36 (s, 1H) ppm.

Step 4: tert-Butyl N-[[4-[5-[3-[bis(tert-butoxycarbonyl)amino]-6-(4-isopropylsulfonylphenyl)pyrazin-2-yl]isoxazol-3-yl]phenyl]-dideuterio-methyl]-N-(trideuteriomethyl)carbamate

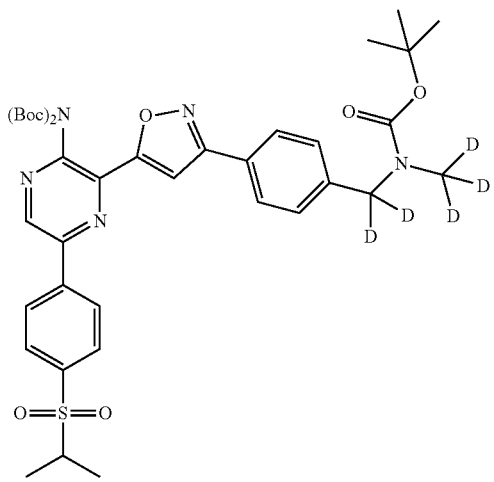

xvi

Et₃N (36.31 mg, 50.01 µL, 0.3588 mmol) was added dropwise to a stirred solution of tert-butyl N-tert-butoxycarbonyl-N-[3-ethynyl-5-(4-isopropylsulfonylphenyl)pyrazin-2-yl]carbamate (150 mg, 0.2990 mmol) and tert-butyl N-[[4-[chloro-N-hydroxy-carbonimidoyl]phenyl]-dideuteriomethyl]-N-(trideuteriomethyl)carbamate (90.84 mg, 0.2990 mmol) in anhydrous THF (3 mL) and the reaction mixture heated at 65° C. for 3.5 hours. The reaction mixture was cooled to ambient temperature and diluted with EtOAc/brine. Water was added until the aqueous layer became clear and the layers were separated. The aqueous layer was extracted with EtOAc (×1) and the combined organic extracts were washed with brine (×1), dried (MgSO4), filtered and concentrated in vacuo. The residue was purified by column chromatography (ISCO Companion, 40 g column, eluting with 0 to 35% EtOAc/Petroleum Ether, loaded in DCM) to give the sub-title product as a white solid (158 mg, 69% Yield); 1H NMR (400 MHz, DMSO) δ 1.22 (d, J=6.8 Hz, 6H)), 1.44 (d, J=22.0 Hz, 9H), 3.56 (dt, J=13.5, 6.7 Hz, 2H), 7.43 (d, J=8.2 Hz, 3H), 8.02 (d, J=6.9 Hz, 2H), 8.08 (d, J=8.7 Hz, 2H), 8.65 (d, J=8.8 Hz, 2H) and 9.51 (s, 1H) ppm; MS (ES+) 669.3 (M-Boc).

Step 5: 3-[3-[4-[dideuterio-(trideuteriomethylamino)methyl]phenyl]isoxazol-5-yl]-5-(4-isopropylsulfonylphenyl)pyrazin-2-amine (compound II-2)

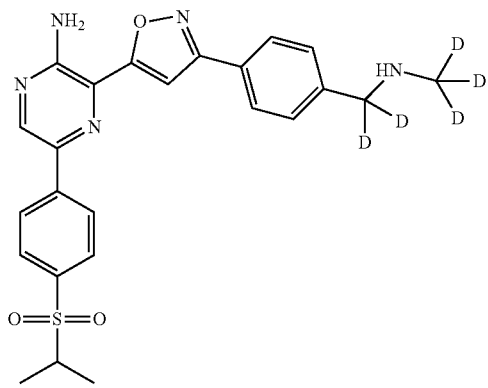

II-2

3M HCl in MeOH (1.361 mL of 3 M, 4.084 mmol) was added to a stirred solution of tert-butyl N-[[4-[5-[3-[bis(tert-butoxycarbonyl)amino]-6-(4-isopropylsulfonylphenyl) pyrazin-2-yl]isoxazol-3-yl]phenyl]-dideuterio-methyl]-N-(trideuteriomethyl)carbamate (157 mg, 0.2042 mmol) in DCM (5 mL) and the reaction heated at reflux for 16 hours. The reaction was cooled to ambient temperature and the resultant precipitate was isolated by filtration and dried under vacuum at 40° C. to give the di-HCl salt of the title compound as a yellow solid (72.5 mg, 66% Yield); 1H NMR (400 MHz, DMSO) δ 1.20 (d, J=6.8 Hz, 6H), 3.48 (dq, J=13.6, 6.7 Hz, 1H), 7.21 (s, 2H), 7.68-7.78 (m, 2H), 7.85 (s, 1H), 7.91-7.99 (m, 2H), 8.08-8.13 (m, 2H), 8.36-8.42 (m, 2H), 8.96 (s, 1H) and 9.14 (s, 2H) ppm; MS (ES+) 469.1.

Example 4: Synthesis of 5-(4-isopropylsulfonylphenyl)-3-[3-[4-[(trideuteriomethylamino)methyl]phenyl]isoxazol-5-yl]pyrazin-2-amine (Compound II-3)

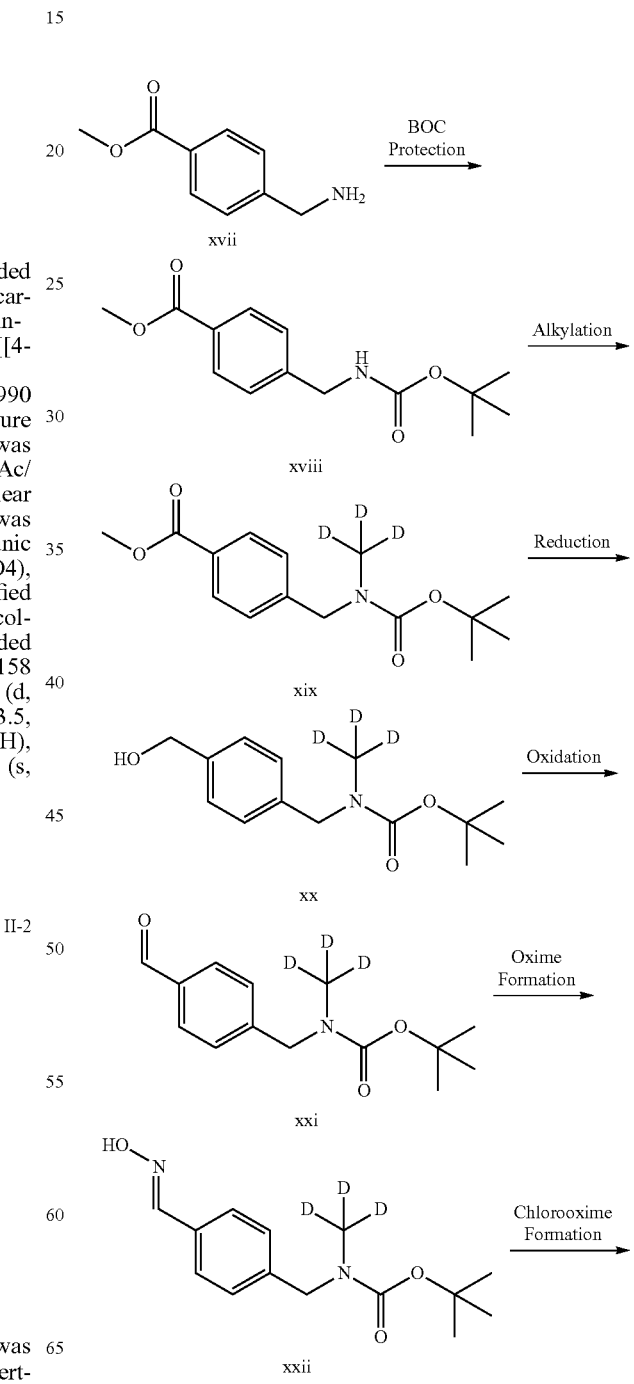

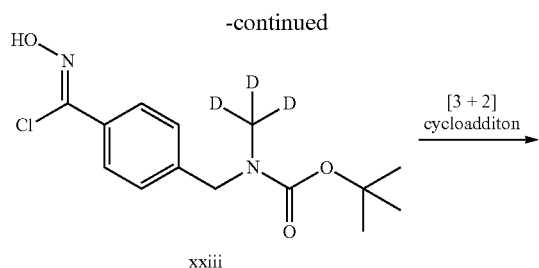

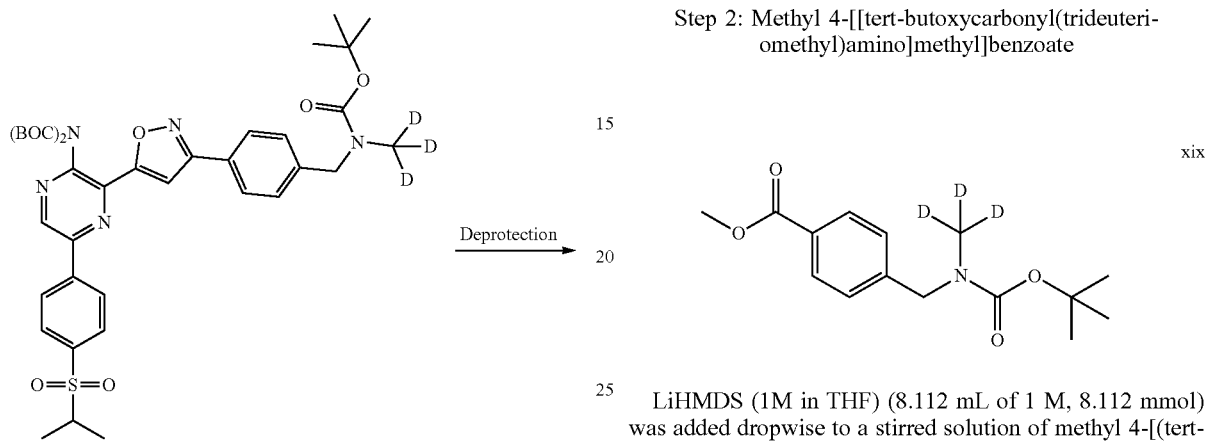

Step 1: Methyl 4-[(tert-butoxycarbonylamino)methyl]benzoate

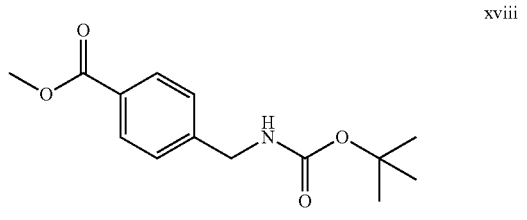 [SMILES: COC(=O)c1ccc(CNC(=O)OC(C)(C)C)cc1]

Et₃N (1.882 g, 2.592 mL, 18.60 mmol) was added to a stirred suspension of methyl 4-(aminomethyl)benzoate (Hydrochloric Acid (1)) (1.5 g, 7.439 mmol) in THF (20 mL) at 0° C. The reaction was allowed to stir at this temperature for 30 minutes then Boc₂O (1.705 g, 1.795 mL, 7.811 mmol) was added in portions. The reaction was allowed to warm to ambient temperature and stirred for 18 hours. The mixture was diluted with EtOAc. The organic layer was washed with 1M aqueous HCl (×2), saturated aqueous NaHCO₃ (×2) and brine (×1). The organic layer was dried (MgSO₄), filtered and concentrated in vacuo to give the sub-title compound as a white solid that was used without further purification (1.93 g, 98% Yield); 1H NMR (400 MHz, DMSO) δ 1.40 (s, 9H), 3.85 (s, 3H), 4.20 (d, J=6.1 Hz, 2H), 7.38 (d, J=8.2 Hz, 2H), 7.49 (t, J=6.1 Hz, 1H) and 7.92 (d, J=8.2 Hz, 2H) ppm; MS (ES+) 251.1 (M-Me).

Step 2: Methyl 4-[[tert-butoxycarbonyl(trideuteriomethyl)amino]methyl]benzoate

LiHMDS (1M in THF) (8.112 mL of 1 M, 8.112 mmol) was added dropwise to a stirred solution of methyl 4-[(tert-butoxycarbonylamino)methyl]benzoate (1.93 g, 7.275 mmol) in THF (10 mL) at −78° C. The solution was stirred at this temperature for 30 minutes then trideuterio(iodo)methane (1.360 g, 9.385 mmol) was added dropwise and the mixture allowed to warm to ambient temperature over 3 hours. The reaction was cooled to −78° C. and a further portion of LiHMDS (1M in THF) (2.182 mL of 1 M, 2.182 mmol) was added. After 10 minutes a further portion of trideuterio(iodo)methane (527.4 mg, 3.638 mmol) was added and the reaction allowed to warm to ambient temperature over 17 hours. The mixture was diluted with EtOAc and the organic layer washed with saturated aqueous NaHCO₃ (×2), brine (×1), dried (MgSO4) filtered and concentrated in vacuo. The residue was purified by column chromatography (ISCO Companion, 120 g column, eluting with 0 to 30% EtOAc/Petroleum Ether, loaded in DCM) to give the sub-title product as a pale yellow oil (1.37 g, 67% Yield); 1H NMR (400 MHz, DMSO) δ 1.38 (d, J=44.2 Hz, 9H), 3.83 (s, 3H), 4.43 (s, 2H), 7.33 (d, J=8.2 Hz, 2H) and 7.94 (d, J=8.1 Hz, 2H) ppm; MS (ES+) 268.1 (M-Me)

Step 3: tert-Butyl N-[[4-(hydroxymethyl)phenyl]methyl]-N-(trideuteriomethyl)carbamate LiBH₄ (158.5 mg, 7.278 mmol) was added to a stirred solution of methyl 4-[[tert-butoxycarbonyl(trideuteriomethyl)amino]methyl]benzoate (1.37 g, 4.852 mmol) in THF (10 mL) and the reaction warmed to 85° C. for 15 hours. A further portion of LiBH₄ (158.5 mg, 7.278 mmol) was added and the reaction stirred at 65° C. for a further 7 hours. The reaction mixture was cooled to ambient temperature then poured onto crushed ice and whilst stirring, 1M HCl was added dropwise until no effervescence was observed. The mixture was stirred for 10 minutes then saturated aqueous NaHCO₃ was added until the mixture was at pH 8. The aqueous layer was extracted with EtOAc (×3) and the combined organic extracts dried (MgSO4), filtered and concentrated in vacuo. The residue was purified by column chromatography (ISCO Companion, 120 g column, eluting with 0 to 100% EtOAc/Petroleum Ether, loaded in DCM) to give the sub-title product as a colourless oil (1.03 g, 84% Yield); 1H NMR (400 MHz, DMSO) δ 1.42 (d, J=14.6 Hz, 9H), 4.35 (s, 2H), 4.48 (d, J=5.7 Hz, 2H), 5.15 (t, J=5.7 Hz, 1H), 7.18 (d, J=7.9 Hz, 2H) and 7.30 (d, J=7.7 Hz, 2H) ppm; MS (ES+) 181.1 (M-O^tBu).

Step 4: tert-Butyl N-[(4-formylphenyl)methyl]-N-(trideuteriomethyl)carbamate

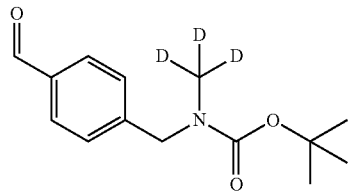

xxi

MnO₂ (5.281 g, 1.051 mL, 60.75 mmol) was added to a stirred solution of tert-butyl N-[[4-(hydroxymethyl)phenyl]methyl]-N-(trideuteriomethyl)carbamate (1.03 g, 4.050 mmol) in DCM (10 mL) and the reaction stirred at ambient temperature for 20 hours. The reaction was filtered through a pad of Celite and washed with DCM. The filtrate was concentrated in vacuo to give the sub-title compound as a colourless oil (891 mg, 88% Yield); 1H NMR (400 MHz, DMSO) δ 1.40 (d, J=43.4 Hz, 9H), 4.48 (s, 2H), 7.43 (d, J=8.0 Hz, 2H), 7.91 (d, J=7.9 Hz, 2H) and 10.00 (s, 1H), ppm.

Step 5: tert-butyl N-[[4-[hydroxyiminomethyl]phenyl]methyl]-N-(trideuteriomethyl)carbamate

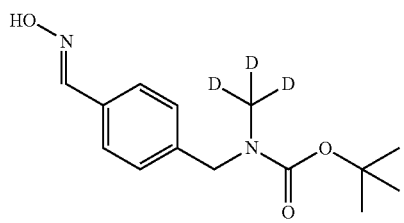

xxii

Hydroxylamine (466.0 μL of 50% w/v, 7.054 mmol) was added to a stirred solution of tert-butyl N-[(4-formylphenyl)methyl]-N-(trideuteriomethyl)carbamate (890 mg, 3.527 mmol) in ethanol (5 mL) and the reaction mixture stirred at ambient temperature for 45 minutes. The reaction mixture was concentrated in vacuo and the residue taken up in water and extracted with EtOAc (×3). The combined organic extracts were washed with brine (×1), dried (MgSO₄), filtered and concentrated in vacuo. The residue was triturated from petroleum ether and the precipitate isolated by filtration to give the sub-title product as a white solid (837 mg, 89% Yield); 1H NMR (400 MHz, DMSO) δ 1.41 (d, J=25.8 Hz, 9H), 4.38 (s, 2H), 7.24 (d, J=8.0 Hz, 2H), 7.58 (d, J=8.0 Hz, 2H), 8.13 (s, 1H) and 11.20 (s, 1H) ppm; MS (ES+) 212.0 (M-^tBu).

Step 6: tert-Butyl N-[[4-[chloro-N-hydroxy-carbonimidoyl]phenyl]methyl]-N-(trideuteriomethyl)carbamate

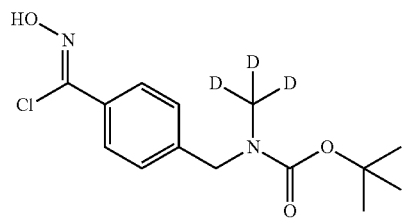

xxiii tert-butyl N-[[4-[hydroxyiminomethyl]phenyl]methyl]-N-(trideuteriomethyl)carbamate (250 mg, 0.9351 mmol) in DMF (2.5 mL) was treated with NCS (124.9 mg, 0.9351 mmol) and the reaction warmed to 65° C. for 1 hour. The reaction was cooled to ambient temperature and diluted with water. The mixture was extracted with EtOAc (×2) and the combined organic extracts washed with brine (×4), dried (MgSO₄), filtered and concentrated in vacuo to give the sub-title compound as a white solid (259 mg, 92% Yield); 1H NMR (400 MHz, DMSO) δ 1.41 (d, J=29.6 Hz, 9H), 4.42 (s, 2H), 7.31 (d, J=8.3 Hz, 2H), 7.78 (d, J=8.0 Hz, 2H), and 12.38 (s, 1H), ppm.

Step 7: tert-Butyl N-[[4-[5-[3-[bis(tert-butoxycarbonyl)amino]-6-(4-isopropylsulfonylphenyl)pyrazin-2-yl]isoxazol-3-yl]phenyl]methyl]-N-(trideuteriomethyl)carbamate

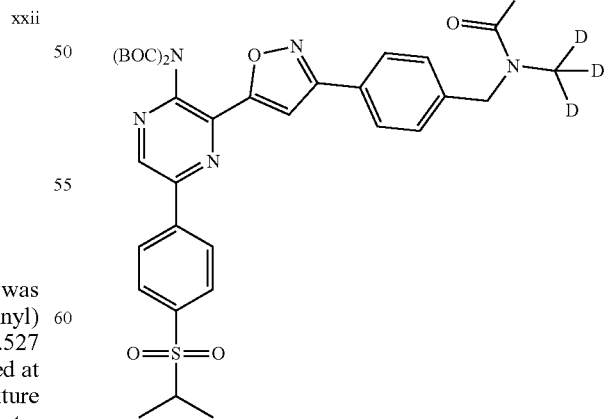

xxiv

Et₃N (48.41 mg, 66.68 μL, 0.4784 mmol) was added dropwise to a stirred solution of tert-butyl N-tert-butoxycarbonyl-N-[3-ethynyl-5-(4-isopropylsulfonylphenyl)pyrazin-2-yl]carbamate (200 mg, 0.3987 mmol) and tert-butyl N-[[4-[chloro-N-hydroxy-carbonimidoyl]phenyl]methyl]-N-(trideuteriomethyl)carbamate (120.3 mg, 0.3987 mmol) in anhydrous THF (5 mL) and the reaction mixture heated at 65° C. for 2.5 hours. The reaction mixture was cooled to ambient temperature and diluted with EtOAc/brine. Water was added until the aqueous layer became clear and the layers were separated. The aqueous layer was extracted with EtOAc (×1) and the combined organic extracts were washed with brine (×1), dried (MgSO₄), filtered and concentrated in vacuo. The residue was purified by column chromatography (ISCO Companion, 40 g column, eluting with 0 to 20% EtOAc/Petroleum Ether, loaded in DCM) to give the subtitle product as a white solid (213.5 mg, 70% Yield); 1H NMR (400 MHz, DMSO) δ 1.22 (d, J=6.8 Hz, 6H), 1.31 (s, 18H), 1.43 (d, J=26.2 Hz, 9H), 3.51-3.60 (m, 1H), 4.47 (s, 2H), 7.42 (d, J=8.1 Hz, 2H), 8.03 (d, J=5.2 Hz, 3H), 8.08 (d, J=8.6 Hz, 2H), 8.65 (d, J=8.6 Hz, 2H) and 9.52 (s, 1H) ppm; MS (ES+) 667.4 (M-Boc).

Step 8: 5-(4-Isopropylsulfonylphenyl)-3-[3-[4-[(trideuteriomethylamino)methyl]phenyl]isoxazol-5-yl]pyrazin-2-amine (Compound II-3)

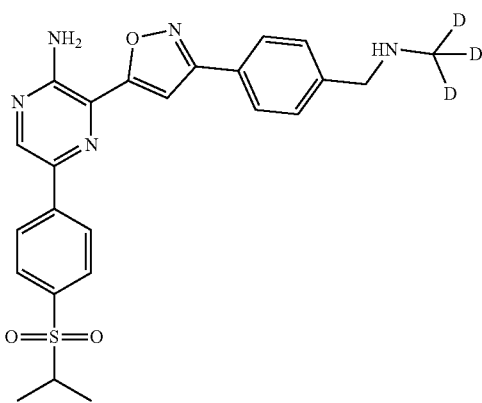

3M HCl in MeOH (1.5 mL of 3 M, 4.500 mmol) was added to a stirred solution of tert-butyl N-[[4-[5-[3-[bis(tert-butoxycarbonyl)amino]-6-(4-isopropylsulfonylphenyl)pyrazin-2-yl]isoxazol-3-yl]phenyl]methyl]-N-(trideuteriomethyl)carbamate (213 mg, 0.2777 mmol) in DCM (6 mL) and the reaction heated at reflux for 15 hours. A further portion of 3M HCl in MeOH (0.5 mL of 3 M, 1.500 mmol) was added and the reaction heated at reflux for a further 7 hours. The reaction was cooled to ambient temperature and the resultant precipitate was isolated by filtration and dried under vacuum at 40° C. to give the di-HCl salt of the title compound as a yellow solid (97.6 mg, 65% Yield); 1H NMR (400 MHz, DMSO) δ 1.20 (d, J=6.8 Hz, 6H), 3.47 (tt, J=14.0, 6.9 Hz, 1H), 4.19-4.25 (m, 2H), 7.23 (s, 2H), 7.72 (d, J=8.4 Hz, 2H), 7.85 (s, 1H), 7.95 (d, J=8.7 Hz, 2H), 8.11 (d, J=8.4 Hz, 2H), 8.39 (d, J=8.7 Hz, 2H), 8.97 (s, 1H) and 9.11 (s, 2H) ppm; MS (ES+) 467.2.

Example 5: Synthesis of 3-[3-[4-(Methylaminomethyl)phenyl]isoxazol-5-yl]-5-[4-[1,2,2,2-tetradeuterio-1-(trideuteriomethyl)ethyl]sulfonylphenyl]pyrazin-2-amine (Compound II-4)

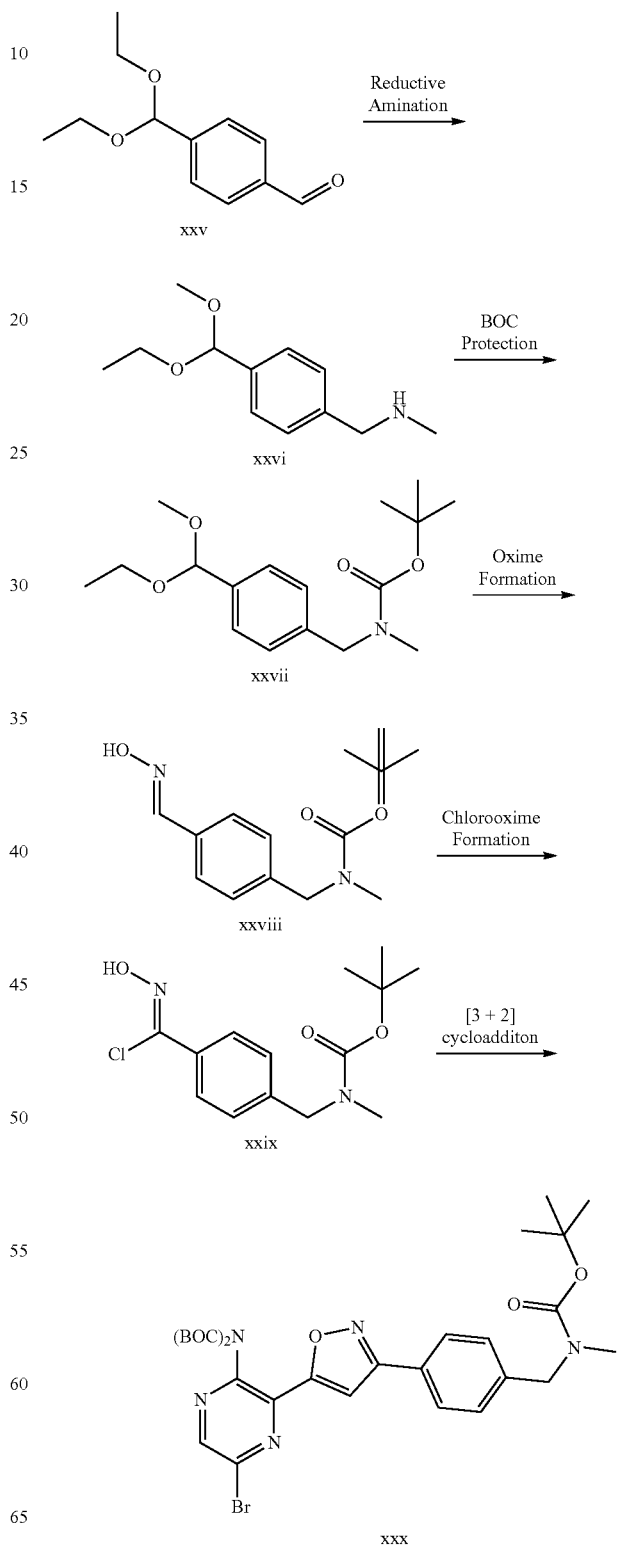

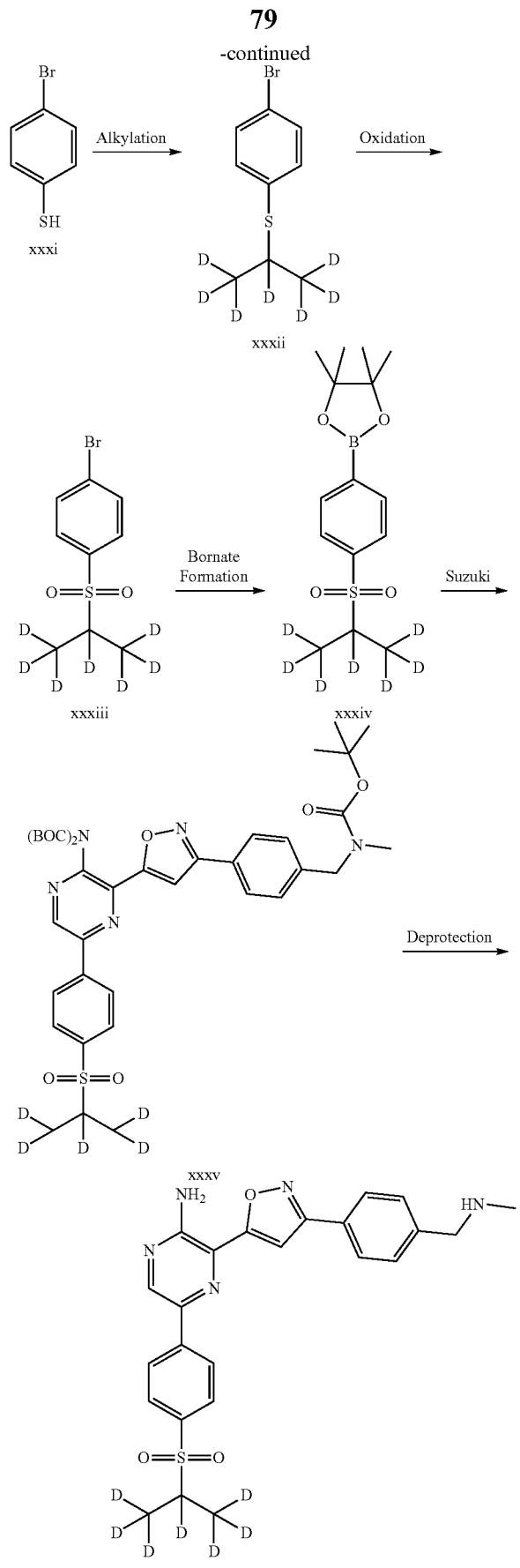

Step 1: 1-[4-(Diethoxymethyl)phenyl]-N-methyl-methanamine

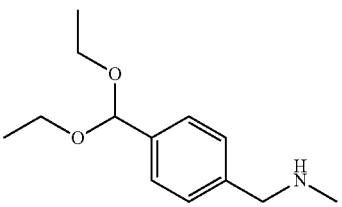

xxvi 2M methylamine in MeOH (288.1 mL, 576.2 mmol) was diluted with methanol (1.000 L) and stirred at ~20 OC. 4-(Diethoxymethyl)benzaldehyde (100 g, 480.2 mmol) was added dropwise over 1 minute and the reaction stirred at ambient temperature for 1.25 hours. Sodium borohydride (29.07 g, 30.76 mL, 768.3 mmol) was added portionwise over 20 minutes while maintaining the temperature between 20 and 30° C. with an ice-water bath. The reaction solution was stirred at ambient temperature overnight then quenched by the dropwise addition of NaOH (960.4 mL of 1.0 M, 960.4 mmol) over 20 minutes. The reaction was stirred for 30 minutes and concentrated in vacuo to remove MeOH. The reaction was partitioned with MTBE (1.200 L) and the phases separated. The organic phase was washed with water (300.0 mL), dried (Na$_2$SO$_4$), and concentrated in vacuo to give the title compound as a yellow oil (102.9 g, 96% Yield); 1H NMR (400 MHz, CDCl$_3$) δ 1.25 (t, 6H), 2.46 (s, 3H), 3.45-3.65 (m, 4H), 3.75 (s, 2H), 5.51 (s, 1H), 7.32 (d, 2H) and 7.44 (d, 2H) ppm.

Step 2: tert-Butyl N-[[4-(diethoxymethyl)phenyl]methyl]-N-methyl-carbamate

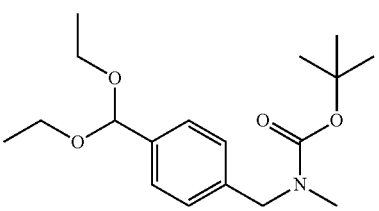

xxvii

A 1-L glass-jacketed reactor was fitted with an overhead stirrer, thermocouple, and chiller. A solution of 1-[4-(diethoxymethyl)phenyl]-N-methyl-methanamine (80.0 g, 358.2 mmol) in DCM (480.0 mL) was stirred at 18° C. A solution of Boc anhydride (79.75 g, 83.95 mL, 365.4 mmol) in DCM (160.0 mL) was added over 10 minutes and the solution was stirred at 20-25° C. overnight. The reaction mixture was filtered, rinsed with DCM (3×50 mL) and the filtrate concentrated in vacuo to afford give the title compound as a pale yellow liquid (116.6 g, quantitative yield); 1H NMR (400 MHz, CDCl$_3$) δ 1.25 (t, 6H), 1.49-1.54 (2×s, 9H), 2.78-2.83 (2×s, 3H), 3.50-3.66 (m, 4H), 4.42 (s, 2H), 5.49 (s, 1H), 7.22 (d, 2H) and 7.45 (d, 2H) ppm.

Step 3: tert-Butyl N-[[4-[hydroxyiminomethyl]phenyl]methyl]-N-methyl-carbamate

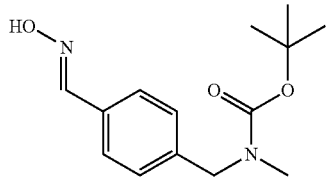

xxviii

A biphasic solution of tert-butyl N-[[4-(diethoxymethyl)phenyl]methyl]-N-methyl-carbamate (50.0 g, 154.6 mmol) in 2-MeTHF (400.0 mL) and $Na_2SO_4$ (100.0 mL of 10% w/v, 70.40 mmol) was stirred at 8-10° C. in a 1-L, glass-jacketed reactor. Hydroxylamine hydrochloride (46.38 mL of 5.0 M, 231.9 mmol) was added and the biphasic solution was stirred at 30° C. for 16 hours. The reaction was diluted with MTBE (200.0 mL) and the layers separated. The organic phase was washed with water (200.0 mL), dried ($Na_2SO_4$), filtered and concentrated in vacuo. The residue was diluted with heptane (200.0 mL) and the resultant suspension was stirred at ambient temperature for 30 minutes. The solid was collected by filtration to give the title compound as a white solid (36.5 g, 89% Yield); 1H NMR (400 MHz, $CDCl_3$) δ 1.50 (s, 9H), 2.88 (br s, 3H), 4.60 (s, 2H), 7.26 (d, 2H), 7.52 (d, 2H) and 8.15 (s, 1H) ppm.

Step 4: tert-Butyl N-[[4-[chloro-N-hydroxy-carbonimidoyl]phenyl]methyl]-N-methyl-carbamate

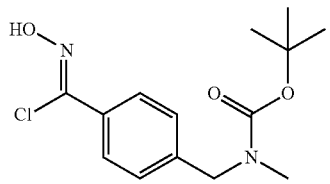

xxix

A suspension of tert-butyl N-[[4-[hydroxyiminomethyl]phenyl]methyl]-N-methyl-carbamate (100 g, 378.3 mmol) in isopropyl acetate (1.000 L) was stirred at ambient temperature. N-Chlorosuccinimide (53.04 g, 397.2 mmol) was added and stirred at ambient temperature for 16 hours. The reaction was partitioned with water (500.0 mL) and the phases separated. The organic phase was washed with water (500.0 mL) (2×), dried ($Na_2SO_4$), filtered and concentrated in vacuo to remove most of the solvent. Heptane (1.000 L) was added and the mixture concentrated in vacuo to remove most of the solvent. Heptane (1.000 L) was added and the resultant precipitate isolated by filtration. The filter-cake was washed with heptane (500 mL) and air-dried to give the title compound as an off-white powder (105.45 g, 93% Yield); 1H NMR (400 MHz, $CDCl_3$) δ 1.48 (2×s, 9H), 2.90 (2×s, 3H), 4.47 (s, 2H), 7.26 (d, 2H), 7.77 (d, 2H) and 8.82 (s, 1H) ppm.

Step 5: tert-Butyl N-[[4-[5-[3-[bis(tert-butoxycarbonyl)amino]-6-bromo-pyrazin-2-yl]isoxazol-3-yl]phenyl]methyl]-N-methyl-carbamate

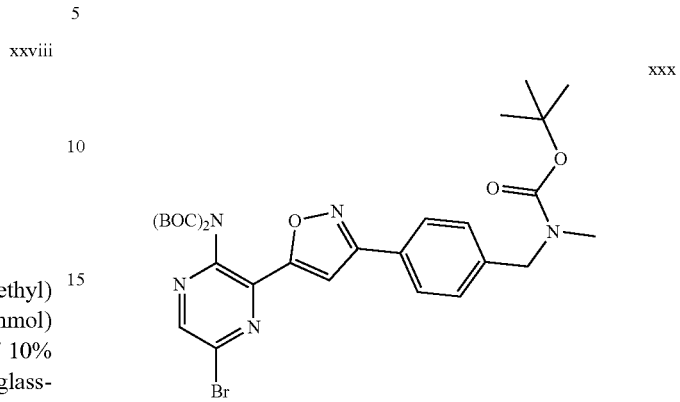

xxx

A suspension of tert-butyl N-[[4-[chloro-N-hydroxy-carbonimidoyl]phenyl]methyl]-N-methyl-carbamate (100.0 g, 334.7 mmol) and tert-butyl N-tert-butoxycarbonyl-N-[3-ethynyl-5-(4-isopropylsulfonylphenyl)pyrazin-2-yl]carbamate (121.2 g, 304.3 mmol) in DCM (1.212 L) was stirred at ambient temperature. Triethylamine (33.87 g, 46.65 mL, 334.7 mmol) was added in one portion and the reaction stirred at ambient temperature for 16 hours. The reaction was partitioned with water (606.0 mL) and the phases separated. The organic phase was washed with water (606.0 mL), dried ($Na_2SO_4$), filtered and concentrated in vacuo to near dryness. Heptane (363.6 mL) was added and the mixture concentrated to about 300 mL. Further heptane (1.212 L) was added and the mixture heated to 90° C. with stirring. The mixture was slowly cooled to ambient temperature and stirred at this temperature for 1 hour. The resultant precipitate was isolated by filtration and the filter-cake washed with heptane (2×363.6 mL) and air-dried to give the title compound as a beige solid (181.8 g, 90% Yield); 1H NMR (400 MHz, $CDCl_3$) δ 1.41 (s, 18H), 1.51 (s, 9H), 2.88 (2×s, 3H), 4.50 (s, 2H), 7.36-7.38 (m, 3H), 7.86 (d, 2H) and 8.65 (s, 1H) ppm.

Step 6: 1-Bromo-4-[1,2,2,2-tetradeuterio-1-(trideuteriomethyl)ethyl]sulfanyl-benzene

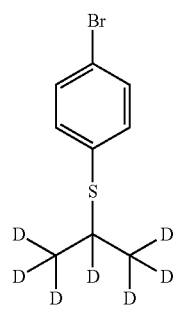

xxxii

Sodium hydride (246.5 mg, 6.163 mmol) was added portionwise to a stirred solution of 4-bromobenzenethiol (compound xxxi) (970.9 mg, 5.135 mmol) in DMF (10 mL) at 0° C. After stirring at this temperature for 15 minutes 1,1,1,2,3,3,3-heptadeuterio-2-iodo-propane (1 g, 5.649 mmol) was added and the reaction allowed to warm to ambient temperature over 18 hours. The reaction was quenched by the addition of water and the mixture stirred for 10 minutes. The mixture was extracted with diethyl ether (×3) and the combined organic extracts washed with water (×2), brine (×2), dried (MgSO$_4$), filtered and concentrated in vacuo to give the sub-title compound that was used directly without further purification assuming 100% Yield and purity; 1H NMR (500 MHz, DMSO) δ 7.25-7.37 (m, 2H) and 7.48-7.55 (m, 2H) ppm.

Step 7: 1-Bromo-4-[1,2,2,2-tetradeuterio-1-(trideuteriomethyl)ethyl]sulfonyl-benzene

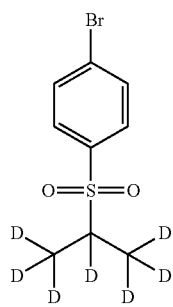

xxxiii mCPBA (2.875 g, 12.83 mmol) was added in portions to a stirred solution of 1-bromo-4-[1,2,2,2-tetradeuterio-1-(trideuteriomethyl)ethyl]sulfanyl-benzene (1.223 g, 5.134 mmol) in DCM (20 mL) at 0° C. and the reaction allowed to warm to ambient temperature over 17 hours. The mixture was washed 1M aqueous NaOH (×2), saturated aqueous Na$_2$S$_2$O$_3$ (×3), brine (×1), dried (MgSO4), filtered and concentrated in vacuo. The residue was purified by column chromatography (ISCO Companion, 80 g column, eluting with 0 to 40% EtOAc/Petroleum Ether, loaded in DCM) to give the sub-title compound as a colourless oil (1.19 g, 86% Yield); 1H NMR (500 MHz, DMSO) δ 7.77-7.81 (m, 2H) and 7.88-7.92 (m, 2H) ppm.

Step 8: 4,4,5,5-Tetramethyl-2-[4-[1,2,2,2-tetradeuterio-1-(trideuteriomethyl)ethyl]sulfonylphenyl]-1,3,2-dioxaborolane

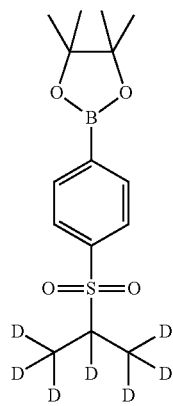

xxxiv

Pd(dppf)Cl$_2$.DCM (179.8 mg, 0.2202 mmol) was added to a stirred suspension of 1-bromo-4-[1,2,2,2-tetradeuterio-1-(trideuteriomethyl)ethyl]sulfonyl-benzene (1.19 g, 4.404 mmol), bis(dipinacolato)diboron (1.342 g, 5.285 mmol) and KOAc (1.296 g, 13.21 mmol) in dioxane (10 mL). The reaction placed under an atmosphere of nitrogen via 5×nitrogen/vacuum cycles and the mixture was heated at 80° C. for 4.5 hours. The reaction was cooled to ambient temperature and the solvent removed in vacuo. The residue was partitioned between Et$_2$O and water and the layers separated. The organic layer was dried (MgSO$_4$), filtered and concentrated in vacuo. The residue was dissolved in 30% EtOAc/Petroleum ether (35 mL) and 1.2 g of Florosil was added. The mixture was stirred for 30 minutes then filtered, washing the solids with further alliquots of 30% EtOAc/Petrol (×3). The filtrate was concentrated in vacuo and tritruated from 10% EtOAc/petroleum ether. The resultant solid was isolated by filtration, washed with petroleum ether and dried in vacuo to give the sub-title compound as an off-white solid (1052.1 mg, 75% Yield); 1H NMR (400 MHz, DMSO) δ 1.33 (s, 12H), 7.87 (d, J=8.4 Hz, 2H) and 7.94 (d, J=8.4 Hz, 2H) ppm.

Step 9: tert-Butyl N-[[4-[5-[3-[bis(tert-butoxycarbonyl)amino]-6-[4-[1,2,2,2-tetradeuterio-1-(trideuteriomethyl)ethyl]sulfonylphenyl]pyrazin-2-yl]isoxazol-3-yl]phenyl]methyl]-N-methyl-carbamate

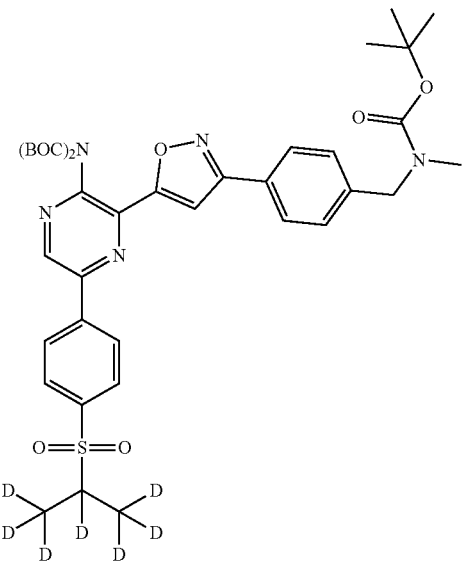

xxxv

[1,1'-Bis(di-tert-butylphosphino)ferrocene]dichloropalladium(II) (106.8 mg, 0.1639 mmol) was added to a mixture of 4,4,5,5-tetramethyl-2-[4-[1,2,2,2-tetradeuterio-1-(trideuteriomethyl)ethyl]sulfonylphenyl]-1,3,2-dioxaborolane (1.3 g, 4.098 mmol), tert-butyl N-[[4-[5-[3-[bis(tert-butoxycarbonyl)amino]-6-bromo-pyrazin-2-yl]isoxazol-3-yl]phenyl] methyl]-N-methyl-carbamate (2.707 g, 4.098 mmol) and K$_2$CO$_3$ (1.133 g, 8.200 mmol) in toluene (9.100 mL), EtOH (2.600 mL) and water (2.600 mL) and the reaction mixture was degassed with a flow of nitrogen (5 cycles). The mixture was heated at 75° C. for 1.5 hours. The reaction was cooled to ambient temperature and water (5.2 mL) was added. After stirring the layers were separated and the organic layer dried (Na$_2$SO$_4$), filtered, and concentrated in vacuo. The residue was triturated with IPA and the resultant precipitate isolated by filtration, washed with IPA (3×4 mL) and dried in vacuo at 50° C. to give the title compound as a white solid (2.4 g, 76% Yield); 1H NMR (400 MHz, CDCl$_3$) δ 1.41 (s, 18H), 1.50 (s, 9H), 2.85-2.89 (m, 3H), 4.50 (s, 2H), 7.36-7.38 (m, 3H), 7.87 (d, 2H), 8.09 (d, 2H), 8.35 (d, 2H) and 9.06 (s, 1H) ppm.

Step 10: 3-[3-[4-(Methylaminomethyl)phenyl]isoxazol-5-yl]-5-[4-[1,2,2,2-tetradeuterio-1-(trideuteriomethyl)ethyl]sulfonylphenyl]pyrazin-2-amine (compound II-4)

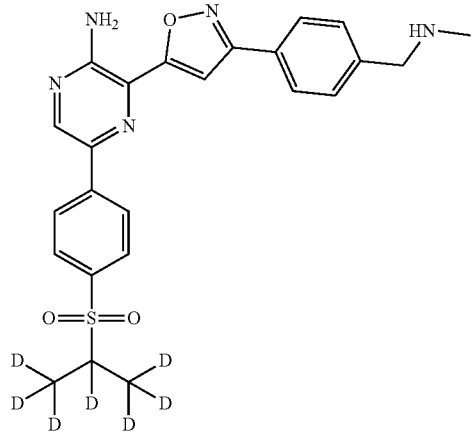

II-4

Concentrated HCl (3.375 g, 2.812 mL of 37% w/w, 34.25 mmol) was added to a solution of tert-butyl N-[[4-[5-[3-[bis(tert-butoxycarbonyl)amino]-6-[4-[1,2,2,2-tetradeuterio-1-(trideuteriomethyl)ethyl]sulfonyphenyl]pyrazin-2-yl]isoxazol-3-yl]phenyl]methyl]-N-methyl-carbamate (2.2 g, 2.854 mmol) in acetone (28.60 mL) and the reaction heated at reflux for 7 hours. The reaction was cooled to ambient temperature and the resultant precipitate isolated by filtration, washed with acetone (2×4.5 mL) and dried in vacuo at 50° C. to give the di-HCl salt of the title compound as a yellow solid (1.42 g, 92% Yield); 1H NMR (400 MHz, DMSO) δ 2.58 (t, 3H), 4.21 (t, 2H), 5.67 (br s, 2H), 7.74 (d, 2H), 7.85 (s, 1H), 7.94 (d, 2H), 8.10 (d, 2H), 8.38 (d, 2H), 8.96 (s, 1H) and 9.33 (br s, 2H) ppm; MS (ES+) 471.8.

Example 6: Synthesis of 5-(4-(tert-butylsulfonyl)phenyl)-3-(3-(4-((methylamino)methyl)phenyl)isoxazol-5-yl)pyrazin-2-amine (Compound I-2)

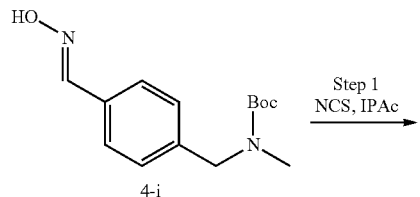

4-i

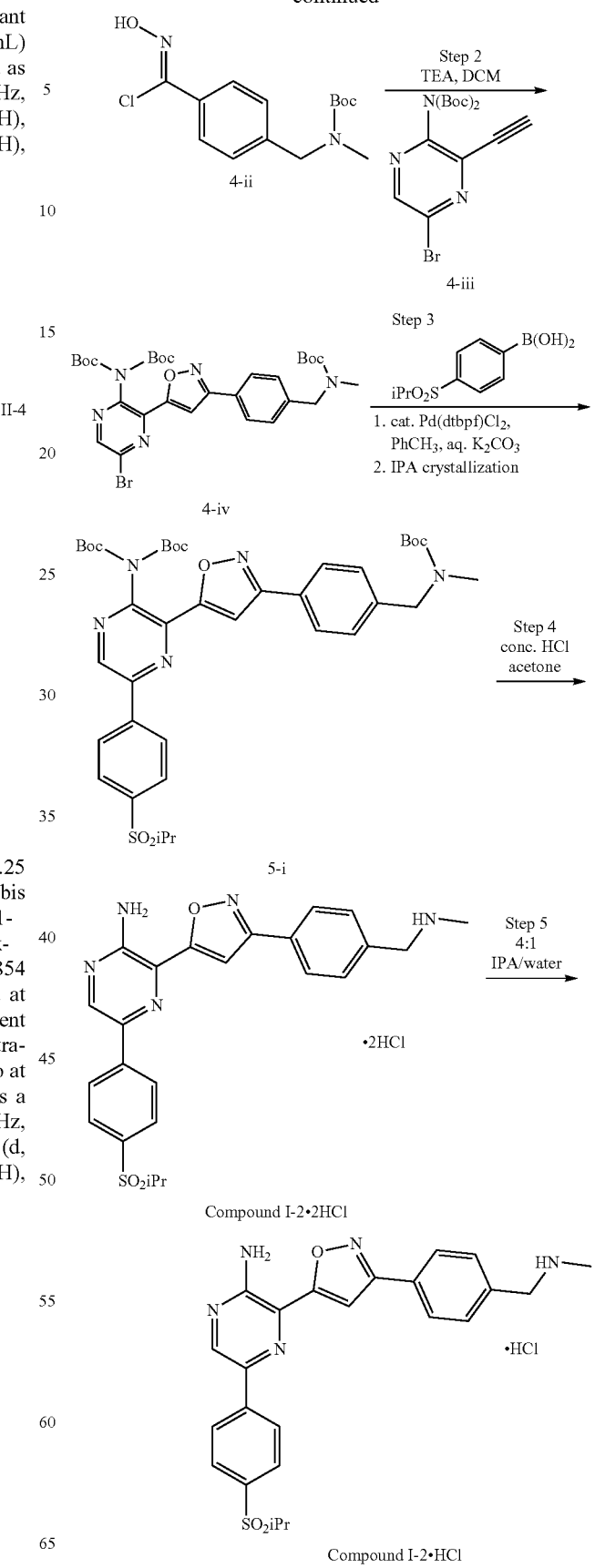

Step 1: Preparation of Compound 4-ii

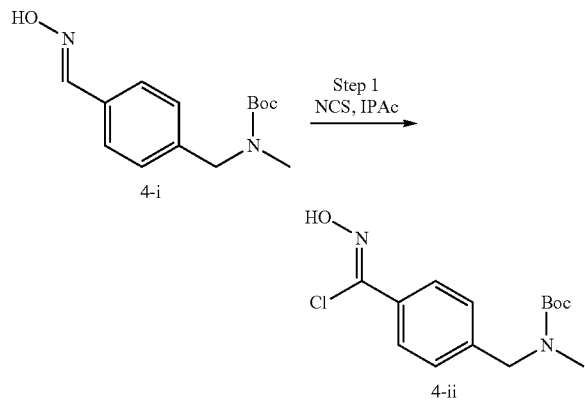

A suspension of tert-butyl 4-((hydroxyimino)methyl)benzyl (methyl)carbamate (Compound 4-i) (650 g, 2.46 mol) in isopropyl acetate (6.5 L) is stirred at ambient temperature. N-Chlorosuccinimide (361 g, 2.71 mol) is added and the reaction temperature maintained overnight at 20-28° C. to ensure complete reaction. The reaction mixture is diluted with water (3.25 L) and EtOAc (1.3 L) and the phases are separated. The organic phase is washed with water (2×3.25 L), dried (Na$_2$SO$_4$), and concentrated to a wet-cake. The concentrate is diluted with heptane (9.1 L), ~2 L of solvent removed, and then stirred at ambient temperature for 2-20 h. The solid is collected by filtration. The filter-cake is washed with heptane (2×975 mL) and dried to afford Compound 4-ii (692 g; 94% yield, 99.2 area % purity by HPLC) as a colorless powder.

Step 2: Preparation of tert-butyl (5-bromo-3-(3-(4-(((tert-butoxycarbonyl)(methyl)amino) methyl)phenyl)isoxazol-5-yl)pyrazin-2-yl)(tert-butoxycarbonyl) carbamate (Compound 4-iv)

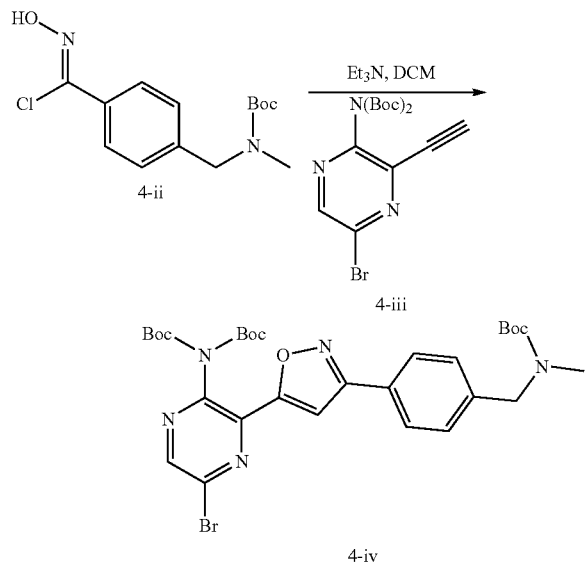

A suspension of tert-butyl N-(5-bromo-3-ethynylpyrazin-2-yl)-N-tert-butoxycarbonylcarbamate (Compound 4-iii) (1.59 kg, 3.99 mol) and tert-butyl 4-(chloro(hydroxyimino) methyl)benzyl(tetrahydro-2H-pyran-4-yl)carbamate (1.31 kg, 4.39 mol; 1.10 equiv.) in CH$_2$Cl$_2$ (12.7 L) is stirred at ambient temperature. Triethylamine (444 g, 611 mL, 4.39 mol) is added to the suspension and the reaction temperature is maintained between 20-30° C. for 20-48 h to ensure complete reaction. The reaction mixture is diluted with water (8 L) and thoroughly mixed, then the phases are separated. The organic phase is washed with water (8 L), dried (Na$_2$SO$_4$), and then concentrated until about 1 L of CH$_2$Cl$_2$ remains. The concentrate is diluted with heptane (3.2 L) and re-concentrated at 40° C./200 torr until no distillate is observed. The concentrate is stirred and further diluted with heptane (12.7 L) to precipitate a solid. The suspension is stirred overnight. The solid is collected by filtration, washed with heptane (2×3 L) then dried to afford Compound 4-iv (2.42 kg; 92% yield, 100 area % purity by HPLC) as a light tan powder. $^1$H NMR (400 MHz, CDCl$_3$) δ 8.61 (s, 1H), 7.82 (d, J=8.2 Hz, 2H), 7.31 (m, 3H), 4.46 (br s, 2H), 2.84 (br d, 3H), 1.57 (s, 2H), 1.44 (br s, 9H), 1.36 (s, 18H).

Step 3: Preparation of Compound 5-i

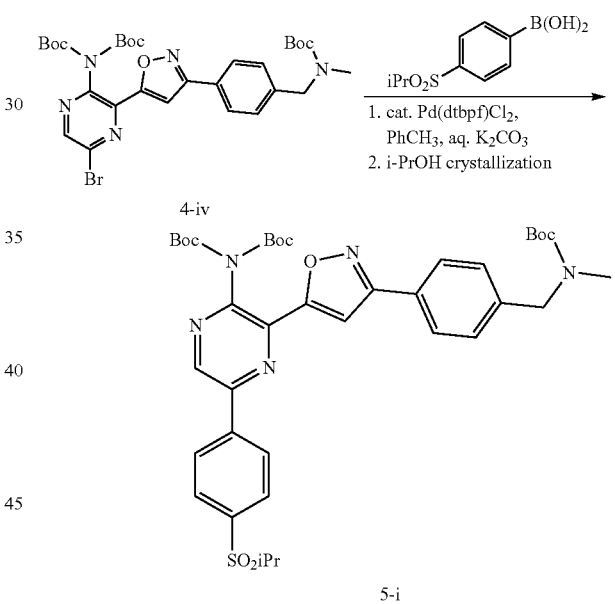

A mixture of tert-butyl (5-bromo-3-(3-(4-(((tert-butoxycarbonyl)(methyl)amino)methyl)phenyl)isoxazol-5-yl) pyrazin-2-yl)(tert-butoxycarbonyl)carbamate (Compound 4-iv)(1.00 kg, 1.51 mol), K$_2$CO$_3$ (419 g, 3.02 mol), and (4-(isopropylsulfonyl)phenyl)boronic acid (345 g, 1.51 mol) in toluene (7.0 L) and water (2.0 L) was stirred and degassed with N$_2$ for 30 min. 1,1'-bis(di-t-butylphosphino)ferrocendichloro-palladium(II) [Pd(dtbpf)Cl$_2$; 19.7 g, 30.3 mmol] was then added and degassed an additional 20 min. The reaction mixture was warmed at 70° C. for at least 1 h to ensure complete reaction. The reaction mixture was cooled to ambient temperature then filtered through Celite. The reaction vessel and filter pad are rinsed with toluene (2×700 mL). The filtrates are combined and the phases are separated. The organic phase is stirred with Biotage MP-TMT resin (170 g) for 4-20 h. The resin is removed by filtration through Celite and the filter pad is washed with toluene (2×700 mL). The filtrate and washings are combined and concentrated to near dryness then diluted with i-PrOH (5.75 L) and re-concentrated. The concentrate is again dissolved in warm (45° C.) i-PrOH (5.75 L) and then cooled to ambient temperature with stirring to induce crystallization then stirred for around 16-20 h. The solid is collected by filtration, washed with i-PrOH (2×1 L), and dried to afford VRT-1018729 (967 g; 84%) as a beige powder. $^1$H NMR (400 MHz, CDCl$_3$) δ 9.04 (s, 1H), 8.33 (d, J=8.6 Hz, 2H), 8.06 (d, J=8.5 Hz, 2H), 7.85 (d, J=8.1 Hz, 2H), 7.34 (m, 3H), 4.47 (br s, 2H), 3.25 (hept, J=7.0 Hz, 1H), 2.85 (br d, 3H), 1.47 (s, 9H), 1.38 (s, 18H), 1.33 (d, J=6.9 Hz, 6H).

Step 4: Preparation of Compound I-2.2HCl

A solution of Compound 5-i (950 g, 1.24 mol) in acetone (12.35 L) is warmed to 40° C. then concentrated HCl (1.23 kg, 1.02 L of 37% w/w, 12.4 mol) is added at a rate to maintain the reaction temperature between 40-45° C. for at least 5 h to ensure complete reaction. The suspension is cooled to below 30° C. and the solid collected by filtration. The filter-cake is washed with acetone (2×950.0 mL) then dried to afford Compound I-2.2HCl (578 g; 87% yield, 99.5 area % purity by HPLC) as a yellow powder. $^1$H NMR (400 MHz, DMSO) δ 9.53 (br d, J=4.8 Hz, 2H), 8.93 (s, 1H), 8.37 (d, J=8.5 Hz, 2H), 8.07 (d, J=8.3 Hz, 2H), 7.92 (d, J=8.6 Hz, 2H), 7.84 (s, 1H), 7.75 (d, J=8.3 Hz, 2H), 4.23-4.15 (m, 2H), 3.43 (hept, J=6.8 Hz, 1H), 2.55 (t, J=5.3 Hz, 3H), 1.17 (d, J=6.8 Hz, 6H).

Step 5: Preparation of Compound I-2.HCl from Compound I-2.2HCl

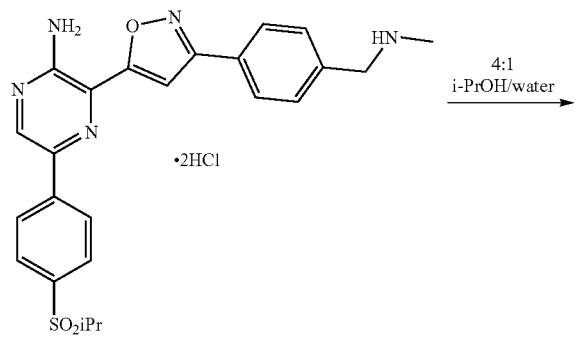

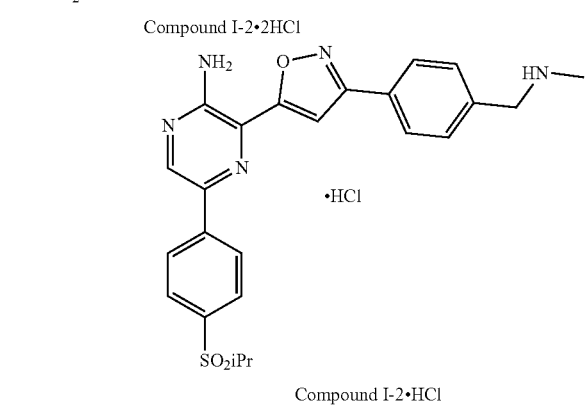

Two-Pot Process

A stirred suspension of Compound I-2.2HCl (874 g, 1.63 mol) in i-PrOH (3.50 L) and water (0.87 L) is warmed at 50° C. for 1-2 h, cooled to ambient temperature, and stirred for 1-20 h. XRPD is performed on a small sample to ensure that Compound I-2.2HCl has been converted to another form. The suspension is cooled to 5° C. and stirred for 1 h. The solid is collected by filtration then the filter-cake is washed with 80/20 i-PrOH/water (2×874 mL), and briefly dried.

If XRPD shows the Compound I-2.HCl/anhydrate form, the solid is dried to afford Compound I-2.HCl/anhydrate (836 g, 99% yield, 99.2 area % purity by HPLC) as a yellow solid. $^1$H NMR (400 MHz, DMSO) δ 9.38 (s, 2H), 8.96 (s, 1H), 8.46-8.34 (m, 2H), 8.10 (d, J=8.3 Hz, 2H), 7.94 (d, J=8.6 Hz, 2H), 7.85 (s, 1H), 7.75 (d, J=8.3 Hz, 2H), 7.23 (br s, 2H), 4.21 (s, 2H), 3.47 (hept, J=6.7 Hz, 1H), 2.58 (s, 3H), 1.19 (d, J=6.8 Hz, 6H).

If XRPD shows the Compound I-2.HCl/hydrate form the solid is stirred in fresh i-PrOH (3.50 L) and water (0.87 L) at 50° C. for at least 2 h until XRPD shows complete conversion to Compound I-2.HCl/anhydrate. The suspension is then cooled to 5° C. and stirred for 1 h. The solid is collected by filtration then the filter-cake is washed with 80/20 i-PrOH/water (2×874 mL) then dried to afford Compound I-2*HCl/anhydrate.

Alternative Procedure (Single Pot) Used

Compound I-2.2HCl (392 g) is charged to the reactor. 4:1 IPA/water (8 L) is charged to a reactor and stirred at ambient temperature overnight. XRPD is used to confirm the conversion to the mono-HCl salt mono-hydrate form. The mixture is heated to 50° C. Seeds of Compound I-2.HCl/anhydrate (16 g) are added and the mixture heated at 50° C. until XRPD confirms complete conversion to the desired anhydrate form. The mixture is to cooled to ambient, filtered and the solid washed with 4:1 IPA/water (2×800 mL) then dried to afford Compound I-2.HCl/anhydrate (343 g, 94% yield).

Step 4: Alternate Method 1: Preparation of Compound I-2 Free Base

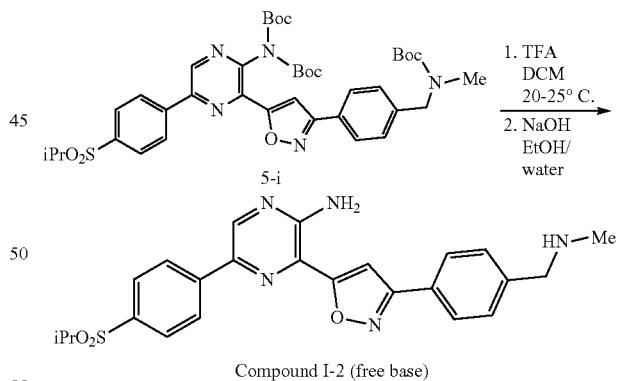

A solution of Compound 5-i (100 g, 131 mmol) in DCM (200 mL) was stirred at ambient temperature then TFA (299 g, 202 mL, 2.62 mol) was added. After 2 h reaction solution was cooled to 5° C. The reaction mixture was diluted with EtOH (1.00 L) over about 5 min resulting in a bright yellow suspension. The suspension was cooled to 10° C. then NaOH (1.64 L of 2.0 M, 3.28 mol) was added over 30 min then stirred at ambient temperature overnight. The solid was collected by filtration then washed with water (2×400 mL), EtOH (2×200 mL) then dried to afford Compound I-2 free-base (57.0 g, 94% yield, 99.7 area % purity by HPLC)

as a fine, yellow powder. ¹H NMR (400 MHz, DMSO) δ 8.95 (s, 1H), 8.39 (d, J=8.5 Hz, 2H), 7.95 (dd, J=11.6, 8.4 Hz, 4H), 7.78 (s, 1H), 7.51 (d, J=8.2 Hz, 2H), 7.21 (br s, 2H), 3.72 (s, 2H), 3.47 (hept, J=6.8 Hz, 1H), 2.29 (s, 3H), 1.19 (d, J=6.8 Hz, 6H).

Step 4: Alternate Method 2: Preparation of Compound I-2.HCl

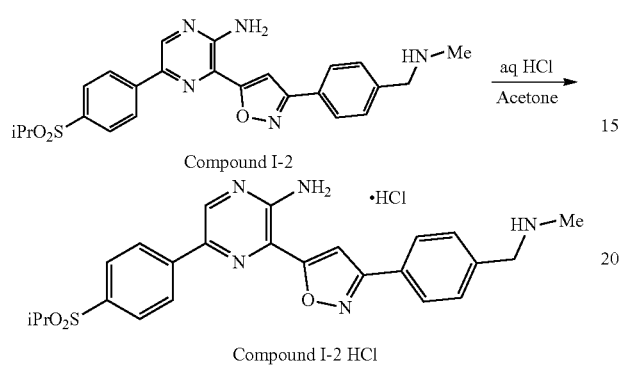

A suspension of Compound I-2 free base (10.0 g, 21.6 mmol) in acetone (80 mL) was stirred and heated to 35° C. An aqueous solution of HCl (11.9 mL of 2.0 M, 23.8 mmol) diluted with water (8.0 mL) was added and the mixture heated at 50° C. for 4 h. The suspension was allowed to cool to ambient temperature then stirred overnight. The solid was collected by filtration. The filter-cake was washed with acetone (2×20 mL) then dried to afford 10.2 g Compound I-2 hydrochloride (95% yield) as a yellow powder.

Example 7: Synthesis of 5-(4-(Isopropylsulfonyl) phenyl)-3-(3-(4-(tetrahydropyran-4-ylamino)methyl) phenyl) isoxazol-5-yl)pyrazin-2-amine (Compound Scheme: Example Synthesis of Compound I-3

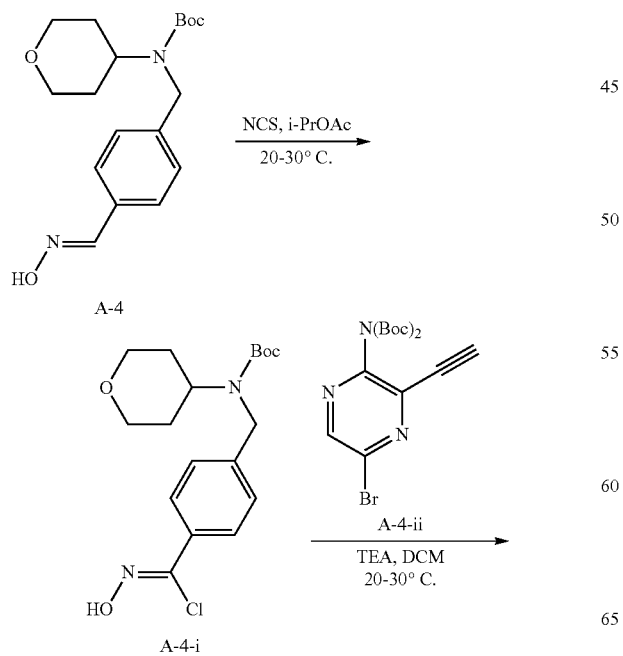

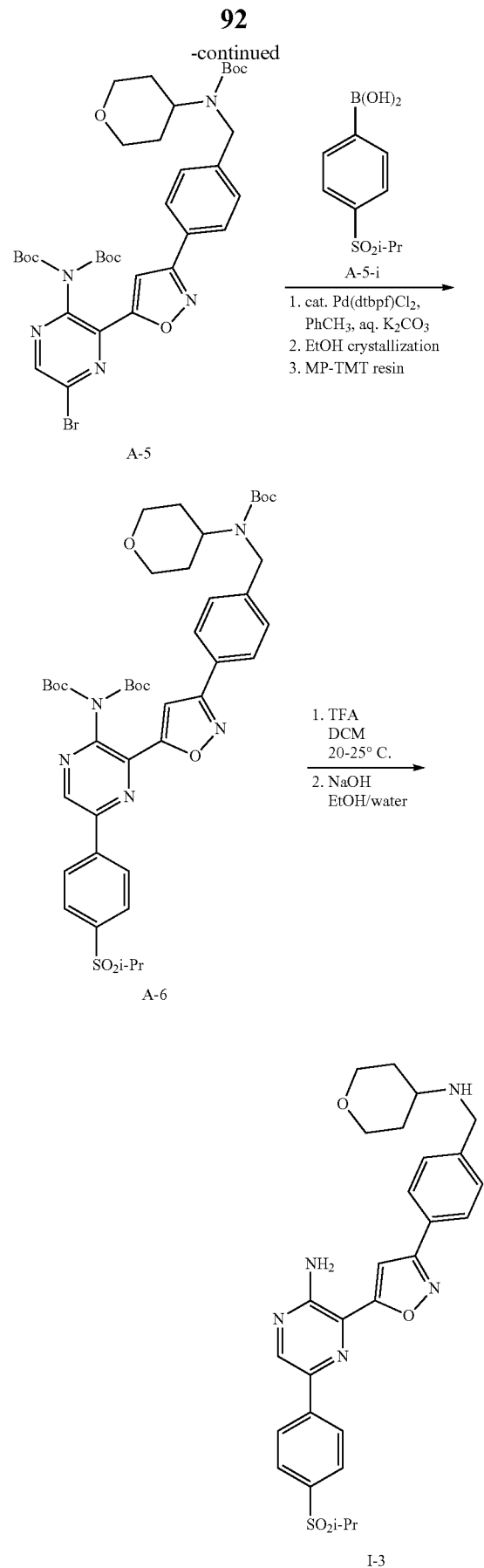

Step 1: Preparation of N-(4-(diethoxymethyl)benzyl)tetrahydro-2H-pyran-4-amine (A-2)

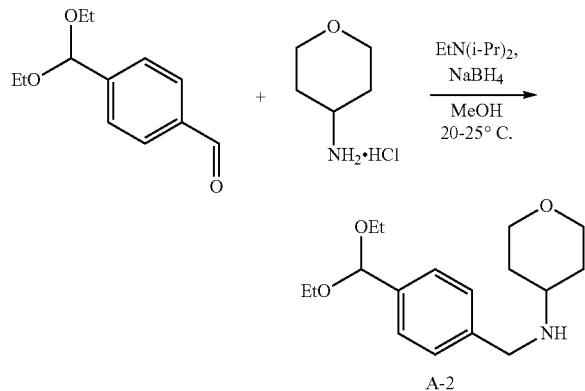

A solution of tetrahydro-2H-pyran-4-amine hydrochloride (1.13 kg, 8.21 mol) in MeOH (14.3 L) is stirred at about 20° C. then Et$_3$N (1.06 kg, 1.43 L, 8.21 mol) is added. The mixture is stirred for at least 5 min then terephthalaldehyde diethyl acetal (1.43 kg, 6.84 mol) is added while maintaining the reaction temperature between 20-25° C. The mixture is stirred for at least 45 min to form the imine. NaBH$_4$ caplets (414 g, 11.0 mol) are added while maintaining the reaction temperature below about 25° C. The mixture is stirred for 1 h after the addition is completed. The reaction mixture is quenched by adding 1 M NaOH (13.7 L) then extracted with MTBE. The organic solution was washed with brine (7.13 L) then dried (Na$_2$SO$_4$) and concentrated to afford Compound A-2 (2197 g; 109% yield, 94.4 area % purity by HPLC) as a hazy oil. $^1$H NMR (400 MHz, CDCl$_3$) δ 7.43 (d, J=8.1 Hz, 2H), 7.31 (d, J=8.1 Hz, 2H), 5.49 (s, 1H), 4.66 (br s, 1H), 4.03-3.91 (m, 2H), 3.82 (s, 2H), 3.69-3.47 (m, 4H), 3.38 (td, J=11.6, 2.1 Hz, 2H), 2.78-2.65 (m, 1H), 1.90-1.81 (m, 2H), 1.53-1.37 (m, 2H), 1.23 (t, J=7.1 Hz, 6H).

Step 2: Preparation of tert-butyl 4-(diethoxymethyl)benzyl(tetrahydro-2H-pyran-4-yl)carbamate (A-3)

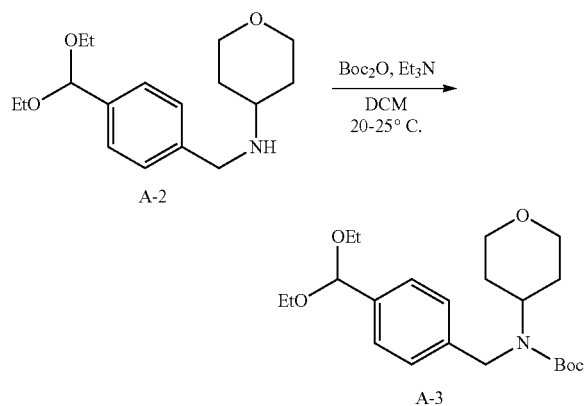

A mixture of N-(4-(diethoxymethyl)benzyl)tetrahydro-2H-pyran-4-amine (A-2) (2195 g, 7.48 mol) in CH$_2$Cl$_2$ (22.0 L) is stirred at 25° C. then di-t-butyl dicarbonate (1.71 kg, 7.86 mol) is added. Et$_3$N (795 g, 1.10 L) is then added while maintaining the reaction temperature between 20-25° C. The reaction mixture is stirred at about 25° C. for 12-20 h. After the reaction is completed, the mixture is cooled to about 20° C. and quenched with 0.5 M aqueous citric acid (7.48 L, 3.74 mol) while maintaining the reaction temperature between 20-25° C. The organic phase is collected, washed with sat. NaHCO$_3$ (6.51 L, 7.48 mol), washed with brine (6.59 L), and dried (Na$_2$SO$_4$) then concentrated to afford tert-butyl 4-(diethoxymethyl)benzyl(tetrahydro-2H-pyran-4-yl)carbamate (A-3) (2801 g; 95% yield, 98.8 area % purity by HPLC) as a thick, amber oil. $^1$H NMR (400 MHz, CDCl$_3$) δ 7.40 (d, J=8.1 Hz, 2H), 7.21 (d, J=7.9 Hz, 2H), 5.49 (s, 1H), 4.39 (br s, 3H), 3.93 (br dd, J=10.8, 3.8 Hz, 2H), 3.67-3.47 (m, 4H), 3.40 (br m, 2H), 1.68-1.59 (m, 4H), 1.39 (br s, 9H), 1.23 (t, J=7.1 Hz, 6H).

Step 3: Preparation of tert-butyl 4-((hydroxyimino)methyl)benzyl(tetrahydro-2H-pyran-4-yl)carbamate (A-4)

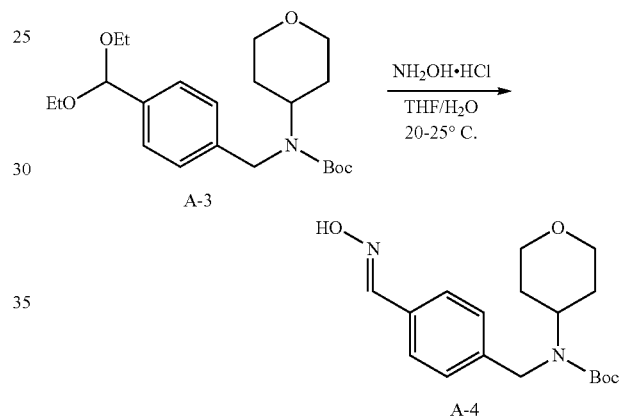

A solution of tert-butyl 4-(diethoxymethyl)benzyl(tetrahydro-2H-pyran-4-yl)carbamate (A-3) (2.80 kg, 7.12 mol) in THF (28.0 L) and water (2.80 L) is stirred at about 20° C. Hydroxylamine hydrochloride (593 g, 8.54 mol) is added while maintaining the reaction temperature between 20-25° C. The reaction mixture is stirred at about 20° C. for 16-20 h then diluted with CH$_2$Cl$_2$ (8.4 L) and 50% brine (11.2 L) and stirred for at least 5 min. The phases are separated then the organic phase is washed with 50% brine (2×2.8 L), dried (Na$_2$SO$_4$) and concentrated. The concentrate is diluted with MeOH (1.4 L) and re-concentrated. The concentrate is diluted with MeOH (14.0 L) and transferred to a reaction vessel. The solution is warmed to about 25° C. then water (14.0 L) is added over about 1-1.5 h; after about 10 L of water is added, the mixture is seeded and a hazy suspension is observed. Additional water (8.4 L) is added over 1.5 h to further precipitate the product. After aging, the solid is collected by filtration. The filter-cake is washed with heptane (5.6 L) and dried to afford tert-butyl 4-((hydroxyimino)methyl)benzyl(tetrahydro-2H-pyran-4-yl)carbamate (A-4) (1678 g; 71%, 91.5 area % purity by HPLC) as an off-white powder. $^1$H NMR (400 MHz, CDCl$_3$) δ 8.12 (s, 1H), 7.51 (d, J=8.2 Hz, 2H), 7.24 (d, J=7.9 Hz, 2H), 4.40 (br s, 3H), 3.96 (dd, J=10.4, 3.6 Hz, 2H), 3.41 (br m, 2H), 1.69-1.61 (m, 4H), 1.39 (br s, 9H).

Step 4: Preparation of (tert-butyl 4-(chloro(hydroxi-mino)methyl)benzyl (tetrahydro-2H-pyran-4-yl) carbamate (A-4-i)

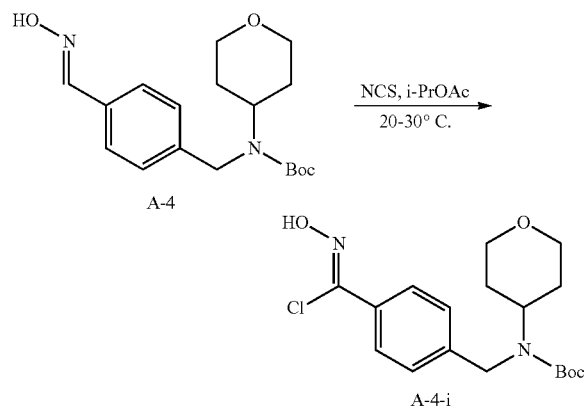

A suspension of (E)-tert-butyl 4-((hydroxyimino)methyl)benzyl(tetrahydro-2H-pyran-4-yl)carbamate (A-4) (1662 g, 4.97 mol) in i-PrOAc (16.6 L) is stirred at 20° C. in a reactor. N-chlorosuccinimide (730 g, 5.47 mol) is added maintaining about 20° C. The suspension is stirred at about 20° C. to complete the reaction. The suspension is diluted with water (8.3 L) and stirred to dissolve the solid. The phases are separated and the organic phase is washed with water (8.3 L). The organic phase is concentrated then diluted with i-PrOAc (831 mL). Heptane (13.3 L; 8 V) is slowly added to induce crystallization. The thick suspension is then stirred for 1 h. The solid is collected by filtration; the filter-cake is washed with heptane (2×1.6 L; 2×1 V) and dried to afford (Z)-tert-butyl 4-(chloro(hydroxyimino)methyl)benzyl (tetrahydro-2H-pyran-4-yl)carbamate (A-4-i) (1628 g; 89%, 98.0 area % purity by HPLC) as a white powder.

Step 5: Preparation of tert-butyl (5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl)carbamate (A-5)

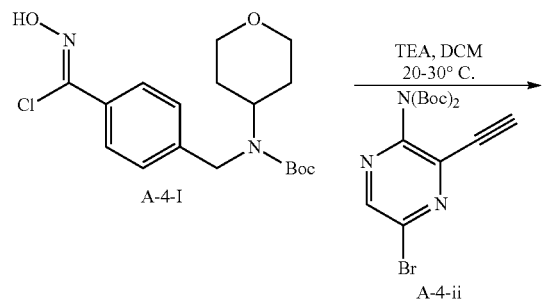

A solution of tert-butyl 4-(chloro(hydroxyimino)methyl)benzyl(tetrahydro-2H-pyran-4-yl)carbamate (A-4-i) (1.60 kg, 4.34 mol) and tert-butyl N-(5-bromo-3-ethynylpyrazin-2-yl)-N-tert-butoxycarbonylcarbamate (Compound A-4-ii) (1.73 kg, 4.34 mol) in $CH_2Cl_2$ (12.8 L) is stirred at 20° C. $Et_3N$ (483 g, 665 mL; 4.77 mol) is added and the reaction temperature maintained below 30° C. The suspension stirred at 20° C. to complete the reaction then diluted with water (8.0 L) and agitated. The phases are separated and the organic phase is washed with water (8.0 L) and then concentrated. i-PrOAc (1.6 L) is added and the mixture and heated at 50° C. Heptane (4.0 L) was slowly added then the suspension is allowed to cool to ambient temperature and stirred overnight. Additional heptane (7.2 L) is added to the suspension and it is stirred for 1 h. The solid is collected by filtration. The filter-cake is washed with heptane (2×1.6 L) and dried to afford tert-butyl (5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl) carbamate (A-5) (2.478 kg; 78%, 97.8 area % purity by HPLC) as a fine, tan powder. $^1$H NMR (400 MHz, $CDCl_3$) δ 8.60 (s, 1H), 7.78 (d, J=8.3 Hz, 2H), 7.31 (m, 3H), 4.42 (br m, 3H), 4.03-3.82 (m, 2H), 3.38 (br s, 2H), 1.60 (m, 4H), 1.36 (s, 27H).

Step 6: Preparation of tert-butyl tert-butoxycarbonyl (3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate

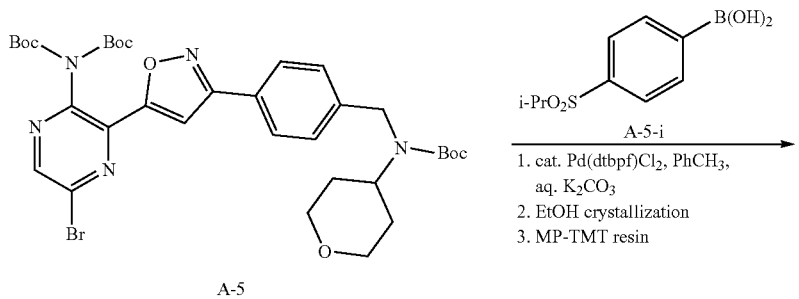

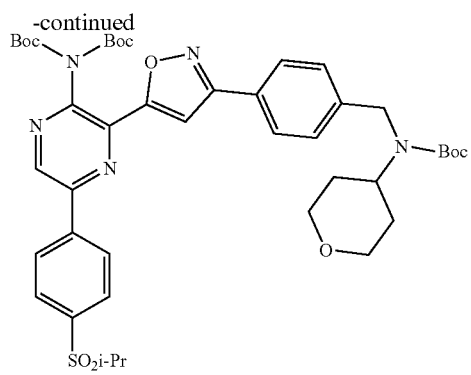

A-6

A mixture of tert-butyl (5-bromo-3-(3-(4-(((tert-butoxycarbonyl)(tetrahydro-2H-pyran-4-yl)amino)methyl)phenyl)isoxazol-5-yl)pyrazin-2-yl)(tert-butoxycarbonyl)carbamate (A-5) (425 g, 582 mmol), $K_2CO_3$ (161 g, 1.16 mol; 2.0 equiv.), and (4-(isopropylsulfonyl)phenyl)boronic acid (133 g, 582 mmol) in toluene (2.98 L) and water (850 mL) is stirred and degassed with $N_2$ at ambient temperature. The catalyst [1,1'-bis(di-tert-butylphosphino)ferrocene]dichloropalladium(II), (Pd(dtbpf)Cl$_2$; 1.90 g, 2.91 mmol) is added and the mixture is degassed for an additional 10 min. The mixture is heated at 70° C. until the reaction is complete. The mixture is cooled to 50° C., diluted with water (850 mL) and filtered through a bed of Celite. The phases are separated. The organic phase is concentrated then the residue is diluted with EtOH (1.70 L) and re-concentrated. With mixing at 40° C., the concentrate is diluted with EtOH (1.70 L) to induce crystallization. The suspension is cooled to 20° C. and stirred for 4 h. The solid is collected by filtration. The filter-cake is washed with EtOH (2×425 mL) and air-dried to afford tert-butyl tert-butoxycarbonyl(3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) as a beige powder. The solid is dissolved in THF (2.13 L) and slurried with Biotage MP-TMT resin (48 g) at ambient temperature. The resin is removed by filtration and the filtrate concentrated to remove most of the THF. The concentrate is diluted with EtOH (970 mL) and re-concentrated to about half the original volume. The concentrate is diluted again with EtOH (970 mL) and mixed for 1 h at 40° C. The suspension is cooled to ambient temperature and the solid is collected by filtration then dried to afford tert-butyl tert-butoxycarbonyl(3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) (416 g; 86% yield, 99.3 area % purity by HPLC) as a white powder. $^1$H NMR (400 MHz, CDCl$_3$) δ 9.04 (s, 1H), 8.38-8.28 (m, 2H), 8.10-8.01 (m, 2H), 7.82 (d, J=8.2 Hz, 2H), 7.34 (m, 3H), 4.44 (br s, 2H), 3.94 (dd, J=10.5, 3.5 Hz, 2H), 3.40 (br s, 2H), 3.25 (hept, J=6.8 Hz, 1H), 1.65 (m, 4H), 1.38 (br s, 27H), 1.33 (d, J=6.9 Hz, 6H).

Step 7: Preparation of 5-(4-(isopropylsulfonyl)phenyl)-3-(3-(4-(((tetrahydro-2H-pyran-4-yl)amino)methyl)phenyl)isoxazol-5-yl)pyrazin-2-amine (1-3) freebase form

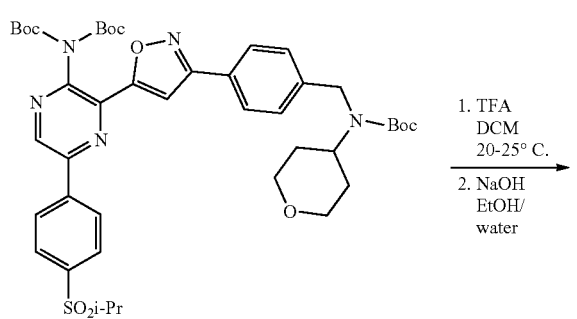

A-6

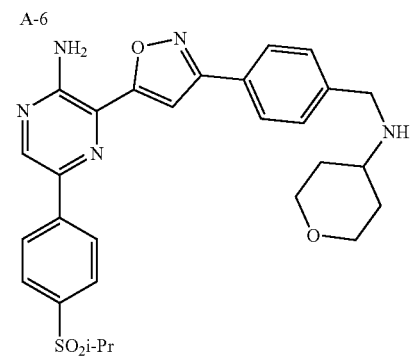

I-3

A suspension of tert-butyl tert-butoxycarbonyl(3-(3-(4-(((tert-butoxycarbonyl)(tetrahydro-2H-pyran-4-yl)amino)methyl)phenyl)isoxazol-5-yl)-5-(4-(isopropylsulfonyl)phenyl)pyrazin-2-yl)carbamate (A-6) (410 g; 492 mmol) in CH$_2$Cl$_2$ (410 mL) is stirred at ambient temperature in a flask. TFA (841 g, 568 mL; 7.4 mol) is added while maintaining the reaction temperature between 20-25° C. The solution is stirred at ambient temperature for about 3 h when analysis shows reaction completion. The solution is cooled to about 5-10° C. and diluted with EtOH (3.3 L) while maintaining the temperature below 20° C. A 5.0 M aqueous solution of NaOH (1.77 L; 8.85 mol) is added while allowing the reaction temperature to rise from about 14° C. to about 42°

C. The suspension is heated at 70-75° C. for 6 h while removing distillate. The suspension is allowed to cool to ambient temperature. The solid is collected by filtration and the filter-cake is washed with water (4×1.64 L). The filter-cake is washed with EtOH (2×820 mL) and dried to afford 5-(4-(isopropylsulfonyl)phenyl)-3-(3-(4-(((tetrahydro-2H-pyran-4-yl)amino)methyl)phenyl) isoxazol-5-yl)pyrazin-2-amine (Compound I-1) (257 g; 98% yield, 99.5 area % purity by HPLC) as a yellow powder.

$^1$H NMR (400 MHz, DMSO) δ 8.94 (s, 1H), 8.44-8.33 (m, 2H), 7.94 (t, J=8.2 Hz, 4H), 7.76 (s, 1H), 7.53 (d, J=8.2 Hz, 2H), 7.20 (s, 2H), 3.83 (m, 1H), 3.80 (s, 3H), 3.46 (hept, J=6.8 Hz, 1H), 3.25 (td, J=11.4, 2.1 Hz, 2H), 2.66-2.54 (m, 1H), 1.79 (br dd, 2H), 1.36-1.22 (m, 2H), 1.19 (d, J=6.8 Hz, 6H). $^{13}$C NMR (101 MHz, DMSO) δ 167.57, 151.76, 141.07, 137.58, 135.75, 129.16, 128.53, 126.57, 126.41, 125.69, 124.52, 102.13, 65.83, 54.22, 52.60, 49.19, 33.18, 15.20.

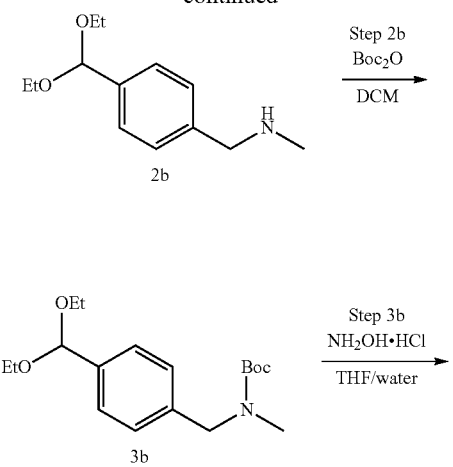

| | | Compound Analytical Data | |
|---|---|---|---|
| Cmpd No. | LCMS ES+ | LCMS (Rt min) | HNMR |
| I-1 | — | — | $^1$H NMR (400 MHz, DMSO) δ 9.63 (d, J = 4.7 Hz, 2H), 9.05 (s, 1H), 8.69 (d, J = 5.2 Hz, 1H), 8.21 (s, 1H), 8.16-8.03 (m, 3H), 7.84 (t, J = 4.1 Hz, 3H), 7.34 (br s, 2H), 4.40-4.18 (m, 2H), 3.94 (dd, J = 11.2, 3.9 Hz, 2H), 3.32 (t, J = 11.2 Hz, 3H), 2.17-2.00 (m, 2H), 1.81 (s, 6H), 1.75 (dd, J = 12.1, 4.3 Hz, 2H). |
| I-2 | — | — | $^1$H NMR (400 MHz, DMSO) δ 8.94 (s, 1H), 8.44-8.33 (m, 2H), 7.94 (t, J = 8.2 Hz, 4H), 7.76 (s, 1H), 7.53 (d, J = 8.2 Hz, 2H), 7.20 (s, 2H), 3.83 (m, 1H), 3.80 (s, 3H), 3.46 (hept, J = 6.8 Hz, 1H), 3.25 (td, J = 11.4, 2.1 Hz, 2H), 2.66-2.54 (m, 1H), 1.79 (br dd, 2H), 1.36-1.22 (m, 2H), 1.19 (d, J = 6.8 Hz, 6H). |
| II-1 | 466.2 | 0.83 | 1H NMR (500 MHz, DMSO) 9.10 (d, J = 5.8 Hz, 2H), 8.97 (s, 1H), 8.42-8.37 (m, 2H), 8.15-8.08 (m, 2H), 7.99-7.92 (m, 2H), 7.85 (s, 1H), 7.75-7.69 (m, 2H), 7.22 (br s, 2H), 3.48 (hept, J = 6.8 Hz, 1H), 2.60 (t, J = 5.4 Hz, 3H), 1.20 (d, J = 6.8 Hz, 6H). |
| II-2 | 469.1 | 0.82 | 1H NMR (500 MHz, DMSO) 9.14 (s, 2H), 8.96 (s, 1H), 8.42-8.36 (m, 2H), 8.13-8.08 (m, 2H), 7.99-7.91 (m, 2H), 7.85 (s, 1H), 7.78-7.68 (m, 2H), 7.21 (s, 2H), 3.48 (dq, J = 13.6, 6.7 Hz, 1H), 1.20 (d, J = 6.8 Hz, 6H). |
| II-3 | 467.2 | 0.78 | 1H NMR (500 MHz, DMSO) 9.11 (s, 2H), 8.97 (s, 1H), 8.39 (d, J = 8.7 Hz, 2H), 8.11 (d, J = 8.4 Hz, 2H), 7.95 (d, J = 8.7 Hz, 2H), 7.85 (s, 1H), 7.72 (d, J = 8.4 Hz, 2H), 7.23 (s, 2H), 4.25-4.19 (m, 2H), 3.47 (tt, J = 14.0, 6.9 Hz, 1H), 1.20 (d, J = 6.8 Hz, 6H). |
| II-4 | 471.8 | 0.83 | 1H NMR (400 MHz, DMSO) δ 2.58 (t, 3H), 4.21 (t, 2H), 5.67 (br s, 2H), 7.74 (d, 2H), 7.85 (s, 1H), 7.94 (d, 2H), 8.10 (d, 2H), 8.38 (d, 2H), 8.96 (s, 1H) and 9.33 (br s, 2H) ppm |

INTERMEDIATES

Example 8: Preparation of Oxime 5a

SCHEME BB:

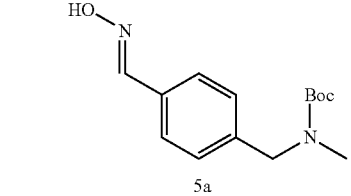

Step 1b

Add MeOH (28.00 L) and 4-(diethoxymethyl)benzaldehyde (Compound 1b) (3500 g, 16.81 mol) into a reactor at 20° C. Add methylamine, 33% in EtOH (1.898 kg, 2.511 L of 33% w/w, 20.17 mol) maintaining 20-30° C. then stir for 1.5 h to form the imine. Add NaBH$_4$ (381.7 g, 10.09 mol) caplets maintaining the temperature between 20-30° C. Stir at room temperature for at least 30 min to ensure complete reaction. Add aqueous NaOH (16.81 L of 2.0 M, 33.62 mol) maintaining approximately 20° C. Add MTBE (17.50 L) and brine (7.0 L), stir for at least 5 min then allow the phases to separate. Extract the aqueous layer with MTBE (7.0 L) then combine the organic phases and wash with brine (3.5 L) then dry (Na$_2$SO$_4$) then concentrate to 6 L. The biphasic mixture was transferred to a separatory funnel and the aqueous phase removed. The organic phase was concentrated to afford 1-(4-(diethoxymethyl)phenyl)-N-methylmethanamine (Compound 2b) (3755 g, 16.82 mol, 100% yield) as an oil. $^1$H NMR (400 MHz, CDCl$_3$) δ 7.43 (d, J=8.1 Hz, 2H), 7.31 (d, J=8.1 Hz, 2H), 5.49 (s, 1H), 3.75 (s, 2H), 3.68-3.46 (m, 4H), 2.45 (s, 3H), 1.23 (t, J=7.1 Hz, 6H).

Steps 2b and 3b

Add 2-MeTHF (15.00 L) and 1-(4-(diethoxymethyl)phenyl)-N-methylmethanamine (Compound 2b) (3750 g, 16.79 mol) to a reactor at 20° C. Add a solution of Boc anhydride (3.848 kg, 4.051 L, 17.63 mol) in 2-MeTHF (7.500 L) maintaining approximately 25° C. Stir for at least 30 min to ensure complete conversion to tert-butyl 4-(diethoxymethyl)benzyl(methyl)carbamate (Compound 3b), then add a solution of Na$_2$SO$_4$ (1.192 kg, 8.395 mol) in water (11.25 L). Heat to 35° C. then add a solution of hydroxylamine hydrochloride (1.750 kg, 25.18 mol) in water (3.75 L) then stir for at least 6 h to ensure complete reaction. Cool to 20° C., stop the stirring and remove the aqueous phase. Wash the organic layer with brine (3.75 L), dry (Na$_2$SO$_4$), filter and concentrate to about 9 L. Add heptane (15.00 L) and crystalline tert-butyl 4-((hydroxyimino)methyl)benzyl (methyl) carbamate (Compound 5a) (1.0 g portions every 10 min) until nucleation was evident, then concentrate to afford a solid slurry. Add heptane (3.75 L) then cool to room temp and filter. Wash with heptane (5.625 L) then dry to afford tert-butyl 4-((hydroxyimino)methyl) benzyl(methyl)carbamate (Compound 5a) (4023 g, 15.22 mol, 91% yield, 97.2 area % purity by HPLC) as a colorless solid. $^1$H NMR (400 MHz, CDCl$_3$) δ 8.13 (s, 1H), 7.54 (d, J=8.1 Hz, 2H), 7.25 (br d, 2H), 4.44 (br s, 2H), 2.83 (br d, 3H), 1.47 (br s, 9H).

Scheme CC: Synthesis of Intermediate A-4-ii

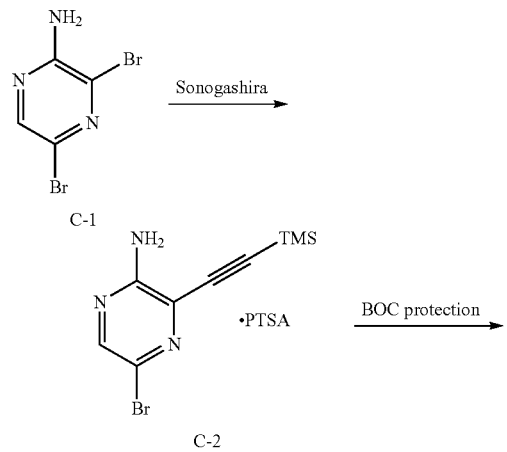

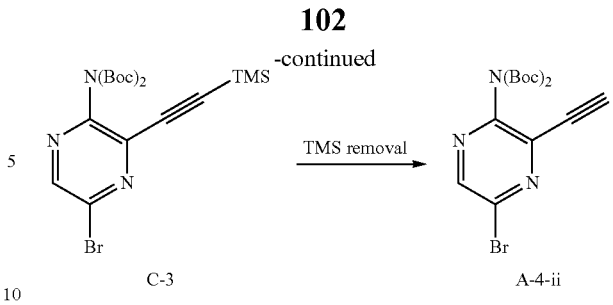

The compound of formula A-4-ii may be made according to the steps outlined in Scheme C. Sonogashira coupling reactions are known in the art (see e.g., Chem. Rev. 2007, 874-922). In some embodiments, suitable Sonogashira coupling conditions comprise adding 1 equivalent of the compound of formula C-1, 1 equivalent of TMS-acetylene, 0.010 equivalents of Pd(PPh$_3$)$_2$Cl$_2$, 0.015 equivalents of CuI and 1.20 equivalents of NMM in isopropanol. The product can be isolated by adding water to the alcoholic reaction mixture.

Amine salts of a product maybe formed by dissolving the amine in a common organic solvent and adding an acid. Examples of suitable solvents include chlorinated solvents (e.g., dichloromethane (DCM), dichloroethane (DCE), CH$_2$Cl$_2$, and chloroform), ethers (e.g., THF, 2-MeTHF and dioxane), esters (e.g., EtOAc, IPAC) and other aprotic solvents. Examples of suitable acids include but are not limited to HCl, H$_3$PO$_4$, H$_2$SO$_4$, MSA, and PTSA. In some embodiments, the solvent is IPAC and the acid is PTSA. In some embodiments, the acid addition salt is converted back to the free amine base in the presence of a suitable solvent and a suitable base. Suitable solvents include EtOAc, IPAC, dichloromethane (DCM), dichloroethane (DCE), CH$_2$Cl$_2$, chloroform, 2-MeTHF, and suitable bases include NaOH, NaHCO$_3$, Na$_2$CO$_3$, KOH, KHCO$_3$, K$_2$CO$_3$, and Cs$_2$CO$_3$. In some embodiments, the suitable solvent is EtOAc and the suitable base is KHCO$_3$.

The amine of Compound C-2 may be protected with various amine protecting groups, such as Boc (tert-butoxycarbonyl). Introduction of Boc protecting groups is known in the art (see e.g. Protecting Groups in Organic Synthesis, Greene and Wuts). In some embodiments, suitable conditions involve adding 1.00 equivalents of the amine, 2.10 equivalents of di-tert-butyl dicarbonate, and 0.03 equivalents of DMAP in EtOAc.

Reduction in Pd is achieved by treating with a metal scavenger (silica gel, functionalized resins, charcoal). In some embodiments, suitable conditions involve adding charcoal.

The TMS (trimethylsilyl) protecting group on Compound C-3 may be removed via conditions known to one of skill in the art. In some embodiments, TMS removal conditions comprise reacting the TMS-protected compound with a suitable base in a suitable solvent. Examples of suitable solvents include chlorinated solvents (e.g., dichloromethane (DCM), dichloroethane (DCE), CH$_2$Cl$_2$, and chloroform), ethers (e.g., THF, 2-MeTHF and dioxane), esters (e.g., EtOAc, IPAC), other aprotic solvents and alcohol solvents (e.g., MeOH, EtOH, iPrOH). Examples of suitable bases include but are not limited to (e.g., NaOH, KOH, K$_2$CO$_3$, Na$_2$CO$_3$). In certain embodiments, suitable conditions comprise adding 1.00 equivalents of the TMS-protected acetylene, 1.10 equivalents of K$_2$CO$_3$, EtOAc and EtOH. In some embodiments, the alcoholic solvent, such as EtOH, is added last in the reaction. In some embodiments the product acetylene is isolated by adding water.

Scheme DD: Example Synthesis of Compound A-4-ii

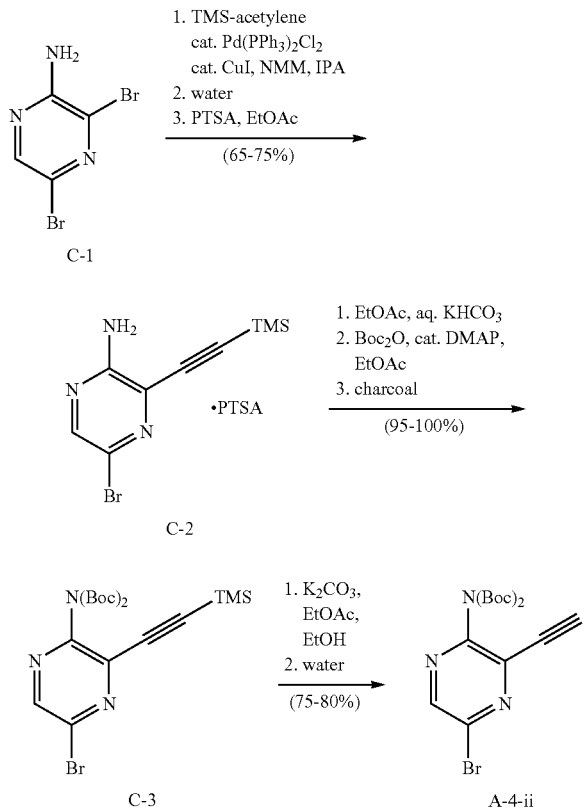

Example 9: Synthesis of Compound A-4-ii

Step 1: Preparation of 5-bromo-3-((trimethylsilyl)ethynyl)pyrazin-2-amine (Compound C-2)

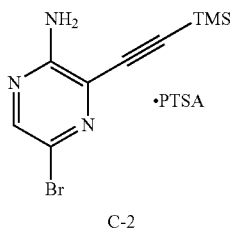

Charge isopropanol (8.0 L) to a reactor the stir and sparge with a stream of $N_2$. Add 3,5-dibromopyrazin-2-amine (Compound C-1) (2000 g, 7.91 moles), Pd(PPh$_3$)$_2$Cl$_2$ (56 g, 0.079 moles), CuI (23 g, 0.119 moles), and NMM (1043 mL, 9.49 moles) to the reactor under a $N_2$ atmosphere. Adjust the reaction temperature to 25° C. Purge the reactor with $N_2$ by doing at least three vacuum/$N_2$ purge cycles. Charge TMS-acetylene (1.12 L, 7.91 moles) to the reaction mixture and maintain the reaction temperature below 30° C. When the reaction is complete lower the temperature of the reaction mixture to 15° C. then add water (10 L) and stir for at least 2 h. The solid is collected by filtration washing the solid with 1:1 IPA/water (2×6 L). The filter cake is dried under vacuum then charged to a reactor and dissolved in EtOAc (12.5 L). PTSA hydrate (1.28 kg, 6.72 mol) is charged as a solid to the reactor. The mixture is stirred at ambient temperature for at least 5 h then the solid is collected by filtration, washed with 1:1 heptane/EtOAc (3.5 L) followed by heptane (3.5 L). The filter cake is dried to afford 5-bromo-3-((trimethylsilyl)ethynyl)pyrazin-2-amine (Compound C-2) as a PTSA salt (2356 g, 67% yield, 98.9 area % purity by HPLC). $^1$H NMR (400 MHz, DMSO) δ 8.12 (s, 1H), 7.48 (d, J=8.1 Hz, 2H), 7.12 (d, J=8.0 Hz, 2H), 2.29 (s, 3H), 0.26 (s, 9H).

Steps 2 and 3

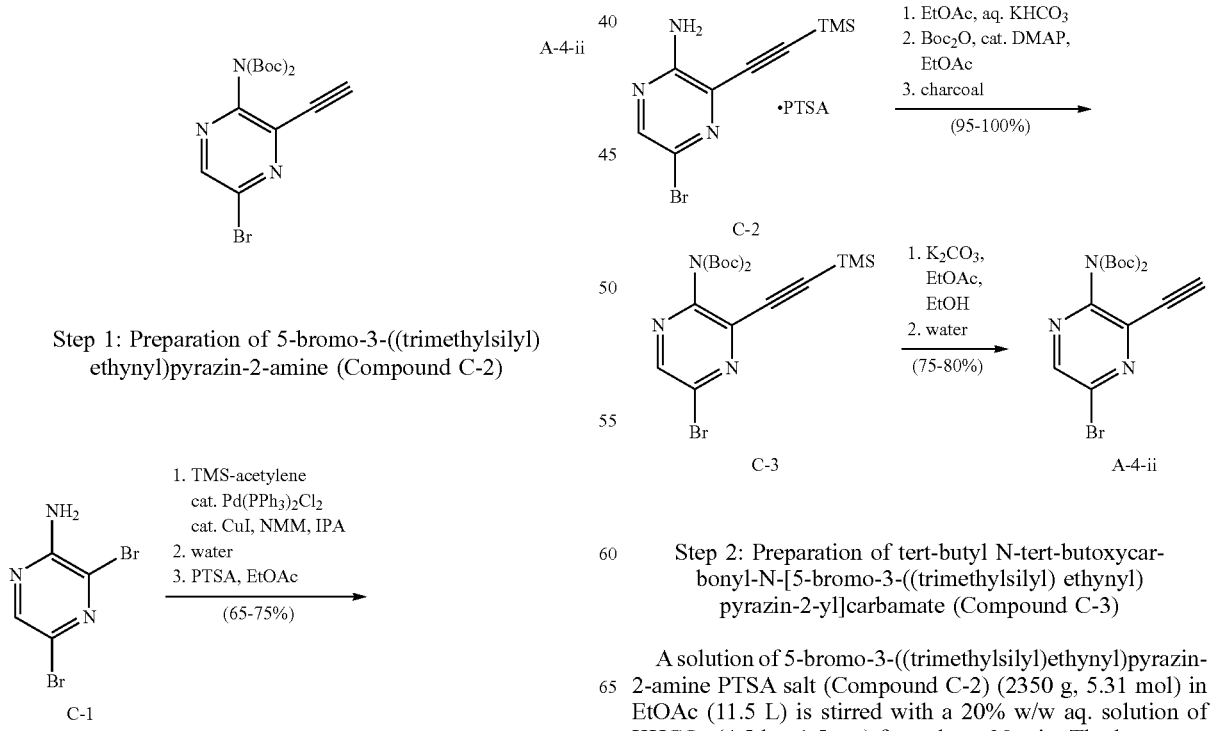

Step 2: Preparation of tert-butyl N-tert-butoxycarbonyl-N-[5-bromo-3-((trimethylsilyl) ethynyl)pyrazin-2-yl]carbamate (Compound C-3)

A solution of 5-bromo-3-((trimethylsilyl)ethynyl)pyrazin-2-amine PTSA salt (Compound C-2) (2350 g, 5.31 mol) in EtOAc (11.5 L) is stirred with a 20% w/w aq. solution of KHCO$_3$ (4.5 kg, 1.5 eq.) for at least 30 min. The layers are separated and the organic layer is concentrated then dissolved in EtOAc (7 L) and added to a reactor. DMAP (19.5 g, 0.16 mol) is added followed a solution of Boc$_2$O (2436 g, 11.16 mol) in EtOAc (3 L) is added lowly. The reaction is stirred for at least 30 min to ensure complete reaction then activated charcoal (Darco G-60, 720 g) and Celite (720 g) are added and stirred for at least 2 h. The mixture is filtered washing the solid pad with EtOAc (2×1.8 L). The filtrate is concentrated to afford tert-butyl N-tert-butoxycarbonyl-N-[5-bromo-3-((trimethylsilyl)ethynyl) pyrazin-2-yl]carbamate (Compound C-3) that is used directly in the next step.

Step 3: Preparation of tert-butyl-N-(5-bromo-3-ethynylpyrazin-2-yl)-N-tert-butoxycarbonylcarbamate (Compound A-4-ii)

K$_2$CO$_3$ (811 g, 5.87 mol) is charged to a reactor followed by a solution of Compound C-3 (2300 g, 4.89 mol) dissolved in EtOAc (4.6 L) agitation started. EtOH (9.2 L) is added slowly and the mixture stirred for at least 1 h to ensure that the reaction is complete then water (4.6 L) is added and stirred for at least 2 h. The solid is collected by filtration and washed with 1:1 EtOH/water (4.6 L followed by 2.3 L) followed by EtOH (2.3 L). The filter cake is dried to afford tert-butyl N-(5-bromo-3-ethynylpyrazin-2-yl)-N-tert-butoxycarbonylcarbamate (Compound A-4-ii) (1568 g, 78% yield, 97.5 area % by HPLC). $^1$H NMR (400 MHz, CDCl$_3$) δ 8.54 (s, 1H), 3.52 (s, 1H), 1.42 (s, 18H).

Solid Forms of Compound I-2

Compound I-2 has been prepared in various solid forms, including salts and co-solvates. The solid forms of the present invention are useful in the manufacture of medicaments for the treatment of cancer. One embodiment provides use of a solid form described herein for treating cancer. In some embodiments, the cancer is pancreatic cancer or non-small cell lung cancer. Another embodiment provides a pharmaceutical composition comprising a solid form described herein and a pharmaceutically acceptable carrier.

Applicants describe herein five novel solid forms of Compound I-2. The names and stoichiometry for each of these solid forms are provided in Table S-1 below:

TABLE S-1

| Example | Forms | Stoichiometry |
|---|---|---|
| Example 13 | Compound I-2 free base | N/A |
| Example 14 | Compound I-2•HCl | 1:1 |
| Example 15 | Compound I-2•2HCl | 1:2 |
| Example 16 | Compound I-2•HCl•H$_2$O | 1:2:1 |
| Example 17 | Compound I-2•HCl•2H$_2$O | 1:1:2 |

Solid state NMR spectra were acquired on the Bruker-Biospin 400 MHz Advance III wide-bore spectrometer equipped with Bruker-Biospin 4 mm HFX probe. Samples were packed into 4 mm ZrO$_2$ rotors (approximately 70 mg or less, depending on sample availability). Magic angle spinning (MAS) speed of typically 12.5 kHz was applied. The temperature of the probe head was set to 275K to minimize the effect of frictional heating during spinning. The proton relaxation time was measured using $^1$H MAS T$_1$ saturation recovery relaxation experiment in order to set up proper recycle delay of the $^{13}$C cross-polarization (CP) MAS experiment. The recycle delay of $^{13}$C CPMAS experiment was adjusted to be at least 1.2 times longer than the measured $^1$H T$_1$ relaxation time in order to maximize the carbon spectrum signal-to-noise ratio. The CP contact time of $^{13}$C CPMAS experiment was set to 2 ms. A CP proton pulse with linear ramp (from 50% to 100%) was employed. The Hartmann-Hahn match was optimized on external reference sample (glycine). Carbon spectra were acquired with SPINAL 64 decoupling with the field strength of approximately 100 kHz. The chemical shift was referenced against external standard of adamantane with its upfield resonance set to 29.5 ppm.

XRPD data for Examples 13-14 were measured on Bruker D8 Advance System (Asset V014333) equipped with a sealed tube Cu source and a Vantec-1 detector (Bruker AXS, Madison, Wis.) at room temperature. The X-ray generator was operating at a voltage of 40 kV and a current of 40 mA. The powder sample was placed in a shallow silicon holder. The data were recorded in a reflection scanning mode (locked coupled) over the range of 3°-40° 2 theta with a step size of 0.0144° and a dwell time of 0.25 s (105 s per step). Variable divergence slits were used.

Example 10: Compound I-2 (Free Base)

Compound I-2 free base can be formed according to the methods described in Example 6, Step 4: Alternate Method 1.

XRPD of Compound I-2 (Free Base)

FIG. 1a shows the X-ray powder diffractogram of the sample which is characteristic of crystalline drug substance.

Representative XRPD peaks from Compound I-2 free base:

| XRPD Peaks | Angle (2-Theta ± 0.2) | Intensity % |
|---|---|---|
| 1 | 23.8 | 100.0 |
| *2 | 14.2 | 43.9 |
| 3 | 22.5 | 39.3 |
| *4 | 25.6 | 31.1 |
| 5 | 19.3 | 28.6 |
| 6 | 27.2 | 27.6 |
| 7 | 17.0 | 25.4 |
| *8 | 18.1 | 25.2 |
| 9 | 17.6 | 19.6 |
| 10 | 20.2 | 17.2 |
| 11 | 28.3 | 15.6 |
| 12 | 20.8 | 14.5 |
| 13 | 29.9 | 14.5 |
| 14 | 33.2 | 14.3 |
| 15 | 30.1 | 13.5 |
| 16 | 26.8 | 13.4 |
| *17 | 22.0 | 12.3 |
| 18 | 36.5 | 12.3 |
| 19 | 31.8 | 12.2 |
| 20 | 34.6 | 11.5 |
| 21 | 31.1 | 11.2 |
| 22 | 34.0 | 11.0 |
| 23 | 30.6 | 10.9 |
| *24 | 11.1 | 10.6 |
| 25 | 13.3 | 10.6 |

Thermo Analysis of Compound I-2 Free Base

Figure 2A:
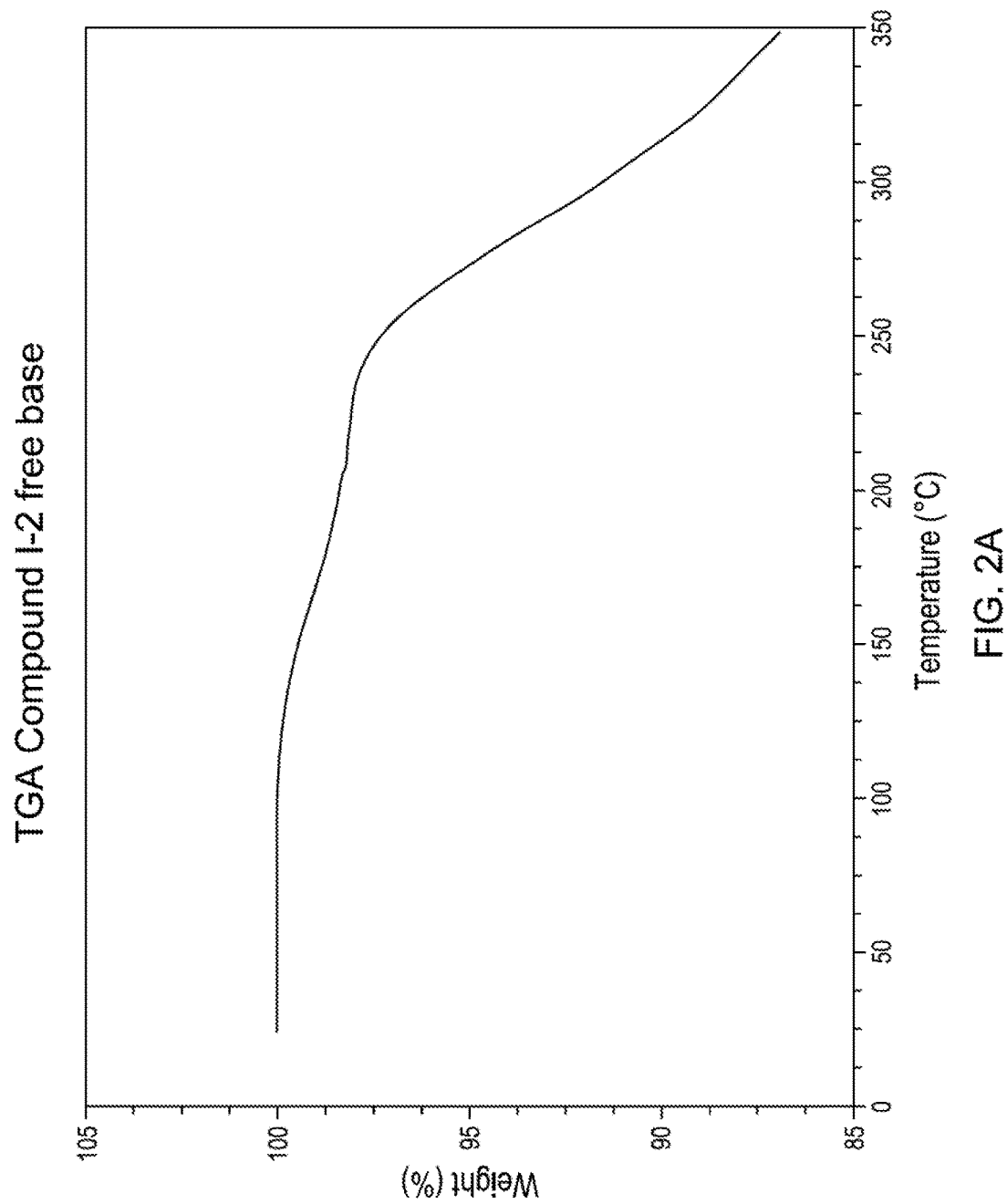
FIG. 2a: TGA Compound I-2 free base

A thermal gravimetric analysis of Compound I-2 free base was performed to determine the percent weight loss as a function of time. The sample was heated from ambient temperature to 350° C. at the rate of 10° C./min on TA Instrument TGA Q5000 (Asset V014258). FIG. 2a shows the TGA result with a one-step weight loss before evaporation or thermal decomposition. From ambient temperature to 215° C., the weight was ~1.9%.

Differential Scanning Calorimetry of Compound I-2 Free Base

Figure 3A:
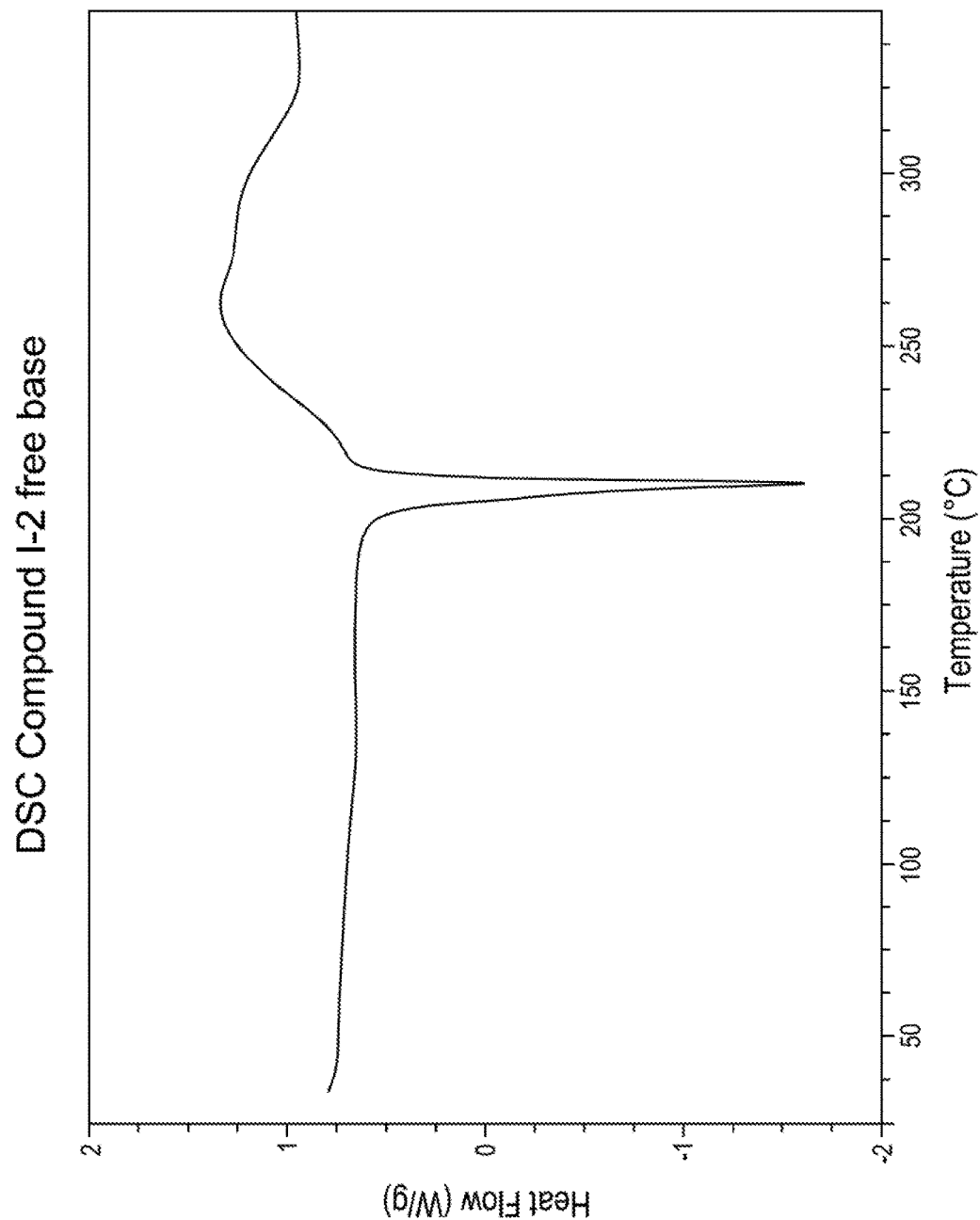
FIG. 3a: DSC Compound I-2 free base
Figure 5A:
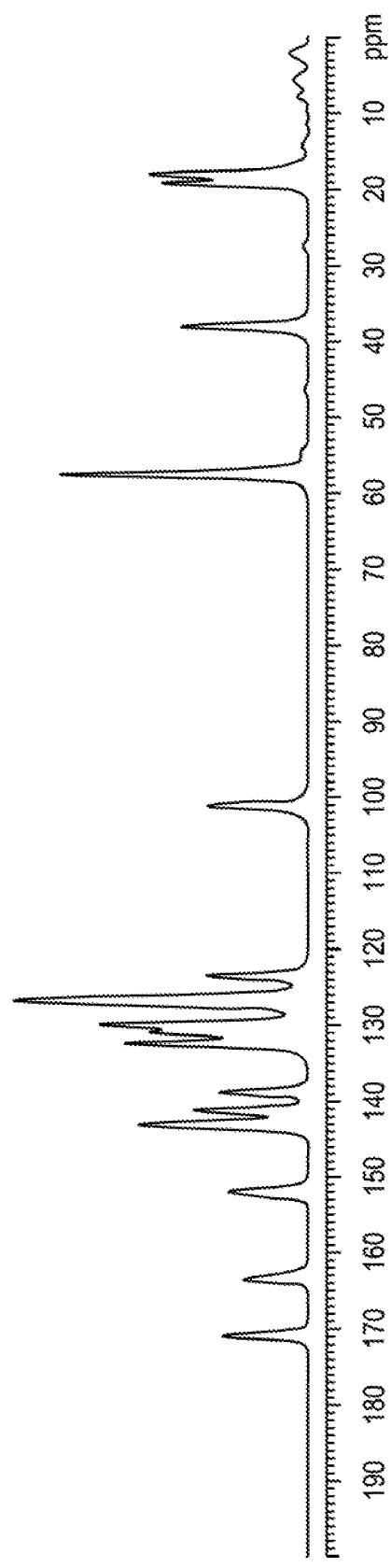
FIG. 5a: Solid State $^{13}$CNMR of Compound I-2 free base

The thermal properties of Compound I-2 free base were measured using the TA Instrument DSC Q2000 (Asset V014259). A Compound I-2 free base sample (1.6900 mg) was weighed in a pre-punched pinhole aluminum hermetic pan and heated from ambient temperature to 350° C. at 10° C./min. One endothermic peak is observed at 210° C. with its onset temperature at 201° C. (FIG. 3a). The enthalpy associated with the endothermic peak is 78 J/g.
Solid State NMR of Compound I-2 free base
13C CPMAS on Compound 1-2 free base
275K; 1H T1=1.30 s
12.5 kHz spinning; ref adamantane 29.5 ppm
For the full spectrum, see FIG. 5a.

| Representative Peaks | | |
|---|---|---|
| Peak # | Chem Shift [ppm] | Intensity [rel] |
| 1* | 171.0 | 28.7 |
| 2 | 163.7 | 21.4 |
| 3* | 152.1 | 26.3 |
| 4 | 143.1 | 57.3 |
| 5* | 141.2 | 38.8 |
| 6 | 138.8 | 30.0 |
| 7 | 132.4 | 62.1 |
| 8 | 130.9 | 52.3 |
| 9 | 130.0 | 70.7 |
| 10* | 126.6 | 100.0 |
| 11 | 123.5 | 34.3 |
| 12 | 101.3 | 34.1 |
| 13 | 57.6 | 84.3 |
| 14* | 38.1 | 42.6 |
| 15* | 19.2 | 48.8 |
| 16 | 18.1 | 53.3 |

Crystal Structure of Compound I-2 Free Base

The free form of Compound I-2 was prepared from the Compound I-2 HCl salt. 200 mg Compound I-2 HCl salt was added to 1 mL of 6N NaOH solution. 20 mL of dichloromethane was used to extract the free form. The dichloromethane layer was dried over $K_2CO_3$. The solution was filtered off and 5 mL of n-heptane was added to it. Crystals were obtained by slow evaporation of the solution at room temperature over night.

Most crystals obtained were thin plates. Some prismatic shape crystals were found among them.

A yellow prismatic crystal with dimensions of 0.2×0.1× 0.1 mm$^3$ was selected, mounted on a MicroMount and centered on a Bruker APEX II diffractometer. Three batches of 40 frames separated in reciprocal space were obtained to provide an orientation matrix and initial cell parameters. Final cell parameters were obtained and refined after data collection was completed based on the full data set.

A diffraction data set of reciprocal space was obtained to a resolution of 116.96° 2θ angle using 0.5° steps with 10 s exposure for each frame. Data were collected at 100 (2) K temperature with a nitrogen flow cryosystem. Integration of intensities and refinement of cell parameters were accomplished using APEXII software.

| CRYSTAL DATA |
|---|
| $C_{24}H_{25}N_5O_3S$ |
| $M_r$ = 463.55 |
| Monoclinic, $P2_1/n$ |
| a = 8.9677 (1) Å |
| b = 10.1871 (1) Å |
| c = 24.5914 (3) Å |
| β = 100.213 (1)° |
| V = 2210.95 (4) Å$^3$ |
| Z = 4 |

Example 11: Compound 1-2.HCl

Compound 1-2.HCl can be formed according to the methods described in Example 6, Step 4: Alternate Method 2 and Example 6, Step 5.
XRPD of Compound I-2.HCl
FIG. 1b shows the X-ray powder diffractogram of the sample which is characteristic of crystalline drug substance.
Representative XRPD peaks from Compound 1-2.HCl

| XRPD Peaks | Angle (2-Theta ± 0.2) | Intensity % |
|---|---|---|
| 1 | 14.4 | 100.0 |
| *2 | 13.5 | 89.1 |
| 3 | 20.9 | 45.8 |
| 4 | 16.4 | 41.9 |
| 5 | 23.6 | 33.8 |
| 6 | 27.2 | 29.6 |
| *7 | 28.8 | 26.0 |
| 8 | 16.8 | 23.3 |
| 9 | 27.6 | 21.3 |
| *10 | 15.0 | 21.1 |
| *11 | 18.8 | 20.8 |
| 12 | 30.5 | 13.3 |
| *13 | 15.4 | 13.0 |
| 14 | 26.9 | 12.7 |

Thermo Analysis of Compound I-2.HCl

Figure 2B:
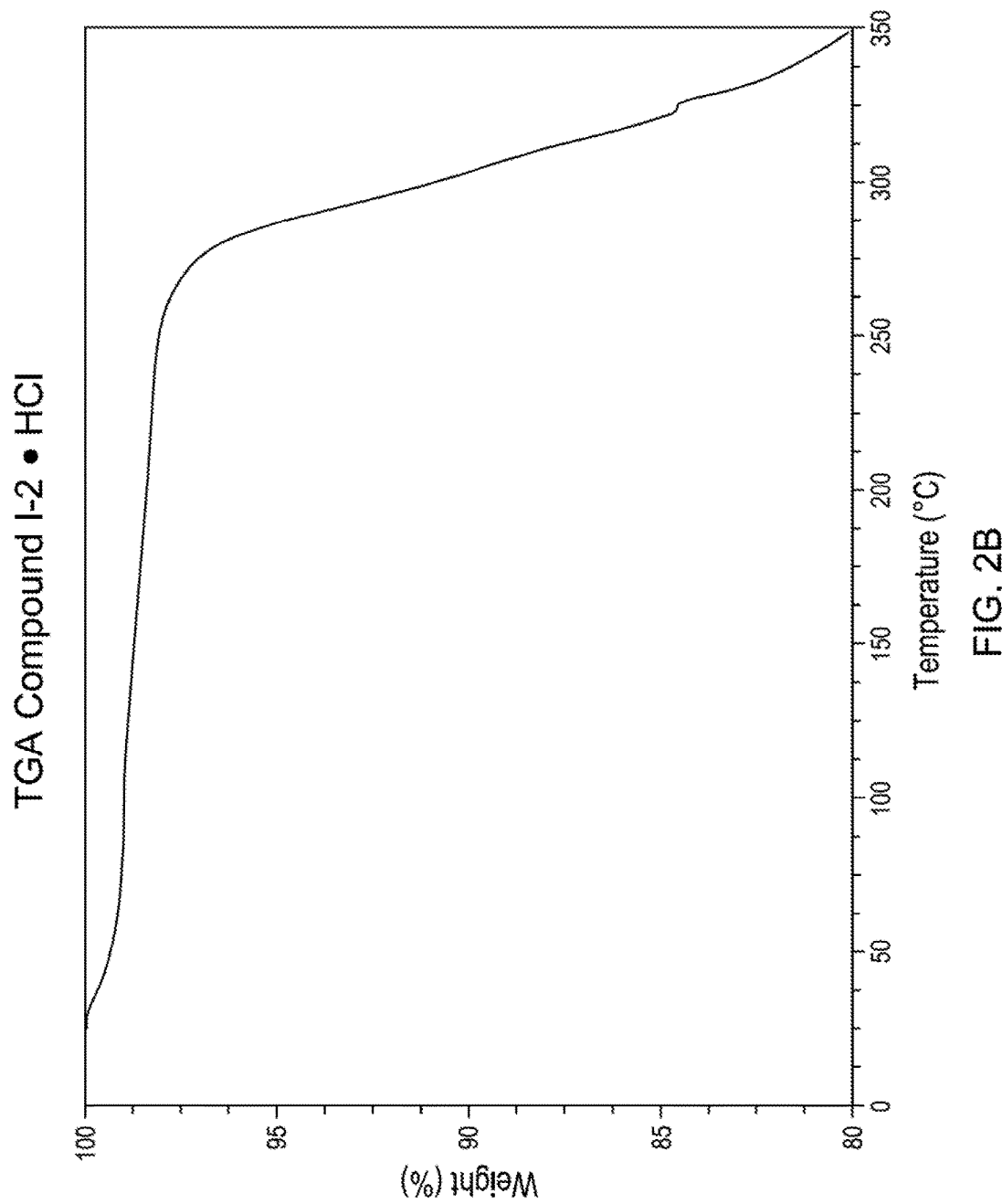
FIG. 2b: TGA Compound I-2.HCl

A thermal gravimetric analysis of Compound I-2.HCl was performed to determine the percent weight loss as a function of time. The sample was heated from ambient temperature to 350° C. at the rate of 10° C./min on TA Instrument TGA Q5000 (Asset V014258). FIG. 2b shows the TGA result with a two-step weight loss before evaporation or thermal decomposition. From ambient temperature to 100° C., the weight was ~1.1%, and from 110° C. to 240° C. the weight loss is ~0.8%.

Differential Scanning Calorimetry of Compound I-2.HCl

Figure 3B:
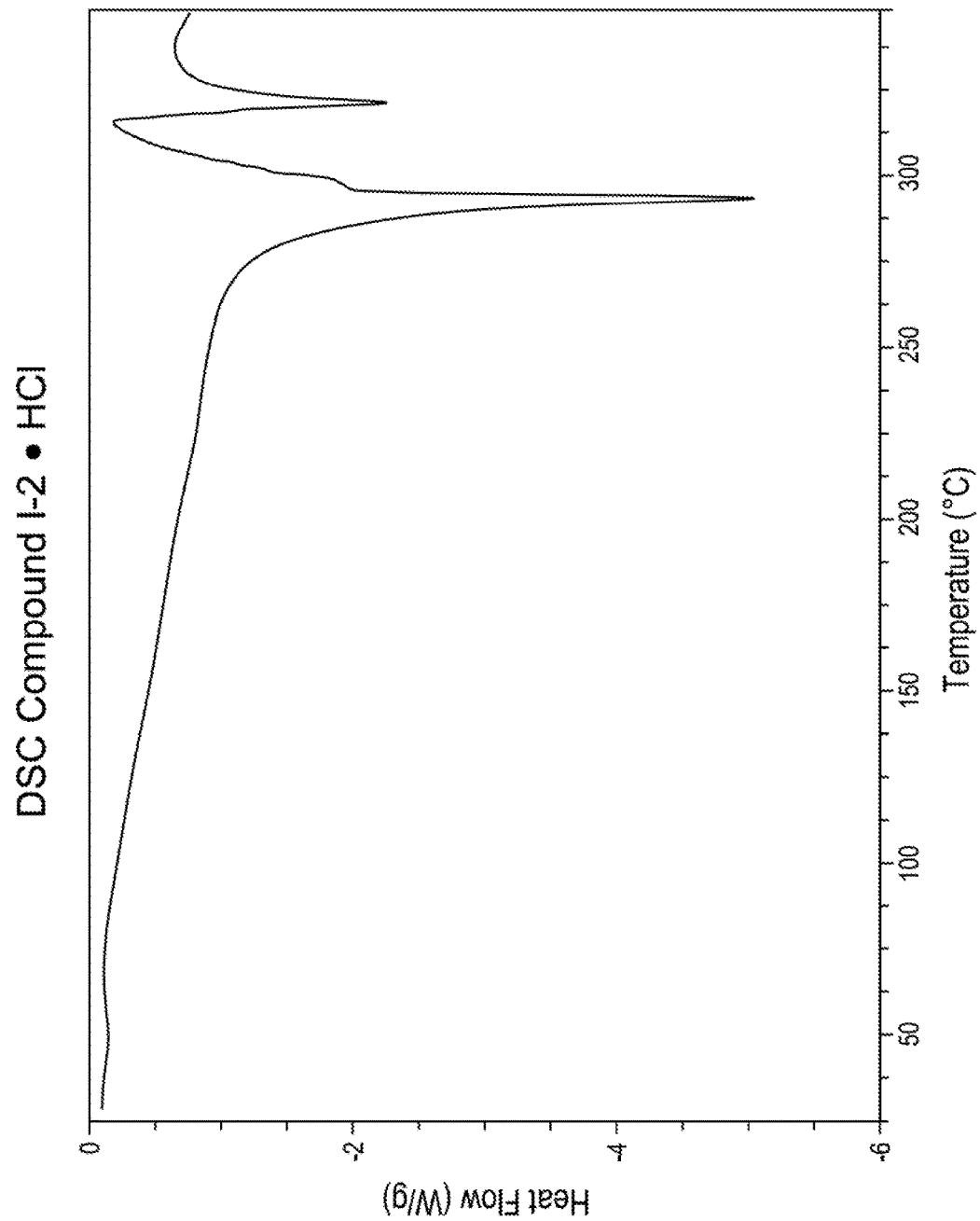
FIG. 3b: DSC Compound I-2.HCl
Figure 5B:
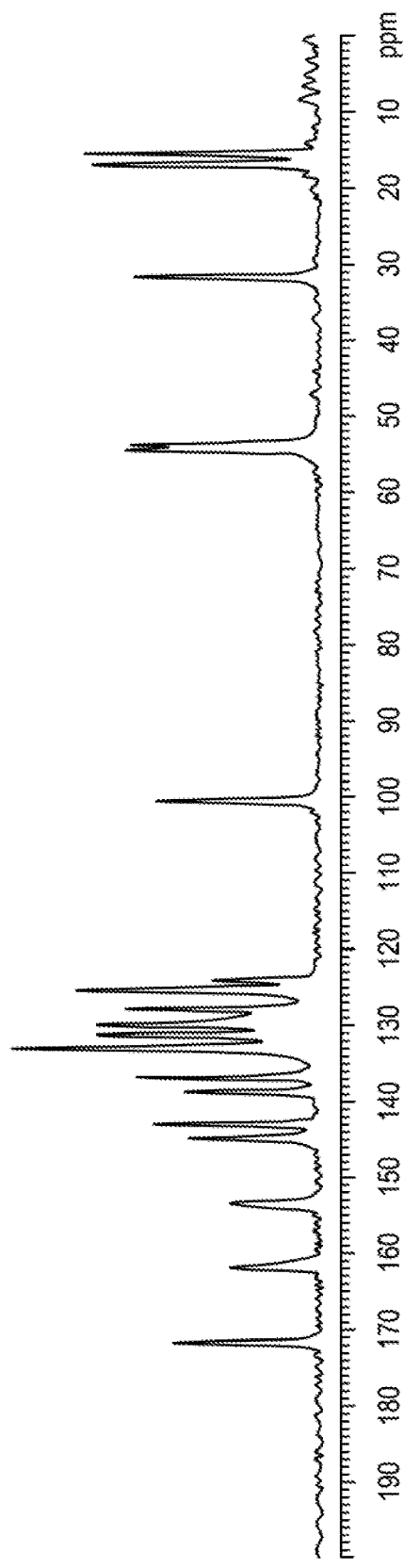
FIG. 5b: Solid State $^{13}$CNMR of Compound I-2.HCl

The thermal properties of Compound I-2.HCl were measured using the TA Instrument DSC Q2000 (Asset V014259). A Compound I-2.HCl sample (3.8110 mg) was weighed in a pre-punched pinhole aluminum hermetic pan and heated from ambient temperature to 350° C. at 10° C./min. One endothermic peak is observed at 293° C. with its onset temperature at 291° C. (FIG. 3b). The enthalpy associated with the endothermic peak is 160.3 J/g. The second endothermic peak is around 321° C. Both peaks were coupled with sample evaporation and decomposition.
Solid State NMR of Compound I-2.HCl
15CPMAS on Compound 1-2.HCl
275K;_12.5 kHz spinning; ref adamantane 29.5 ppm
For the full spectrum, see FIG. 5b.

| Representative Peaks | | |
|---|---|---|
| Peak # | Chem Shift [ppm] | Intensity [rel] |
| 1* | 171.7 | 47.42 |
| 2 | 161.9 | 28.72 |
| 3* | 153.4 | 28.94 |
| 4 | 144.8 | 42.57 |
| 5 | 142.9 | 54.14 |
| 6 | 138.7 | 44.06 |
| 7 | 136.7 | 60.06 |
| 8* | 132.9 | 100 |
| 9 | 131.2 | 72.62 |
| 10 | 129.8 | 73.58 |
| 11 | 127.9 | 63.71 |

-continued

Representative Peaks

| Peak # | Chem Shift [ppm] | Intensity [rel] |
|---|---|---|
| 12 | 125.4 | 79.5 |
| 13 | 124.1 | 34.91 |
| 14 | 100.7 | 53.52 |
| 15 | 54.5 | 62.56 |
| 16 | 53.9 | 61.47 |
| 17* | 31.8 | 61.15 |
| 18 | 17.0 | 74.78 |
| 19* | 15.7 | 77.79 |

Crystal Structure of Compound I-2.HCl 180 mg Compound I-2.HCl was added to a vial with 0.8 mL 2-propanol and 0.2 mL water. The sealed vial was kept in an oven at 70° C. for two weeks. Diffraction quality crystals were observed.

A yellow needle shape crystal with dimensions of 0.15× 0.02×0.02 $mm^3$ was selected, mounted on a MicroMount and centered on a Bruker APEX II diffractometer (V011510). Three batches of 40 frames separated in reciprocal space were obtained to provide an orientation matrix and initial cell parameters. Final cell parameters were collected and refined was completed based on the full data set.

A diffraction data set of reciprocal space was obtained to a resolution of 106° 2θ angle using 0.5° steps with exposure times 20 s each frame for low angle frames and 60 s each frame for high angle frames. Data were collected at room temperature.

To obtain the data in table 1, dry nitrogen was blown to the crystal at 6 Liter/min speed to keep the ambient moisture out. Data in table 2 was obtained without nitrogen. Integration of intensities and refinement of cell parameters were conducted using the APEXII software. The water occupancy can vary between 0 and 1.

TABLE 1

$C_{24}H_{26}ClN_5O_3S$ $M_r$ = 500.01
Monoclinic, $P2_1/n$
a = 5.3332 (2) Å
b = 35.4901 (14) Å
c = 13.5057 (5) Å
β = 100.818 (2)°
V = 2510.87 (17) Å$^3$

TABLE 2

$C_{24}H_{28}ClN_5O_4S$

Mr = 518.02
Monoclinic, P21/n
a = 5.4324 (5) Å
b = 35.483 (4) Å
c = 13.3478 (12) Å
β = 100.812 (5)°
V = 2527.2 (4) Å$^3$ CHN Elemental Analysis CHN elemental analysis of Compound I-2.HCl suggest a mono HCl salt.

| Element | C | H | N | Cl |
|---|---|---|---|---|
| % Theory $C_{24}H_{25}N_5O3S \cdot HCl$ | 57.60 | 5.20 | 14.00 | 7.10 |
| % Found | 56.52 | 5.38 | 13.69 | 7.18 |

Example 12: Compound I-2.2HCl

Compound I-2.2HCl can be formed according to the methods described in Example 6, Step 4.

XRPD of Compound I-2.2HCl

The XRPD patterns are acquired at room temperature in reflection mode using a Bruker D8 Discover system (Asset Tag V012842) equipped with a sealed tube source and a Hi-Star area detector (Bruker AXS, Madison, Wis.). The X-Ray generator is operated at a voltage of 40 kV and a current of 35 mA. The powder sample is placed in a nickel holder. Two frames are registered with an exposure time of 120 s each. The data is subsequently integrated over the range of 4.5°-39° 2θ with a step size of 0.02° and merged into one continuous pattern.

Figure 1C:
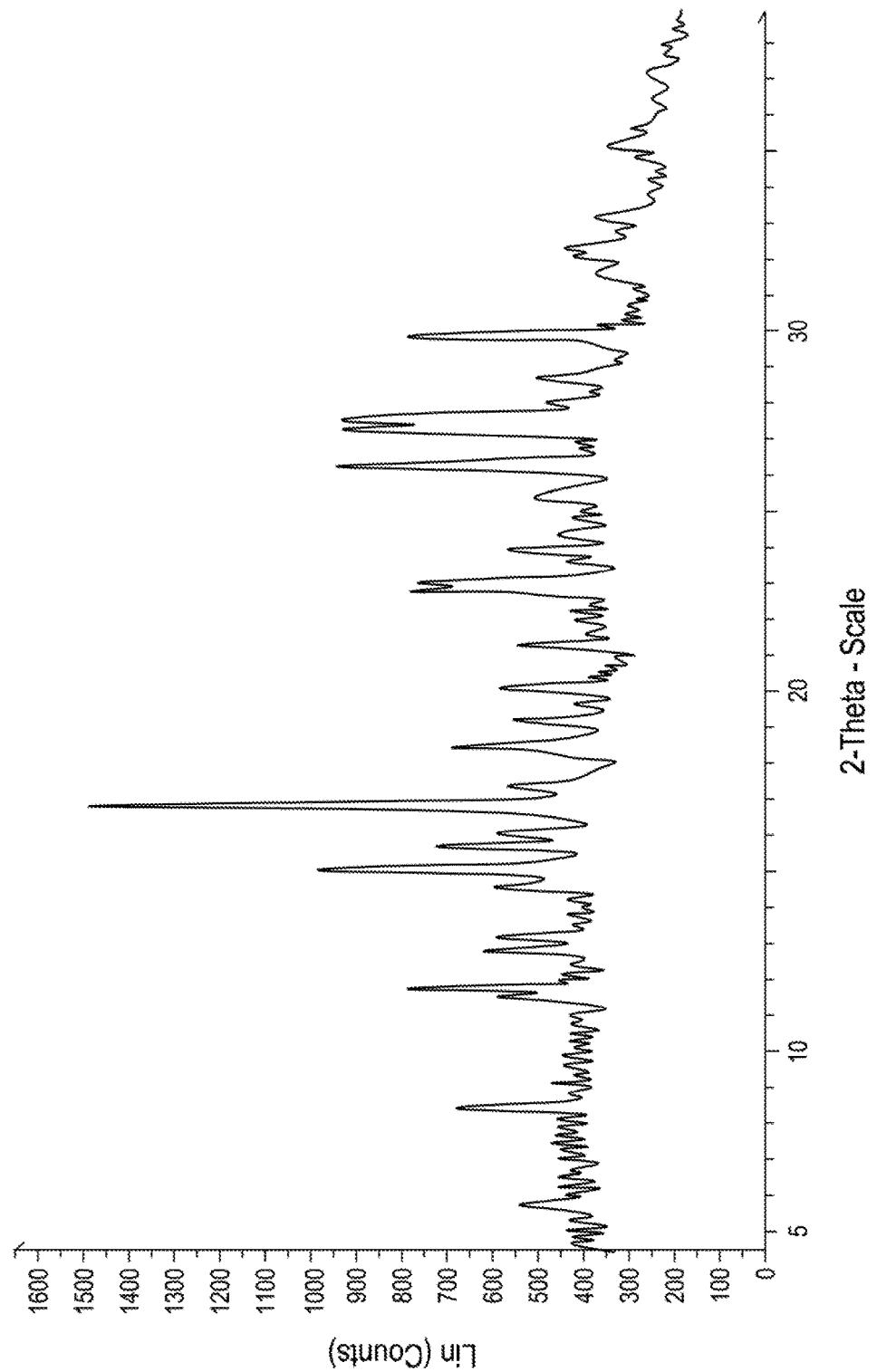
FIG. 1c: XRPD Compound I-2.2HCl

FIG. 1c shows the X-ray powder diffractogram of the sample which is characteristic of crystalline drug substance.

Representative XRPD peaks from Compound I-2.2HCl

| XRPD Peaks | Angle (2-Theta ± 0.2) | Intensity % |
|---|---|---|
| 1 | 16.8 | 100.0 |
| *2 | 15.1 | 92.2 |
| 3 | 26.2 | 91.3 |
| 4 | 27.5 | 91.3 |
| 5 | 27.2 | 91.2 |
| 6 | 11.8 | 89.0 |
| 7 | 29.8 | 89.0 |
| 8 | 22.8 | 88.8 |
| 9 | 15.7 | 88.1 |
| *10 | 18.5 | 87.5 |
| 11 | 8.4 | 87.4 |
| 12 | 12.8 | 86.6 |
| *13 | 11.5 | 86.0 |
| 14 | 14.6 | 86.0 |
| 15 | 20.1 | 86.0 |
| *16 | 13.1 | 85.9 |
| 17 | 16.0 | 85.9 |
| 18 | 17.3 | 85.7 |
| 19 | 23.9 | 85.7 |
| 20 | 19.2 | 85.4 |
| *21 | 5.7 | 85.2 |
| 22 | 21.3 | 85.2 |
| 23 | 25.3 | 84.9 |
| 24 | 28.7 | 84.7 |
| 25 | 24.3 | 84.1 |

Thermo Analysis of Compound I-2.2HCl

Figure 2C:
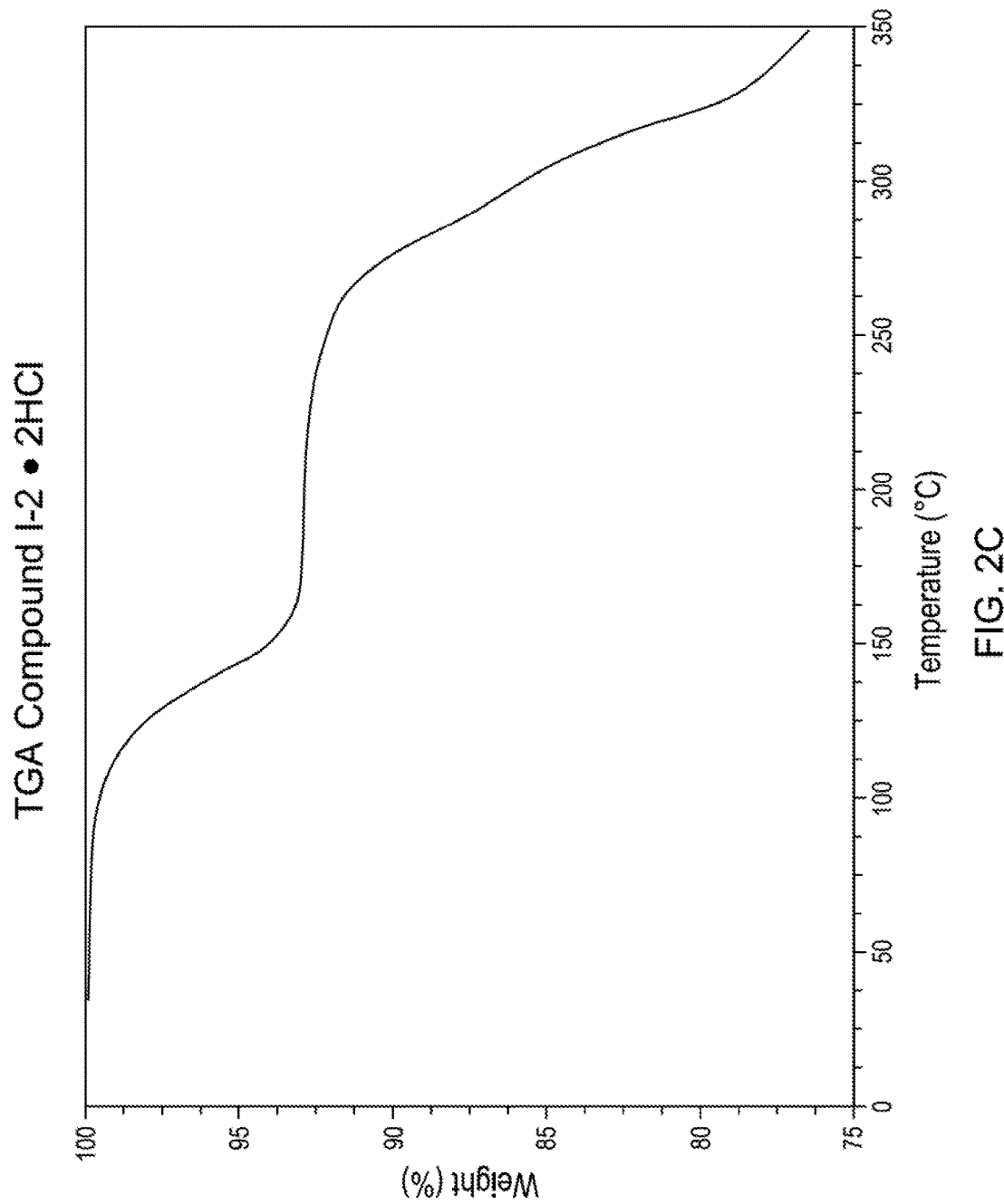
FIG. 2c: TGA Compound I-2.2HCl

A thermal gravimetric analysis of Compound I-2.2HCl was performed on the TA Instruments TGA model Q5000. Compound I-2.2HCl was placed in a platinum sample pan and heated at 10° C./min to 350° C. from room temperature. FIG. 2c shows the TGA result, which demonstrates a weight loss of 7.0% from room temperature to 188° C., which is consistent with the loss of 1 equivalent of HCl (6.8%). The onset temperature of degradation/melting is 263° C.

Differential Scanning Calorimetry of Compound I-2.2HCl

Figure 3C:
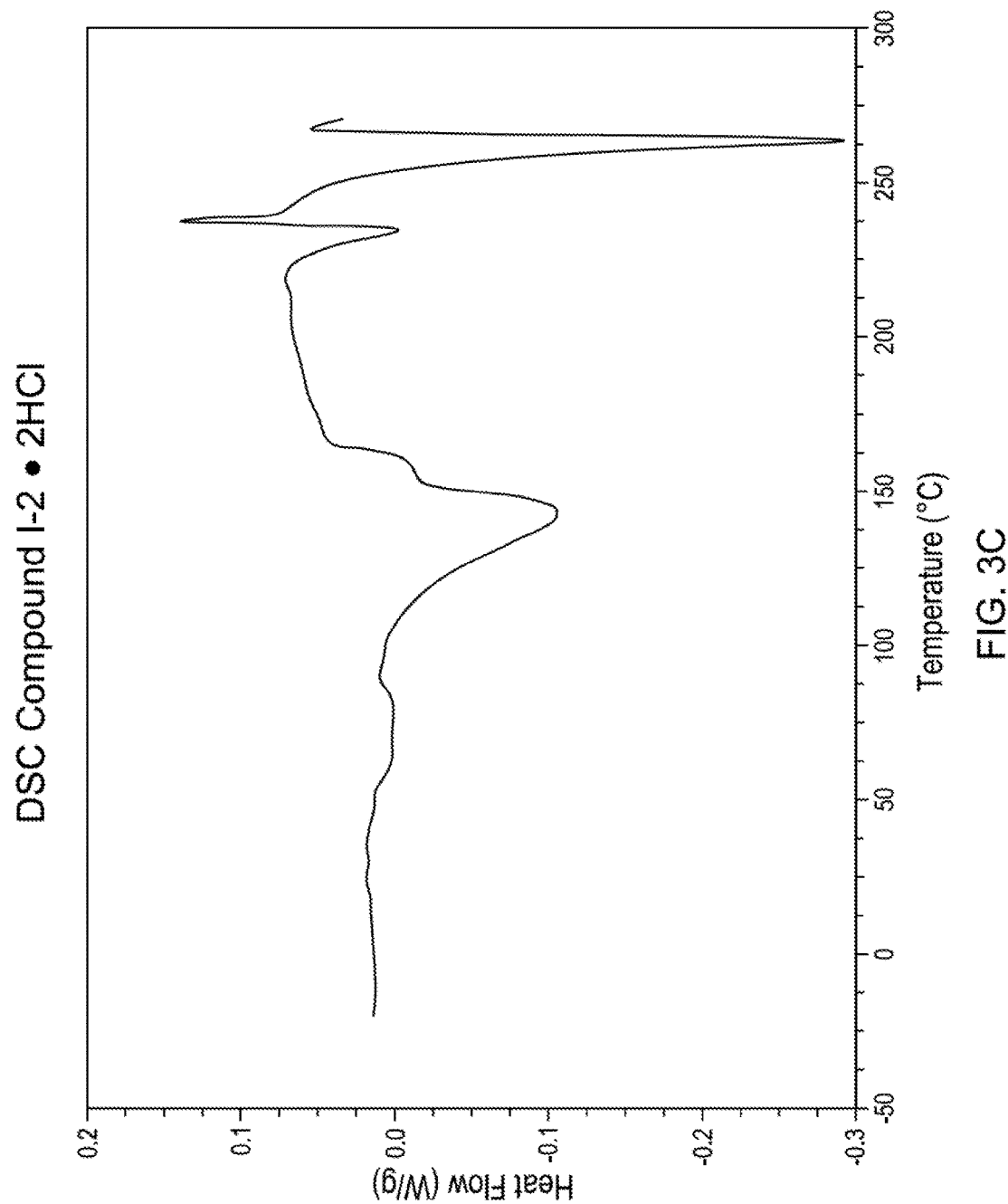
FIG. 3c: DSC Compound I-2.2HCl

A DSC thermogram for Compound I-2.2HCl drug substance lot 3 was obtained using TA Instruments DSC Q2000. Compound I-2.2HCl was heated at 2° C./min to 275° C. from −20° C., and modulated at ±1° C. every 60 sec. The DSC thermogram (FIG. 3c) reveals an endothermic peak below 200° C., which could corresponds to the loss of 1 equivalent of HCl. Melting/recrystallization occurs between 215-245° C., followed by degradation.

Figure 4A:
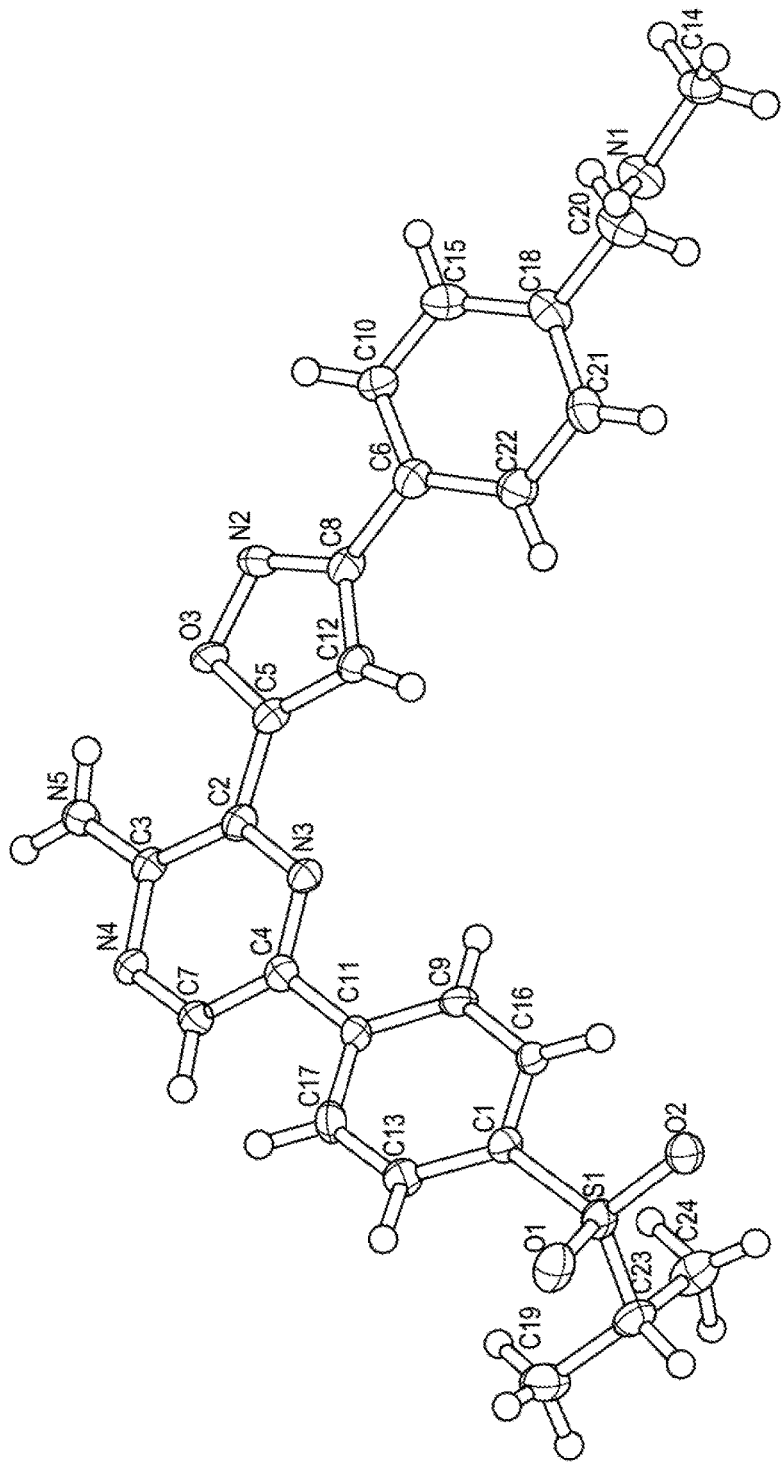
FIG. 4a: ORTEP plot of the asymmetric unit of the Compound 1-2 free form single crystal structure
Figure 4B:
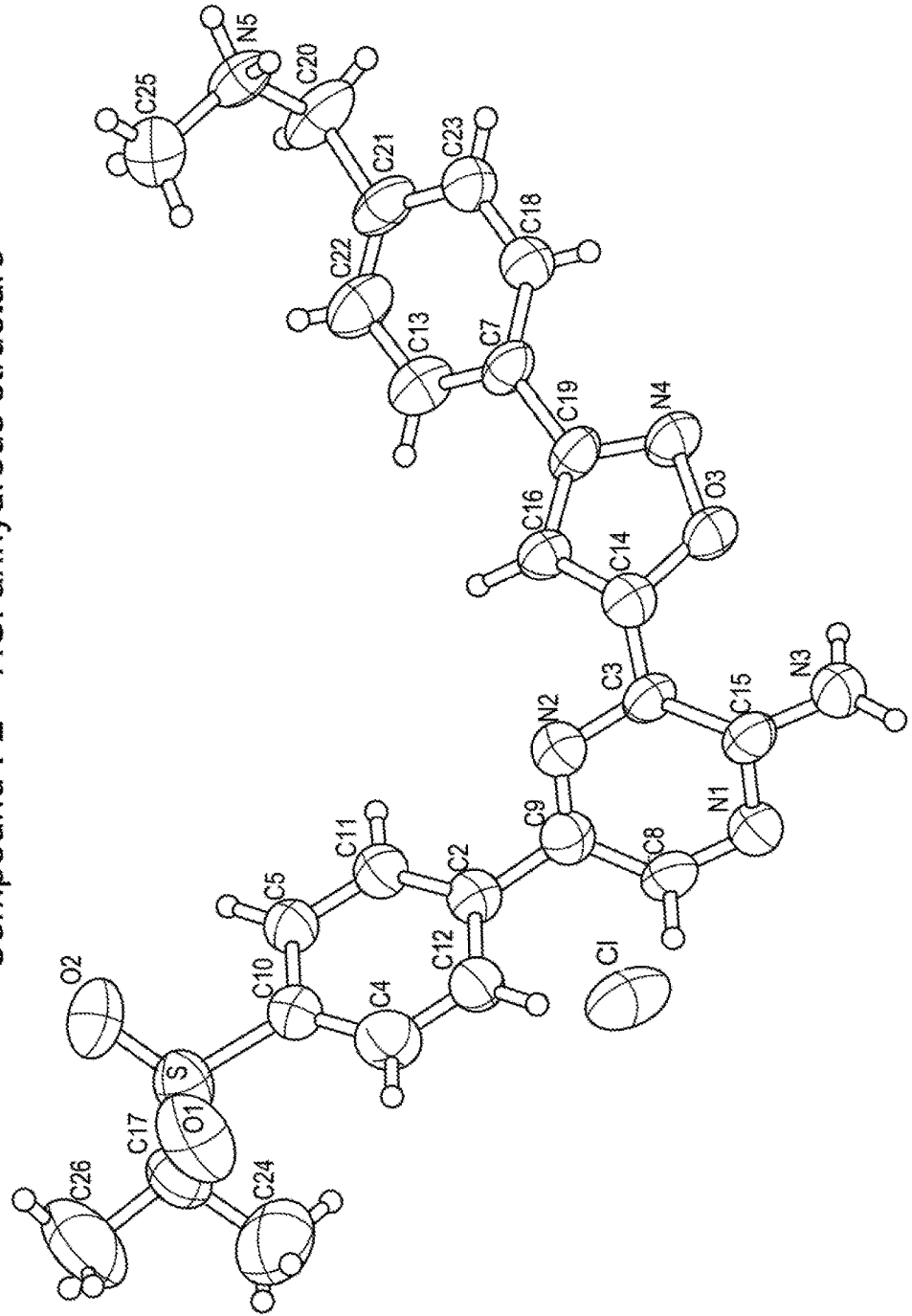
FIG. 4b: ORTEP plot of the asymmetric unit of the Compound I-2.HCl anhydrous structure.
Figure 4C:
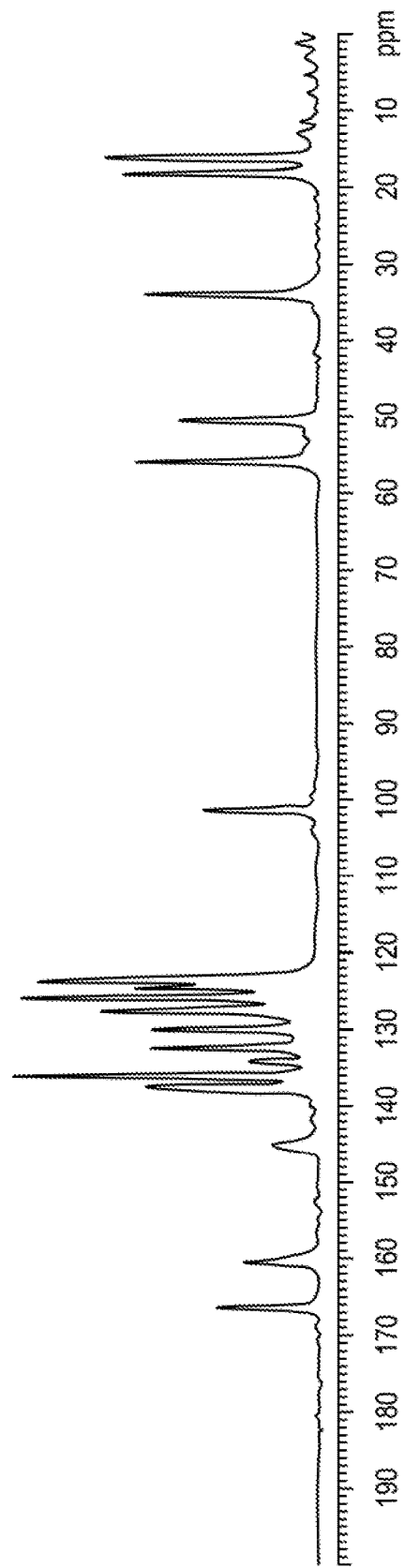
FIG. 4c: Solid State $^{13}$CNMR of Compound I-2.2HCl

Solid State NMR of Compound I-2.2HCl
$^{13}$C CPMAS on Compound I-2.2HCl
275K; 1H T1=1.7 s
12.5 kHz spinning; ref. adamantane 29.5 ppm
For the full spectrum, see FIG. 4c

| Peak # | Chem Shift [ppm] | Intensity [rel] |
|---|---|---|
| 1* | 166.5 | 32.6 |
| 2 | 160.7 | 24.7 |
| 3 | 145.3 | 15.0 |
| 4* | 137.6 | 56.0 |
| 5* | 136.1 | 100.0 |
| 6 | 134.2 | 22.7 |
| 7 | 132.4 | 55.9 |
| 8 | 130.0 | 54.9 |
| 9 | 127.7 | 70.7 |
| 10 | 125.9 | 97.1 |
| 11 | 124.7 | 59.0 |
| 12 | 123.8 | 91.4 |
| 13 | 123.2 | 56.0 |
| 14 | 101.6 | 37.7 |
| 15 | 56.1 | 60.3 |
| 16 | 50.7 | 45.6 |
| 17* | 34.2 | 56.8 |
| 18 | 18.4 | 63.5 |
| 19* | 16.4 | 70.32 |

Crystal Structure of Compound I-2.2HCl 180 mg Compound I-2.HCl was added to a vial with 0.8 mL 2-propanol and 0.2 mL water. The sealed vial was kept in an oven at 70° C. for two weeks. Diffraction quality crystals were observed.

A yellow needle shape crystal with dimensions of 0.15× 0.02×0.02 mm$^3$ was selected, mounted on a MicroMount and centered on a Bruker APEX II diffractometer (V011510). Three batches of 40 frames separated in reciprocal space were obtained to provide an orientation matrix and initial cell parameters. Final cell parameters were collected and refined was completed based on the full data set.

A diffraction data set of reciprocal space was obtained to a resolution of 106° 2θ angle using 0.5° steps with exposure times 20 s each frame for low angle frames and 60 s each frame for high angle frames. Data were collected at room temperature. Dry nitrogen was blown to the crystal at 6 Liter/min speed to keep the ambient moisture out. Integration of intensities and refinement of cell parameters were conducted using the APEXII software.

| CRYSTAL DATA |
|---|
| $C_{24}H_{26}ClN_5O_3S$ |
| $M_r$ = 500.01 |
| Monoclinic, $P2_1/n$ |
| a = 5.3332 (2) Å |
| b = 35.4901 (14) Å |
| c = 13.5057 (5) Å |
| β = 100.818 (2)° |
| V = 2510.87 (17) Å$^3$ |

Example 13: Compound I-2.HCl.H$_2$O

Compound I-2.HCl.H$_2$O can be formed from Compound I-2.2 HCl. (E29244-17) A suspension of Compound I-2.2 HCl (10.0 g, 18.6 mmol) in isopropyl alcohol (40 mL) and water (10 mL) is warmed at 50° C. for about 1 h and then cooled to below 10° C. The solid is collected by filtration. The filter-cake is washed with 80/20 isopropyl alcohol/water (2×10 mL) and air-dried to afford Compound I-2.HCl.2H$_2$O as a yellow powder.

XRPD of Compound I-2.HCl.H$_2$O

The XRPD patterns are acquired at room temperature in reflection mode using a Bruker D8 Discover system (Asset Tag V012842) equipped with a sealed tube source and a Hi-Star area detector (Bruker AXS, Madison, Wis.). The X-Ray generator is operated at a voltage of 40 kV and a current of 35 mA. The powder sample is placed in a nickel holder. Two frames are registered with an exposure time of 120 s each. The data is subsequently integrated over the range of 4.5°-39° 2 θtheta with a step size of 0.02° and merged into one continuous pattern.

Figure 1D:
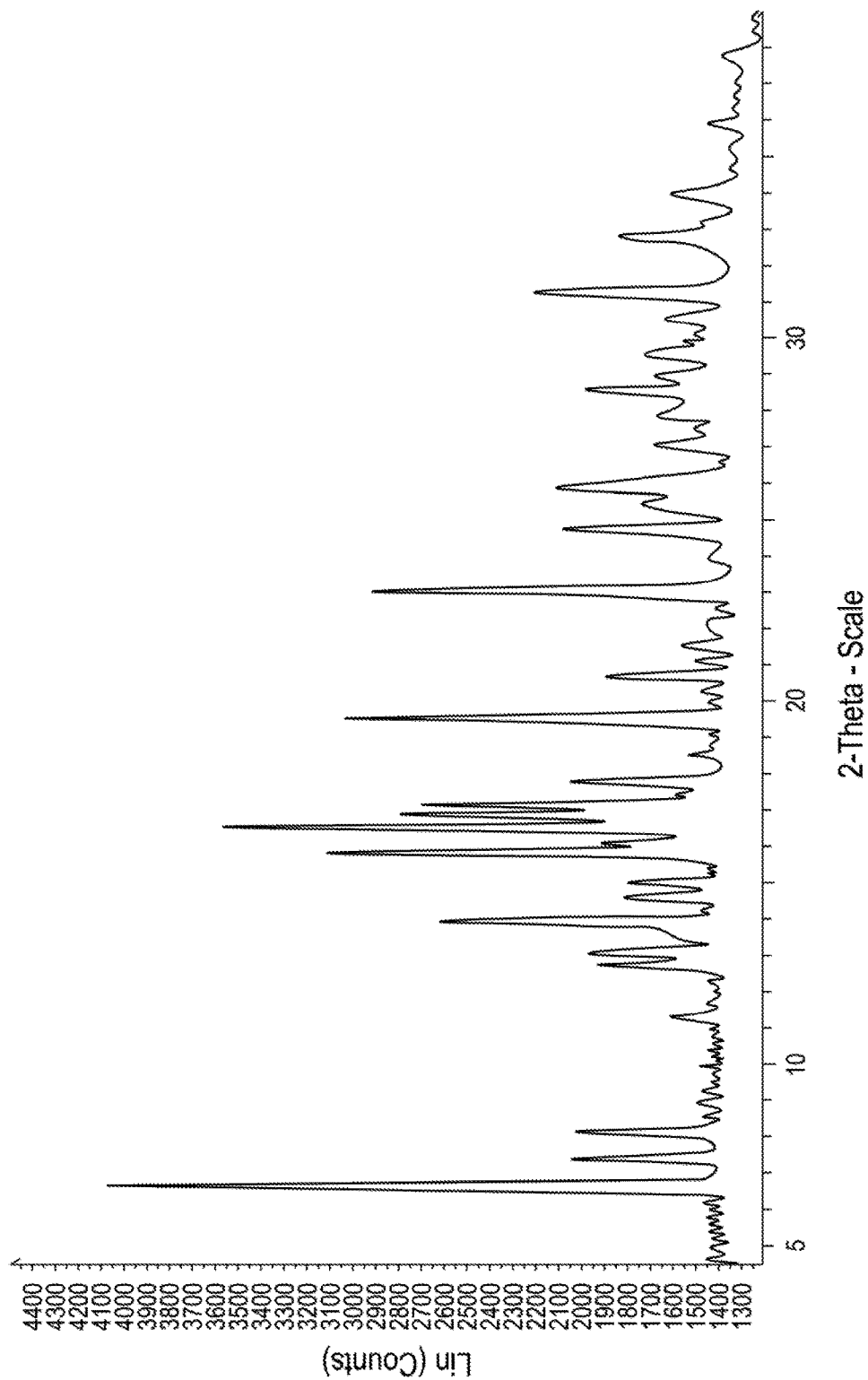
FIG. 1d: XRPD Compound I-2.HCl monohydrate
Figure 1E:
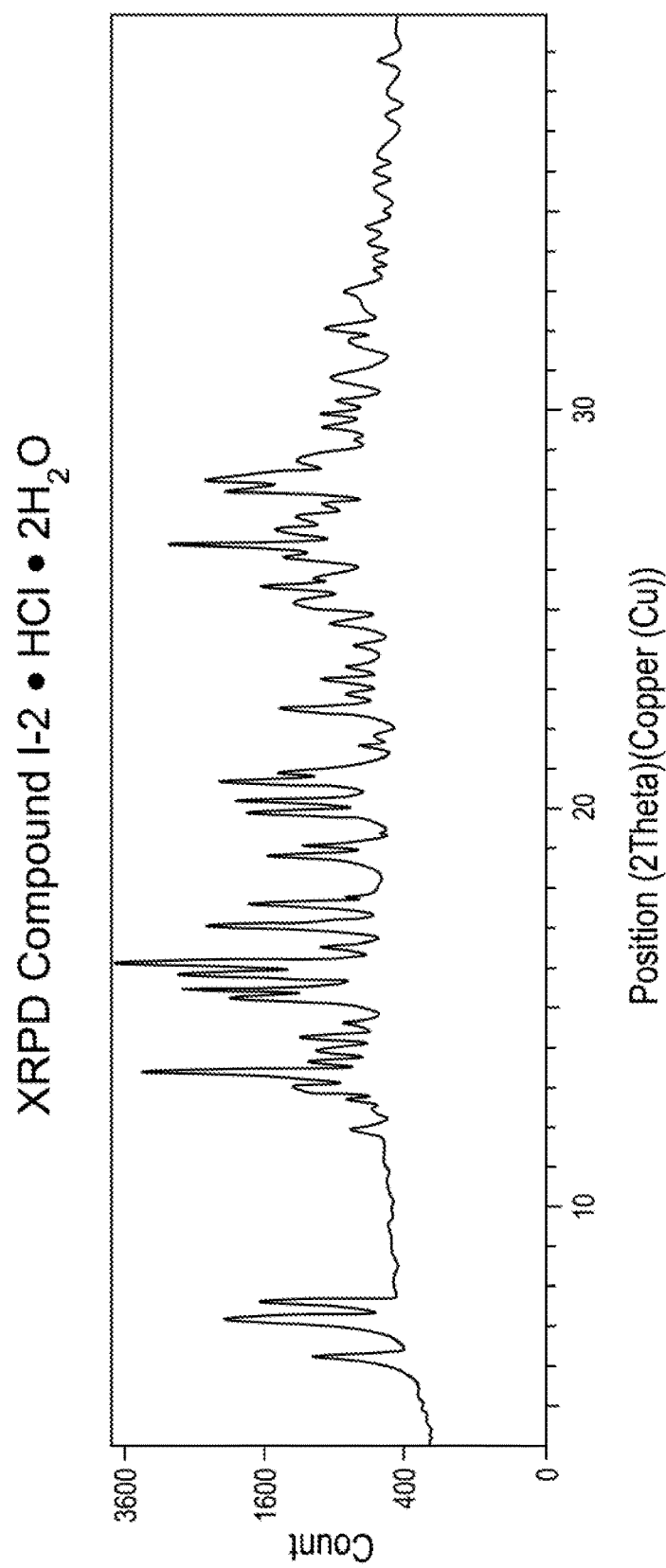
FIG. 1e: XRPD Compound I-2.HCl.2H$_2$O

FIG. 1d shows the X-ray powder diffractogram of the sample which is characteristic of crystalline drug substance.

Representative XRPD peaks from Compound I-2.HCl.H$_2$O

| XRPD Peaks | Angle (2-Theta ± 0.2) | Intensity % |
|---|---|---|
| *1 | 6.6 | 100.0 |
| *2 | 19.5 | 46.5 |
| 3 | 16.8 | 37.8 |
| 4 | 22.9 | 36.0 |
| 5 | 13.9 | 27.0 |
| 6 | 7.3 | 23.4 |
| 7 | 13.0 | 22.7 |
| 8 | 16.5 | 21.2 |
| *9 | 24.7 | 20.9 |
| 10 | 17.7 | 20.8 |
| 11 | 31.1 | 19.6 |
| 12 | 15.8 | 19.3 |
| *13 | 8.1 | 18.5 |
| 14 | 17.1 | 18.4 |
| 15 | 12.7 | 17.2 |
| 16 | 16.0 | 17.2 |
| 17 | 14.5 | 16.5 |
| 18 | 20.6 | 16.0 |
| 19 | 32.7 | 15.5 |
| *20 | 11.2 | 15.2 |
| 21 | 33.9 | 11.3 |

Thermo Analysis of Compound I-2.HCl.H$_2$O

Figure 2D:
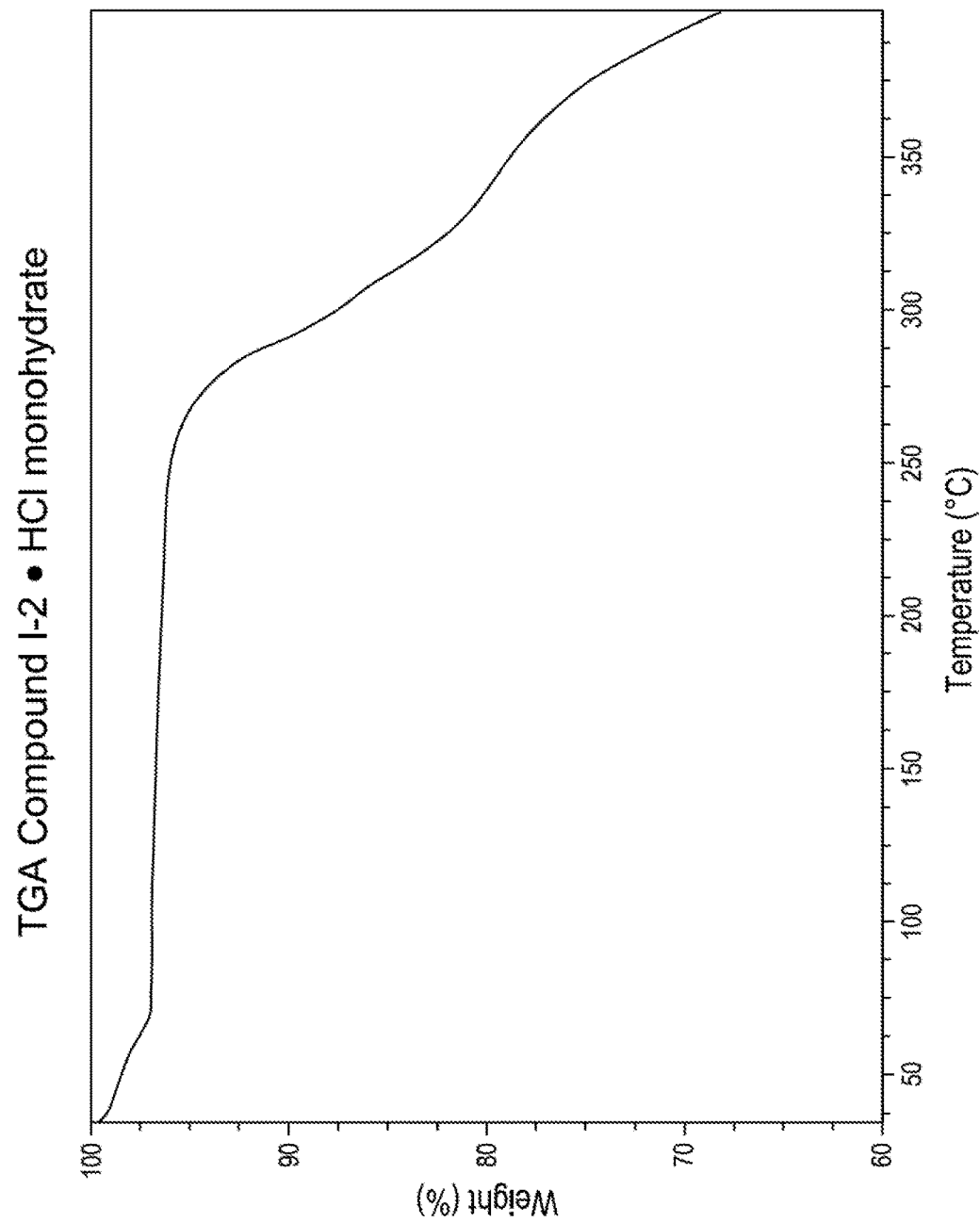
FIG. 2d: TGA Compound I-2.HCl monohydrate
Figure 2E:
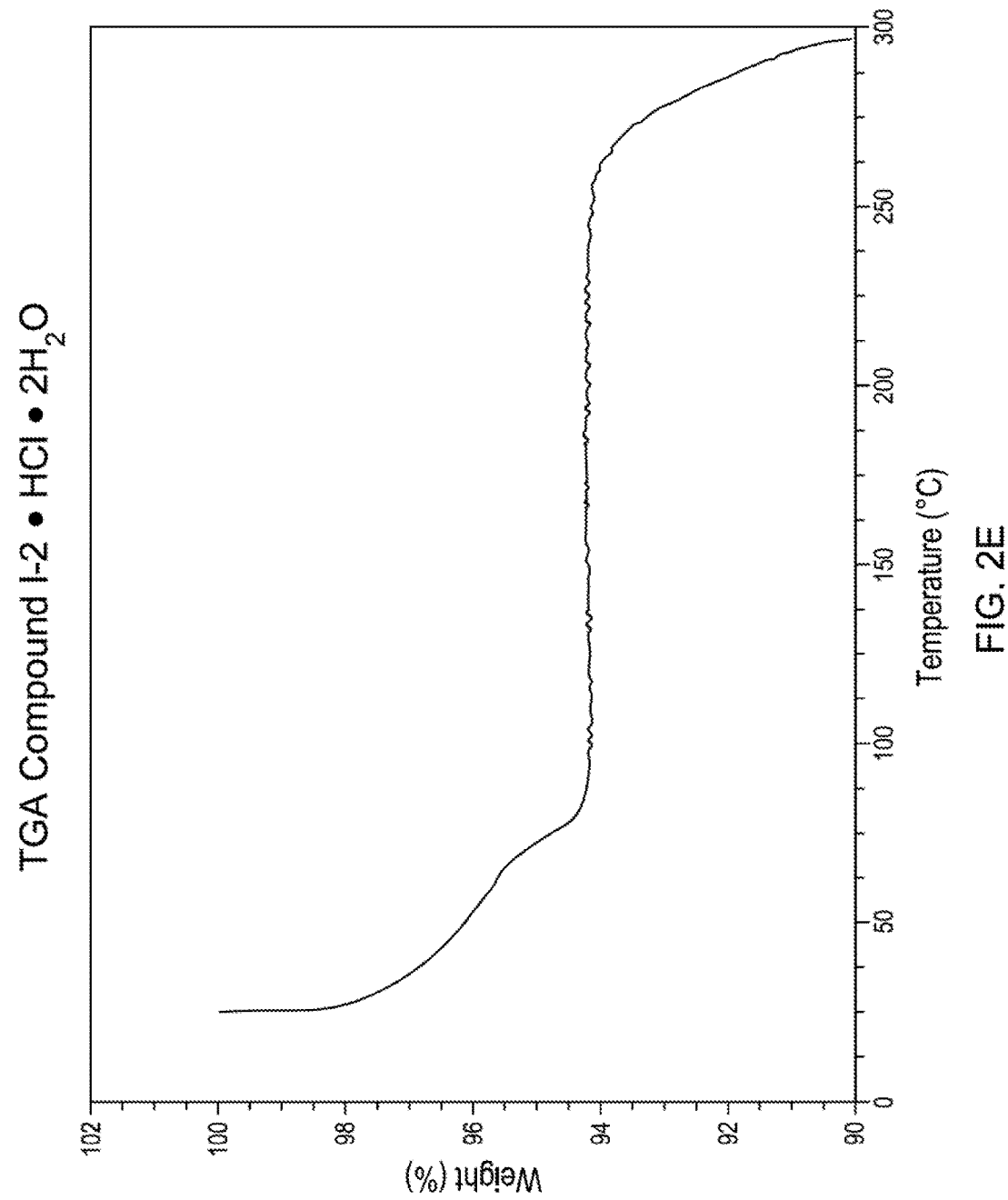
FIG. 2e: TGA Compound I-2.HCl.2H$_2$O

Thermogravimetric analysis (TGA) for Compound I-2.HCl.H$_2$O was performed on the TA Instruments TGA model Q5000. Compound I-2.HCl.H$_2$O was placed in a platinum sample pan and heated at 10° C./min to 400° C. from room temperature. The thermogram (FIG. 2d) demonstrates a weight loss of 2.9% from room temperature to 100° C., and a weight loss of 0.6% from 100° C. to 222° C., which is consistent with theoretical monohydrate (3.5%).

Differential Scanning Calorimetry of Compound I-2.HCl.H$_2$O

Figure 3D:
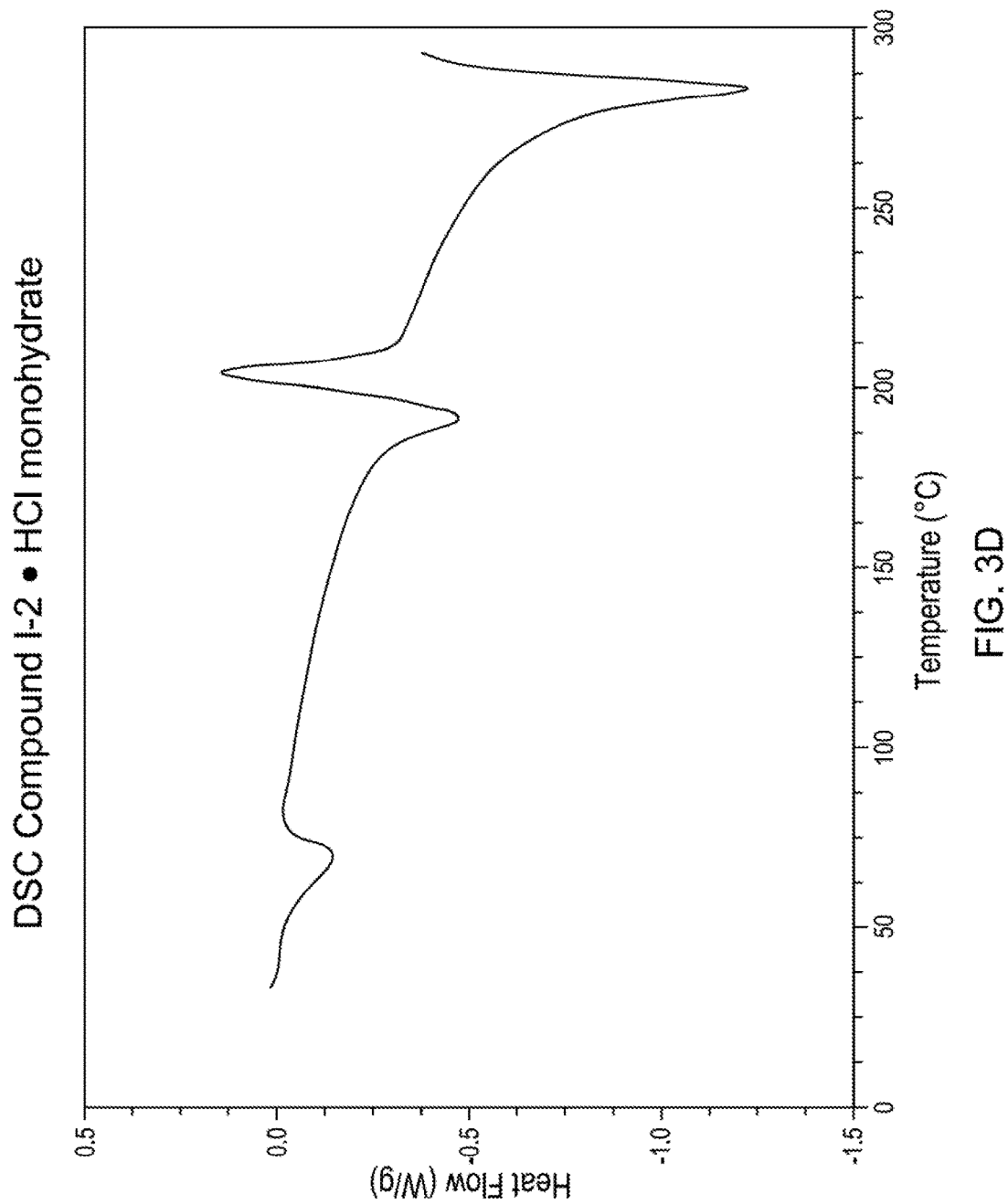
FIG. 3d: DSC Compound I-2.HCl monohydrate
Figure 3E:
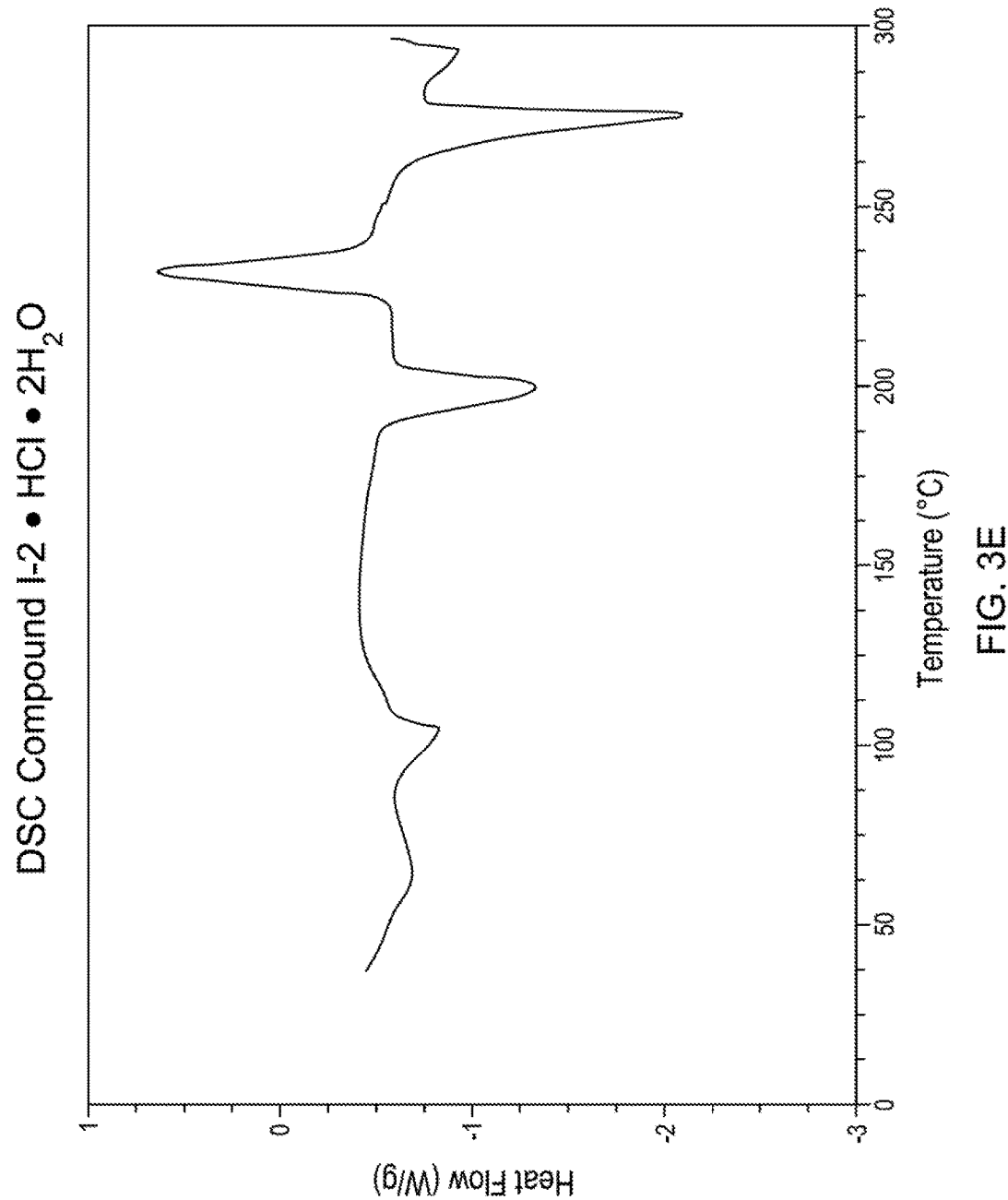
FIG. 3e: DSC Compound I-2.HCl.2H$_2$O

A DSC thermogram for Compound I-2.HCl.H$_2$O was obtained using TA Instruments DSC Q2000. Compound I-2.HCl.H$_2$O was heated at 2° C./min to 275° C. from −20° C., and modulated at ±1° C. every 60 sec. The DSC thermogram (FIG. 3d) reveals an endothermic peak below 200° C., which could corresponds to the loss of 1 equivalent of HCl. Melting/recrystallization occurs between 215-245° C., followed by degradation.

Example 14: Compound I-2.HCl.2H$_2$O

Compound I-2.HCl.2H$_2$O can be formed from Compound I-2.2 HCl. (E29244-17) A suspension of Compound I-2.2

HCl (10.0 g, 18.6 mmol) in isopropyl alcohol (40 mL) and water (10 mL) is warmed at 50° C. for about 1 h and then cooled to below 10° C. The solid is collected by filtration. The filter-cake is washed with 80/20 isopropyl alcohol/water (2×10 mL) and air-dried to afford Compound I-2.HCl.2H$_2$O as a yellow powder.

XRPD of Compound I-2.HCl.2H$_2$O

The powder x-ray diffraction measurements were performed using PANalytical's X-pert Pro diffractometer at room temperature with copper radiation (1.54060° A). The incident beam optic was comprised of a variable divergence slit to ensure a constant illuminated length on the sample and on the diffracted beam side, a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

FIG. 1d shows the X-ray powder diffractogram of the sample which is characteristic of crystalline drug substance.

Representative XRPD peaks from Compound I-2.HCl.2H$_2$O

| XRPD Peaks | Angle (2-Theta ± 0.2) | Intensity % |
|---|---|---|
| 1 | 16.2 | 100.0 |
| 2 | 13.4 | 82.0 |
| *3 | 26.6 | 69.2 |
| 4 | 15.9 | 66.3 |
| 5 | 15.5 | 63.8 |
| 6 | 17.1 | 55.3 |
| 7 | 28.3 | 55.3 |
| 8 | 7.2 | 51.8 |
| 9 | 20.7 | 49.7 |
| 10 | 15.3 | 46.2 |
| 11 | 20.2 | 44.6 |
| 12 | 28.0 | 41.2 |
| 13 | 19.9 | 40.4 |
| 14 | 17.6 | 39.1 |
| 15 | 26.3 | 39.0 |
| *16 | 7.6 | 36.1 |
| 17 | 27.3 | 33.6 |
| 18 | 25.6 | 33.5 |
| 19 | 18.8 | 32.2 |
| 20 | 27.0 | 29.1 |
| 21 | 20.8 | 28.7 |
| 22 | 22.5 | 28.0 |
| 23 | 13.0 | 23.8 |
| *24 | 6.3 | 22.6 |
| 25 | 25.2 | 22.6 |
| 26 | 14.3 | 22.4 |
| 27 | 19.1 | 20.8 |
| 28 | 25.1 | 19.7 |
| 29 | 13.7 | 19.0 |
| 30 | 14.0 | 17.4 |
| 31 | 33.0 | 16.2 |
| *32 | 23.3 | 15.7 |
| 33 | 16.6 | 15.1 |
| 34 | 29.6 | 14.9 |
| 35 | 29.9 | 14.8 |
| 36 | 27.6 | 14.8 |
| 37 | 32.1 | 13.3 |
| *38 | 24.6 | 13.1 |
| 39 | 30.8 | 11.1 |

Thermo Analysis of Compound I-2.HCl.2H$_2$O

The TGA (Thermogravimetric Analysis) thermographs were obtained using a TA instrument TGA Q500 respectively at a scan rate of 10° C./min over a temperature range of 25-300° C. For TGA analysis, samples were placed in an open pan. The thermogram demonstrates a weight loss of ~6 from room temperature to 100° C., which is consistent with theoretical dihydrate (6.7%).

Differential Scanning Calorimetry of Compound I-2.HCl.2H$_2$O

A DSC (Differential Scanning Calorimetry) thermographs were obtained using a TA instruments DSC Q2000 at a scan rate of 10° C./min over a temperature range of 25-300° C. For DSC analysis, samples were weighed into aluminum hermetic T-zero pans that were sealed and punctured with a single hole. The DSC thermogram reveals dehydration between room temperature and 120° C. followed by melting/recrystallization between 170-250° C.

Crystal Structure of Compound I-2.HCl with Water 180 mg Compound I-2.HCl was added to a vial with 0.8 mL 2-propanol and 0.2 mL water. The sealed vial was kept in an oven at 70° C. for two weeks. Diffraction quality crystals were observed.

A yellow needle shape crystal with dimensions of 0.15× 0.02×0.02 mm$^3$ was selected, mounted on a MicroMount and centered on a Bruker APEX II diffractometer (V011510). Then a kapton tube with water inside covered the pin. The tube was sealed to make sure the crystal is equilibrated with water for two days before the diffraction experiments. Three batches of 40 frames separated in reciprocal space were obtained to provide an orientation matrix and initial cell parameters. Final cell parameters were collected and refined was completed based on the full data set.

A diffraction data set of reciprocal space was obtained to a resolution of 106° 2θ angle using 0.5° steps with exposure times 20 s each frame for low angle frames and 60 s each frame for high angle frames. Data were collected at room temperature. Integration of intensities and refinement of cell parameters were conducted using the APEXII software.

| CRYSTAL DATA C$_{24}$H$_{28}$ClN$_5$O$_4$S |
|---|
| M$_r$ = 518.02 |
| Monoclinic, P2$_1$/n |
| a = 5.4324 (5) Å |
| b = 35.483 (4) Å |
| c = 13.3478 (12) Å |
| β = 100.812 (5)° |
| V = 2527.2 (4) Å$^3$ |

Example 15: Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5 A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% CO$_2$. Compounds are then added to the cell media from a final concentration of 25 μM in 3-fold serial dilutions and the cells are incubated at 37° C. in 5% CO$_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50 s for intracellular ATR inhibition are determined using Prism software (GraphPad Prism version 3.0 cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry,* 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 16: ATR Inhibition Assay

Compounds can be screened for their ability to inhibit ATR kinase using a radioactive-phosphate incorporation assay. Assays are carried out in a mixture of 50 mM Tris/HCl (pH 7.5), 10 mM $MgCl_2$ and 1 mM DTT. Final substrate concentrations are 10 µM [γ-33P]ATP (3mCi 33P ATP/mmol ATP, Perkin Elmer) and 800 µM target peptide (ASEL-PASQPQPFSAKKK).

Assays are carried out at 25° C. in the presence of 5 nM full-length ATR. An assay stock buffer solution is prepared containing all of the reagents listed above, with the exception of ATP and the test compound of interest. 13.5 µL of the stock solution is placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate is pre-incubated for 10 minutes at 25° C. and the reaction initiated by addition of 15 µL [γ-33P]ATP (final concentration 10 µM).

The reaction is stopped after 24 hours by the addition of 30 µL 0.1M phosphoric acid containing 2 mM ATP. A multiscreen phosphocellulose filter 96-well plate (Millipore, Cat no. MAPHN0B50) is pretreated with 100 µL 0.2M phosphoric acid prior to the addition of 45 µL of the stopped assay mixture. The plate is washed with 5×200 µL 0.2M phosphoric acid. After drying, 100 µL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0 cx for Macintosh, GraphPad Software, San Diego Calif., USA).

In general, the compounds of the present invention are effective for inhibiting ATR. Compounds I-1, I-2, II-1, 11-2, II-3 and II-4 inhibit ATR at Ki values below 0.001 µM.

Example 17: Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150l of McCoy's 5 A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 M as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

Example 18: Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 µl of McCoy's 5 A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Data for Examples 18-21

| Cmpd No. | Single agent HT116 IC50 (nM) | ATR inhibition Ki (nM) | ATR cellular IC50 (nM) | Cisplatin sensitization (nM) |
|---|---|---|---|---|
| II-1 | 62 | <1 | 18 | 39 |
| II-2 | 46 | <1 | — | 29 |
| II-3 | 66 | 0.148 | 10 | 39 |
| II-4 | — | 0.2 | — | — |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A process for preparing a compound of formula I:

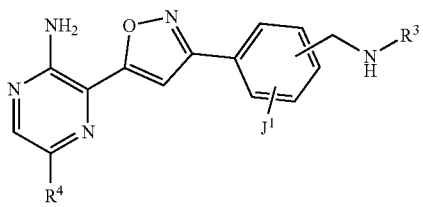

I wherein
$R^4$ is

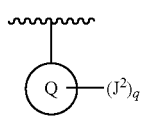

$J^1$ is H, halo, $C_{1-4}$alkyl, or $C_{1-4}$alkoxy;
Q is phenyl, pyridyl, or an N-alkylated pyridine;
$J^2$ is halo; CN; phenyl; oxazolyl; or a $C1_{1-6}$ aliphatic group wherein up to 2 methylene units are optionally replaced with O, C(O), S, S(O), or S(O)$_2$; said $C1_{1-6}$aliphatic group is optionally substituted with 1-3 fluoro or CN;
q is 0, 1, or 2; and
$R^3$ is hydrogen, $C_{1-6}$alkyl, or a 3-6 membered saturated or partially unsaturated heterocyclyl having 1-2 heteroatoms selected from the group consisting of oxygen, nitrogen, and sulfur;
wherein the heterocyclyl is optionally substituted with 1 occurrence of halo or $C_{1-3}$alkyl,
wherein the process comprises the step of preparing a compound of formula 4:

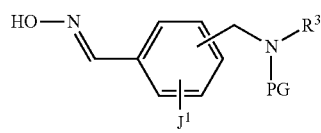

4 from a compound of formula 3:

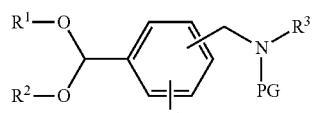

3 under suitable oxime formation conditions;
wherein:
$R^1$ is $C_{1-6}$alkyl;
$R^2$ is $C_{1-6}$alkyl;
or $R^1$ and $R^2$, together with the oxygen atoms to which they are attached, form an optionally substituted 5 or 6 membered saturated heterocyclic ring having two oxygen atoms;
$R^3$ is hydrogen, $C_{1-6}$alkyl, or a 3-6 membered saturated or partially unsaturated heterocyclyl having 1-2 heteroatoms selected from the group consisting of oxygen, nitrogen, and sulfur;
wherein the heterocyclyl is optionally substituted with 1 occurrence of halo or $C_{1-3}$alkyl;
$J^1$ is H, halo, $C_{1-4}$alkyl, or $C_{1-4}$alkoxy; and
PG is a carbamate protecting group.

2. The process of claim 1, further comprising the step of protecting a compound of formula 2:

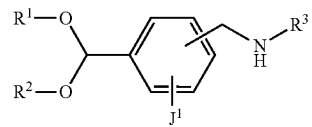

2 under suitable protection conditions to form the compound of formula 3.

3. The process of claim 2, further comprising the step of reacting a compound of formula 1:

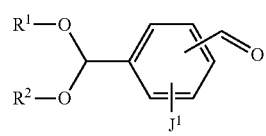

1 with a suitable ligand under suitable reductive amination conditions to form the compound of formula 2.

4. The process of claim 3, wherein the suitable ligand is an amine.

5. The process of claim 1, comprising one or more of the following limitations:
a) $R^1$ is ethyl and $R^2$ ethyl;
b) $R^3$ is $CH_3$ or

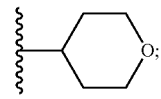 [SMILES: *C1CCOCC1]

and
c) $J^1$ is H.

6. The process of claim 1, wherein $R^4$ is

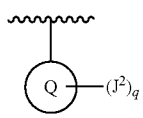

wherein Q is phenyl, q is 1, and $J^2$ is a $C_{1-6}$ aliphatic group wherein up to 1 methylene unit is optionally replaced with —S(O)$_2$—.

7. The process of claim 6, wherein $J^2$ is —S(O)$_2$—($C_{1-5}$alkyl).

8. The process of claim 2, wherein
$R^1$ is ethyl; $R^2$ is ethyl;
$R^3$ is $CH_3$ or

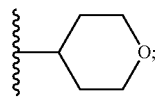

PG is Boc or Cbz;
$J^1$ is H;
$R^4$ is

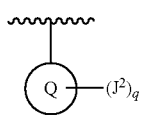

wherein Q is phenyl; $J^2$ is —S(O)$_2$—CH(CH$_3$)$_2$; and q is 1.

9. The process of claim 1, wherein the suitable oxime formation conditions comprise treating the compound of formula 3 with NH$_2$OH—HCl in a mixture of THF and water.

10. The process of claim 1, wherein the suitable oxime formation conditions comprise treating the compound of formula 3 with NH$_2$OH—HCl in a mixture of 2-MeTHF and water.

11. The process of claim 9 or 10, wherein the suitable oxime formation conditions further comprise an amount of Na$_2$SO$_4$ as buffer.

12. The process of claim 10, wherein 1 equivalent of the compound of formula 3 is combined with 1.1 equivalents of NH$_2$OH—HCl in a 10:1 v/v mixture of 2-MeTHF/water optionally buffered with Na$_2$SO$_4$.

13. The process of claim 1, wherein the compound of formula 4 is a compound of formula 4-i:

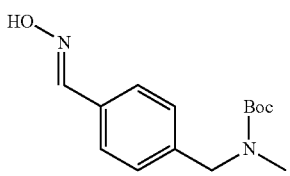

and wherein the compound of formula 3 is a compound of formula 3b:

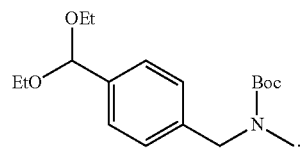

14. The process of claim 13, further comprising reacting the compound of formula 4-i:

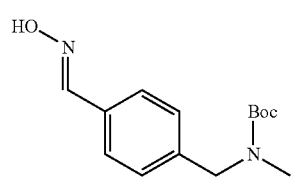

under suitable chlorooxime formation conditions to provide a compound of formula 4-ii:

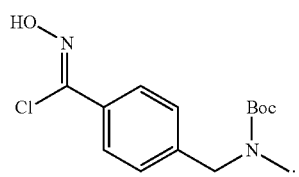

15. The process of claim 14, wherein the suitable chlorooxime formation conditions comprise exposing the compound of formula 4-i to N-chlorosuccinimide (NCS) in a suitable solvent.

16. The process of claim 15, wherein the suitable solvent comprises an aprotic solvent.

17. The process of claim 15, wherein the suitable solvent comprises an alkyl acetate.

18. The process of claim 17, wherein the alkyl acetate is selected from isopropyl acetate and ethyl acetate.

19. The process of claim 1, wherein the compound of formula I is:

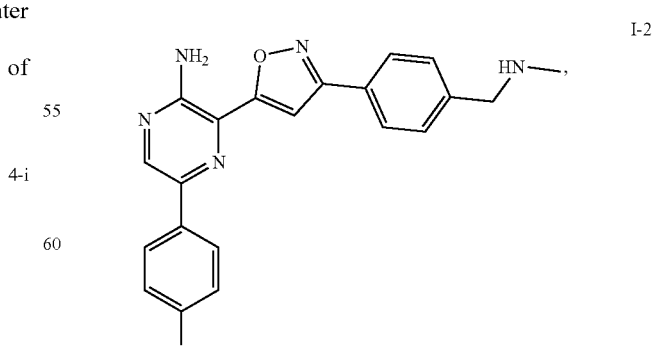

or a pharmaceutically acceptable salt thereof.

20. A process for preparing a compound of formula 4:

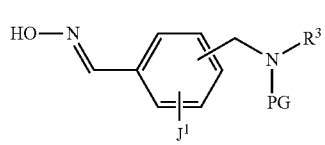

comprising the step of reacting a compound of formula 3:

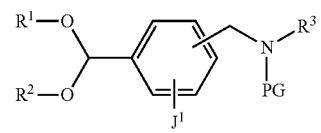

under suitable oxime formation conditions;
wherein:
R$^1$ is C$_{1-6}$alkyl;
R$^2$ is C$_{1-6}$alkyl;
or R$^1$ and R$^2$, together with the oxygen atoms to which they are attached, form an optionally substituted 5 or 6 membered saturated heterocyclic ring having two oxygen atoms;
R$^3$ is hydrogen, C$_{1-6}$alkyl, or a 3-6 membered saturated or partially unsaturated heterocyclyl having 1-2 heteroatoms selected from the group consisting of oxygen, nitrogen, and sulfur;
wherein the heterocyclyl is optionally substituted with 1 occurrence of halo or C$_{1-3}$alkyl;
J$^1$ is H, halo, C$_{1-4}$alkyl, or C$_{1-4}$alkoxy; and
PG is a carbamate protecting group.

21. The process of claim 20, further comprising the step of protecting a compound of formula 2:

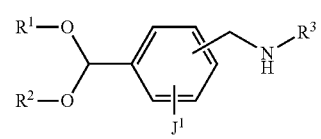

under suitable protection conditions to form the compound of formula 3.

22. The process of claim 21, further comprising the step of reacting a compound of formula 1:

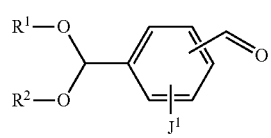

with a suitable ligand under suitable reductive amination conditions to form the compound of formula 2.

23. The process of claim 22, wherein the suitable ligand is an amine.

24. A process for preparing a compound of formula 4-ii:

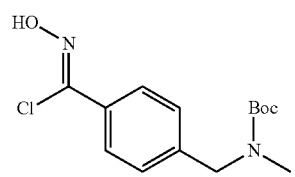

comprising reacting a compound of formula 4-i:

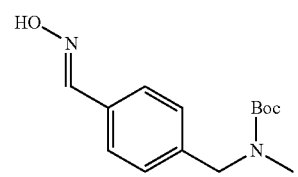

under suitable chlorooxime formation conditions to form the compound of formula 4-ii.

25. The process of claim 24, wherein the suitable chlorooxime formation conditions comprise exposing the compound of formula 4-i to N-chlorosuccinimide (NCS) in a suitable solvent.

26. The process of claim 25, wherein the suitable solvent comprises an aprotic solvent.

27. The process of claim 25, wherein the suitable solvent comprises an alkyl acetate.

28. The process of claim 27, wherein the alkyl acetate is selected from isopropyl acetate and ethyl acetate.

29. The process of claim 24, further comprising the step of preparing the compound of formula 4-i:

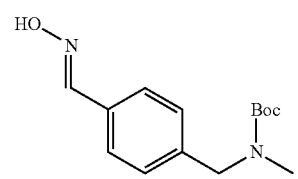

comprising reacting a compound of formula 3b:

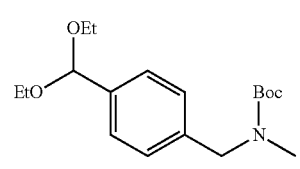

under suitable oxime formation conditions to form the compound of formula 4-i.

30. The process of claim 29, wherein the suitable oxime formation conditions comprise treating the compound of formula 3b with NH$_2$OH-HCl in a mixture of THF and water.

31. The process of claim 29, wherein the suitable oxime formation conditions comprise treating the compound of formula 3b with NH$_2$OH-HCl in a mixture of 2-MeTHF and water.

32. The process of claim 30 or 31, wherein the suitable oxime formation conditions further comprise an amount of Na$_2$SO$_4$ as buffer.

33. The process of claim 29, wherein 1 equivalent of the compound of formula 3b is combined with 1.1 equivalents of NH$_2$OH-HCl in a 10:1 v/v mixture of 2-MeTHF/water optionally buffered with Na$_2$SO$_4$.

34. The process of claim 29, further comprising the step of preparing the compound of formula 3b:

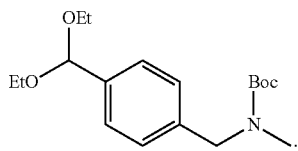
3b comprising reacting a compound of formula 2b:

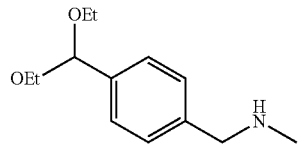
2b under suitable Boc protection conditions to form the compound of formula 3b.

35. The process of claim 34, further comprising the step of preparing the compound of formula 2b:

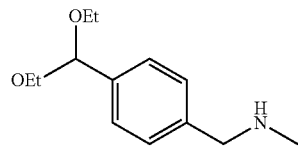
2b comprising reacting a compound of formula 1b:

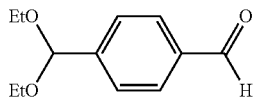

with methylamine under suitable reductive amination conditions to form a compound of formula 2b.

* * * * *